US010130619B2

(12) United States Patent
Machin et al.

(10) Patent No.: US 10,130,619 B2
(45) Date of Patent: Nov. 20, 2018

(54) AMIDO THIADIAZOLE DERIVATIVES AS NADPH OXIDASE INHIBITORS

(71) Applicant: GENKYOTEX SUISSE SA, Plan-les-Ouates (CH)

(72) Inventors: Peter Machin, London (GB); Andrew Sharpe, Saffron Walden (GB); Christopher James Lock, Saffron Walden (GB); Mark S. Chambers, Saffron Walden (GB); Alastair Hodges, Saffron Walden (GB); Vivienne Allen, Saffron Walden (GB); John M. Ellard, Saffron Walden (GB)

(73) Assignee: GENKYOTEX SUISSE SA, Plan-les-Ouates (CH)

( * ) Notice: Subject to any disclaimer, the term of this patent is extended or adjusted under 35 U.S.C. 154(b) by 0 days.

(21) Appl. No.: 15/536,800

(22) PCT Filed: Dec. 16, 2015

(86) PCT No.: PCT/IB2015/059659
§ 371 (c)(1),
(2) Date: Jun. 16, 2017

(87) PCT Pub. No.: WO2016/098005
PCT Pub. Date: Jun. 23, 2016

(65) Prior Publication Data
US 2017/0348296 A1 Dec. 7, 2017

(30) Foreign Application Priority Data
Dec. 17, 2014 (EP) .................................... 14198597

(51) Int. Cl.
| | | |
|---|---|---|
| *A61K 31/506* | (2006.01) | |
| *A61K 31/4439* | (2006.01) | |
| *C07D 417/04* | (2006.01) | |
| *C07D 417/14* | (2006.01) | |
| *A61K 31/4545* | (2006.01) | |
| *A61K 31/496* | (2006.01) | |
| *A61K 31/5355* | (2006.01) | |

(52) U.S. Cl.
CPC ...... *A61K 31/4439* (2013.01); *A61K 31/4545* (2013.01); *A61K 31/496* (2013.01); *A61K 31/506* (2013.01); *A61K 31/5355* (2013.01); *C07D 417/04* (2013.01); *C07D 417/14* (2013.01)

(58) Field of Classification Search
CPC ............................ A61K 31/506; C07D 417/14
USPC .......................................... 514/256; 544/333
See application file for complete search history.

(56) References Cited

U.S. PATENT DOCUMENTS

| | | |
|---|---|---|
| 2007/0037883 A1 | 2/2007 | Dusting et al. |
| 2007/0082910 A1 | 4/2007 | Yamamoto et al. |
| 2008/0176934 A1 | 7/2008 | Verbeuren et al. |
| 2012/0040984 A1 | 2/2012 | Fett et al. |
| 2014/0323500 A1 | 10/2014 | Brandes et al. |

FOREIGN PATENT DOCUMENTS

| | | |
|---|---|---|
| WO | WO 97/19679 | 6/1997 |
| WO | WO 2004/041813 | 5/2004 |
| WO | WO 2010/086551 | 8/2010 |
| WO | WO 2012/170752 | 12/2012 |
| WO | WO 2013/038136 | 3/2013 |
| WO | WO 2013/068972 | 5/2013 |
| WO | WO 2014/106649 | 7/2014 |
| WO | WO 2014/153227 | 9/2014 |

OTHER PUBLICATIONS

Brigham, K. L. "Role of Free Radicals in Lung Injury" *Chest*, Jun. 1986, pp. 859-863, vol. 89, No. 6.
Cai, H. et al. "The vascular NAD(P)H oxidases as therapeutic targets in cardiovascular diseases" *Trends in Pharmacological Sciences*, Sep. 2003, pp. 471-478, vol. 24, No. 9.
Carnesecchi, S. et al. "NADPH Oxidase-1 Plays a Crucial Role in Hyperoxia-induced Acute Lung Injury in Mice" *American Journal of Respiratory and Critical Care Medicine*, Aug. 6, 2009, pp. 972-981, vol. 180, No. 10.
Cheng, G. et al. "Homologs of gp91phox: cloning and tissue expression of Nox3, Nox4, and Nox5" *Gene*, 2001, pp. 131-140, vol. 269.
Djordjevic, T. et al. "Human Urotensin II Is a Novel Activator of NADPH Oxidase in Human Pulmonary Artery Smooth Muscle Cells" *Arterioscler Thromb Vasc Biol.*, Mar. 2005, pp. 519-525, vol. 25.
Ellis, E. A. et al. "Increased $H_2O_2$, Vascular Endothelial Growth Factor and Receptors in the Retina of the BBZ/WOR Diabetic Rat" *Free Radical Biology & Medicine*, 2000, pp. 91-101, vol. 28, No. 1.
Garrido-Urbani, S. et al. "Targeting Vascular NADPH Oxidase 1 Blocks Tumor Angiogenesis through a PPARα Mediated Mechanism" *PLoS ONE*, Feb. 2011, pp. 1-13, vol. 6, No. 2, e14665.
Gianni, D. et al. "A Novel and Specific NADPH Oxidase-1 (Nox1) Small-Molecule Inhibitor Blocks the Formation of Functional Invadopodia in Human Colon Cancer Cells" *ACS Chemical Biology*, 2010, pp. 981-993, vol. 5, No. 10.
Girouard, H. et al. "Neurovascular coupling in the normal brain and in hypertension, stroke, and Alzheimer disease" *J Appl Physiol*, 2006, pp. 328-335, vol. 100.
Lambeth, J. D. et al. "NOX enzymes as novel targets for drug development" *Semin Immunophathol*, 2008, pp. 1-25, vol. 30.
Leto, T. L. et al. "Role of Nox Family NADPH Oxidases in Host Defense" *Antioxidants & Redox Signaling*, 2006, pp. 1549-1561, vol. 8, Nos. 9-10.

(Continued)

*Primary Examiner* — Jeffrey H Murray
(74) *Attorney, Agent, or Firm* — Saliwanchik, Lloyd & Eisenschenk

(57) ABSTRACT

The present invention is related to amino thiazole derivatives of Formula (I), pharmaceutical composition thereof and to their use for the treatment and/or prophylaxis of disorders or conditions related to Nicotinamide adenine dinucleotide phosphate oxidase (NADPH Oxidase).

12 Claims, No Drawings

(56) References Cited

OTHER PUBLICATIONS

Liu, J. Q. et al. "Extracellular superoxide enhances 5-HT-induced murine pulmonary artery vasoconstriction" *Am J Physiol Lung Cell Mol Physiol*, Mar. 12, 2004, pp. L111-L118, vol. 287.

Mougenot, P. et al. "Thiadiazoles as new inhibitors of diacylglycerol acyltransferase type 1" *Bioorganic & Medicinal Chemistry Letters*, Feb. 2, 2012, pp. 2497-2502, vol. 22, No. 7.

Nunomura, A. et al. "Oxidative Damage Is the Earliest Event in Alzheimer Disease" *Journal of Neuropathology and Experimental Neurology*, Aug. 2001, pp. 759-767, vol. 60, No. 8.

Palicz, A. et al. "Phosphatidic Acid and Diacylglycerol Directly Activate NADPH Oxidase by Interacting with Enzyme Components" *The Journal of Biological Chemistry*, Feb. 2, 2001, pp. 3090-3097, vol. 276, No. 5.

Pillarisetti, S. et al. "Role of oxidative stress and inflammation in the origin of Type 2 diabetes—a paradigm shift" *Expert Opin. Ther. Targets*, 2004, pp. 401-408, vol. 8, No. 5.

Ranayhossaini, D. J. et al. "Selective Recapitulation of Conserved and Nonconserved Regions of Putative NOXA1 Protein Activation Domain Confers Isoform-specific Inhibition of Nox1 Oxidase and Attenuation of Endothelial Cell Migration" *The Journal of Biological Chemistry*, Dec. 20, 2013, pp. 36437-36450, vol. 288, No. 51.

Shi, Y. et al. "Increased NAD(P)H Oxidase and Reactive Oxygen Species in Coronary Arteries After Balloon Injury" *Arterioscler Thromb Vasc Biol.*, May 2001, pp. 739-745, vol. 21.

Thabut, G. et al. "Tumor Necrosis Factor-α Increases Airway Smooth Muscle Oxidants Production through a NADPH Oxidase-like System to Enhance Myosin Light Chain Phosphorylation and Contractility" *The Journal of Biological Chemistry*, Jun. 21, 2002, pp. 22814-22821, vol. 277, No. 25.

Vernet, P. et al. "Analysis of Reactive Oxygen Species Generating Systems in Rat Epididymal Spermatozoa" *Biology of Reproduction*, 2001, pp. 1102-1113, vol. 65.

Wilkinson-Berka, J. L. et al. "NADPH Oxidase, NOX1, Mediates Vascular Injury in Ischemic Retinopathy" *Antioxidants & Redox Signaling*, 2014, pp. 2726-2740, vol. 20, No. 17.

Yang, S. et al. "Characterization of Interferon Gamma Receptors on Osteoclasts: Effect of Interferon Gamma on Osteoclastic Superoxide Generation" *Journal of Cellular Biochemistry*, 2002, pp. 645-654. vol. 84.

Written Opinion in International Application No. PCT/IB2015/059659, dated Mar. 10, 2016, pp. 1-6.

Asaba, K. et al. "Effects of NADPH oxidase inhibitor in diabetic nephropathy" *Kidney International*, 2005, pp. 1890-1898, vol. 67.

Baumer, A. T. et al. "The NAD(P)H Oxidase Inhibitor Apocynin Improves Endothelial NO/Superoxide Balance and Lowers Effectively Blood Pressure in Spontaneously Hypertensive Rats: Comparison to Calcium Channel Blockade" *Clinical and Experimental Hypertension*, 2007, pp. 287-299, vol. 29.

Chirino, Y. I. et al. "Protective effects of apocynin against cisplatin-induced oxidative stress and nephrotoxicity" *Tosicology*, 2008, pp. 18-23, vol. 245.

Chan, E. C. et al. "Regulation of cell proliferation by NADPH oxidase-mediated signaling: Potential roles in tissue repair, regenerative medicine and tissue engineering" *Pharnacology & Therapeutics*, 2009, pp. 97-108, vol. 122.

Peters, E. A. et al. "Effect of Apocynin on Ozone-Induced Airway Hyperresponsiveness to Methacholine in Asthmatics" *Free Radical Biology & Medicine*, 2001, pp. 1442-1447, vol. 31, No. 11.

Rachmilewitz, D. et al. "Sulphydryl blocker induced small intestinal inflammation in rats: a new model mimicking Crohn's disease" *Gut*, 1997, pp. 358-365, vol. 41.

Tang, X. N. et al. "Apocynin Improves Outcome in Experimental Stroke with a Narrow Dose Range" *Neuroscience*, 2008, pp. 556-562, vol. 154.

Wang, W. et al. "Effect of the NADPH Oxidase Inhibitor Apocynin on Septic Lung Injury in Guinea Pigs" *American Journal of Respiratory and Critical Care Medicine*, 1994, pp. 1449-1452, vol. 150.

Zhao, W. et al. "Kidney Fibrosis in Hypertensive Rats: Role of Oxidative Stress" *Am J Nephrol*, 2008, pp. 548-554, vol. 28.

Klees, R. F. et al. "Apocynin Derivatives Interrupt Intracellular Signaling Resulting in Decreased Migration in Breast Cancer Cells" *Journal of Biomedicine and Biotechnology*, 2006, pp. 1-10, vol. 2006.

Bedard, K. et al. "The NOX Family of ROS-Generating NADPH Oxidases: Physiology and Pathophysiology" *Physiological Reviews*, Jan. 2007, pp. 245-313, vol. 87.

Qian, L. et al. "Sinomenine, a natural dextrorotatory morphinan analog, is anti-inflammatory and neuroprotective through inhibition of microglial NADPH oxidase" *Journal of Neuroinflammation*, 2007, pp. 1-14, vol. 4, No. 23.

Hougee, S. et al. "Oral administration of the NADPH-oxidase inhibitor apocynin partially restores diminished cartilage proteoglycan synthesis and reduces inflammation in mice" *European Journal of Pharmacology*, 2006, pp. 264-269, vol. 531.

Vaquero, V. C. et al. "Reactive Oxygen Species Produced by NAD(P)H Oxidase Inhibit Apoptosis in Pancreatic Cancer Cells" *The Journal of Biological Chemistry*, Aug. 13, 2004, pp. 34643-34654, vol. 279, No. 33.

Lu, J. P. et al. "Androgens induce oxidative stress and radiation resistance in prostate cancer cells though NADPH oxidase" *Prostate Cancer and Prostatic Diseases*, 2010, pp. 39-46, vol. 13.

Lafeber, F. P. J. G. et al. "Apocynin, a plant-derived, cartilage-saving drug, might be useful in the treatment of rheumatoid arthritis" *Rheumatology*, 1999, pp. 1088-1093, vol. 38.

Cayatte, A. J. et al. "S17834, a New Inhibitor of Cell Adhesion and Atherosclerosis That Targets NADPH Oxidase" *Arteriosclerosis, Thrombosis, and Vascular Biology*, 2001, pp. 1577-1584, vol. 21.

Jin, L. et al. "NADPH oxidase: recent evidence for its role in erectile dysfunction" *Asian Journal of Andrology*, 2008, pp. 6-13, vol. 10, No. 1.

Sedeek, M. et al. "Molecular mechanisms of hypertension: role of Nox family NADPH oxidases" *Current Opinion in Nephrology and Hypertension*, Mar. 2009, pp. 122-127, vol. 18, No. 2.

AMIDO THIADIAZOLE DERIVATIVES AS NADPH OXIDASE INHIBITORS

CROSS-REFERENCE TO RELATED APPLICATION

This application is the U.S. national stage application of International Patent Application No. PCT/IB2015/059659, filed Dec. 16, 2015.

FIELD OF THE INVENTION

The present invention relates to amido thiadiazole derivatives of Formula (I), pharmaceutical composition thereof and to their use for the preparation of a medicament for the treatment and/or prophylaxis of Nicotinamide adenine dinucleotide phosphate oxidase (NADPH Oxidase) related disorders such as cardiovascular diseases, neurodegenerative diseases, inflammatory disorders and cancers. Specifically, the present invention is related to amido thiadiazole derivatives useful for the preparation of a pharmaceutical formulation for the modulation, notably the inhibition of the activity or function of the Nicotinamide adenine dinucleotide phosphate oxidase (NADPH Oxidase).

BACKGROUND OF THE INVENTION

NADPH oxidases (NOX) are proteins that transfer electrons across biological membranes. In general, the electron acceptor is oxygen and the product of the electron transfer reaction is superoxide. The biological function of NOX enzymes is therefore the generation of reactive oxygen species (ROS) from oxygen. Reactive oxygen species (ROS) are oxygen-derived small molecules, including oxygen radicals (super-oxide anion $[.O_2^-]$, hydroxyl [HO.], peroxyl [ROO.], alkoxyl [RO.] and hydroperoxyl [HOO.]) and certain non-radicals that are either oxidizing agents and/or are easily converted into radicals. Nitrogen-containing oxidizing agents, such as nitric oxide are also called reactive nitrogen species (RNS). ROS generation is generally a cascade of reactions that starts with the production of superoxide. Superoxide rapidly dismutates to hydrogen peroxide either spontaneously, particularly at low pH or catalyzed by superoxide dismutase. Other elements in the cascade of ROS generation include the reaction of superoxide with nitric oxide to form peroxynitrite, the peroxidase-catalyzed formation of hypochlorous acid from hydrogen peroxide, and the iron-catalyzed Fenton reaction leading to the generation of hydroxyl radical.

ROS avidly interact with a large number of molecules including other small inorganic molecules as well as DNA, proteins, lipids, carbohydrates and nucleic acids. This initial reaction may generate a second radical, thus multiplying the potential damage. ROS are involved not only in cellular damage and killing of pathogens, but also in a large number of reversible regulatory processes in virtually all cells and tissues. However, despite the importance of ROS in the regulation of fundamental physiological processes, ROS production can also irreversibly destroy or alter the function of the target molecule. Consequently, ROS have been increasingly identified as major contributors to damage in biological organisms, so-called "oxidative stress".

During inflammation, NADPH oxidase is one of the most important sources of ROS production in vascular cells under inflammatory conditions (Thabut et al., 2002, *J. Biol. Chem.*, 277:22814-22821).

In the lung, tissues are constantly exposed to oxidants that are generated either endogenously by metabolic reactions (e.g. by mitochondrial respiration or activation of recruited inflammatory cells) or exogenously in the air (e.g. cigarette smoke or air pollutants). Further, the lungs, constantly exposed to high oxygen tensions as compared to other tissues, have a considerable surface area and blood supply and are particularly susceptible to injury mediated by ROS (Brigham, 1986, *Chest*, 89(6): 859-863). NADPH oxidase-dependent ROS generation has been described in pulmonary endothelial cells and smooth muscle cells. NADPH oxidase activation in response to stimuli has been thought to be involved in the development of respiratory disorders such as pulmonary hypertension and enhancement of pulmonary vasoconstriction (Djordjevic et al., 2005, *Arterioscler. Thromb. Vasc. Biol.*, 25, 519-525; Liva et al., 2004, *Am. J. Physiol. Lung, Cell. Mol. Physiol.*, 287: L111-118). Further, pulmonary fibrosis has been characterized by lung inflammation and excessive generation of ROS.

Osteoclasts, which are macrophage-like cells that play a crucial role in bone turn-over (e.g. bone resorption), generate ROS through NADPH oxidase-dependent mechanisms (Yang et al., 2002, *J. Cell. Chem.* 84, 645-654).

Diabetes is known to increase oxidative stress (e.g. increased generation of ROS by auto-oxidation of glucose) both in humans and animals and increased oxidative stress has been said to play an important role in the development of diabetic complications. It has been shown that increased peroxide localization and endothelial cell dysfunction in the central retina of diabetic rats coincides with the areas of NADPH oxidase activity in the retinal endothelial cells (Ellis et al., 2000, *Free Rad. Biol. Med.*, 28:91-101). Further, it has been suggested that controlling oxidative stress (ROS) in mitochondria and/or inflammation may be a beneficial approach for the treatment of diabetes (Pillarisetti et al., 2004, *Expert Opin. Ther. Targets*, 8(5):401-408).

ROS are also strongly implicated in the pathogenesis of atherosclerosis, cell proliferation, hypertension and reperfusion injury cardiovascular diseases in general (Cai et al., 2003, *Trends Pharmacol. Sci.*, 24:471-478). Not only is superoxide production, for example in the arterial wall, increased by all risk factors for atherosclerosis, but ROS also induce many "proatherogenic" in vitro cellular responses. An important consequence of the formation of ROS in vascular cells is the consumption of nitric oxide (NO). NO inhibits the development of vascular diseases, and loss of NO is important in the pathogenesis of cardiovascular diseases. The increase in NADPH oxidase activity in vascular wall after balloon injury has been reported (Shi et al., 2001, *Throm. Vasc. Biol.*, 2001, 21, 739-745)

It is believed that oxidative stress or free radical damage is also a major causative factor in neurodegenerative diseases. Such damages may include mitochondrial abnormalities, neuronal demyelination, apoptosis, neuronal death and reduced cognitive performance, potentially leading to the development of progressive neurodegenerative disorders (Nunomura et al., 2001, *J. Neuropathol. Exp. Neurol.*, 60:759-767; Girouard, 2006, *J. Appl. Physiol.* 100:328-335).

Further, the generation of ROS by sperm has been demonstrated in a large number of species and has been suggested to be attributed to an NADPH oxidase within spermatozoa (Vernet et al., *Biol. Reprod.*, 2001, 65:1102-1113). Excessive ROS generation has been suggested to be implicated in sperm pathology, including male infertility and also in some penile disorders and prostate cancer.

Oxidative stress through reactive oxygen species generation by an NADPH oxidase has been shown to be responsible of neuropathological alterations in a rat model of chronic psychosocial stress and involved in psychotic disorders and social isolation processes.

Further, ROS have been shown to be associated with increased mitotic rate, angiogenesis, migration of adenocarcinoma cells and cell differentiation Lambeth et al. 2008, *Semin. Immunopathol.*, 2008, 30, 339-363) and NOX inhibitors have been shown able to reduce tumour vascularization (tumour angiogenesis) and tumour growth in a curative model in a similar extent to that of an anti-VEGFR2 antibody (DC101) (Garrido-Urbani, 2011, *PLoS ONE*, 6(2)).

NADPH oxidases are multi-subunit enzymes made up of a membrane-bound cytochrome b558 domain and three cytosolic protein subunits, p47phox, p67phox and a small GTPase, Rac. Seven isoforms of NOX enzymes have been identified including NOX1, NOX2, NOX3, NOX4, NOX5, DUOX1 and DUOX2 (Leto et al., 2006, *Antioxid. Redox Signal*, 8(9-10):1549-61; Cheng et al., 2001, *Gene*, 16; 269(1-2):131-40).

In particular, excessive vascular and colon epithelial ROS production by Nox1 isoform has been found as being implicated in the development and progression of a wide spectrum of diseases a number of disease states, including cardiovascular disorders and in particular hypertension and atherosclerosis, neurodegenerative diseases, liver fibrosis, cancer, in particular in colon cancer, ischemic conditions, in particular ischemic retinopathies and neoplasia.

It has been found that ROS generation by the Nox1 member of the Nox family is necessary for the formation of extracellular matrix (ECM)-degrading, actin-rich cellular structures known as invadopodia. A peptide mimicking a putative activation domain of the NOX1 activator NOXA1 was developed as Nox-1 inhibitor and was described as being able to attenuate endothelial cell migration (Rynayhossani et al., 2013, *J. Bio. Chem.*, 288(51):36437-50). A subset of phenothiazines, 2-acetylphenothiazine (referred to as ML171 and its related 2-(trifluoromethyl)-phenothiazine) have been found to be Nox1 inhibitors that potently block Nox1-dependent ROS generation. ML171 also blocks the ROS-dependent formation of ECM-degrading invadopodia in colon cancer cells (Gianni et al., 2010, ACS Chem. Biol., 5(10):981:93). Further, NOX1 selective inhibition has been found to be a potential strategy for ECM-degrading invadopodia in colon cancer cells (Gianni et al., 2010, *ACS Chem. Biol.*, 5(10):981:93). Further, NOX1 selective inhibition has been found to be a potential strategy for treatment for a range of ischemic retinopathies (Wilkinson-Berka et al., 2014, *Antioxid. Redox Signal*, 20(17):2726-40) since NOX1 has been reported to mediate vascular injury in ischemic retinopathy. Very recently, peptidic inhibitors of Nox1 have been developed (WO 2014/106649) for treating and/or preventing cancer, atherosclerosis, angiogenesis, and aging and other Nox1 inhibitors have been developed for the protection of pancreatic beta cells (WO 2014/153227). Further, it was recently determined that NOX1 is an important contributor to ROS production and cell death of the alveolocapillary barrier in acute lung injury and that NOX1 silencing prevented ROS generation and cell death in lung epithelial cells (Carnesecchi et al., 2009, *American Journal of Respiratory and Critical Care Medicine*; 180(10):972-981).

Thus, ROS derived from NOX1 contribute to the pathogenesis of numerous diseases, and therefore, it would be highly desirable to develop new active agents clinically useful inhibitors of the Nox enzymes, in particular selective for Nox1.

SUMMARY OF THE INVENTION

The present invention is directed towards new molecules useful in the treatment and/or prophylaxis of Nicotinamide adenine dinucleotide phosphate oxidase (NADPH Oxidase) related disorders such as cardiovascular diseases, neurodegenerative diseases, kidney diseases, liver disorders, inflammatory disorders, cancers, fibrotic disorders, psychotic disorders, angiogenesis, infectious diseases, and angiogenesis-dependent conditions. Notably, the invention is related to new molecules useful in the inhibition or reduction of ROS production in cells.

A first aspect of the invention provides amido thiadiazole derivatives according to Formula (I), wherein $A_1$ and $A_2$; X and Y; $R^1$; $R^2$, $R^3$, $R^4$, $R^5$, $R^6$, $R^7$, $R^8$, $R^9$, $R^{10}$, $R^{11}$ and n are as defined below, as well as tautomers, geometrical isomers, optically active forms, pharmaceutically acceptable salts and pharmaceutically active derivative thereof.

A second aspect of the invention relates to an amido thiadiazole derivative according to Formula (I), wherein $A_1$ and $A_2$; X and Y; $R^1$; $R^2$, $R^3$, $R^4$, $R^5$, $R^6$, $R^7$, $R^8$, $R^9$, $R^{10}$, $R^{11}$ and n are as defined below, as well as tautomers, geometrical isomers, optically active forms, pharmaceutically acceptable salts and pharmaceutically active derivative thereof for use as a medicament.

A third aspect of the invention relates to a pharmaceutical composition containing at least one amido thiadiazole derivative according to the invention, as well as tautomers, geometrical isomers, optically active forms, pharmaceutically acceptable salts and pharmaceutically active derivative thereof.

A fourth aspect of the invention resides in a use of an amido thiadiazole derivative according to the invention as tautomers, geometrical isomers, optically active forms, pharmaceutically acceptable salts and pharmaceutically active derivative thereof for the preparation of a pharmaceutical composition for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, fibrotic disorders, psychotic disorders, infectious diseases, allergic disorders, traumatisms, septic, hemorrhagic and anaphylactic shock, diseases or disorders of the gastrointestinal system, angiogenesis and angiogenesis-dependent and/or other diseases and disorders associated with Nicotinamide adenine dinucleotide phosphate oxidase (NADPH Oxidase).

A fifth aspect of the invention relates to a method for treating a patient suffering from a disease or condition selected from cardiovascular disorders, respiratory disorders, metabolic disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, fibrotic disorders, psychotic disorders, infectious diseases, allergic disorders, traumatisms, septic, hemorrhagic and anaphylactic shock, diseases or disorders of the gastrointestinal system, angiogenesis and angiogenesis-dependent and other diseases and/or disorders associated with Nicotinamide adenine dinucleotide phosphate oxidase (NADPH Oxidase). The method comprises administering an amido thiadiazole derivative according to Formula (I), wherein $A_1$ and $A_2$; X and Y; $R^1$; $R^2$, $R^3$, $R^4$, $R^5$, $R^6$, $R^7$, $R^8$, $R^9$, $R^{10}$, $R^{11}$ and n are as defined below, as well as tautomers, geometrical isomers, optically active forms, pharmaceutically acceptable salts and pharmaceutically active derivative thereof in a patient in need thereof.

A sixth aspect of the invention relates to an amido thiadiazole derivative according to Formula (I), wherein $A_1$ and $A_2$; X and Y; $R^1$; $R^2$, $R^3$, $R^4$, $R^5$, $R^6$, $R^7$, $R^8$, $R^9$, $R^{10}$, $R^{11}$ and n are as defined below, as well as tautomers, geometrical isomers, optically active forms, pharmaceutically acceptable salts and pharmaceutically active derivative thereof for the treatment of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, fibrotic disorders, psychotic disorders, infectious diseases, allergic disorders, traumatisms, septic, hemorrhagic and anaphylactic shock, diseases or disorders of the gastrointestinal system, angiogenesis and angiogenesis-dependent and other diseases and/or disorders associated with Nicotinamide adenine dinucleotide phosphate oxidase (NADPH Oxidase).

Other features and advantages of the invention will be apparent from the following detailed description.

DETAILED DESCRIPTION OF THE INVENTION

The following paragraphs provide definitions of the various chemical moieties that make up the compounds according to the invention and are intended to apply uniformly through-out the specification and claims, unless an otherwise expressly set out definition provides a broader definition.

The term "alkyl" when used alone or in combination with other terms, comprises a straight chain or branched $C_1$-$C_{20}$ alkyl which refers to monovalent alkyl groups having 1 to 20 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl, n-nonadecyl, and n-eicosanyl and the like. Preferably, these include $C_1$-$C_9$ alkyl, more preferably $C_1$-$C_6$ alkyl, especially preferably $C_1$-$C_4$ alkyl, which, by analogy, refer respectively to monovalent alkyl groups having 1 to 9 carbon atoms, monovalent alkyl groups having 1 to 6 carbon atoms and monovalent alkyl groups having 1 to 4 carbon atoms. Particularly, those include $C_1$-$C_6$ alkyl.

The term "alkenyl" when used alone or in combination with other terms, comprises a straight chain or branched $C_2$-$C_{20}$ alkenyl. It may have any available number of double bonds in any available positions, and the configuration of the double bond may be the (E) or (Z) configuration. This term is exemplified by groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 1-heptenyl, 1-octenyl, geranyl, 1-decenyl, 1-tetradecenyl, 1-octadecenyl, 9-octadecenyl, 1-eicosenyl, and 3,7,11,15-tetramethyl-1-hexadecenyl, and the like. Preferably, these include $C_2$-$C_8$ alkenyl, more preferably $C_2$-$C_6$ alkenyl. Among others, especially preferred are vinyl or ethenyl (—CH═$CH_2$), n-2-propenyl (allyl, —$CH_2$CH═$CH_2$), isopropenyl, 1-propenyl, 2-methyl-1-propenyl, 1-butenyl, 2-butenyl, and 3-methyl-2-butenyl and the like.

The term "alkynyl" when used alone or in combination with other terms, comprises a straight chain or branched $C_2$-$C_{20}$ alkynyl. It may have any available number of triple bonds in any available positions. This term is exemplified by groups such as alkynyl groups that may have a carbon number of 2-20, and optionally a double bond, such as ethynyl (—C≡CH), 1-propynyl, 2-propynyl (propargyl: —$CH_2$C≡CH), 2-butynyl, 2-pentene-4-ynyl, and the like. Particularly, these include $C_2$-$C_8$ alkynyl, more preferably $C_2$-$C_6$ alkynyl and the like. Preferably those include $C_2$-$C_6$ alkynyl which refers to groups having 2 to 6 carbon atoms and having at least 1 or 2 sites of alkynyl unsaturation.

The term "heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl and the like.

The term "aryl" refers to an unsaturated aromatic carbocyclic group of from 6 to 14 carbon atoms having a single ring (e.g., phenyl) or multiple condensed rings (e.g., indenyl, naphthyl). Aryl include phenyl, naphthyl, anthryl, phenanthrenyl and the like.

The term "$C_1$-$C_6$ alkyl aryl" refers to aryl groups having a $C_1$-$C_6$ alkyl substituent, including methyl phenyl, ethyl phenyl and the like.

The term "aryl $C_1$-$C_6$ alkyl" refers to $C_1$-$C_6$ alkyl groups having an aryl substituent, including 3-phenylpropanyl, benzyl and the like.

The term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "$C_1$-$C_6$ alkyl heteroaryl" refers to heteroaryl groups having a $C_1$-$C_6$ alkyl substituent, including methyl furyl and the like.

The term "heteroaryl $C_1$-$C_6$ alkyl" refers to $C_1$-$C_6$ alkyl groups having a heteroaryl substituent, including furyl methyl and the like.

The term "$C_2$-$C_6$ alkenyl aryl" refers to an aryl groups having a $C_2$-$C_6$ alkenyl substituent, including vinyl phenyl and the like.

The term "aryl $C_2$-$C_6$ alkenyl" refers to a $C_2$-$C_6$ alkenyl groups having an aryl substituent, including phenyl vinyl and the like.

The term "$C_2$-$C_6$ alkenyl heteroaryl" refers to heteroaryl groups having a $C_2$-$C_6$ alkenyl substituent, including vinyl pyridinyl and the like.

The term "heteroaryl $C_2$-$C_6$ alkenyl" refers to $C_1$-$C_6$ alkenyl groups having a heteroaryl substituent, including pyridinyl vinyl and the like.

The term "$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl includes cyclopentyl, cyclohexyl, norbornyl and the like.

The term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidinyl, piperidinyl, piperazinyl, morpholinyl, tetrahydrofuranyl and the like.

The term "$C_1$-$C_6$ alkyl $C_3$-$C_8$-cycloalkyl" refers to $C_3$-$C_8$-cycloalkyl groups having a $C_1$-$C_6$ alkyl substituent, including methyl cyclopentyl and the like.

The term "$C_3$-$C_8$-cycloalkyl $C_1$-$C_6$ alkyl" refers to $C_1$-$C_6$ alkyl groups having a $C_3$-$C_8$-cycloalkyl substituent, including 3-cyclopentyl propyl and the like.

The term "$C_1$-$C_6$ alkyl heterocycloalkyl" refers to heterocycloalkyl groups having a $C_1$-$C_6$ alkyl substituent, including 4-methylpiperidinyl and the like.

The term "heterocycloalkyl $C_1$-$C_6$ alkyl" refers to $C_1$-$C_6$ alkyl groups having a heterocycloalkyl substituent, including (1-methylpiperidin-4-yl) methyl and the like.

The term "carboxy" refers to the group —C(O)OH.

The term "carboxy $C_1$-$C_6$ alkyl" refers to $C_1$-$C_6$ alkyl groups having a carboxy substituent, including 2-carboxyethyl and the like.

The term "acyl" refers to the group —C(O)R where R includes H, "$C_1$-$C_6$ alkyl," preferably "$C_1$-$C_6$ alkyl," "aryl," "heteroaryl," "$C_3$-$C_8$-cycloalkyl," "heterocycloalkyl," "aryl $C_1$-$C_6$ alkyl," "heteroaryl $C_1$-$C_6$ alkyl," "$C_3$-$C_8$-cycloalkyl $C_1$-$C_6$ alkyl" or "heterocycloalkyl $C_1$-$C_6$ alkyl", including acetyl and the like.

The term "acyl $C_1$-$C_6$ alkyl" to $C_1$-$C_6$ alkyl groups having an acyl substituent, including 2-acetylethyl and the like.

The term "acyl aryl" refers to aryl groups having an acyl substituent, including 2-acetylphenyl and the like.

The term "acyloxy" refers to the group —OC(O)R where R includes H, "$C_1$-$C_6$ alkyl", "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", including acetyloxy and the like.

The term "acyloxy $C_1$-$C_6$ alkyl" refers to $C_1$-$C_6$ alkyl groups having an acyloxy substituent, including 2-(ethylcarbonyloxy) ethyl and the like.

The term "alkoxy" refers to the group —O—R where R includes "$C_1$-$C_6$ alkyl", "aryl", "heteroaryl", "aryl $C_1$-$C_6$ alkyl" or "heteroaryl $C_1$-$C_6$ alkyl". Preferred alkoxy groups include for example, methoxy, ethoxy, phenoxy and the like.

The term "alkoxy $C_1$-$C_6$ alkyl" refers to $C_1$-$C_6$ alkyl groups having an alkoxy substituent, including methoxyethyl and the like.

The term "alkoxycarbonyl" refers to the group —C(O)OR where R includes "$C_1$-$C_6$ alkyl", "aryl", "heteroaryl", "aryl $C_1$-$C_6$ alkyl", "heteroaryl $C_1$-$C_6$ alkyl" or "heteroalkyl".

The term "alkoxycarbonyl $C_1$-$C_6$ alkyl" refers to $C_1$-$C_6$ alkyl groups having an alkoxycarbonyl substituent, including 2-(benzyloxycarbonyl)ethyl and the like.

The term "aminocarbonyl" refers to the group —C(O)NRR' where R and R' are independently H, $C_1$-$C_6$ alkyl, aryl, heteroaryl, "aryl $C_1$-$C_6$ alkyl" or "heteroaryl $C_1$-$C_6$ alkyl," including N-phenyl carbonyl and the like.

The term "aminocarbonyl $C_1$-$C_6$ alkyl" refers to alkyl groups having an aminocarbonyl substituent, including 2-(dimethylaminocarbonyl)ethyl, N-ethyl acetamidyl, N,N-Diethyl-acetamidyl and the like.

The term "acylamino" refers to the group —NRC(O)R' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl", including acetylamino and the like.

The term "acylamino $C_1$-$C_6$ alkyl" refers to $C_1$-$C_6$ alkyl groups having an acylamino substituent, including 2-(propionylamino)ethyl and the like.

The term "ureido" refers to the group —NRC(O)NR'R" where R, R' and R" are independently H, "$C_1$-$C_6$ alkyl," "$C_2$-$C_6$ alkenyl," "alkynyl," "$C_3$-$C_8$-cycloalkyl," "heterocycloalkyl," "$C_1$-$C_6$ aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl," and where R' and R," together with the nitrogen atom to which they are attached, can optionally form a 3-8-membered heterocycloalkyl ring.

The term "ureido $C_1$-$C_6$ alkyl" refers to $C_1$-$C_6$ alkyl groups having an ureido substituent, including 2-(N'-methylureido) ethyl and the like.

The term "carbamate" refers to the group —NRC(O)OR' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "$C_1$-$C_6$ alkyl aryl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl" and optionally R can also be hydrogen.

The term "amino" refers to the group —NRR' where R and R' are independently H, "$C_1$-$C_6$ alkyl", "aryl", "heteroaryl", "$C_1$-$C_6$ alkyl aryl", "$C_1$-$C_6$ alkyl heteroaryl," "cycloalkyl," or "heterocycloalkyl," and where R and R', together with the nitrogen atom to which they are attached, can optionally form a 3-8-membered heterocycloalkyl ring.

The term "amino alkyl" refers to alkyl groups having an amino substituent, including 2-(1-pyrrolidinyl)ethyl and the like.

The term "ammonium" refers to a positively charged group —$N^+$RR'R" where R, R' and R" are independently "$C_1$-$C_6$ alkyl", "$C_1$-$C_6$ alkyl aryl", "$C_1$-$C_6$ alkyl heteroaryl," "cycloalkyl," or "heterocycloalkyl," and where R and R', together with the nitrogen atom to which they are attached, can optionally form a 3-8-membered heterocycloalkyl ring.

The term "ammonium alkyl" refers to alkyl groups having an ammonium substituent, including 1-ethylpyrrolidinium and the like.

The term "halogen" refers to fluoro, chloro, bromo and iodo atoms.

The term "sulfonyloxy" refers to a group —$OSO_2$—R wherein R is selected from "$C_1$-$C_6$ alkyl," "$C_1$-$C_6$ alkyl" substituted with halogens, e.g., an —$OSO_2$—$CF_3$ group, "$C_2$-$C_6$ alkenyl," "alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl alkyl".

The term "sulfonyloxy $C_1$-$C_6$ alkyl" refers to alkyl groups having a sulfonyloxy substituent, including 2-(methylsulfonyloxy) ethyl and the like.

The term "sulfonyl" refers to group "—$SO_2$—R" wherein R is selected from "aryl," "heteroaryl," "$C_1$-$C_6$ alkyl," "$C_1$-$C_6$ alkyl" substituted with halogens, e.g., an —$SO_2$—$CF_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl".

The term "sulfonyl $C_1$-$C_6$ alkyl" refers to alkyl groups having a sulfonyl substituent, including 2-(methylsulfonyl) ethyl and the like.

The term "sulfinyl" refers to a group "—S(O)—R" wherein R is selected from "alkyl," "alkyl" substituted with halogens, e.g., a —SO—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfinyl alkyl" refers to alkyl groups having a sulfinyl substituent, including 2-(methylsulfinyl) ethyl and the like.

The term "sulfanyl" refers to groups —S—R where R includes H, "$C_1$-$C_6$ alkyl," "$C_1$-$C_6$ alkyl" substituted with halogens, e.g., a —S—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "alkynylheteroaryl," "cycloalkyl $C_1$-$C_6$ alkyl," or "heterocycloalkyl $C_1$-$C_6$ alkyl". Preferred sulfanyl groups include methylsulfanyl, ethylsulfanyl, and the like.

The term "sulfanyl $C_1$-$C_6$ alkyl" refers to $C_1$-$C_5$-alkyl groups having a sulfanyl substituent, including 2-(ethylsulfanyl) ethyl and the like.

The term "sulfonylamino" refers to a group —NRSO$_2$—R' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfonylamino $C_1$-$C_6$ alkyl" refers to alkyl groups having a sulfonylamino substituent, including 2-(ethylsulfonylamino) ethyl and the like.

The term "aminosulfonyl" refers to a group —SO$_2$—NRR' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", and where R and R', together with the nitrogen atom to which they are attached, can optionally form a 3-8-membered heterocycloalkyl ring. Aminosulfonyl groups include cyclohexylaminosulfonyl, piperidinylsulfonyl and the like.

The term "aminosulfonyl $C_1$-$C_6$ alkyl" refers to $C_1$-$C_6$ alkyl groups having an aminosulfonyl substituent, including 2-(cyclohexylaminosulfonyl)ethyl and the like.

Unless otherwise constrained by the definition of the individual substituent, all the above substituents should be understood as being all optionally substituted.

Unless otherwise constrained by the definition of the individual substituent, the term "substituted" refers to groups substituted with from 1 to 5 substituents selected from the group consisting of "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "$C_1$-$C_6$ alkyl cycloalkyl," "$C_1$-$C_6$ alkyl heterocycloalkyl," "cycloalkyl $C_1$-$C_6$ alkyl," "heterocycloalkyl $C_1$-$C_6$ alkyl," "amino," "aminosulfonyl," "ammonium," "alkoxy," "acyl amino," "amino carbonyl," "aryl," "aryl $C_1$-$C_6$ alkyl," "heteroaryl," "heteroaryl $C_1$-$C_6$ alkyl," "sulfinyl," "sulfonyl," "sulphonamide", "alkoxy," "alkoxy carbonyl," "carbamate," "sulfanyl," "halogen," "carboxy," trihalomethyl, cyano, hydroxy, mercapto, nitro, and the like.

The term "pharmaceutically acceptable salts or complexes" refers to salts or complexes of the below-specified compounds of Formula (I). Examples of such salts include, but are not restricted, to base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from acid addition such as salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. The prodrug is a derivative of the compound according to the invention and presenting NADPH oxidase inhibiting activity that has a chemically or metabolically decomposable group, and a compound that may be converted into a pharmaceutically active compound in vivo by solvolysis under physiological conditions. The invention further encompasses any tautomers of the compounds according to the invention.

The term "cardiovascular disorder or disease" comprises atherosclerosis, especially diseases or disorders associated with endothelial dysfunction including but not limited to hypertension, cardiovascular complications of Type I or Type II diabetes, intimal hyperplasia, coronary heart disease, cerebral, coronary or arterial vasospasm, endothelial dysfunction, heart failure including congestive heart failure, peripheral artery disease, restenosis, trauma caused by a stent, stroke, ischemic attack, vascular complications such as after organ transplantation, myocardial infarction, hypertension, formation of atherosclerotic plaques, platelet aggregation, angina pectoris, aneurysm, aortic dissection, ischemic heart disease, ischemic retinopathies, cardiac hypertrophy, pulmonary embolus, thrombotic events including deep vein thrombosis, injury caused after ischemia by restoration of blood flow or oxygen delivery as in organ transplantation, open heart surgery, angioplasty, hemorrhagic shock, angioplasty of ischemic organs including heart, brain, liver, kidney, retina and bowel.

The term "respiratory disorder or disease" comprises bronchial asthma, bronchitis, allergic rhinitis, adult respiratory syndrome, cystic fibrosis, lung viral infection (influenza), pulmonary hypertension, idiopathic pulmonary fibrosis and chronic obstructive pulmonary diseases (COPD).

The term "infectious disorder or disease" includes a disorder caused by organisms such as bacteria, viruses or parasites. Many organisms live in and on our bodies. It includes but is not limited to infectious diseases of the lung, influenza and other conditions caused by virus infections.

The term "allergic disorder" includes hay fever and asthma.

The term "traumatism" includes polytraumatism.

The term "disease or disorder affecting the metabolism" includes obesity, metabolic syndrome and Type II diabetes.

The term "skin disease" or disorder" includes psoriasis, eczema, scleroderma, xeroderma pigmentosum, skin cancers, melanoma, erythropoietic protoporphyria, discoid lupus erythematosus, solar urticaria, polymorphous light eruption, dermatitis, wound healing and scar formation.

The term "bone disorder" includes osteoporosis, osteoarthritis, osteosclerosis, periodontitis, and hyperparathyroidism.

The term "neurodegenerative disease or disorder" comprises a disease or a state characterized by a central nervous system (CNS) degeneration or alteration, especially at the level of the neurons such as Alzheimer's disease, Parkinson's disease, Huntington's disease, amyotrophic lateral sclerosis, epilepsy and muscular dystrophy. It further comprises neuro-inflammatory and demyelinating states or diseases such as leukoencephalopathies, and leukodystrophies.

The term "demyelinating" is referring to a state or a disease of the CNS comprising the degradation of the myelin around the axons. In the context of the invention, the term demyelinating disease is intended to comprise conditions which comprise a process that demyelinate cells such as multiple sclerosis, progressive multifocal leukoencephalopathy (PML), myelopathies, any neuroinflammatory condition involving autoreactive leukocyte within the CNS, congenital metabolic disorder, a neuropathy with abnormal myelination, drug induced demyelination, radiation induced demyelination, a hereditary demyelinating condition, a prion induced demyelinating condition, encephalitis induced demyelination or a spinal cord injury. Preferably, the condition is multiple sclerosis.

The term "psychotic disorder" includes disorders also known as behavioural disorders or mood disorders and refers to a group of disorders characterized by dramatic changes or extremes of mood which can be for example diagnosed as described in Diagnostic and Statistical Manual of Mental Disorders-4th Edition Text Revision (DMS-IV-TR), American Psychiatric Press, 2000. It includes schizophrenia, schizoaffective disorder, schizophreniform disorder, delusional disorder, psychotic depression, or mania with psychosis.

The term "kidney disease or disorder" includes diabetic nephropathy, renal failure, glomerulonephritis, nephrotoxicity of aminoglycosides and platinum compounds and hyperactive bladder. In a particular embodiment, the term according to the invention includes chronic kidney diseases or disorders.

The term "reproduction disorder or disease" includes erectile dysfunction, fertility disorders, prostatic hypertrophy and benign prostatic hypertrophy.

The term "disease or disorder affecting the eye and/or the lens" includes cataract including diabetic cataract, re-opacification of the lens post cataract surgery, diabetic and other forms of retinopathies like Glaucoma, Aged-related Macular degeneration (AMD), Dry eye syndrome and allergic conjonctivits.

The term "conditions affecting the inner ear" includes presbyacusis, tinnitus, Meniere's disease and other balance problems, utriculolithiasis, vertigo, vestibular migraine, and noise induced hearing loss and drug induced hearing loss (ototoxicity).

The term "inflammatory disorder or disease" means inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, heart failure, myocardial infarction, psoriasis, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis or juvenile ankylosing spondylitis, reactive arthritis, infectious arthritis or arthritis after infection, gonococcal arthritis, syphilitic arthritis, Lyme disease, arthritis induced by "angiitis syndrome," polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, disorders by repetitive use (typing), mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis and Crohn's disease or diseases like relapsing polychondritis, chronic inflammatory bowel diseases (IBD), colitis or the related diseases which require the administration to a mammal in a therapeutic effective dose of a compound expressed by Formula (I) in a sufficient dose to inhibit NADPH oxidase.

The term "liver diseases or disorders" include liver fibrosis, alcohol induced fibrosis, steatosis and non alcoholic steatohepatitis.

The term "arthritis" means acute rheumatic arthritis, chronic rheumatoid arthritis, chlamydial arthritis, chronic absorptive arthritis, chylous arthritis, arthritis based on bowel disease, filarial arthritis, gonorrheal arthritis, gouty arthritis, hemophilic arthritis, hypertrophic arthritis, juvenile chronic arthritis, Lyme arthritis, neonatal foal arthritis, nodular arthritis, ochronotic arthritis, psoriatic arthritis or suppurative arthritis, or the related diseases which require the administration to a mammal in a therapeutic effective dose of a compound expressed by Formula (I) in a sufficient dose to inhibit NADPH oxidase.

The term "pain" includes hyperalgesia associated with inflammatory pain and neurogenic pain, such as arthritic pain.

The term "cancer" means carcinoma (e.g., fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, renal cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, lung adenocarcinoma, bladder cancer or epithelial cancer, melanoma), neoplasia or the related diseases which require the administration to a mammal in a therapeutic effective dose of a compound expressed by the Formula (I) in a sufficient dose to inhibit NADPH oxidase. In particular, disorders induced by the toxicity of some drugs such as cancer therapies (e.g. Doxorubicin).

The term "disease or disorders of the gastrointestinal system", includes gastric mucosa disorders ischemic bowel disease management, enteritis/colitis/Crohn's Disease, cancer chemotherapy, or neutropenia.

The term "angiogenesis" includes sprouting angiogenesis, intussusceptive angiogenesis, vasculogenesis, arteriogenesis and lymphangiogenesis. Angiogenesis is the formation of new blood vessels from pre-existing capillaries or post-capillary venules and occurs in pathological conditions such as cancers, arthritis and inflammation. A large variety of tissues, or organs comprised of organized tissues, can support angiogenesis in disease conditions including skin, muscle, gut, connective tissue, joints, bones and the like tissue in which blood vessels can invade upon angiogenic stimuli. As used herein, the term "angiogenesis-dependent condition" is intended to mean a condition where the process of angiogenesis or vasculogenesis sustains or augments a pathological condition. Vasculogenesis results from the formation of new blood vessels arising from angioblasts which are endothelial cell precursors. Both processes result in new blood vessel formation and are included in the meaning of the term angiogenesis-dependent conditions. Similarly, the term "angiogenesis" as used herein is intended to include de novo formation of vessels such as those arising from vasculogenesis as well as those arising from branching and sprouting of existing vessels, capillaries and venules.

The term "angiogenesis inhibitory" means which is effective in the decrease in the extent, amount, or rate of neovascularization. Effecting a decrease in the extent, amount, or rate of endothelial cell proliferation or migration in the tissue is a specific example of inhibiting angiogenesis. Angiogenesis inhibitory activity is particularly useful in the treatment of any cancers as it targets tumor growth process and in the absence of neovascularization of tumor tissue, the tumor tissue does not obtain the required nutrients, slows in growth, ceases additional growth, regresses and ultimately becomes necrotic resulting in killing of the tumor. Further, an angiogenesis inhibitory activity is particularly useful in the treatment of any cancers as it is particularly effective against the formation of metastases because their formation also requires vascularization of a primary tumor so that the metastatic cancer cells can exit the primary tumor and their establishment in a secondary site requires neovascularization to support growth of the metastases.

The term "fibrotic disease or disorder" refers to diseases or disorders characterized by the development of excess fibrous connective tissue as a reparative response to injury or damage and includes pulmonary fibrosis, kidney fibrosis, liver fibrosis, retroperitoneal fibrosis and heart fibrosis.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions. Treatment can be as single agent or in combination with other therapies.

The term "subject" as used herein refers to mammals. For examples, mammals contemplated by the present invention include human, primates, domesticated animals such as cattle, sheep, pigs, horses and the like.

The term "inhibitor" used in the context of the invention is defined as a molecule that inhibits completely or partially the activity of NADPH oxidase and/or inhibit or reduce the generation of reactive oxygen species (ROS).

Compounds According to the Invention

In one embodiment, the invention provides an amido thiadiazole derivative according to Formula (I):

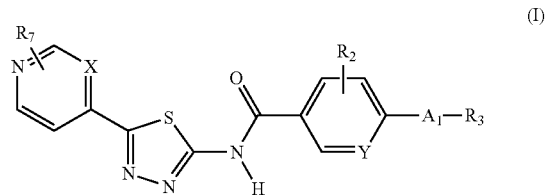

(I)

wherein X is selected from $CR^1$ and N; Y is selected from CH or N; $A_1$ is selected from —$OCHR^5$—, —$NR^4$—$CHR^5$—, —$CH_2NR^4$— and —$CH_2$—O—; $R^1$ is selected from H, halogen and optionally substituted $C_1$-$C_6$ alkyl; $R^2$ is selected from H, halogen (e.g. chloro, fluoro), optionally substituted alkoxy such optionally substituted methoxy (e.g. methoxy, (tetrahydro-2H-pyran-4-yl)methoxy, piperidin-4-ylmethoxy) or optionally substituted ethoxy (e.g. 2-(dimethylamino)ethoxy, 2-hydroxy ethoxy, 1-phenyl ethoxy, 2-methoxy ethoxy), optionally substituted alkoxy $C_1$-$C_6$ alkyl, optionally substituted $C_1$-$C_6$ alkyl such as optionally substituted methyl, optionally substituted amino such as optionally substituted $C_1$-$C_6$ alkyl amino (e.g. methyl amino, tetrahydro-2H-pyran-4-yl)methyl)amino, (1-methylpiperidin-4-yl)methyl)amino, di-methyl amino, optionally substituted ethyl amino such as 2-morpholino ethyl amino or 2-(dimethylamino) ethyl amino or methoxy ethyl amino, optionally substituted methyl amino such as 1-methyl-1H-imidazol-4-yl methyl amino or 2-hydroxyethyl)amino, optionally substituted propyl amino such as dimethylamino propyl amino), optionally substituted heterocycloalkyl such as optionally substituted piperazine (e.g. methylpiperazin-1-yl), optionally substituted $C_1$-$C_6$ alkyl heterocycloalkyl such as optionally substituted $C_1$-$C_6$ alkyl piperazine (e.g. methylpiperazin-1-yl), optionally substituted amino $C_1$-$C_6$ alkyl, optionally substituted alkoxy $C_1$-$C_6$ alkyl, —O—$R^8$ and —$NR^9R^{10}$; $R^3$ is a group of formula —$(CHR^6)_n$-$A_2$ or $R^3$ forms with the moiety $CHR^5$ from $A_1$ an optionally substituted ring selected from optionally substituted aryl such as an optionally substituted phenyl (e.g. phenyl or phenyl substituted by halogen such as fluoro phenyl substituted by alkoxy such as methoxy) and optionally substituted heteroaryl such as optionally substituted 1,3-dihydro-1H-indenyl (e.g. 1-(dimethylamino)-2,3-dihydro-1H-inden-2-yl, 2,3-dihydro-1H-inden-2-yl, 2,3-dihydro-1H-inden-1-yl) or optionally substituted 6,7-dihydro-5H-cyclopenta pyridinyl (e.g. 6,7-dihydro-5H-cyclopenta[b]pyridin-5-yl, 2-methylpyridin-3-yl, 5-methylpyridin-2-yl) or optionally substituted 1,2,3,4-tetrahydronaphthalenyl (e.g. 1,2,3,4-tetrahydronaphthalen-1-yl) or optionally substituted 2,3-dihydrobenzofuranyl (e.g. 2,3-dihydrobenzofuran-3-yl, 2,3-dihydro-1H-inden-1-yl) or optionally substituted thiadiazolyl (e.g. 1,3,4-thiadiazol-2-yl) or optionally substituted isoxazolyl (e.g. 5-methylisoxazol-3-yl) or optionally substituted pyrazolyl (e.g. 1-methyl-1H-pyrazol-3-yl) or optionally substituted imidazolyl (e.g. 1-methyl-1H-imidazol-2-yl), or $R^3$ forms with the moiety $NR^4$ from $A_1$ an optionally substituted ring selected from optionally substituted aryl and optionally substituted heteroaryl such as optionally substituted isoindolinyl (e.g. isoindolin-2-yl, 1H-indol-1-yl)); n is an integer from 0 to 4 (such as 0, 1, 2, 3 or 4); $R^4$ is selected from H and optionally substituted alkyl such as optionally substituted methyl; $A_2$ is an optionally substituted ring selected from optionally substituted aryl such as optionally substituted phenyl (e.g. methoxy phenyl, fluoro phenyl, chloro phenyl), optionally substituted heteroaryl such as optionally substituted pyridin (e.g. pyridin-2-yl, pyridin-3-yl, pyridin-4-yl, 2-methyl pyridin-3-yl, 5-methyl substituted pyridin (e.g. pyridin-2-yl, pyridin-3-yl, pyridin-4-yl, 2-methyl pyridin-3-yl, 5-methyl pyridin-2-yl) or optionally substituted pyrazolyl (e.g. 1,3-dimethyl-1H-pyrazol-5-yl, 1-methyl-1H-pyrazol-3-y) or optionally substituted thiadiazolyl (e.g. 1,3,4-thiadiazol-2-yl) or optionally substituted imidazolyl (e.g. 1H-imidazol-4-yl, 1-methyl-1H-imidazol-2-yl, 1-methyl-1H-imidazol-5-yl) or optionally substituted 1,2,4-triazolyl (e.g. 1-methyl-1H-1,2,4-triazol-5-yl) or optionally substituted isoxazolyl (e.g. 1-cyclopropylisoxazol-3-yl) or optionally substituted oxadiazolyl (e.g. 5-methyl-1,2,4-oxadiazol-3-yl) or optionally substituted pyrimidinyl (e.g. pyrimidinyl-2-yl); $R^5$ is selected from H, optionally substituted $C_1$-$C_6$ alkyl such as optionally substituted methyl (e.g. methoxy methyl, 3,3-difluoropyrrolidin-1-yl methyl, 4-methylpiperazin-1-yl methyl, hydroxyl methyl) or optionally substituted ethyl or optionally substituted propyl (e.g. methyl, hydroxy methyl, hydroxy ethyl, 2-propanolyl, hydroxyl isopropyl), optionally substituted amino $C_1$-$C_6$ alkyl such as optionally substituted amino methyl (e.g. dimethylamino methyl, methylamino methyl), optionally substituted alkoxy $C_1$-$C_6$ alkyl, optionally substituted heterocycloalkyl $C_1$-$C_6$ alkyl such as optionally substituted heterocycloalkyl methyl for example optionally substituted pyrrolidin $C_1$-$C_6$ alkyl (e.g. 3,3-difluoropyrrolidin-1-yl methyl) or substituted piperazine $C_1$-$C_6$ alkyl (e.g. 4-methylpiperazin-1-yl methyl) or heterocycloalkyl ethyl for example optionally substituted morpholino $C_1$-$C_6$ alkyl (e.g. morpholino methyl, morpholino ethyl) or optionally substituted pyrrolidin $C_1$-$C_6$ alkyl (e.g. pyrrolidin methyl, pyrrolidin ethyl), optionally substituted aminocarbonyl (e.g. dimethyl aminocarbonyl), optionally substituted $C_2$-$C_8$ cycloalkyl such as optionally substituted cyclopropyl and optionally substituted amino $C_1$-$C_6$ alkyl such as optionally substituted amino ethyl (e.g. di-methyl amino ethyl) or optionally substituted amino methyl (e.g. di-methyl amino methyl); $R^6$ is selected from H, optionally substituted $C_1$-$C_6$ alkyl such as optionally substituted methyl, optionally substituted amino optionally substituted $C_1$-$C_6$ alkyl amino (e.g. dimethyl amino) and hydroxy and wherein $R^6$ groups are independently selected for each repeating unit ($CHR^6$); $R^7$ is selected from H, halogen (e.g. fluoro) and optionally substituted $C_1$-$C_6$ alkyl such as methyl; $R^8$ is selected from H, optionally substituted $C_1$-$C_6$ alkyl such as optionally substituted methyl or optionally substituted ethyl (e.g. methoxy ethyl, 2-(dimethylamino)ethyl, hydroxy ethyl), optionally substituted amino $C_1$-$C_6$ alkyl, optionally substituted heterocycloalkyl, optionally substituted $C_2$-$C_8$ cycloalkyl, optionally substituted heterocycloalkyl $C_1$-$C_6$ alkyl such as optionally substituted heterocycloalkyl methyl, for example optionally substituted tetrahydropyran $C_1$-$C_6$ alkyl (e.g. tetrahydro-2H-pyran-4-yl) or optionally substituted piperidine alkyl (e.g. 1-methylpiperidin-4-yl), optionally substituted $C_2$-$C_8$ cycloalkyl $C_1$-$C_6$ alkyl, optionally substituted alkoxy, optionally substituted amino $C_1$-$C_6$ alkyl such optionally substituted amino ethyl (e.g. 2-(dimethylamino)ethyl); optionally substituted aryl $C_1$-$C_6$ alkyl and optionally substituted heteroaryl $C_1$-$C_6$ alkyl; $R^9$ and $R^{10}$ are independently selected from H, optionally substituted $C_1$-$C_6$ alkyl such a optionally substituted methyl (e.g. 1-methyl-1H-imidazol-4-yl)methyl)) or optionally substituted ethyl (e.g. 2-methoxy ethyl), optionally substituted amino $C_1$-$C_6$ alkyl such as optionally substituted amino ethyl (e.g. dimethyl amino ethyl) or such as optionally substituted amino propyl (e.g. dimethylamino)propyl), optionally substituted heterocycloalkyl such as optionally substituted piperidine (e.g. 1-methylpiperidin), optionally substituted $C_2$-$C_8$ cycloalkyl, optionally substituted heterocycloalkyl $C_1$-$C_6$ alkyl such as optionally substituted heterocycloalkyl ethyl for example optionally substituted morpholino $C_1$-$C_6$ alkyl (e.g. 2-morpholino ethyl) or optionally substituted heterocycloalkyl methyl for example optionally substituted tetrahydrofuran $C_1$-$C_6$ alkyl (e.g. tetrahydro-2H-pyran-4-yl methyl) or piperidin $C_1$-$C_6$ alkyl (e.g. 1-methylpiperidin-4-yl) methyl or optionally substituted imidazoly $C_1$-$C_6$ alkyl (e.g. 1methyl-1H-imidazol-4-yl)methyl) optionally substituted $C_2$-$C_8$ cycloalkyl $C_1$-$C_6$ alkyl, optionally substituted alkoxy, optionally substituted alkoxy $C_1$-$C_6$ alkyl such as optionally substituted alkoxy ethyl (e.g. 2-methoxy ethyl), optionally substituted aryl $C_1$-$C_6$ alkyl and optionally substituted heteroaryl $C_1$-$C_6$ alkyl such as heteroaryl $C_1$-$C_6$ alkyl methyl, for example optionally substituted imidazolyl $C_1$-$C_6$ alkyl (e.g. 1-methyl-1H-imidazol-4-yl methyl), optionally substituted amino $C_1$-$C_6$ alkyl such optionally substituted amino ethyl or optionally substituted amino propyl (e.g. 2-(dimethylamino)ethyl, 2-(dimethylamino)propyl)); as well as tautomers, geometrical isomers, optically active forms, pharmaceutically acceptable salts and pharmaceutically active derivative thereof.

In a particular embodiment, the invention provides an amido thiadiazole derivative according to Formula (I) wherein X is N.

In another particular embodiment, the invention provides an amido thiadiazole derivative according to Formula (I) wherein X is $CR^1$.

In a further particular embodiment, the invention provides an amido thiadiazole derivative according to Formula (I) wherein X is CH or CF.

In another particular embodiment, the invention provides an amido thiadiazole derivative according to Formula (I) wherein Y is CH;

In another particular embodiment, the invention provides an amido thiadiazole derivative according to Formula (I) wherein Y is N;

In another particular embodiment, the invention provides an amido thiadiazole derivative according to Formula (I) wherein $A_1$ is —$OCHR^5$—;

In another particular embodiment, the invention provides an amido thiadiazole derivative according to Formula (I) wherein $A_1$ is —$NR^4$—$CHR^5$.

In another particular embodiment, the invention provides an amido thiadiazole derivative according to Formula (I) wherein $A_1$ is —$CH_2NR^4$.

In another particular embodiment, the invention provides an amido thiadiazole derivative according to Formula (I) wherein $A_1$ is —$CH_2$—O—.

In another particular embodiment, the invention provides an amido thiadiazole derivative according to Formula (I) wherein $R^2$ is H.

In another particular embodiment, the invention provides an amido thiadiazole derivative according to Formula (I) wherein $R^2$ is halogen.

In another particular embodiment, the invention provides an amido thiadiazole derivative according to Formula (I) wherein $R^2$ is optionally substituted alkoxy.

In another particular embodiment, the invention provides an amido thiadiazole derivative according to Formula (I) wherein $R^2$ is optionally substituted $C_1$-$C_6$ alkyl.

In another particular embodiment, the invention provides an amido thiadiazole derivative according to Formula (I) wherein $R^2$ is optionally substituted heterocycloalkyl.

In another particular embodiment, the invention provides an amido thiadiazole derivative according to Formula (I) wherein $R^2$ is —O—$R^8$;

In another particular embodiment, the invention provides an amido thiadiazole derivative according to Formula (I) wherein $R^2$ is $NR^9R^{10}$.

In another particular embodiment, the invention provides an amido thiadiazole derivative according to Formula (I) wherein $R^3$ is a group of formula —$(CHR^6)_n$-$A_2$.

In a further particular embodiment, the invention provides an amido thiadiazole derivative according to Formula (I) wherein $R^3$ is a group of formula —$(CHR^6)_n$-$A_2$ where n is zero and $A_2$ is optionally substituted aryl.

In another particular embodiment, the invention provides an amido thiadiazole derivative according to Formula (I) wherein $R^3$ forms with the moiety $CHR^5$ from $A_1$ an optionally substituted ring selected from optionally substituted aryl and optionally substituted heteroaryl.

In another particular embodiment, the invention provides an amido thiadiazole derivative according to Formula (I) wherein $R^3$ forms with the moiety $NR^4$ from $A_1$ an optionally substituted ring selected from optionally substituted aryl and optionally substituted heteroaryl.

In another particular embodiment, the invention provides an amido thiadiazole derivative according to Formula (I) wherein n is 0.

In another particular embodiment, the invention provides an amido thiadiazole derivative according to Formula (I) wherein n is 1.

In another particular embodiment, the invention provides an amido thiadiazole derivative according to Formula (I) wherein n is 2.

In another particular embodiment, the invention provides an amido thiadiazole derivative according to Formula (I) wherein $R^4$ is H.

In another particular embodiment, the invention provides an amido thiadiazole derivative according to Formula (I) wherein $R^4$ is optionally substituted alkyl.

In another particular embodiment, the invention provides an amido thiadiazole derivative according to Formula (I) wherein $A_2$ is an optionally substituted aryl.

In another particular embodiment, the invention provides an amido thiadiazole derivative according to Formula (I) wherein $A_2$ is an optionally substituted heteroaryl.

In another particular embodiment, the invention provides an amido thiadiazole derivative according to Formula (I) wherein $R^5$ is H.

In another particular embodiment, the invention provides an amido thiadiazole derivative according to Formula (I) wherein $R^5$ is selected from optionally substituted $C_1$-$C_6$ alkyl, optionally substituted amino $C_1$-$C_6$ alkyl and optionally substituted heterocycloalkyl $C_1$-$C_6$ alkyl.

In another particular embodiment, the invention provides an amido thiadiazole derivative according to Formula (I) wherein $R^5$ is optionally substituted $C_1$-$C_6$ alkyl.

In another particular embodiment, the invention provides an amido thiadiazole derivative according to Formula (I) wherein $R^5$ is optionally substituted aminocarbonyl.

In another particular embodiment, the invention provides an amido thiadiazole derivative according to Formula (I) wherein $R^5$ is optionally substituted amino $C_1$-$C_6$ alkyl.

In another particular embodiment, the invention provides an amido thiadiazole derivative according to Formula (I) wherein $R^5$ is optionally substituted alkoxy $C_1$-$C_6$ alkyl.

In another particular embodiment, the invention provides an amido thiadiazole derivative according to Formula (I) wherein $R^5$ is optionally substituted heterocycloalkyl $C_1$-$C_6$ alkyl.

In another particular embodiment, the invention provides an amido thiadiazole derivative according to Formula (I) wherein $R^5$ is optionally substituted optionally substituted $C_2$-$C_8$ cycloalkyl.

In another particular embodiment, the invention provides an amido thiadiazole derivative according to Formula (I) wherein $R^6$ is H.

In another particular embodiment, the invention provides an amido thiadiazole derivative according to Formula (I) wherein $R^6$ is optionally substituted $C_1$-$C_6$ alkyl.

In another particular embodiment, the invention provides an amido thiadiazole derivative according to Formula (I) wherein $R^6$ is optionally substituted $C_1$-$C_6$ alkyl amino.

In another particular embodiment, the invention provides an amido thiadiazole derivative according to Formula (I) wherein $R^6$ is optionally substituted hydroxy.

In another particular embodiment, the invention provides an amido thiadiazole derivative according to Formula (I) wherein $R^7$ is H.

In another particular embodiment, the invention provides an amido thiadiazole derivative according to Formula (I) wherein $R^7$ is halogen.

In another particular embodiment, the invention provides an amido thiadiazole derivative according to Formula (I) wherein $R^7$ is optionally substituted $C_1$-$C_6$ alkyl.

In another particular embodiment, the invention provides an amido thiadiazole derivative according to Formula (I) wherein $R^8$ is optionally substituted $C_1$-$C_6$ alkyl.

In another particular embodiment, the invention provides an amido thiadiazole derivative according to Formula (I) wherein $R^8$ is optionally substituted heterocycloalkyl $C_1$-$C_6$ alkyl.

In another particular embodiment, the invention provides an amido thiadiazole derivative according to Formula (I) wherein $R^8$ is optionally substituted amino $C_1$-$C_6$ alkyl.

In another particular embodiment, the invention provides an amido thiadiazole derivative according to Formula (I) wherein $R^9$ is H.

In another particular embodiment, the invention provides an amido thiadiazole derivative according to Formula (I) wherein $R^9$ is optionally substituted $C_1$-$C_6$ alkyl.

In another particular embodiment, the invention provides an amido thiadiazole derivative according to Formula (I) wherein $R^{10}$ is H.

In another particular embodiment, the invention provides an amido thiadiazole derivative according to Formula (I) wherein $R^{10}$ is optionally substituted $C_1$-$C_6$ alkyl.

In another particular embodiment, the invention provides an amido thiadiazole derivative according to Formula (I) wherein $R^{10}$ is optionally substituted heterocycloalkyl.

In another particular embodiment, the invention provides an amido thiadiazole derivative according to Formula (I) wherein $R^{10}$ is optionally substituted heterocycloalkyl $C_1$-$C_6$ alkyl.

In another particular embodiment, the invention provides an amido thiadiazole derivative according to Formula (I) wherein $R^{10}$ is optionally substituted amino $C_1$-$C_6$ alkyl.

In another particular embodiment, the invention provides an amido thiadiazole derivative according to Formula (I) wherein X is CH or CF, Y is CH, $A_1$ is —OCHR$^5$—R$^2$ is optionally substituted alkoxy; $R^3$ is a group of formula —(CHR$^6$)$_n$-A$_2$ where n is zero and A$_2$ is optionally substituted aryl and $R^5$ is selected from optionally substituted $C_1$-$C_6$ alkyl, optionally substituted amino $C_1$-$C_6$ alkyl and optionally substituted heterocycloalkyl $C_1$-$C_6$ alkyl.

Compositions

The invention provides pharmaceutical or therapeutic agents as compositions and methods for treating a patient, preferably a mammalian patient, and most preferably a human patient who is suffering from a medical disorder, and in particular a disorder mediated by NADPH oxidase, such as a cardiovascular disorder or disease, a respiratory disorder or disease, a disease or disorder affecting the metabolism, a skin disorder, a bone disorder, a neuroinflammatory disorder, a neurodegenerative disorder, a kidney disease, a reproduction disorder, a disease or disorder affecting the eye and/or the lens, a condition affecting the inner ear, an inflammatory disorder or disease, a liver disease, pain, a cancer, a fibrotic disorder, a psychotic disorder, infectious diseases, angiogenesis, angiogenesis-dependent conditions and/or a disease or disorders of the gastrointestinal system.

Pharmaceutical compositions of the invention can contain one or more amino thiadiazole derivative in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. According to one aspect compositions according to the invention are oral compositions.

Compositions of this invention may also be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as formulation processing techniques and the like are set out in Part 5 of Part 5 of Remington's "*The Science and Practice of Pharmacy*", 22nd Edition, 2012, University of the Sciences in Philadelphia, Lippincott Williams & Wilkins the content of which is incorporated herein by reference. Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum.

The compounds of this invention can also be administered in sustained release forms or from sustained release drug delivery systems. A description of representative sustained release materials can also be found in the incorporated materials in *Remington's Pharmaceutical Sciences.*

Mode of Administration

Compositions of this invention may be administered in any manner, including, but not limited to, orally, parenterally, sublingually, transdermally, rectally, transmucosally, topically, via inhalation, via buccal or intranasal administration, or combinations thereof. Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v. infusion. In a particular embodiment, aminothiadiazole derivatives according to the invention are orally.

This invention is further illustrated by the following examples that are not intended to limit the scope of the invention in any way.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Combination

According to one embodiment of the invention, the compounds according to the invention and pharmaceutical formulations thereof can be administered alone or in combination with a co-agent useful in the treatment of cancer, such as substances used in conventional chemotherapy directed against solid tumors and for control of establishment of metastases or substances used in hormonotherapy or any other molecule that act by triggering programmed cell death, for example a co-agent selected from the category of drugs that stop the synthesis of pre DNA molecule building blocks such as methotrexate (Abitrexate®), fluorouracil (Adrucil®), hydroxyurea (Hydrea® ), and mercaptopurine (Purinethol® ), for example a co-agent selected from the category of drugs that directly damage the DNA in the nucleus of the cell such as cisplatin (Platinol® ) and antibiotics —daunorubicin (Cerubidine® ), doxorubicin (Adriamycin® ), and etoposide (VePesid® ), for example a co-agent selected from the category of drugs that effect the synthesis or breakdown of the mitotic spindles such as Vinblastine (Velban® ), Vincristine (Oncovin® ) and Pacitaxel (Taxol® ).

According to another embodiment of the invention, the compounds according to the invention and pharmaceutical formulations thereof can be administered in combination with agents targeting cell-surface proteins such as gene transfer of cytokine receptor chain and receptor-targeted cytotoxin administration According to another embodiment of the invention, the compounds according to the invention and pharmaceutical formulations thereof can be administered in combination with radiation therapy.

The invention encompasses the administration of a compound according to the invention or of a pharmaceutical formulation thereof, wherein the compound according to the invention or the pharmaceutical formulation thereof is administered to an individual prior to, simultaneously or sequentially with other therapeutic regimens or co-agents useful in the treatment of cancers (e.g. multiple drug regimens), in a therapeutically effective amount. Compounds according to the invention or the pharmaceutical formulations thereof that are administered simultaneously with said co-agents can be administered in the same or different composition(s) and by the same or different route(s) of administration.

In another particular embodiment, the compounds and methods of the invention are contemplated for use in the treatment of cancers wherein the administration of a compound according to the invention is typically conducted during or after chemotherapy, hormonotherapy or radiotherapy.

In another particular embodiment, the compounds and methods of the invention are contemplated for use in the treatment of cancers wherein the administration of a compound according to the invention is typically conducted after a regimen of chemotherapy, hormonotherapy or radiotherapy at times where the tumor tissue will be responding to the toxic assault by inducing angiogenesis to recover by the provision of a blood supply and nutrients to the tumor tissue.

In another embodiment, the administration of a compound according to the invention is performed after surgery where solid tumors have been removed as a prophylaxis against metastases.

Patients

In an embodiment, patients according to the invention are patients suffering from a cardiovascular disorder or disease, in particular of hypertension, atherosclerosis and ischemic conditions.

In another embodiment, patients according to the invention are patients suffering from a respiratory disorder or disease.

In another embodiment, patients according to the invention are patients suffering from a disease or disorder affecting the metabolism, in particular diabetic disorders.

In another embodiment, patients according to the invention are patients suffering from a skin disorder.

In another embodiment, patients according to the invention are patients suffering from a bone disorder.

In another embodiment, patients according to the invention are patients suffering from a neuroinflammatory disorder and/or a neurodegenerative disorder, in particular Parkinson's disease.

In another embodiment, patients according to the invention are patients suffering from a kidney disease.

In another embodiment, patients according to the invention are patients suffering from a reproduction disorder.

In another embodiment, patients according to the invention are patients suffering from a disease or disorder affecting the eye and/or the lens and/or a condition affecting the inner ear.

In another embodiment, patients according to the invention are patients suffering from an inflammatory disorder or disease, in particular colitis.

In another embodiment, patients according to the invention are patients suffering from a liver disease.

In another embodiment, patients according to the invention are patients suffering from pain, such as inflammatory pain, in particular arthritic pain.

In another embodiment, patients according to the invention are patients suffering from a cancer, in particular colon cancer.

In another embodiment, patients according to the invention are patients suffering from a fibrotic disorder, in particular liver fibrosis.

In another embodiment, patients according to the invention are patients suffering from a psychotic disorder.

In another embodiment, patients according to the invention are patients suffering from an infectious disease, in particular a viral lung infection or influenza.

In another embodiment, patients according to the invention are suffering from angiogenesis or an angiogenesis-dependent condition.

In another embodiment, patients according to the invention are patients suffering from allergic disorders.

In another embodiment, patients according to the invention are patients suffering from traumatisms.

In another embodiment, patients according to the invention are patients suffering from septic, hemorrhagic and anaphylactic shock.

In another embodiment, patients according to the invention are patients suffering from a disease or disorders of the gastrointestinal system.

Use According to the Invention

In another embodiment, the invention provides an amido thiadiazole derivative according to Formula (I) wherein $A_1$ and $A_2$; X and Y; $R^1$; $R^2$, $R^3$, $R^4$, $R^5$, $R^6$, $R^7$, $R^8$, $R^9$, $R^{10}$, $R^{11}$ and n are as defined in the detailed description; as well as pharmaceutically acceptable salts and pharmaceutically active derivative thereof for use as a medicament.

In another embodiment, the invention provides a use of an amido thiadiazole derivative according to Formula (I) wherein $A_1$ and $A_2$; X and Y; $R^1$; $R^2$, $R^3$, $R^4$, $R^5$, $R^6$, $R^7$, $R^8$, $R^9$, $R^{10}$, $R^{11}$ and n are as defined in the detailed description, as well as tautomers, geometrical isomers, optically active forms, pharmaceutically acceptable salts and pharmaceutically active derivative thereof for the preparation of a pharmaceutical composition for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, fibrotic disorders, allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase).

In another embodiment, the invention provides an amido thiadiazole derivative according to Formula (I) wherein $A_1$ and $A_2$; X and Y; $R^1$; $R^2$, $R^3$, $R^4$, $R^5$, $R^6$, $R^7$, $R^8$, $R^9$, $R^{10}$ and $R^{11}$, n are as defined in the detailed description, as well as tautomers, geometrical isomers, optically active forms, pharmaceutically acceptable salts and pharmaceutically active derivative thereof for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, fibrotic disorders, psychotic disorders, infectious diseases, allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase).

In another embodiment, the invention provides an amido thiadiazole derivative for use according to the invention wherein the disorder is selected from a melanoma, a skin cancer, a breast cancer, a hemangioma or angiofibroma and the like cancer where there is neovascularization of a tumor of the skin, lung, pancreas, breast, colon, laryngeal, ovarian, prostate, colorectal, head, neck, testicular, lymphoid, marrow, bone, sarcoma, renal, sweat gland tissues.

In another embodiment, the invention provides an amido thiadiazole derivative for use according to the invention wherein the disorder is a glioblastoma.

In another embodiment, the invention provides an amido thiadiazole derivative for use according to the invention wherein the disorder is an inflammatory disorder where there is neovascularization of an inflamed tissue such as arthritic tissue or psoriatic tissue.

Compounds of the present invention include in particular those selected from the following group:

4-(1-phenylethoxy)-3-(piperidin-4-ylmethoxy)-N-(5-(pyridin-4-yl)-1,3,4-thiadiazol-2-yl)benzamide;

3-(2-hydroxyethoxy)-4-(1-phenylethoxy)-N-(5-(pyridin-4-yl)-1,3,4-thiadiazol-2-yl)benzamide;

5-chloro-6-(2-(dimethylamino)-1-(pyridin-2-yl)ethoxy)-N-(5-(pyridin-4-yl)-1,3,4-thiadiazol-2-yl)nicotinamide;

3-methoxy-4-(1-phenylethoxy)-N-(5-(pyridin-4-yl)-1,3,4-thiadiazol-2-yl)benzamide;

3-methoxy-4-(1-(pyridin-2-yl)ethoxy)-N-(5-(pyridin-4-yl)-1,3,4-thiadiazol-2-yl)benzamide;

4-(2-(dimethylamino)-1-phenylethoxy)-3-methoxy-N-(5-(pyridin-4-yl)-1,3,4-thiadiazol-2-yl)benzamide;

4-(2-hydroxy-1-phenylethoxy)-3-methoxy-N-(5-(pyridin-4-yl)-1,3,4-thiadiazol-2-yl)benzamide;

4-(3-hydroxy-1-phenylpropoxy)-3-methoxy-N-(5-(pyridin-4-yl)-1,3,4-thiadiazol-2-yl)benzamide;

3-methoxy-4-(1-phenyl-3-(pyrrolidin-1-yl)propoxy)-N-(5-(pyridin-4-yl)-1,3,4-thiadiazol-2-yl)benzamide;

3-methoxy-4-(1-phenyl-2-(pyrrolidin-1-yl)ethoxy)-N-(5-(pyridin-4-yl)-1,3,4-thiadiazol-2-yl)benzamide;

4-(3-(dimethylamino)-1-phenylpropoxy)-3-methoxy-N-(5-(pyridin-4-yl)-1,3,4-thiadiazol-2-yl)benzamide;

3-methoxy-4-(2-(methylamino)-1-phenylethoxy)-N-(5-(pyridin-4-yl)-1,3,4-thiadiazol-2-yl)benzamide;

3-methoxy-4-(1-(pyridin-3-yl)ethoxy)-N-(5-(pyrimidin-4-yl)-1,3,4-thiadiazol-2-yl)benzamide;

N-(5-(3-fluoropyridin-4-yl)-1,3,4-thiadiazol-2-yl)-3-methoxy-4-(1-(pyridin-3-yl)ethoxy)benzamide;

3-methoxy-N-(5-(3-methylpyridin-4-yl)-1,3,4-thiadiazol-2-yl)-4-(1-phenylethoxy)benzamide;

3-methoxy-N-(5-(2-methylpyridin-4-yl)-1,3,4-thiadiazol-2-yl)-4-(1-phenylethoxy)benzamide;

4-((1H-imidazol-4-yl)methoxy)-3-methoxy-N-(5-(pyridin-4-yl)-1,3,4-thiadiazol-2-yl)benzamide;

3-methoxy-N-(5-(pyridin-4-yl)-1,3,4-thiadiazol-2-yl)-4-(pyrimidin-2-ylmethoxy)benzamide;

3-methoxy-4-((1-methyl-1H-imidazol-2-yl)methoxy)-N-(5-(pyridin-4-yl)-1,3,4-thiadiazol-2-yl)benzamide;

5-methyl-6-(1-phenylethoxy)-N-(5-(pyridin-4-yl)-1,3,4-thiadiazol-2-yl)nicotinamide;

5-chloro-6-(1-phenylethoxy)-N-(5-(pyridin-4-yl)-1,3,4-thiadiazol-2-yl)nicotinamide;

5-((2-methoxyethyl)amino)-6-(1-phenylethoxy)-N-(5-(pyridin-4-yl)-1,3,4-thiadiazol-2-yl)nicotinamide;

6-(benzyloxy)-5-chloro-N-(5-(pyridin-4-yl)-1,3,4-thiadiazol-2-yl)nicotinamide;
6-(benzyloxy)-5-(4-methylpiperazin-1-yl)-N-(5-(pyridin-4-yl)-1,3,4-thiadiazol-2-yl)nicotinamide;
5-methoxy-6-((1-phenylethyl)amino)-N-(5-(pyridin-4-yl)-1,3,4-thiadiazol-2-yl)nicotinamide;
6-(3-(dimethylamino)-1-phenylpropoxy)-5-methoxy-N-(5-(pyridin-4-yl)-1,3,4-thiadiazol-2-yl)nicotinamide;
6-(2-hydroxy-1-phenylethoxy)-5-methoxy-N-(5-(pyridin-4-yl)-1,3,4-thiadiazol-2-yl)nicotinamide;
6-(2-hydroxy-2-phenylethoxy)-5-methoxy-N-(5-(pyridin-4-yl)-1,3,4-thiadiazol-2-yl)nicotinamide;
5-chloro-6-(2-hydroxy-2-methyl-1-phenylpropoxy)-N-(5-(pyridin-4-yl)-1,3,4-thiadiazol-2-yl)nicotinamide;
5-chloro-6-(2-(dimethylamino)-1-(pyridin-2-yl)ethoxy)-N-(5-(pyridin-4-yl)-1,3,4-thiadiazol-2-yl)nicotinamide;
6-(2-(dimethylamino)-1-phenylethoxy)-N-(5-(pyridin-4-yl)-1,3,4-thiadiazol-2-yl)nicotinamide;
6-((1-(dimethylamino)-2,3-dihydro-1H-inden-2-yl)oxy)-N-(5-(pyridin-4-yl)-1,3,4-thiadiazol-2-yl)nicotinamide;
6-((1-(dimethylamino)-3-phenylpropan-2-yl)oxy)-N-(5-(pyridin-4-yl)-1,3,4-thiadiazol-2-yl)nicotinamide;
6-((1-phenylpropan-2-yl)oxy)-N-(5-(pyridin-4-yl)-1,3,4-thiadiazol-2-yl)nicotinamide;
6-(1-(pyridin-3-yl)ethoxy)-N-(5-(pyridin-4-yl)-1,3,4-thiadiazol-2-yl)nicotinamide;
6-((1-(pyridin-3-yl)ethyl)amino)-N-(5-(pyridin-4-yl)-1,3,4-thiadiazol-2-yl)nicotinamide;
6-(1-phenylethoxy)-N-(5-(pyridin-4-yl)-1,3,4-thiadiazol-2-yl)-5-((tetrahydro-2H-pyran-4-yl)methoxy)nicotinamide;
6-(3-morpholino-1-phenylpropoxy)-N-(5-(pyridin-4-yl)-1,3,4-thiadiazol-2-yl)nicotinamide;
6-(2-morpholino-1-phenylethoxy)-N-(5-(pyridin-4-yl)-1,3,4-thiadiazol-2-yl)nicotinamide;
4-(isoindolin-2-ylmethyl)-3-methoxy-N-(5-(pyridin-4-yl)-1,3,4-thiadiazol-2-yl)benzamide;
6-(benzyloxy)-5-methoxy-N-(5-(pyridin-4-yl)-1,3,4-thiadiazol-2-yl)nicotinamide;
5-methoxy-6-(1-phenyl ethoxy)-N-(5-(pyridin-4-yl)-1,3,4-thiadiazol-2-yl) nicotinamide;
2-methyl-6-(1-phenylethoxy)-N-(5-(pyridin-4-yl)-1,3,4-thiadiazol-2-yl)nicotinamide;
2-methyl-6-(1-(pyridin-2-yl)ethoxy)-N-(5-(pyridin-4-yl)-1,3,4-thiadiazol-2-yl)nicotinamide;
6-(benzyloxy)-2-methyl-N-(5-(pyridin-4-yl)-1,3,4-thiadiazol-2-yl)nicotinamide;
5-methoxy-6-(1-(pyridin-2-yl)ethoxy)-N-(5-(pyridin-4-yl)-1,3,4-thiadiazol-2-yl)nicotinamide;
5-chloro-6-(1-(pyridin-2-yl)ethoxy)-N-(5-(pyridin-4-yl)-1,3,4-thiadiazol-2-yl)nicotinamide;
6-(benzyloxy)-5-((2-(dimethylamino)ethyl)amino)-N-(5-(pyridin-4-yl)-1,3,4-thiadiazol-2-yl)nicotinamide;
6-(benzyloxy)-5-methyl-N-(5-(pyridin-4-yl)-1,3,4-thiadiazol-2-yl)nicotinamide;
5-((2-(dimethylamino)ethyl)amino)-6-(1-phenylethoxy)-N-(5-(pyridin-4-yl)-1,3,4-thiadiazol-2-yl)nicotinamide;
6-(1-phenylethoxy)-N-(5-(pyridin-4-yl)-1,3,4-thiadiazol-2-yl)-5-(((tetrahydro-2H-pyran-4-yl)methyl)amino)nicotinamide;
5-(((1-methylpiperidin-4-yl)methyl)amino)-6-(1-phenylethoxy)-N-(5-(pyridin-4-yl)-1,3,4-thiadiazol-2-yl)nicotinamide;
5-(methylamino)-6-(1-phenylethoxy)-N-(5-(pyridin-4-yl)-1,3,4-thiadiazol-2-yl)nicotinamide;
6-(benzyloxy)-5-(methylamino)-N-(5-(pyridin-4-yl)-1,3,4-thiadiazol-2-yl)nicotinamide;
6-(3-(dimethylamino)-1-phenylpropoxy)-5-methyl-N-(5-(pyridin-4-yl)-1,3,4-thiadiazol-2-yl)nicotinamide;
5-chloro-6-(3-(dimethylamino)-1-phenylpropoxy)-N-(5-(pyridin-4-yl)-1,3,4-thiadiazol-2-yl)nicotinamide;
6-(2-(dimethylamino)-1-phenylethoxy)-5-methoxy-N-(5-(pyridin-4-yl)-1,3,4-thiadiazol-2-yl)nicotinamide;
5-chloro-6-(2-(dimethylamino)-1-phenylethoxy)-N-(5-(pyridin-4-yl)-1,3,4-thiadiazol-2-yl)nicotinamide;
6-(2-(dimethylamino)-1-phenylethoxy)-5-methyl-N-(5-(pyridin-4-yl)-1,3,4-thiadiazol-2-yl)nicotinamide;
5-((3-(dimethylamino)propyl)amino)-6-(1-phenylethoxy)-N-(5-(pyridin-4-yl)-1,3,4-thiadiazol-2-yl)nicotinamide;
5-((2-hydroxyethyl)amino)-6-(1-phenylethoxy)-N-(5-(pyridin-4-yl)-1,3,4-thiadiazol-2-yl)nicotinamide;
5-(((1-methyl-1H-imidazol-4-yl)methyl)amino)-6-(1-phenylethoxy)-N-(5-(pyridin-4-yl)-1,3,4-thiadiazol-2-yl)nicotinamide;
5-((1-methylpiperidin-4-yl)amino)-6-(1-phenylethoxy)-N-(5-(pyridin-4-yl)-1,3,4-thiadiazol-2-yl)nicotinamide;
5-((2-morpholinoethyl)amino)-6-(1-phenylethoxy)-N-(5-(pyridin-4-yl)-1,3,4-thiadiazol-2-yl)nicotinamide;
5-(4-methylpiperazin-1-yl)-6-(1-phenylethoxy)-N-(5-(pyridin-4-yl)-1,3,4-thiadiazol-2-yl)nicotinamide;
5-(dimethylamino)-6-(1-phenylethoxy)-N-(5-(pyridin-4-yl)-1,3,4-thiadiazol-2-yl)nicotinamide;
5-methoxy-6-((1-(pyridin-3-yl)ethyl)amino)-N-(5-(pyridin-4-yl)-1,3,4-thiadiazol-2-yl)nicotinamide;
6-(2-(dimethylamino)-1-(pyridin-2-yl)ethoxy)-5-methoxy-N-(5-(pyridin-4-yl)-1,3,4-thiadiazol-2-yl)nicotinamide;
5-(dimethylamino)-6-(3-(dimethylamino)-1-phenylpropoxy)-N-(5-(pyridin-4-yl)-1,3,4-thiadiazol-2-yl)nicotinamide;
6-(3-(dimethylamino)-1-phenylpropoxy)-5-(methylamino)-N-(5-(pyridin-4-yl)-1,3,4-thiadiazol-2-yl)nicotinamide;
3-methoxy-N-(5-(pyridin-4-yl)-1,3,4-thiadiazol-2-yl)-4-(pyridin-4-ylmethoxy)benzamide;
3-methoxy-4-(1-(pyridin-3-yl)ethoxy)-N-(5-(pyridin-4-yl)-1,3,4-thiadiazol-2-yl)benzamide;
4-((1,3-dimethyl-1H-pyrazol-5-yl)methoxy)-3-methoxy-N-(5-(pyridin-4-yl)-1,3,4-thiadiazol-2-yl)benzamide;
4-((2,3-dihydro-1H-inden-1-yl)oxy)-3-methoxy-N-(5-(pyridin-4-yl)-1,3,4-thiadiazol-2-yl)benzamide;
3-methoxy-N-(5-(pyridin-4-yl)-1,3,4-thiadiazol-2-yl)-4-(1,2,3,4-tetrahydronaphthalen-1-yl)oxy)benzamide;
3-methoxy-N-(5-(pyridin-4-yl)-1,3,4-thiadiazol-2-yl)-4-(thiazol-4-ylmethoxy)benzamide;
3-methoxy-N-(5-(pyridin-4-yl)-1,3,4-thiadiazol-2-yl)-4-(thiazol-2-ylmethoxy)benzamide;
3-(2-(dimethylamino)ethoxy)-4-(1-phenylethoxy)-N-(5-(pyridin-4-yl)-1,3,4-thiadiazol-2-yl)benzamide;
3-(2-methoxyethoxy)-4-(1-phenylethoxy)-N-(5-(pyridin-4-yl)-1,3,4-thiadiazol-2-yl)benzamide;
3-((1-methylpiperidin-4-yl)methoxy)-4-(1-phenylethoxy)-N-(5-(pyridin-4-yl)-1,3,4-thiadiazol-2-yl)benzamide;
3-methoxy-4-((2-methylpyridin-3-yl)methoxy)-N-(5-(pyridin-4-yl)-1,3,4-thiadiazol-2-yl)benzamide;
3-methoxy-4-((5-methylpyridin-2-yl)methoxy)-N-(5-(pyridin-4-yl)-1,3,4-thiadiazol-2-yl)benzamide;
3-methoxy-4-((5-methylisoxazol-3-yl)methoxy)-N-(5-(pyridin-4-yl)-1,3,4-thiadiazol-2-yl)benzamide;
3-methoxy-4-((4-methoxybenzyl)oxy)-N-(5-(pyridin-4-yl)-1,3,4-thiadiazol-2-yl)benzamide;
4-((2-fluorobenzyl)oxy)-3-methoxy-N-(5-(pyridin-4-yl)-1,3,4-thiadiazol-2-yl)benzamide;
3-methoxy-4-(pyridin-2-ylmethoxy)-N-(5-(pyridin-4-yl)-1,3,4-thiadiazol-2-yl)benzamide;

4-((4-fluorobenzyl)oxy)-3-methoxy-N-(5-(pyridin-4-yl)-1,3,4-thiadiazol-2-yl)benzamide;
3-methoxy-4-((5-methyl-1,2,4-oxadiazol-3-yl)methoxy)-N-(5-(pyridin-4-yl)-1,3,4-thiadiazol-2-yl)benzamide;
4-((5-cyclopropylisoxazol-3-yl)methoxy)-3-methoxy-N-(5-(pyridin-4-yl)-1,3,4-thiadiazol-2-yl)benzamide;
3-methoxy-4-((1-methyl-1H-1,2,4-triazol-5-yl)methoxy)-N-(5-(pyridin-4-yl)-1,3,4-thiadiazol-2-yl)benzamide;
3-methoxy-4-((1-methyl-1H-imidazol-5-yl)methoxy)-N-(5-(pyridin-4-yl)-1,3,4-thiadiazol-2-yl)benzamide;
3-methoxy-4-(2-(1-methyl-1H-imidazol-2-yl)ethoxy)-N-(5-(pyridin-4-yl)-1,3,4-thiadiazol-2-yl)benzamide;
3-methoxy-4-(1-(pyridin-2-yl)ethoxy)-N-(5-(pyrimidin-4-yl)-1,3,4-thiadiazol-2-yl)benzamide;
N-(5-(3-fluoropyridin-4-yl)-1,3,4-thiadiazol-2-yl)-3-methoxy-4-(1-(pyridin-2-yl)ethoxy)benzamide;
N-(5-(3-fluoropyridin-4-yl)-1,3,4-thiadiazol-2-yl)-4-(3-hydroxy-1-phenylpropoxy)-3-methoxybenzamide;
N-(5-(3-fluoropyridin-4-yl)-1,3,4-thiadiazol-2-yl)-4-(2-hydroxy-1-phenylethoxy)-3-methoxybenzamide;
4-(2-(dimethylamino)-1-phenylethoxy)-N-(5-(3-fluoropyridin-4-yl)-1,3,4-thiadiazol-2-yl)-3-methoxybenzamide;
6-(3-(dimethylamino)-1-phenylpropoxy)-N-(5-(pyridin-4-yl)-1,3,4-thiadiazol-2-yl)-5-((tetrahydro-2H-pyran-4-yl)methoxy)nicotinamide;
5-chloro-6-(2-hydroxy-1-phenylethoxy)-N-(5-(pyridin-4-yl)-1,3,4-thiadiazol-2-yl)nicotinamide;
4-(3-hydroxy-1-phenylpropoxy)-3-methoxy-N-(5-(pyrimidin-4-yl)-1,3,4-thiadiazol-2-yl)benzamide;
4-(2-hydroxy-1-phenylethoxy)-3-methoxy-N-(5-(pyrimidin-4-yl)-1,3,4-thiadiazol-2-yl)benzamide;
4-(benzyloxy)-3-methoxy-N-(5-(pyrimidin-4-yl)-1,3,4-thiadiazol-2-yl)benzamide;
4-(benzyloxy)-N-(5-(3-fluoropyridin-4-yl)-1,3,4-thiadiazol-2-yl)-3-methoxybenzamide;
4-(2-(dimethylamino)-1-phenylethoxy)-3-methoxy-N-(5-(3-methylpyridin-4-yl)-1,3,4-thiadiazol-2-yl)benzamide;
6-(2-(dimethylamino)-1-phenylethoxy)-5-methoxy-N-(5-(pyrimidin-4-yl)-1,3,4-thiadiazol-2-yl)nicotinamide;
4-(2-(dimethylamino)-1-phenylethoxy)-3-methoxy-N-(5-(2-methylpyridin-4-yl)-1,3,4-thiadiazol-2-yl)benzamide;
3-methoxy-4-((1-phenylpropan-2-yl)oxy)-N-(5-(pyridin-4-yl)-1,3,4-thiadiazol-2-yl)benzamide;
4-(2-(dimethylamino)-1-phenylethoxy)-3-methoxy-N-(5-(pyrimidin-4-yl)-1,3,4-thiadiazol-2-yl)benzamide;
4-(benzyloxy)-N-(5-(pyridin-4-yl)-1,3,4-thiadiazol-2-yl)benzamide;
3-methoxy-4-((methyl(pyridin-2-yl)amino)methyl)-N-(5-(pyridin-4-yl)-1,3,4-thiadiazol-2-yl)benzamide;
4-((1H-indol-1-yl)methyl)-3-methoxy-N-(5-(pyridin-4-yl)-1,3,4-thiadiazol-2-yl)benzamide;
3-methoxy-4-(phenoxymethyl)-N-(5-(pyridin-4-yl)-1,3,4-thiadiazol-2-yl)benzamide;
3-methoxy-4-((methyl(phenyl)amino)methyl)-N-(5-(pyridin-4-yl)-1,3,4-thiadiazol-2-yl)benzamide;
6-(2-hydroxy-2-methyl-1-phenylpropoxy)-N-(5-(pyridin-4-yl)-1,3,4-thiadiazol-2-yl)nicotinamide;
6-((1-phenylpropan-2-yl)oxy)-N-(5-(pyridin-4-yl)-1,3,4-thiadiazol-2-yl)nicotinamide;
6-((1,3-dimethyl-1H-pyrazol-5-yl)methoxy)-N-(5-(pyridin-4-yl)-1,3,4-thiadiazol-2-yl)nicotinamide;
N-(5-(pyridin-4-yl)-1,3,4-thiadiazol-2-yl)-6-(thiophen-3-ylmethoxy)nicotinamide;
6-(3-(dimethylamino)-1-phenylpropoxy)-N-(5-(3-fluoropyridin-4-yl)-1,3,4-thiadiazol-2-yl)nicotinamide;
6-(1-phenylpropoxy)-N-(5-(pyridin-4-yl)-1,3,4-thiadiazol-2-yl)nicotinamide;
6-(1-(4-chlorophenyl)propoxy)-N-(5-(pyridin-4-yl)-1,3,4-thiadiazol-2-yl)nicotinamide;
6-((2,3-dihydro-1H-inden-1-yl)oxy)-N-(5-(pyridin-4-yl)-1,3,4-thiadiazol-2-yl)nicotinamide;
6-((6,7-dihydro-5H-cyclopenta[b]pyridin-5-yl)oxy)-N-(5-(pyridin-4-yl)-1,3,4-thiadiazol-2-yl)nicotinamide;
6-(3-(dimethylamino)-1-phenylpropoxy)-N-(5-(pyridin-4-yl)-1,3,4-thiadiazol-2-yl)nicotinamide;
6-(3-hydroxy-3-phenylpropoxy)-N-(5-(pyridin-4-yl)-1,3,4-thiadiazol-2-yl)nicotinamide;
6-(1-phenylethoxy)-N-(5-(pyridin-4-yl)-1,3,4-thiadiazol-2-yl)nicotinamide;
6-(benzyloxy)-N-(5-(pyridin-4-yl)-1,3,4-thiadiazol-2-yl)nicotinamide;
6-(methyl(1-phenylethyl)amino)-N-(5-(pyridin-4-yl)-1,3,4-thiadiazol-2-yl)nicotinamide;
6-((2-(dimethylamino)-2-phenylethyl)amino)-N-(5-(pyridin-4-yl)-1,3,4-thiadiazol-2-yl)nicotinamide;
6-((2,3-dihydro-1H-inden-2-yl)amino)-N-(5-(pyridin-4-yl)-1,3,4-thiadiazol-2-yl)nicotinamide;
6-((1-(pyridin-2-yl)ethyl)amino)-N-(5-(pyridin-4-yl)-1,3,4-thiadiazol-2-yl)nicotinamide;
6-((1-(pyridin-3-yl)propan-2-yl)amino)-N-(5-(pyridin-4-yl)-1,3,4-thiadiazol-2-yl)nicotinamide;
6-((1-phenylethyl)amino)-N-(5-(pyridin-4-yl)-1,3,4-thiadiazol-2-yl)nicotinamide;
4-((6,7-dihydro-5H-cyclopenta[b]pyridin-5-yl)oxy)-3-methoxy-N-(5-(pyridin-4-yl)-1,3,4-thiadiazol-2-yl)benzamide;
4-((2,3-dihydrobenzofuran-3-yl)oxy)-3-methoxy-N-(5-(pyridin-4-yl)-1,3,4-thiadiazol-2-yl)benzamide;
4-(cyclopropyl(phenyl)methoxy)-3-methoxy-N-(5-(pyridin-4-yl)-1,3,4-thiadiazol-2-yl)benzamide;
3-methoxy-4-(1-phenylethoxy)-N-(5-(pyrimidin-4-yl)-1,3,4-thiadiazol-2-yl)benzamide;
4-((2,3-dihydro-1H-inden-2-yl)oxy)-3-methoxy-N-(5-(pyridin-4-yl)-1,3,4-thiadiazol-2-yl)benzamide;
3-methoxy-4-(1-phenylpropoxy)-N-(5-(pyridin-4-yl)-1,3,4-thiadiazol-2-yl)benzamide;
3-methoxy-4-phenethoxy-N-(5-(pyridin-4-yl)-1,3,4-thiadiazol-2-yl)benzamide;
3-methoxy-4-((1-methyl-1H-pyrazol-3-yl)methoxy)-N-(5-(pyridin-4-yl)-1,3,4-thiadiazol-2-yl)benzamide;
3-methoxy-4-(pyridin-3-ylmethoxy)-N-(5-(pyridin-4-yl)-1,3,4-thiadiazol-2-yl)benzamide;
4-(benzyloxy)-3-chloro-N-(5-(pyridin-4-yl)-1,3,4-thiadiazol-2-yl)benzamide;
4-(benzyloxy)-2-chloro-N-(5-(pyridin-4-yl)-1,3,4-thiadiazol-2-yl)benzamide;
4-(pyridin-3-ylmethoxy)-N-(5-(pyridin-4-yl)-1,3,4-thiadiazol-2-yl)benzamide;
4-(1-phenylethoxy)-N-(5-(pyridin-4-yl)-1,3,4-thiadiazol-2-yl)benzamide;
4-(benzyloxy)-2-fluoro-N-(5-(pyridin-4-yl)-1,3,4-thiadiazol-2-yl)benzamide;
4-(benzyloxy)-3-methoxy-N-(5-(pyridin-4-yl)-1,3,4-thiadiazol-2-yl)benzamide;
4-phenoxy-N-(5-(pyridin-4-yl)-1,3,4-thiadiazol-2-yl)benzamide;
6-phenoxy-N-(5-(pyridin-4-yl)-1,3,4-thiadiazol-2-yl)nicotinamide;
6-((1-(dimethylamino)-1-oxo-3-phenylpropan-2-yl)oxy)-N-(5-(pyridin-4-yl)-1,3,4-thiadiazol-2-yl)nicotinamide;
6-((4-phenylbutan-2-yl)oxy)-N-(5-(pyridin-4-yl)-1,3,4-thiadiazol-2-yl)nicotinamide;
6-(2-phenylpropoxy)-N-(5-(pyridin-4-yl)-1,3,4-thiadiazol-2-yl)nicotinamide;

6-(3-(4-methoxyphenyl)propoxy)-N-(5-(pyridin-4-yl)-1,3,4-thiadiazol-2-yl)nicotinamide;

5-methyl-6-(2-morpholino-1-phenylethoxy)-N-(5-(pyridin-4-yl)-1,3,4-thiadiazol-2-yl)nicotinamide;

3-methoxy-4-(2-methoxy-1-phenylethoxy)-N-(5-(pyridin-4-yl)-1,3,4-thiadiazol-2-yl) benzamide;

3-methoxy-4-(2-morpholino-1-phenylethoxy)-N-(5-(pyridin-4-yl)-1,3,4-thiadiazol-2-yl) benzamide;

3-methoxy-4-(2-morpholino-1-phenylethoxy)-N-(5-(pyridin-4-yl)-1,3,4-thiadiazol-2-yl) benzamide;

6-(3-(dimethylamino)-1-phenylpropoxy)-5-methoxy-N-(5-(pyrimidin-4-yl)-1,3,4-thiadiazol-2-yl)nicotinamide;

6-(2-(3,3-difluoropyrrolidin-1-yl)-1-phenylethoxy)-N-(5-(pyridin-4-yl)-1,3,4-thiadiazol-2-yl)nicotinamide;

6-(2-(4-methylpiperazin-1-yl)-1-phenylethoxy)-N-(5-(pyridin-4-yl)-1,3,4-thiadiazol-2-yl) nicotinamide;

6-(1-phenyl-3-(pyrrolidin-1-yl)propoxy)-N-(5-(pyridin-4-yl)-1,3,4-thiadiazol-2-yl) nicotinamide;

5-methoxy-6-(1-phenyl-2-(pyrrolidin-1-yl)ethoxy)-N-(5-(pyrimidin-4-yl)-1,3,4-thiadiazol-2-yl)nicotinamide;

5-methoxy-6-(1-phenyl-2-(pyrrolidin-1-yl)ethoxy)-N-(5-(pyridin-4-yl)-1,3,4-thiadiazol-2-yl)nicotinamide;

5-methyl-6-(1-phenyl-2-(pyrrolidin-1-yl)ethoxy)-N-(5-(pyridin-4-yl)-1,3,4-thiadiazol-2-yl) nicotinamide;

5-methoxy-6-(1-phenylethoxy)-N-(5-(pyrimidin-4-yl)-1,3,4-thiadiazol-2-yl)nicotinamide;

4-(2-(dimethylamino)-1-phenylethoxy)-3-fluoro-N-(5-(pyridin-4-yl)-1,3,4-thiadiazol-2-yl)benzamide;

3-chloro-4-(2-(dimethylamino)-1-phenylethoxy)-N-(5-(pyridin-4-yl)-1,3,4-thiadiazol-2-yl)benzamide;

4-(1-(4-fluorophenyl)-2-hydroxyethoxy)-3-methoxy-N-(5-(pyridin-4-yl)-1,3,4-thiadiazol-2-yl)benzamide; and 4-(2-(dimethylamino)-1-(4-fluorophenyl)ethoxy)-3-methoxy-N-(5-(pyridin-4-yl)-1,3,4-thiadiazol-2-yl)benzamide.

In another embodiment, the invention provides a method for treating a patient suffering from a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, fibrotic disorders, psychotic disorders, infectious diseases, allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase). The method comprises administering a compound according to Formula (I) in a patient in need thereof.

In another embodiment, the invention provides a method for inhibiting or preventing angiogenesis in a patient in need thereof, wherein the method comprises administering an angiogenesis inhibiting dose of a compound of Formula (I) to a patient or a tissue in need thereof.

In another embodiment, the invention provides a method of inhibiting or preventing tumor neovascularization by inhibiting tumor angiogenesis according to the present methods. Similarly, the invention provides a method for inhibiting tumor growth by practicing the angiogenesis-inhibiting methods.

In a particular embodiment, the compounds and methods of the invention are contemplated for use in treatment of a tumor tissue of a patient with a tumor, solid tumor, a metastasis, a cancer, a melanoma, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present compounds and methods include, but are not limited to, tumors of the skin, melanoma, lung, pancreas, breast, colon, laryngeal, ovarian, prostate, colorectal, head, neck, testicular, lymphoid, marrow, bone, sarcoma, renal, sweat gland, and the like tissues. Further examples of cancers treated are glioblastomas.

In another particular embodiment, the compounds and methods of the invention are contemplated for use in treatment of an inflamed tissue and the angiogenesis to be inhibited is inflamed tissue angiogenesis where there is neovascularization of inflamed tissue. In this case, the compound and method according to the invention contemplate the inhibition of angiogenesis in arthritic tissues, such as in a patient with chronic articular rheumatism, in immune or non-immune inflamed tissues, in psoriatic tissue and the like.

In embodiments, the invention contemplates inhibition of angiogenesis in a tissue. The extent of angiogenesis in a tissue, and therefore the extent of inhibition achieved by the present methods, can be evaluated by a variety of methods, such as those which are described herein.

According to an embodiment of the invention, the disease or condition is a cancer.

According to an embodiment of the invention, the compound according to the invention is to be administered in combination with a co-agent useful in the treatment of cancer.

According to an embodiment of the invention, the compound according to the invention is to be administered in combination with radiation therapy.

In another embodiment, the invention provides a pharmaceutical composition containing at least one derivative amido thiadiazole according to Formula (I) and a pharmaceutically acceptable carrier, diluent or excipient thereof.

The compounds of invention have been named according the IUPAC standards used in the ChemDraw (product version 12.0.3).

Compounds according to the present invention comprise a compound according to Formula (I), its tautomers, its geometrical isomers, its optically active forms as enantiomers, diastereomers and its racemate forms, as well as pharmaceutically acceptable salts thereof. References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

The invention having been described, the following examples are presented by way of illustration, and not limitation.

Synthesis of Compounds of the Invention:

The novel derivatives according to Formula (I) can be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The general synthetic approaches for obtaining compounds of Formula (I) is depicted in Schemes 1, 2, 3 and 4 below.

The intermediate compounds according to Formula (1-IV) are further reacted with an aqueous solution of a hydroxide base such as lithium hydroxide or sodium hydroxide in a combination with a solvent such as methanol or tetrahydrofuran using a suitable temperature, for example at

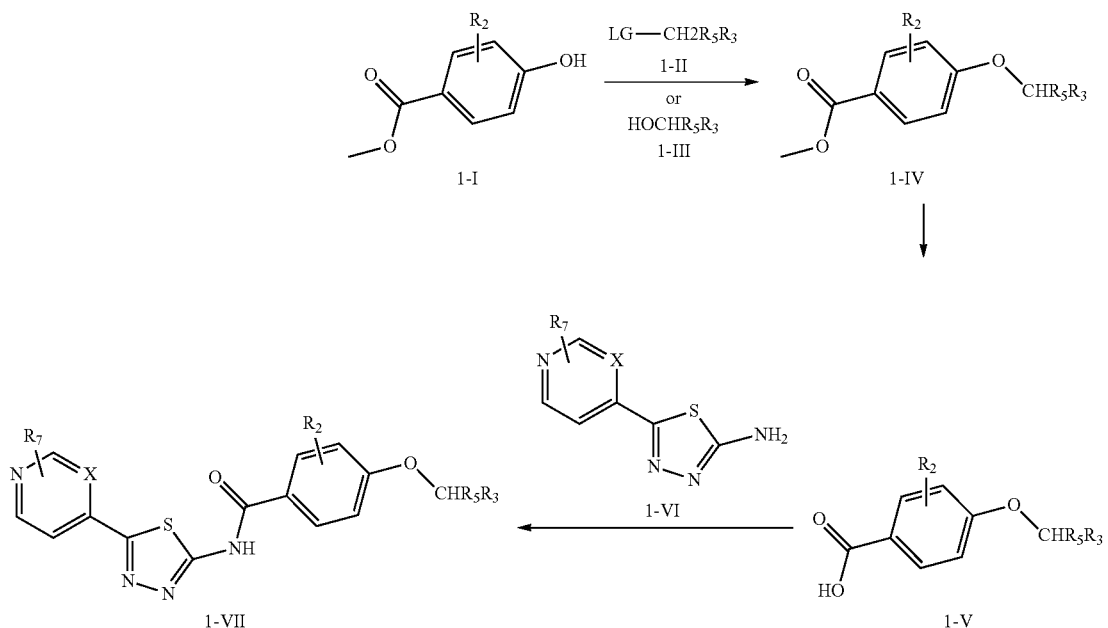

Scheme 1

Amido thiadiazole derivatives according to Formula (1-VII), i.e. of Formula (I) wherein $A_1$ is —OCHR$^5$ and Y is CH, whereby the substituents X, $R^2$, $R^3$, $R^5$ and $R^7$ are as defined above, may be prepared in 2 or 3 chemical steps from custom made or commercially available phenol derivatives, according to Formula (1-I), halides, according to Formula (1-II) or hydroxyl compounds, according to Formula (1-III) and aminothiadiazole derivatives according to Formula (1-VI) following the synthetic protocol outlined in Scheme 1 above. In a more specific method the phenol derivative according to Formula (1-I) is reacted with a compound of the Formula (1-II), wherein LG represents a suitable leaving group such as chlorine, bromine or iodine, in the presence of a suitable inorganic base potassium carbonate in an inert solvent such as N,N-dimethylformamide and at a suitable temperature preferably heating to between 80 and 120° C. over a time depending on the intrinsic reactivity of the compounds according to Formula (1-II) to provide the ether derivatives according to Formula (1-IV). As an alternative this step can be accomplished using a Mitsunobu reaction with a hydroxyl compound according to the Formula (1-III). The conditions employed in a Mitsunobu reaction are well known to those skilled in the art, but in general the phenol derivatives according to the Formula (1-I) and the hydroxyl compound according to the Formula (1-III) are reacted in the presence of a phosphine derivative such as triphenyl phosphine and a azodicarboxylate such as diethylazodicarboxylate in an appropriate inert solvent such as tetrahydrofuran or dichloromethane. The reaction is conducted using a suitable temperature, preferably between 0° C. and 40° C. and reaction time depending on the intrinsic reactivity of compound according to the Formula (1-III) to afford the ether derivative according to the Formula (1-IV).

ambient temperature to 50° C. and over a time depending on the intrinsic reactivity of the compound according to Formula (1-IV) to provide benzoic acid derivatives according to Formula (1-V).

In a subsequent step, a benzoic acid derivative according to the Formula (1-V) is reacted with an aminothiadiazole derivative according to Formula (1-IV) using an appropriate coupling agent such as HATU in the presence of a non-nucleophilic base such as diisopropylethylamine in a suitable inert solvent such as NMP and at an appropriate temperature preferably with heating to 70° C. over a time depending on the intrinsic reactivity of the compounds according to Formula (1-IV) to provide the amidothiadiazole derivative according to Formula (1-VII). Alternatively, this step may be accomplished in a two stage sequence. In such a process the nicotinic acid derivative according to the Formula (2-I) is first converted to the corresponding acid chloride by reaction with a reagent such as thionyl chloride or oxalyl chloride either neat or in the presence of a suitable inert solvent such as acetonitrile or dichloromethane at a suitable temperature which may be up to 70° C. The acid chloride so formed is then further reacted with an aminothiadiazole derivative according to Formula (1-VII) in the presence of a suitable non-nucleophilic base for example pyridine which may also act as the solvent at a suitable temperature and reaction time taking into account the intrinsic reactivity of the compound according to Formula (1-VI). Following this process amido thiadiazole derivatives according to Formula (1-VII) are isolated, using standard conditions well known to the person skilled in the art as shown in Scheme 1.

Scheme 2

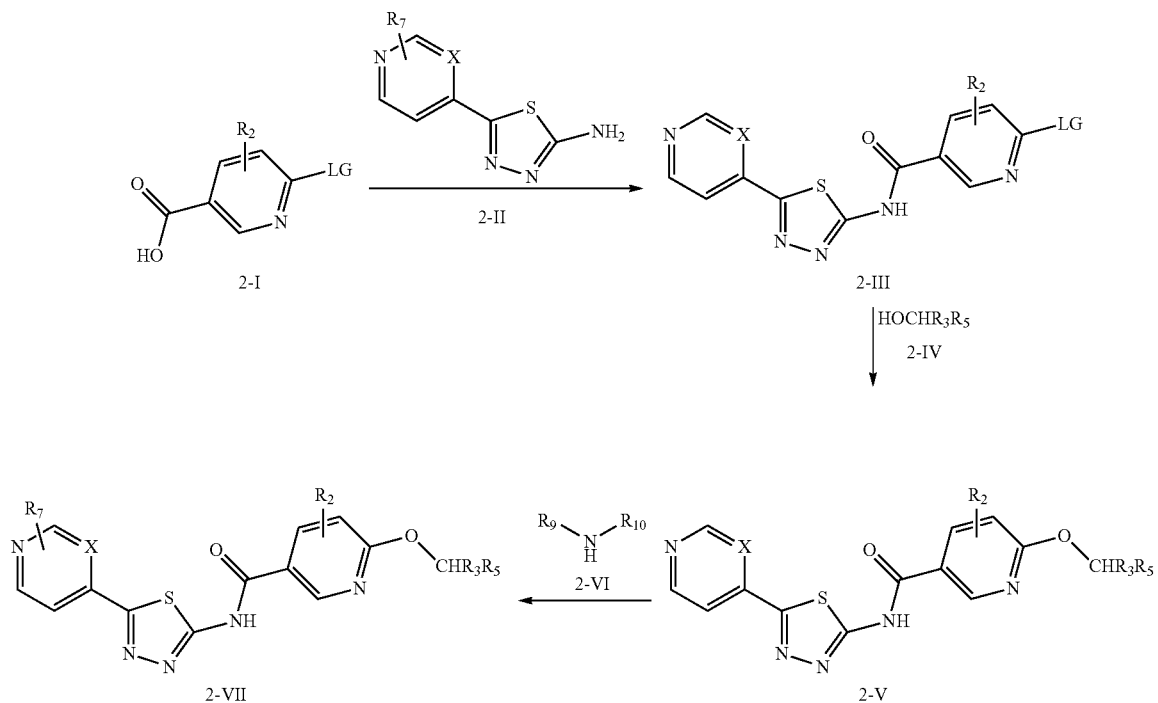

Amidothiadiazole derivatives according to Formula (2-V and 2-VII), i.e. of Formula (I) wherein $A_1$ is —OCHR$^5$ and Y is N, whereby the substituents X, $R^2$, $R^3$, $R^5$, $R^7$, $R^8$, $R^9$ and $R^{10}$ are as defined above may be prepared in 2 or 3 chemical steps from custom made or commercially available nicotinic acid derivatives, according to Formula (2-I), aminothiadiazole derivatives, according to Formula (2-II) and hydroxy derivatives according to Formula (2-IV) following the synthetic protocol outlined in Scheme 2 above. In a more specific method, a nicotinic acid derivative according to Formula (2-I), wherein R2 is as defined above and LG represents a suitable leaving group for example fluorine or chlorine, is reacted with an aminothiadiazole derivative according to Formula (2-II) using an appropriate coupling agent such as HATU in the presence of a non-nucleophilic base such as diisopropylethylamine in a suitable inert solvent such as NMP and at an appropriate temperature for example with heating to 70° C. over a time depending on the intrinsic reactivity of the compounds according to Formula (2-II) to provide the nicotinamide derivative according to Formula (2-III). Alternatively this step may be accomplished in a two stage sequence. In such a process the nicotinic acid derivative according to the Formula (2-I) is first converted to the corresponding acid chloride by reaction with a reagent such as thionyl chloride or oxalyl chloride either neat or in the presence of a suitable inert solvent such as acetonitrile or dichloromethane at a suitable temperature which may be up to 70° C. The acid chloride so formed is then further reacted with an aminothiadiazole derivative according to Formula (2-II) in the presence of a suitable non-nucleophilic base for example pyridine which may also act as the solvent at a suitable temperature a reaction time taking into account the intrinsic reactivity of the compound according to Formula (2-II) to provide the nicotinamide derivative according to Formula (2-III).

The intermediate compound according to Formula (2-III) are further reacted with hydroxyl derivatives according to Formula (2-IV), wherein $R^3$ and $R^5$ are as defined above, in the presence of a suitable base such as sodium hydroxide or caesium carbonate and in an inert solvent such as dimethylsulfoxide and at an appropriate temperature, for example an elevated temperature between 50° C. and 170° C., and reaction time depending on the intrinsic reactivity of the compound according to Formula (2-IV) to afford the amidothiadiazole derivatives according to Formula (2-V).

In a subsequent step the amidothiadiazole derivative according to Formula (2-V), wherein $R^2$ represents a suitable leaving group such as chlorine or bromine, can be further reacted with an amine according to the Formula (2-VI) in the presence of a suitable palladium source and ligand, many of which are known to those skilled in the art, but preferred examples include BrettPhos palladacycle and BrettPhos when the amine is a primary amine or BrettPhos palladacyle and RuPhos when the amine is a secondary amine. These palladium mediated couplings are performed in the presence of a suitable base such as sodium tert-butoxide and in a suitable inert solvent such as 1,4-dioxane or NMP preferably using elevated temperatures, for example between 80 and 90° C. over a suitable period of time depending on the intrinsic reactivity of the compound according to Formula (2-VI).

Following this process amidothiadiazole derivatives according to Formula (2-VIII) are isolated, using standard conditions well known to the person skilled in the art as shown in Scheme 2.

Scheme 3

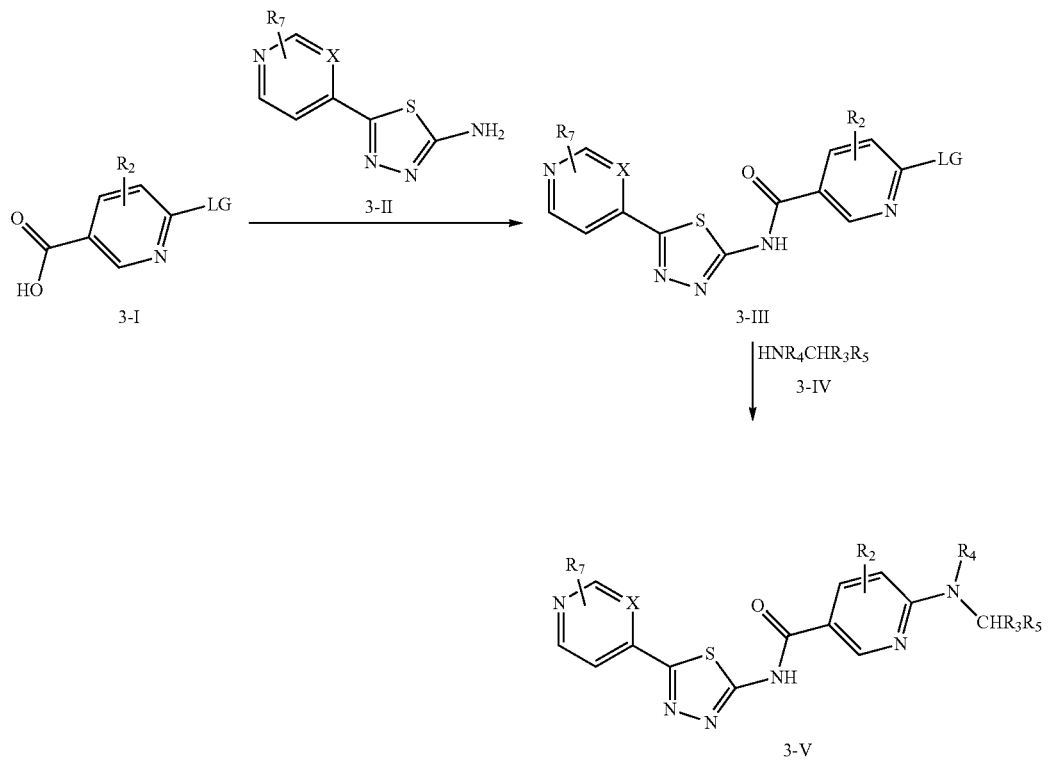

Amidothiadiazole derivatives according to Formula (3-V), i.e. of Formula (I) wherein $A_1$ is —NR$^4$CHR$^5$ and Y is N, whereby the substituents X, R$^2$, R$^3$, R$^4$, R$^5$ and R$^7$ are as defined above, may be prepared in 2 or 3 chemical steps from custom made or commercially available nicotinic acid derivatives, according to Formula (3-I), aminothiadiazole derivatives, according to Formula (3-II) and amino derivatives according to Formula (3-IV) following the synthetic protocol outlined in Scheme 3 above. In a more specific method, a nicotinic acid derivative according to Formula (3-I), wherein R2 is as defined above and LG represents a suitable leaving group for example fluorine or chlorine, is reacted with an aminothiadiazole derivative according to Formula (3-II) using an appropriate coupling agent such as HATU in the presence of a non-nucleophilic base such as diisopropylethylamine in a suitable inert solvent such as NMP and at an appropriate temperature preferably with heating to 70° C. over a time depending on the intrinsic reactivity of the compounds according to Formula (3-II) to provide the nicotinamide derivative according to Formula (3-III). Alternatively this step may be accomplished in a two stage sequence. In such a process the nicotinic acid derivative according to the Formula (3-I) is first converted to the corresponding acid chloride by reaction with a reagent such as thionyl chloride or oxalyl chloride either neat or in the presence of a suitable inert solvent such as acetonitrile or dichloromethane at a suitable temperature which may be up to 70° C. The acid chloride so formed is then further reacted with an aminothiadiazole derivative according to Formula (3-II) in the presence of a suitable non-nucleophilic base for example pyridine which may also act as the solvent at a suitable temperature and reaction time taking into account the intrinsic reactivity of the compound according to Formula (3-II) to provide the nicotinamide derivative according to Formula (3-III).

In a subsequent step the nicotinamide derivative according to the Formula (3-III) is further reacted with an amine according to the Formula (3-IV) in an inert solvent such as DMSO at an elevated temperature, for example with heating to 150° C. for an appropriate period of time depending on the intrinsic reactivity of the compound according to Formula (3-III) to afford the nicotinamide derivatives according to Formula (3-V). Alternatively if LG is a suitable leaving group such as chlorine the nicotinamide derivatives according to Formula (3-III) may be reacted with amine derivatives according to the Formula (3-III) using a suitable palladium source and ligand, many of which are known to those skilled in the art, but preferred examples include BrettPhos palladacycle and BrettPhos when the amine is a primary amine or BrettPhos palladacyle and RuPhos when the amine is a secondary amine. These palladium mediated couplings are performed in the presence of a suitable base such as sodium tert-butoxide and in a suitable inert solvent such as 1,4-dioxane or NMP preferably using elevated temperatures, for example between 80 and 90° C. over a suitable period of time depending on the intrinsic reactivity of the compound according to Formula (3-III). Following this process amidothiadiazole derivatives according to Formula (3-V) are isolated, using standard conditions well known to the person skilled in the art as shown in scheme 3.

Scheme 4

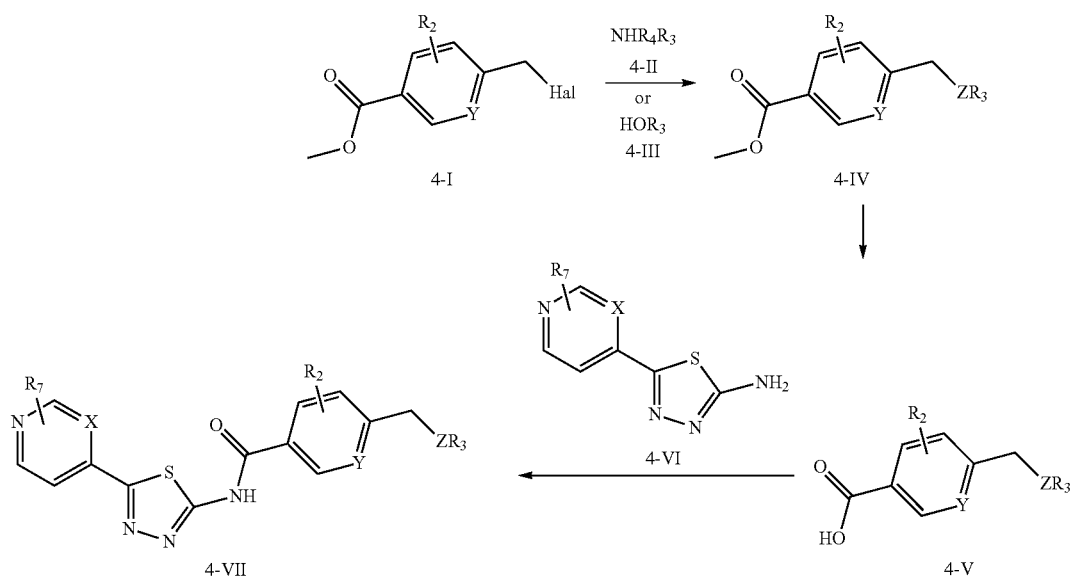

Amidothiadiazole derivatives according to Formula (4-VII), i.e. of Formula (I) wherein $A_1$ is —$CH_2NR^4$ or is —$CH_2O$— and Y is CH or N, whereby the substituents X, Y, $R^2$, $R^3$, $R^4$ and $R^7$ are as defined above and Z may be $NR^4$ or O, may be prepared in 2 or 3 chemical steps from custom made or commercially available halogens, according to Formula (4-I), amines, according to Formula (4-II) or hydroxyl compounds, according to Formula (4-III) and aminothiadiazole derivatives according to Formula (4-VI) following the synthetic protocol outlined in Scheme 4 above. In a more specific method the bromomethyl derivative according to Formula (4-I) is reacted with a compound of the Formula (4-II) or (4-III), in the presence of a suitable base such as potassium carbonate in an inert solvent such as DMF and at a suitable temperature typically between 21° C. and 40° C. over a time depending on the intrinsic reactivity of the compounds according to Formula (4-II) or (4-III) to provide the ether or amine derivatives according to Formula (4-IV). The intermediate compounds according to Formula (4-IV) are further reacted with an aqueous solution of a hydroxide base such as lithium hydroxide or sodium hydroxide in a combination with solvent such as methanol or tetrahydrofuran using a suitable temperature, for example at ambient temperature and over a time depending on the intrinsic reactivity of the compound according to Formula (4-IV) to provide benzoic acid derivatives according to Formula (4-V).

In a subsequent step a benzoic acid derivative according to the Formula (4-V) is reacted with an aminothiadiazole derivative according to Formula (4-IV) using an appropriate coupling agent such as HATU in the presence of a non-nucleophilic base such as diisopropylethylamine in a suitable inert solvent such as NMP and at an appropriate temperature preferably with heating to 70° C. over a time depending on the intrinsic reactivity of the compounds according to Formula (4-IV) to provide the amidothiadiazole derivative according to Formula (4-III). Following this process amidothiadiazole derivatives according to Formula (4-VII) are isolated, using standard conditions well known to the person skilled in the art as shown in Scheme 4.

The Following Abbreviations Refer Respectively to the Definitions Below:

AR (Amplex Red); BrettPhos (2-(Dicyclohexylphosphino)3,6-dimethoxy-2',4',6'-triisopropyl-1,1'-biphenyl), DMEM (Dulbecco's Modified Eagle's medium); DMSO (Dimethyl sulfoxide), ESI (Electrospray Ionisation), FAD (Flavin Adenine Dinucleotide); eq. (equivalent), g (gram), HATU ((1-[Bis(dimethylamino)methylene]-1H-1,2,3-triazolo[4,5-b]pyridinium 3-oxid hexafluorophosphate), HBSS (Hank's Balanced Salt Solution); HPLC (High performance liquid chromatography), HRP (horseradish peroxidase); M (molar), mg (milligram), MHz (Megahertz), mL (milliliter), mmol (millimole), MP (Macroporous), MS (Mass spectrometry), NMP (N-Methyl-2-pyrrolidone), NMR (Nuclear magnetic resonance), PA (Phosphatidic Acid); PBS (Phosphate Buffered Saline); PMA (Phorbol 12-myristate 13-acetate); RuPhos (2-Dicyclohexylphosphino-2',6'-diisopropoxybiphenyl), SFC (Supercritical Fluid Chromatography), THF (Tetrahydrofuran), µL (microliters).

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "Protecting Groups", Georg Thieme Verlag Stuttgart, 2005 and Theodora W. Greene and Peter G. M. Wuts in "Protective Groups in Organic Synthesis", Wiley Interscience, 4$^{th}$ Edition 2006.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following, the present invention shall be illustrated by means of some examples, which are not to be viewed as limiting the scope of the invention.

Mass Spectra

Recorded on a Micromass ZQ™, single quadrapole mass spectrometer.

NMR

1H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Preparative Reverse-phase HPLC Conditions

Preparative HPLC purification was performed by reverse phase HPLC using a Waters Fractionlynx™ preparative HPLC system (2525 pump, 2996/2998 UV/VIS detector, 2767 liquid handler) or an equivalent HPLC system such as a Gilson Trilution® UV directed system. The Waters® 2767 liquid handler acted as both auto-sampler and fraction collector.

The columns used for the preparative purification of the compounds were a Waters Sunfire® OBD Phenomenex Luna® Phenyl Hexyl or Waters Xbridge® Phenyl at 10 μm 19×150 mm or Waters CSH™ Phenyl Hexyl, 19×150, 5 μm column.

Appropriate focused gradients were selected based on acetonitrile and methanol solvent systems under either acidic or basic conditions.

The modifiers used under acidic/basic conditions were formic acid or trifluoroacetic acid (0.1% V/V) and ammonium bicarbonate (10 mM) respectively.

The purification was controlled by Waters Fractionlynx™ software through monitoring at 210-400 nm, and triggered a threshold collection value at 260 nm and, when using the Fractionlynx™, the presence of target molecular ion as observed under APi conditions. Collected fractions were analysed by LCMS (Waters Acquity® systems with Waters® SQD).

Chiral SFC Conditions

The chiral separation of compounds was achieved by Supercritical Fluid Chromatography (SFC) using a Waters® Thar Prep100 preparative SFC system (P200 CO2 pump, 2545 modifier pump, 2998 UV/VIS detector, 2767 liquid handler with Stacked Injection Module). The Waters® 2767 liquid handler acted as both auto-sampler and fraction collector. The column used for the preparative purification of the compounds was a Diacel Chiralpak® IA/IB/IC, a Phenomenex® Lux Cellulose-4, an YMC Amylose-C or an YMC Cellulose-C at 5 μm 250×20-21.2 mm ID. Appropriate isocratic methods were selected based on methanol, ethanol or isopropanol solvent systems under un-modified or basic conditions. The standard SFC method used was modifier, $CO_2$, 100 mL/min, 120 Bars backpressure, 40° C. column temperature. The modifier used under basic conditions was diethylamine (0.1% V/V). The modifier used under acidic conditions was either formic acid (0.1% V/V) or trifluoroacetic acid (0.1% V/V).

The SFC purification was controlled by Waters Fractionlynx™ software through monitoring at 210-400 nm and triggered at a threshold collection value, typically 260 nm. Collected fractions were analysed by SFC (Waters®/Thar SFC systems with Waters® SQD). The fractions that contained the desired product were concentrated by vacuum centrifugation.

EXAMPLE 1

Formation of 4-(1-phenylethoxy)-3-(piperidin-4-ylmethoxy)-N-(5-(pyridin-4-yl)-1,3,4-thiadiazol-2-yl)benzamide (Compound 1-VII, Scheme 1)

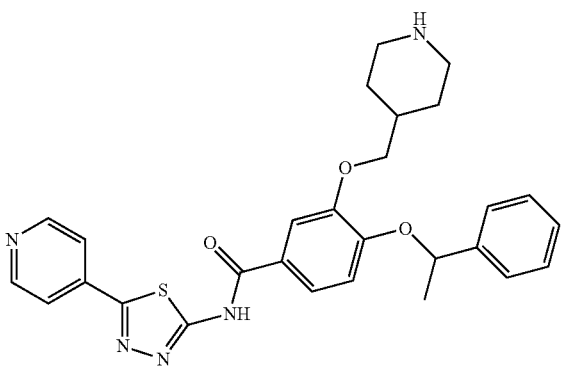

(1)

a) methyl 3-hydroxy-4-(1-phenylethoxy)benzoate (Compound of Formula 1-IV, Scheme 1)

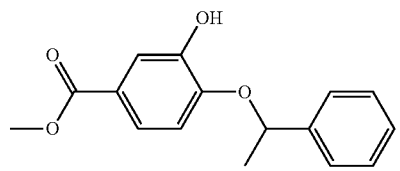 [SMILES: COC(=O)c1ccc(OC(C)c2ccccc2)c(O)c1]

To a stirred solution of methyl 3,4-dihydroxybenzoate (0.2 g, 1.2 mmol, 1 eq.) in N,N-dimethylformamide (6 mL) at 0° C. was added potassium carbonate (0.33 g, 2.4 mmol. 2 eq.) followed by (1-bromoethyl)benzene (0.16 mL, 1.2 mmol, 1 eq.) and the resulting mixture stirred at room temperature for 16 hours. The reaction was diluted with water and ethyl acetate. The aqueous phase was extracted with ethyl acetate (×2). The combined organic phase was washed with water and brine, dried over magnesium sulfate and the solvent removed in vacuo. The residue was purified by silica gel column chromatography using a 0-50% ethyl acetate in iso-hexane gradient to afford methyl 3-hydroxy-4-(1-phenylethoxy)benzoate (0.169 g, 51% yield). $^1$H NMR (400 MHz, CDCl$_3$) 7.58 (1H, d, J=1.5 Hz), 7.43 (1H, dd, J=1.5, 8.3 Hz), 7.39-7.26 (5H, m), 6.70 (1H, d, J=8.3 Hz), 5.78 (1H, s), 5.42 (1H, q, J=6.5 Hz), 3.84 (3H, s), 1.71 (3H, d, J=6.5 Hz).

b) tert-butyl 4-((5-(methoxycarbonyl)-2-(1-phenylethoxy)phenoxy)methyl)piperidine-1-carboxylate (Compound of Formula 1-IV, Scheme 1)

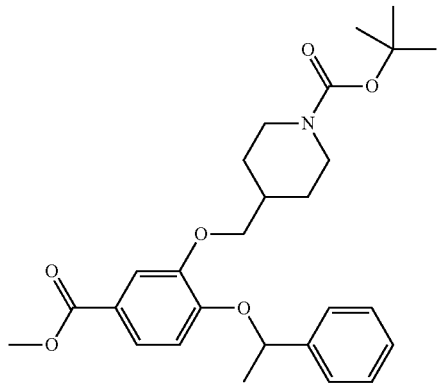 [SMILES: COC(=O)c1ccc(OC(C)c2ccccc2)c(OCC2CCN(C(=O)OC(C)(C)C)CC2)c1]

To a stirred solution of methyl 3-hydroxy-4-(1-phenylethoxy)benzoate (0.154 g, 0.57 mmol, 1 eq.), tert-butyl 4-(hydroxymethyl)piperidine-1-carboxylate (0.202 g, 0.74 mmol, 1.3 eq.) and triphenyl phosphine (0.194 g, 0.74 mmol, 1.3 eq.) in tetrahydrofuran (5 mL) at 0° C. was added diethylazodicarboxylate (135 µL, 0.74 mmol, 1.3 eq.) dropwise. The resulting mixture was then stirred overnight at room temperature. The solvent was removed in vacuo and the residue purified by column chromatography using a 0-50% ethyl acetate in iso-hexane gradient to afford tert-butyl 4-((5-(methoxycarbonyl)-2-(1-phenylethoxy)phenoxy) methyl)piperidine-1-carboxylate (0.203 g, 75% yield). $^1$H NMR (400 MHz, CDCl$_3$) 7.52-7.47 (2H, m), 7.38-7.30 (4H, m), 7.27-7.24 (1H, m), 6.75 (1H, d, J=8.6 Hz), 5.37 (1H, q, J=6.4 Hz), 4.27-4.10 (2H, m), 3.92-3.89 (2H, m), 3.85 (3H, s), 2.84-2.75 (2H, m), 2.09-1.99 (1H, m), 1.92-1.83 (2H, m), 1.67 (3H, d, J=6.6 Hz), 1.48 (9H, s), 1.38-1.22 (2H, m).

c) 3-((1-(tert-butoxycarbonyl)piperidin-4-yl) methoxy)-4-(1-phenylethoxy)benzoic acid (Compound of Formula 1-V, Scheme 1)

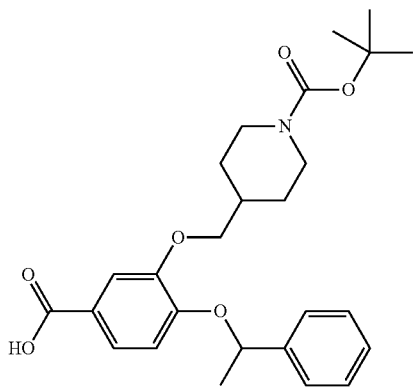 [SMILES: CC(Oc1ccc(C(=O)O)cc1OCC1CCN(C(=O)OC(C)(C)C)CC1)c1ccccc1]

To a solution of tert-butyl 4-((5-(methoxycarbonyl)-2-(1-phenylethoxy)phenoxy)methyl) piperidine-1-carboxylate (0.203 g, 0.43 mmol, 1 eq.) in methanol (5 mL) was added 2M aqueous sodium hydroxide solution (0.5 mL, 1.0 mmol, 2.3 eq.) and the resulting mixture stirred at 60° C. for 48 hours. The methanol was removed in vacuo and the residue partitioned between water and ethyl acetate. The aqueous phase was acidified to pH 3 using 2M hydrochloric acid and then extracted with ethyl acetate (×3). The combined organic phase was washed with brine and the solvent removed in vacuo to afford 3-((1-(tert-butoxycarbonyl)piperidin-4-yl) methoxy)-4-(1-phenylethoxy)benzoic acid (0.192 g, 98% yield). $^1$H NMR (400 MHz, CDCl$_3$) 7.57-7.54 (2H, m), 7.37-7.30 (4H, m), 7.28-7.24 (1H, m), 6.77 (1H, d, J=8.1 Hz), 5.38 (1H, q, J=6.7 Hz), 4.20-4.15 (2H, m), 3.92 (2H, d, J=5.0 Hz), 2.82-2.75 (2H, m), 2.08-1.99 (1H, m), 1.91-1.84 (2H, m), 1.69 (3H, d, J=7.1 Hz), 1.48 (9H, s), 1.38-1.28 (2H, m).

d) tert-butyl 4-((2-(1-phenylethoxy)-5-((5-(pyridin-4-yl)-1,3,4-thiadiazol-2-yl)carbamoyl)phenoxy) methyl)piperidine-1-carboxylate (Compound of Formula 1-VII, Scheme 1)

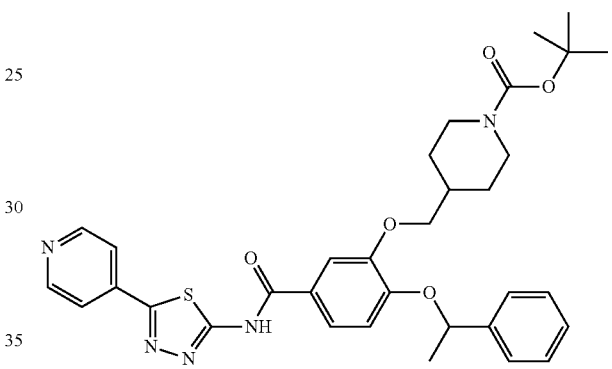

A solution of 3-((1-(tert-butoxycarbonyl)piperidin-4-yl) methoxy)-4-(1-phenylethoxy) benzoic acid (0.192 g, 0.42 mmol, 1 eq.), 5-(4-pyridyl)-1,3,4-thiadiazol-2-yl amine (0.075 g, 0.42 mmol, 1 eq.), HATU (0.240 g, 0.63 mmol, 1.5 eq.) and diisopropylethylamine (90 µL, 0.52 mmol, 1.2 eq.) in NMP (2 mL) was stirred at 70° C. for 24 hours. The solvent was removed in vacuo and the resulting solid triturated with hot methanol. The solid was collected by filtration and washed with saturated sodium bicarbonate solution and water and then dried in vacuo to afford tert-butyl 4-((2-(1-phenylethoxy)-5-((5-(pyridin-4-yl)-1,3,4-thiadiazol-2-yl)carbamoyl)phenoxy)methyl)piperidine-1-carboxylate (0.116 g, 45% yield). $^1$H NMR (400 MHz, DMSO) 13.11 (1H, s), 8.75 (2H, d, J=6.1 Hz), 7.95-7.93 (2H, m), 7.80 (1H, d, J=2.0 Hz), 7.66 (1H, dd, J=2.0, 8.3 Hz), 7.42 (2H, d, J=7.3 Hz), 7.36 (2H, dd, J=7.5, 7.5 Hz), 7.27 (1H, dd, J=7.3, 7.3 Hz), 7.05 (1H, d, J=8.8 Hz), 5.67-5.61 (1H, m), 4.05-3.98 (4H, m), 2.81-2.78 (2H, m), 2.08-2.02 (1H, m), 1.87-1.79 (2H, m), 1.59 (3H, d, J=6.6 Hz), 1.42 (9H, s), 1.34-1.24 (2H, m).

e) 4-(1-phenylethoxy)-3-(piperidin-4-ylmethoxy)-N-(5-(pyridin-4-yl)-1,3,4-thiadiazol-2-yl) benzamide (Compound 1-VII, Scheme 1)

To a stirred suspension of tert-butyl 4-((2-(1-phenylethoxy)-5-((5-(pyridin-4-yl)-1,3,4-thiadiazol-2-yl)carbamoyl)phenoxy)methyl)piperidine-1-carboxylate (0.116 g, 0.19 mmol, 1 eq.) in methanol (5 mL) was added 4M hydrochloric acid in dioxane (1 mL, 4.0 mmol, 21 eq.) and the resulting mixture stirred overnight at room temperature. The solvent was removed in vacuo and the residue purified by preparative HPLC. The resultant material was triturated with hot isopropanol to afford 4-(1-phenylethoxy)-3-(piperidin-4-ylmethoxy)-N-(5-(pyridin-4-yl)-1,3,4-thiadiazol-2-yl) benzamide (0.015 g, 16% yield). $^1$H NMR (400 MHz, DMSO) 8.74 (2H, d, J=4.8 Hz), 7.92 (2H, d, J=4.8 Hz), 7.85 (1H, s), 7.70 (1H, d, J=8.3 Hz), 7.48 (2H, d, J=7.8 Hz), 7.41 (2H, dd, J=7.6, 7.6 Hz), 7.32 (1H, dd, J=7.2, 7.2 Hz), 7.05 (1H, d, J=8.6 Hz), 5.70-5.62 (1H, m), 4.05 (2H, d, J=6.3 Hz), 3.02 (2H, dd, J=12.6, 12.6 Hz), 2.23-2.19 (1H, m), 2.10-2.05 (2H, m), 1.67-1.56 (5H, m), one CH$_2$ is obscured by the residual water signal; MS (ESI$^+$) 516.

EXAMPLE 2

Formation of 3-(2-hydroxyethoxy)-4-(1-phenylethoxy)-N-(5-(pyridin-4-yl)-1,3,4-thiadiazol-2-yl) benzamide (Compound 1-VII, Scheme 1)

(2)

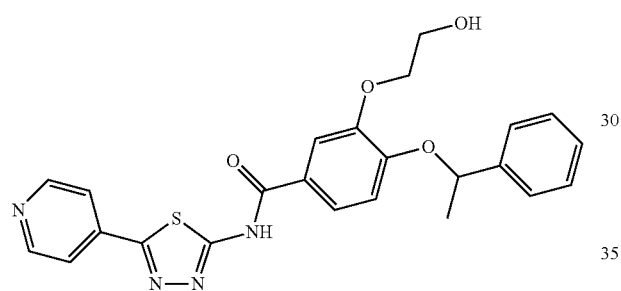

To a solution of lithium chloride (0.019 g, 0.45 mmol, 5 eq.) and water (16 μL, 0.89 mmol, 10 eq.) in dimethyl sulfoxide (0.5 mL) was added 4-(1-phenylethoxy)-N-(5-(pyridin-4-yl)-1,3,4-thiadiazol-2-yl)-3-(2-((tetrahydro-2H-pyran-2-yl)oxy)ethoxy)benzamide (0.050 g, 0.09 mmol, 1 eq. prepared following the general procedure outlined for Example 1 steps a-d, starting from methyl 3,4-dihydroxybenzoate, (1-bromoethyl)benzene, 2-((tetrahydro-2H-pyran-2-yl)oxy)ethanol and 5-(4-pyridyl)-1,3,4-thiadiazol-2-yl amine)) and the resulting mixture stirred at 90° C. overnight. A solution of lithium chloride (0.008 g, 0.19 mmol, 2.1 eq.) and water (7 μL, 0.39 mmol, 4.3 eq.) in dimethyl sulfoxide (0.2 mL) was added and the reaction stirred at 90° C. overnight. The resultant solid was collected by filtration and triturated with dichloromethane to afford 3-(2-hydroxyethoxy)-4-(1-phenylethoxy)-N-(5-(pyridin-4-yl)-1,3,4-thiadiazol-2-yl)benzamide (0.013 g, 33% yield). $^1$H NMR (400 MHz, DMSO) 13.19 (1H, s), 8.81 (2H, d, J=6.1 Hz), 8.01 (2H, d, J=6.1 Hz), 7.88 (1H, d, J=2.0 Hz), 7.70 (1H, dd, J=2.0, 8.6 Hz), 7.49 (2H, d, J=7.3 Hz), 7.41 (2H, dd, J=7.6, 7.6 Hz), 7.32 (1H, t, J=7.3 Hz), 7.09 (1H, d, J=8.6 Hz), 5.73 (1H, q, J=6.1 Hz), 4.92 (1H, s), 4.22 (2H, t, J=5.2 Hz), 3.88 (2H, t, J=5.2 Hz), 1.65 (3H, d, J=6.3 Hz); MS (ESI$^+$) 463.

EXAMPLE 3

Formation of 4-(benzyloxy)-3-(2-methoxyethoxy)-N-(5-(pyridin-4-yl)-1,3,4-thiadiazol-2-yl)benzamide (Compound 1-VII, Scheme 1)

(3)

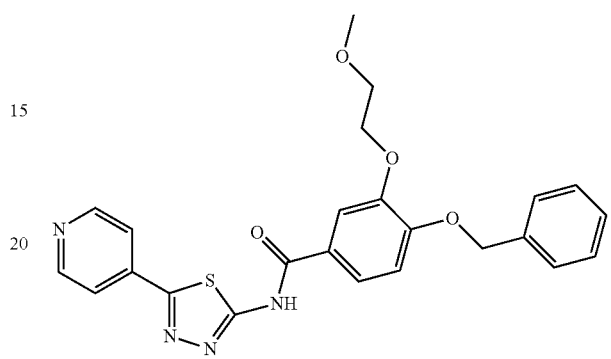

a) methyl 4-(benzyloxy)-3-hydroxybenzoate (Compound of Formula 1-IV, Scheme 1)

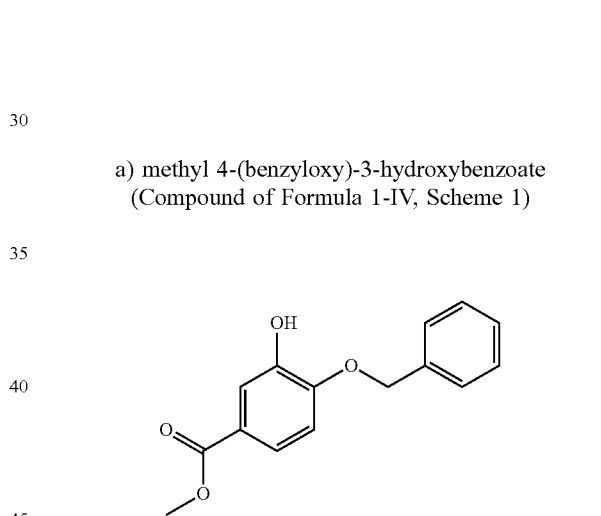

To a stirred solution of methyl 3,4-dihydroxybenzoate (1.1 g, 6.5 mmol, 1 eq.) and potassium carbonate (1.1 g, 7.8 mmol, 1.2 eq.) in N,N-dimethylformamide (11 mL) was added benzyl bromide (0.78 mL, 6.5 mmol, 1 eq.) and the resulting mixture was stirred at room temperature overnight. The solvent was removed in vacuo and the crude product partitioned between water and ethyl acetate, 2M hydrochloric acid was added to adjust the pH to 2, the layers were separated and the aqueous extracted with a further 3 portions of ethyl acetate. The combined extracts were dried with magnesium sulfate and evaporated in vacuo. The residue was purified by silica gel column chromatography using a 5-80% ethyl acetate in iso-hexane gradient to afford methyl 4-(benzyloxy)-3-hydroxybenzoate as a white solid (0.82 g, 49% yield). $^1$H NMR (400 MHz, CDCl$_3$) 7.62-7.62 (2H, m), 7.43-7.4 (5H, m), 6.94 (1H, d, J=8.0 Hz), 5.69 (1H, s), 5.17 (2H, s), 3.88 (3H, s).

b) methyl 4-(benzyloxy)-3-(2-methoxyethoxy)benzoate (Compound of Formula 1-IV, Scheme 1)

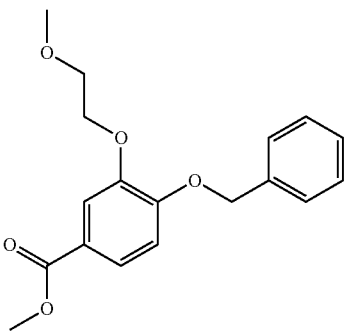 [SMILES: COCCOc1cc(C(=O)OC)ccc1OCc1ccccc1]

To a stirred suspension of methyl 4-(benzyloxy)-3-hydroxybenzoate (0.4 g, 1.5 mmol, 1 eq.) and potassium carbonate (0.415 g, 3 mmol, 2 eq.) in N,N-dimethylformamide (3 mL) was added 1-bromo-2-methoxyethane (160 µL, 1.7 mmol, 1.1 eq.) and the resulting mixture heated to 150° C. for 1.5 hours. The solvent was removed in vacuo and the crude product partitioned between water and ethyl acetate and the aqueous phase extracted with ethyl acetate. The combined extracts were dried with magnesium sulfate and evaporated in vacuo. The residue was purified by silica gel column chromatography using a 5-25% ethyl acetate in iso-hexane gradient to afford methyl 4-(benzyloxy)-3-(2-methoxyethoxy)benzoate as a clear liquid (0.5 g, 100% yield). $^1$H NMR (400 MHz, CDCl$_3$) 7.63-7.62 (2H, m), 7.45-7.44 (2H, m), 7.4-7.3 (3H, m), 6.91 (1H, d, J=8.4 Hz), 5.19 (2H, s), 4.23-4.22 (2H, m), 3.88 (3H, s), 3.80-3.78 (2H, m), 3.45 (3H, s).

c) 4-(benzyloxy)-3-(2-methoxyethoxy)benzoic acid (Compound of Formula 1-V, Scheme 1)

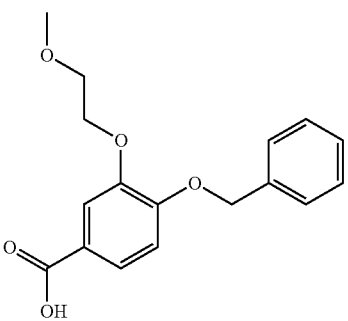 [SMILES: COCCOc1cc(C(=O)O)ccc1OCc1ccccc1]

To a stirred solution of methyl 4-(benzyloxy)-3-(2-methoxyethoxy)benzoate (0.5 g, 1.6 mmol, 1 eq.) in ethanol (6 mL) was added 2M aqueous sodium hydroxide solution (3 mL, 6 mmol, 4 eq.) and the resulting mixture stirred at 40° C. for 3 hours. The ethanol was removed in vacuo, the resultant mixture cooled in an ice bath and acidified with concentrated hydrochloric acid. The crude product was partitioned between water and ethyl acetate and the aqueous phase extracted with ethyl acetate. The combined extracts were dried with magnesium sulfate and evaporated in vacuo to afford 4-(benzyloxy)-3-(2-methoxyethoxy)benzoic acid as a white solid (0.418 g, 86% yield). $^1$H NMR (400 MHz, CDCl$_3$) 7.72-7.7 (1H, m), 7.66-7.65 (1H, m), 7.44-7.42 (2H, m), 7.4-7.2 (3H, m), 6.94-6.93 (1H, m), 5.22 (2H, s), 4.24-4.23 (2H, m), 3.81-3.79 (2H, m), 3.46 (3H, s).

d) 4-(benzyloxy)-3-(2-methoxyethoxy)-N-(5-(pyridin-4-yl)-1,3,4-thiadiazol-2-yl)benzamide (Compound 1-VII, Scheme 1)

Oxalyl chloride (0.1 mL, 1.18 mmol, 4.0 eq.) was added to a solution of 4-(benzyloxy)-3-(2-methoxyethoxy)benzoic acid (0.1 g, 0.33 mmol, 1.15 eq.) in dichloromethane (2 mL) followed by N,N-dimethylformamide (2 drops). The reaction was stirred at room temperature overnight and the solvent was removed in vacuo. A suspension of 5-(pyrimidin-4-yl)-1,3,4-thiadiazol-2-amine (0.051 g, 0.29 mmol, 1 eq.) in pyridine (1.5 mL) was added and the reaction stirred at ambient temperature overnight. The resultant solid was collected by filtration and washed successively with pyridine (0.5 mL), water, saturated sodium bicarbonate solution and water and then dried in vacuo to afford 4-phenoxy-N-(5-(pyridin-4-yl)-1,3,4-thiadiazol-2-yl)benzamide as a white solid (0.026 g, 13% yield). $^1$H NMR (400 MHz, DMSO) 13.19 (1H, s), 8.75 (2H, d, J=6.1 Hz), 7.97-7.94 (2H, m), 7.85 (1H, d, J=2.1 Hz), 7.80 (1H, dd, J=2.1, 8.5 Hz), 7.48 (2H, d, J=7.0 Hz), 7.41 (2H, dd, J=7.3, 7.3 Hz), 7.37-7.33 (1H, m), 7.24 (1H, d, J=8.7 Hz), 5.25 (2H, s), 4.27-4.23 (2H, m), 3.75-3.71 (2H, m), 3.34 (3H, s); MS (ESI+) 463.

EXAMPLE 4

Formation of (S)-3-methoxy-4-(1-phenylethoxy)-N-(5-(pyridin-4-yl)-1,3,4-thiadiazol-2-yl)benzamide (Compound 1-VII, Scheme 1)

(4)

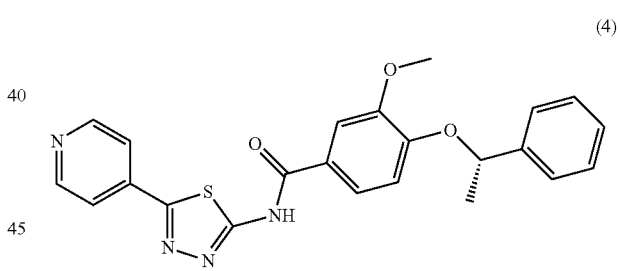

a) (S)-methyl 3-methoxy-4-(1-phenylethoxy)benzoate (Compound of Formula 1-IV, Scheme 1)

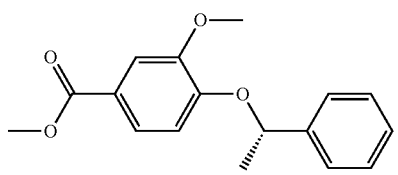 [SMILES: COC(=O)c1ccc(O[C@@H](C)c2ccccc2)c(OC)c1]

To a stirred solution of methyl 4-hydroxy-3-methoxybenzoate (3.0 g, 16.5 mmol, 1 eq.), (R)-1-phenylethanol (4.0 mL, 33.0 mmol, 2 eq.) and triphenylphosphine (8.65 g, 33.0 mmol, 2 eq.) in tetrahydrofuran (100 mL) at 0° C. was added diethylazodicarboxylate (5.2 mL, 33.0 mmol, 2 eq.) dropwise maintaining the internal reaction temperature below 6°

C. The resulting mixture was then stirred overnight at room temperature. The solvent was removed in vacuo and azeotroped with diethyl ether. The residue was dissolved in diethyl ether, the residual solid removed by filtration and the filtrate concentrated. The residue was purified by column chromatography using a 0-50% ethyl acetate in iso-hexane gradient to afford (S)-methyl 3-methoxy-4-(1-phenylethoxy) benzoate as a colourless oil (3.77 g, 80% yield). $^1$H NMR (400 MHz, CDCl$_3$) 7.53 (1H, d, J=2.0 Hz), 7.47 (1H, dd, J=2.0, 8.3 Hz), 7.39-7.30 (4H, m), 7.27-7.24 (1H, m), 6.72 (1H, d, J=8.6 Hz), 5.43-5.37 (1H, m), 3.94 (3H, s), 3.85 (3H, s), 1.71 (3H, d, J=6.3 Hz).

b) (S)-3-methoxy-4-(1-phenylethoxy)benzoic acid (Compound of Formula 1-V, Scheme 1)

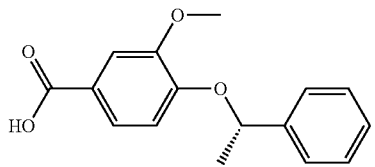 [SMILES: COc1cc(C(=O)O)ccc1O[C@@H](C)c1ccccc1]

To a solution of (S)-methyl 3-methoxy-4-(1-phenylethoxy)benzoate (3.77 g, 13.18 mmol, 1 eq.) in methanol (26.3 mL) was added 2M aqueous sodium hydroxide solution (26.3 mL, 52.72 mmol, 4.0 eq.) and the resulting mixture stirred at 50° C. for 2 hours. The methanol was removed in vacuo and the residue partitioned between water and dichloromethane. The aqueous phase was acidified to pH 1 using 2M hydrochloric acid and the solid precipitate collected by filtration, washed with water then dried in air to afford (S)-3-methoxy-4-(1-phenylethoxy)benzoic acid (2.92 g, 81% yield). $^1$H NMR (400 MHz, DMSO) 12.65 (1H, s), 7.49 (1H, d, J=1.5 Hz), 7.48-7.36 (6H, m), 6.96 (1H, d, J=8.6 Hz), 5.64 (1H, q, J=6.2 Hz), 3.90 (3H, s), 1.63 (3H, d, J=6.3 Hz).

c) (S)-3-methoxy-4-(1-phenylethoxy)-N-(5-(pyridin-4-yl)-1,3,4-thiadiazol-2-yl)benzamide (Compound of Formula 1-VII, Scheme 1)

A solution of (S)-3-methoxy-4-(1-phenylethoxy)benzoic acid (2.92 g, 10.72 mmol, 1 eq.), 5-(4-pyridyl)-1,3,4-thiadiazol-2-yl amine (1.91 g, 10.72 mmol, 1 eq.), HATU (6.11 g., 16.08 mmol, 1.5 eq.) and diisopropylethylamine (2.24 mL, 12.87 mmol, 1.2 eq.) in NMP (48 mL) was stirred at 70° C. for 24 hours. The reaction was diluted with water (200 mL) and the precipitate collected by filtration, washed with water, saturated sodium bicarbonate solution then dried in air. The solid was triturated with hot ethanol to afford (S)-3-methoxy-4-(1-phenylethoxy)-N-(5-(pyridin-4-yl)-1,3,4-thiadiazol-2-yl)benzamide (1.75 g, 37% yield). $^1$H NMR (400 MHz, DMSO) 13.17 (1H, s), 8.81-8.76 (2H, m), 8.00-7.96 (2H, m), 7.85-7.82 (1H, m), 7.69 (1H, d, J=8.6 Hz), 7.47 (2H, d, J=7.6 Hz), 7.40 (2H, dd, J=7.5, 7.5 Hz), 7.32 (1H, dd, J=7.1, 7.1 Hz), 7.05 (1H, d, J=8.6 Hz), 5.74-5.68 (1H, m), 3.97 (3H, s), 1.64 (3H, d, J=6.3 Hz); MS (ESI$^+$) 433.

EXAMPLE 5

Formation of (S)-3-methoxy-4-(1-pyridin-2-yl) ethoxy)-N-(5-(pyridin-4-yl)-1,3,4-thiadiazol-2-yl) benzamide (Compound 1-VII, Scheme 1)

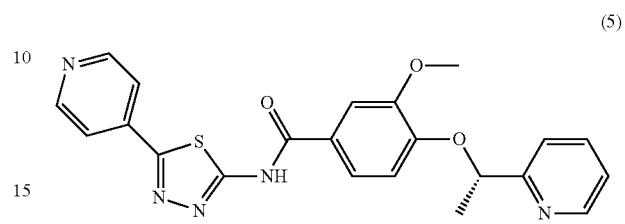

a) (S)-3-methoxy-4-(1-(pyridin-2-yl)ethoxy)benzoic acid (Compound of Formula 1-V, Scheme 1)

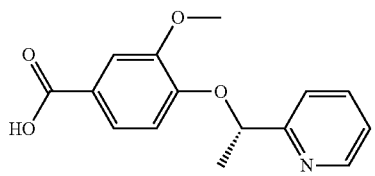 [SMILES: COc1cc(C(=O)O)ccc1O[C@@H](C)c1ccccn1]

To a solution of (S)-methyl 3-methoxy-4-(1-(pyridin-2-yl)ethoxy)benzoate (5.74 g, 11.55 mmol, 1 eq., prepared according to the general procedure outlined for the preparation of Example 4 (step a-b), starting from methyl 4-hydroxy-3-methoxybenzoate and (R)-1-(pyridin-2-yl)ethanol) in methanol (26.3 mL) was added 2M aqueous sodium hydroxide solution (23 mL, 4.62 mmol, 4.0 eq.) and the resulting mixture stirred at 40° C. for 2 hours. The methanol was removed in vacuo and the residue partitioned between water and dichloromethane. The aqueous phase was acidified to pH 5 using 2M hydrochloric acid and the precipitate collected by filtration, washed with water then dried in air to afford (S)-3-methoxy-4-(1-(pyridin-2-yl)ethoxy)benzoic acid. Chiral purification was carried out using SFC (YMC Amylose-C column, 30/70 MeOH/CO$_2$, 5 ml/min, 120 bar, 40° C.) to afford the single enantiomer of the title compound (1.94 g, 61% yield, e.e.=99.8%). $^1$H NMR (400 MHz, DMSO) 12.70 (1H, s), 8.62 (1H, d, J=4.0 Hz), 7.89-7.84 (1H, m), 7.52-7.44 (3H, m), 7.38 (1H, dd, J=4.9, 6.4 Hz), 6.94 (1H, d, J=8.3 Hz), 5.61 (1H, q, J=6.5 Hz), 3.91 (3H, s), 1.67 (3H, d, J=6.6 Hz).

b) (S)-3-methoxy-4-(1-(pyridin-2-yl)ethoxy)-N-(5-(pyridin-4-yl)-1,3,4-thiadiazol-2-yl) benzamide (Compound of Formula 1-VII, Scheme 1)

Following the general method outlined for the preparation of Example 4 (step c), starting from (S)-3-methoxy-4-(1-(pyridin-2-yl)ethoxy)benzoic acid (1.94 g, 7.13 mmol, 1 eq.) and 5-(4-pyridyl)-1,3,4-thiadiazol-2-yl amine (1.27 g, 7.13 mmol, 1 eq.), (S)-3-methoxy-4-(1-(pyridin-2-yl)ethoxy)-N-(5-(pyridin-4-yl)-1,3,4-thiadiazol-2-yl)benzamide (1.70 g, 55% yield) was isolated. $^1$H NMR (400 MHz, DMSO) 13.21 (1H, s), 8.80 (2H, d, J=5.8 Hz), 8.63 (1H, d, J=4.5 Hz), 7.99 (2H, d, J=5.8 Hz), 7.89-7.83 (2H, m), 7.71 (1H, dd, J=1.6, 8.5 Hz), 7.50 (1H, d, J=8.1 Hz), 7.37 (1H, dd, J=5.3, 6.6 Hz), 7.04 (1H, d, J=8.6 Hz), 5.66 (1H, q, J=6.5 Hz), 3.99 (3H, s), 1.69 (3H, d, J=6.3 Hz); MS (ESI$^+$) 434.

EXAMPLE 6

Formation of (R)-4-(2-(dimethylamino)-1-phenylethoxy)-3-methoxy-N-(5-(pyridin-4-yl)-1,3,4-thiadiazol-2-yl)benzamide (Compound 1-VII, Scheme 1)

(6)

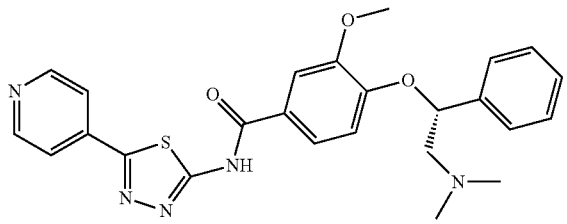

a) (R)-2-(dimethylamino)-1-phenylethanol (Compound of Formula 1-III, Scheme 1)

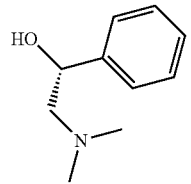

A mixture of (R)-2-amino-1-phenylethanol (5.15 g, 37.6 mmol, 1 eq), formic acid (20 mL) and formaldehyde (37 wt % in water, 35 mL) was stirred at 85° C. for 5.5 hours then at ambient temperature for a further 16 hours. The reaction was evaporated and the resultant residue was partitioned between dichloromethane and water, cooled in an ice bath and basified to pH 14 with concentrated sodium hydroxide (20 mL). The organic phase was separated and the aqueous phase extracted with dichloromethane (×2). The combined extracts were dried with magnesium sulfate and evaporated. The crude product was dissolved in methanol divided into two portions and each portion loaded onto a Biotage SCX-2 cartridge (70 g). The cartridges were washed with methanol (200 mL) and the product eluted with ammonia in methanol (3.5 M), evaporation in vacuo yielded (R)-2-(dimethylamino)-1-phenylethanol as a yellow liquid (5.14 g, 82% yield). $^1$H NMR (400 MHz, CDCl$_3$) 7.39-7.31 (4H, m), 7.29-7.22 (1H, m), 4.69 (1H, dd, J=3.3, 10.6 Hz), 3.61 (1H, s), 2.47 (1H, dd, J=10.6, 12.1 Hz), 2.35 (6H, s).

b) (R)-methyl 4-(2-(dimethylamino)-1-phenylethoxy)-3-methoxybenzoate (Compound of Formula 1-IV, Scheme 1)

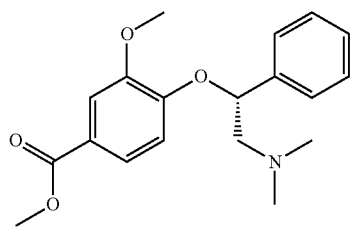 [SMILES: COC(=O)c1ccc(O[C@@H](CN(C)C)c2ccccc2)c(OC)c1]

To a stirred solution of (R)-2-(dimethylamino)-1-phenylethanol (5.1 g, 30.9 mmol, 1 eq.), methyl vanillate (6.2 g, 34 mmol, 1.1 eq.) and triphenyl phosphine (12.1 g, 46.3 mmol, 1.5 eq.) in dichloromethane (150 mL) at 31° C. was added diethylazodicarboxylate (7.6 mL, 46.3 mmol, 1.5 eq.) dropwise over a period of 30 minutes at such a rate so as to maintain the temperature between 33-40° C. The resulting mixture was then stirred at room temperature for 23 hours. The solvent removed in vacuo. The crude product was dissolved in methanol (100 mL) divided into two portions and each portion loaded onto a Biotage SCX-2 cartridge (70 g). The cartridges were washed through with methanol (250 mL) and the product eluted with ammonia in methanol (3.5 M), evaporation in vacuo yielded (R)-4-(2-(dimethylamino)-1-phenylethoxy)-3-methoxybenzoic acid as a yellow liquid (9.21 g, 91% yield). $^1$H NMR (400 MHz, CDCl$_3$) 7.51 (1H, d, J=2.0 Hz), 7.44 (1H, dd, J=2.0, 8.6 Hz), 7.37-7.28 (4H, m), 7.28-7.21 (1H, m), 6.69 (1H, d, J=8.3 Hz), 5.38 (1H, dd, J=3.5, 8.3 Hz), 3.92 (3H, s), 3.84 (3H, s), 3.05 (1H, dd, J=8.5, 13.5 Hz), 2.65 (1H, dd, J=3.5, 13.6 Hz), 2.38 (6H, s).

c) sodium (R)-4-(2-(dimethylamino)-1-phenylethoxy)-3-methoxybenzoate (Compound of Formula 1-V, Scheme 1)

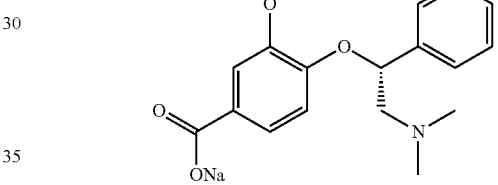

To a stirred solution of (R)-methyl 4-(2-(dimethylamino)-1-phenylethoxy)-3-methoxybenzoate (4.74 g, 14.4 mmol, 1 eq.) in methanol (95 mL) was added 2M aqueous sodium hydroxide solution (14.4 mL, 28.8 mmol, 2 eq.) and the resulting mixture stirred at ambient temperature for 4 days. The methanol was removed in vacuo and water (10 mL) was added. The solid was collected by filtration, washed with water (4 mL, 2×2 mL) and dried in vacuo to afford sodium (R)-4-(2-(dimethylamino)-1-phenylethoxy)-3-methoxybenzoate (3.45 g, 76% yield). $^1$H NMR (400 MHz, DMSO) 7.50 (1H, d, J=1.8 Hz), 7.44 (2H, d, J=7.1 Hz), 7.36 (2H, dd, J=7.5, 7.5 Hz), 7.30-7.26 (2H, m), 6.75 (1H, d, J=8.3 Hz), 5.47 (1H, dd, J=4.8, 7.3 Hz), 3.83 (3H, s), 2.86 (1H, dd, J=7.5, 13.0 Hz), 2.60 (1H, dd, J=4.9, 13.0 Hz), 2.30 (6H, s).

d) (R)-4-(2-(dimethylamino)-1-phenylethoxy)-3-methoxy-N-(5-(pyridin-4-yl)-1,3,4-thiadiazol-2-yl)benzamide (Compound of Formula 1-VII, Scheme 1)

A solution of sodium (R)-4-(2-(dimethylamino)-1-phenylethoxy)-3-methoxybenzoate (2.9 g, 8.6 mmol, 1 eq.), 5-(4-pyridyl)-1,3,4-thiadiazol-2-yl amine (1.53 g, 8.6 mmol, 1 eq.), HATU (4.9 g, 12.9 mmol, 1.5 eq.) and diisopropylethylamine (1.8 mL, 10.3 mmol, 1.2 eq.) in NMP (29 mL) was stirred at 70° C. for 24 hours. 5-(4-pyridyl)-1,3,4-thiadiazol-2-yl amine (0.38 g, 2.1 mmol, 0.25 eq.), HATU (1.0 g, 2.6 mmol, 0.3 eq.) and diisopropylethylamine (400 μL, 2.3 mmol, 0.27 eq.) were added and heating continued for a further 6.5 hours followed by 17 hours at ambient temperature. The reaction was poured into water (150 mL) and the resultant precipitate filtered, washed with water and dried in vacuo. The solid was stirred in refluxing ethanol (25 mL) allowed to cool and the solid filtered and washed with ethanol. This was repeated twice more with ethanol (25 mL) then ethanol (20 mL). The solid was suspended in methanol (100 mL) and a solution of sodium hydrogen carbonate (0.6 g, 7.1 mmol) in water was added. The methanol was removed in vacuo and water (5 mL) added and the solid filtered and washed with water (4×2 mL). The damp solid was suspended in water (10 mL) and the suspension heated to 70° C. The cooled suspension was filtered, washed with water (2 mL) and dried in vacuo to afford (R)-4-(2-(dimethylamino)-1-phenylethoxy)-3-methoxy-N-(5-(pyridin-4-yl)-1,3,4-thiadiazol-2-yl)benzamide as a tan solid (1.19 g, 29%). $^1$H NMR (400 MHz, DMSO) 12.91 (1H, s), 8.78 (2H, d, J=6.1 Hz), 7.97 (2H, d, J=6.1 Hz), 7.83 (1H, d, J=1.8 Hz), 7.67 (1H, dd, J=2.0, 8.6 Hz), 7.48 (2H, d, J=7.3 Hz), 7.40 (2H, dd, J=7.6, 7.6 Hz), 7.32 (1H, dd, J=7.3, 7.3 Hz), 7.09 (1H, d, J=8.6 Hz), 5.71 (1H, dd, J=4.3, 7.8 Hz), 3.98 (3H, s), 2.99 (1H, dd, J=7.8, 13.1 Hz), 2.70 (1H, dd, J=4.0, 13.4 Hz), 2.37 (6H, s); MS (ESI$^+$) 476.

EXAMPLE 7

(R)-4-(2-hydroxy-1-phenylethoxy)-3-methoxy-N-(5-(pyridin-4-yl)-1,3,4-thiadiazol-2-yl)benzamide (Compound 1-VII, Scheme 1)

(7)

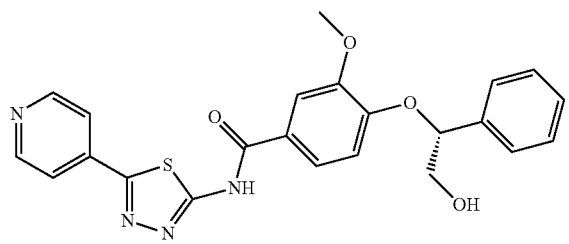

a) (S)-1-phenyl-2-((triisopropylsilyl)oxy)ethanol (Compound of Formula 1-III, Scheme 1)

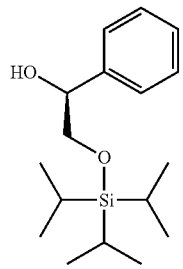 [SMILES: CC(C)[Si](OC[C@@H](O)c1ccccc1)(C(C)C)C(C)C]

To a stirred solution of (S)-1-phenylethane-1,2-diol (3.54 g, 25.6 mmol, 1 eq.) in dichloromethane (140 mL) cooled in an ice bath was added chlorotriisopropylsilane (5.7 mL, 26.9 mmol, 1.05 eq.) followed by imidazole (2.7 g, 39.7 mmol, 1.55 eq.). The reaction was allowed to warm to ambient temperature and stirred for 17 hours. The reaction was quenched with water (50 mL), the layers were separated and the aqueous phase extracted with dichloromethane (50 mL). The combined extracts were dried with magnesium sulfate and evaporated in vacuo to give (S)-1-phenyl-2-((triisopropylsilyl)oxy)ethanol as a clear liquid (8.12 g, 100% yield). $^1$H NMR (400 MHz, CDCl$_3$) 7.40-7.27 (5H, m), 4.78 (1H, dd, J=3.3, 8.8 Hz), 3.85 (1H, dd, J=3.5, 9.9 Hz), 3.65-3.59 (1H, m), 3.07 (1H, s), 1.16-1.09 (3H, m), 1.08-1.04 (18H, m).

b) (R)-methyl 3-methoxy-4-(1-phenyl-2-((triisopropylsilyl)oxy)ethoxy)benzoate (Compound of Formula 1-IV, Scheme 1)

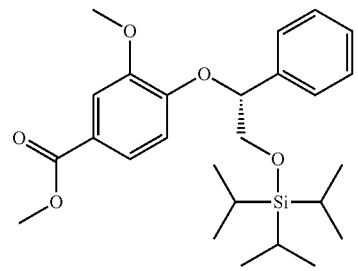 [SMILES: COC(=O)c1ccc(O[C@@H](CO[Si](C(C)C)(C(C)C)C(C)C)c2ccccc2)c(OC)c1]

To a stirred solution of (S)-1-phenyl-2-((triisopropylsilyl)oxy)ethanol (7.5 g, 25.6 mmol, 1 eq.), methyl vanillate (5.12 g, 28.16 mmol, 1.1 eq.) and triphenyl phosphine (10.0 g, 38.4 mmol, 1.5 eq.) in dichloromethane (100 mL) at 3° C. was added diethylazodicarboxylate (6.0 mL, 38.4 mmol, 1.5 eq.) dropwise over a period of 75 minutes at such a rate so as to maintain the temperature below 6° C. The resulting mixture was then stirred at room temperature for 23 hours. The solvent was removed in vacuo, the resulting suspension filtered and the solid washed with dichloromethane (20 mL). The combined filtrates were purified by silica gel column chromatography using 5% ethyl acetate in iso-hexane eluent to afford (R)-methyl 3-methoxy-4-(1-phenyl-2-((triisopropylsilyl)oxy)ethoxy)benzoate (6.6 g, 56% yield). $^1$H NMR (400 MHz, CDCl$_3$) 7.52 (1H, d, J=2.0 Hz), 7.47 (1H, dd, J=2.0, 8.3 Hz), 7.40 (2H, d, J=7.1 Hz), 7.34-7.29 (2H, m), 7.28-7.23 (1H, m), 6.77 (1H, d, J=8.6 Hz), 5.30 (1H, dd, J=5.9, 5.9 Hz), 4.20 (1H, dd, J=6.8, 10.3 Hz), 3.96 (1H, dd, J=5.3, 10.4 Hz), 3.91 (3H, s), 3.84 (3H, s), 1.09-1.03 (3H, m), 1.03-0.97 (18H, m).

c) (R)-3-methoxy-4-(1-phenyl-2-((triisopropylsilyl)oxy)ethoxy)benzoic acid (Compound of Formula 1-V, Scheme 1)

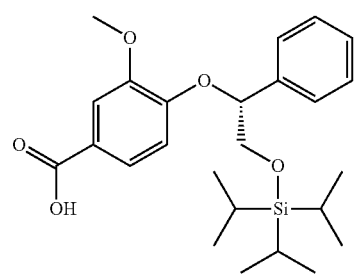 [SMILES: COc1cc(C(=O)O)ccc1O[C@@H](CO[Si](C(C)C)(C(C)C)C(C)C)c1ccccc1]

2 M Aqueous sodium hydroxide (21 mL, 41.9 mmol, 4 eq.) was added to a solution of (R)-methyl 3-methoxy-4-(1- phenyl-2-((triisopropylsilyl)oxy)ethoxy)benzoate (4.8 g, 10.48 mmol, 1 eq.) in methanol (67 mL). Tetrahydrofuran (30 mL) was added and the mixture stirred at ambient temperature for 18.75 hours. The organic solvents were removed in vacuo and dichloromethane (200 mL) was added. The aqueous phase was acidified to pH 5 with citric acid (3 g), the organic layer separated and the aqueous layer extracted with dichloromethane (2×50 mL). The combined extracts were dried with magnesium sulfate, evaporated in vacuo and purified by silica gel column chromatography using a 10-50% ethyl acetate in iso-hexane gradient to afford (R)-3-methoxy-4-(1-phenyl-2-((triisopropylsilyl)oxy) ethoxy)benzoic acid (1.37 g 29% yield). $^1$H NMR (400 MHz, CDCl$_3$) 7.56-7.53 (2H, m), 7.42-7.39 (2H, m), 7.35-7.26 (3H, m), 6.79 (1H, d, J=8.8 Hz), 5.31 (1H, dd, J=5.3, 6.8 Hz), 4.20 (1H, dd, J=6.8, 10.4 Hz), 3.99-3.94 (1H, m), 3.92 (3H, s), 1.10-1.04 (3H, m), 1.03-0.97 (18H, m).

d) (R)-3-methoxy-4-(1-phenyl-2-((triisopropylsilyl) oxy)ethoxy)-N-(5-(pyridin-4-yl)-1,3,4-thiadiazol-2-yl)benzamide (Compound 1-VII, Scheme 1)

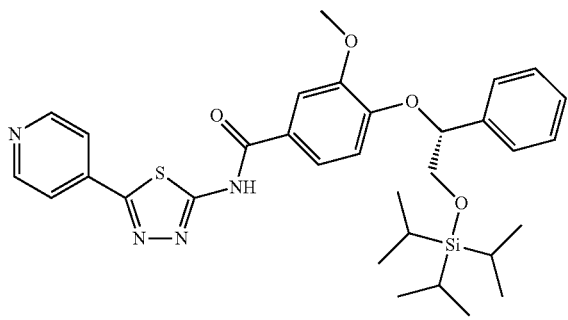 [SMILES: COc1cc(C(=O)Nc2nnc(-c3ccncc3)s2)ccc1O[C@@H](CO[Si](C(C)C)(C(C)C)C(C)C)c1ccccc1]

A solution of (R)-3-methoxy-4-(1-phenyl-2-((triisopropylsilyl)oxy)ethoxy)benzoic acid (0.1.0 g, 2.2 mmol, 1 eq.), 5-(4-pyridyl)-1,3,4-thiadiazol-2-yl amine (0.467 g, 2.6 mmol, 1.2 eq.), HATU (1.35 g, 3.5 mmol, 1.5 eq.) and diisopropylethylamine (480 μL, 2.75 mmol, 1.2 eq.) in NMP (10 mL) was stirred at 70° C. for 16 hours. The cooled reaction mixture was added to water (100 mL) and the crude product filtered and partitioned between dichloromethane (100 mL) and water (15 mL). The layers were separated and the aqueous extracted with a mixture of dichloromethane (100 mL) and methanol (10 mL). The combined extracts were dried with magnesium sulfate, evaporated in vacuo and purified by silica gel column chromatography using a 20-100% ethyl acetate in iso-hexane gradient to afford (R)-3-methoxy-4-(1-phenyl-2-((triisopropylsilyl)oxy) ethoxy)-N-(5-(pyridin-4-yl)-1,3,4-thiadiazol-2-yl)benzamide as a white solid (0.784 g, 60% yield). $^1$H NMR (400 MHz, DMSO) 13.16 (1H, s), 8.79 (2H, dd, J=1.6, 4.5 Hz), 7.99 (2H, dd, J=1.6, 4.4 Hz), 7.84 (1H, d, J=2.0 Hz), 7.68 (1H, dd, J=2.1, 8.6 Hz), 7.52-7.48 (2H, m), 7.40 (2H, dd, J=7.6, 7.6 Hz), 7.37-7.32 (1H, m), 7.09 (1H, d, J=8.9 Hz), 5.62 (1H, dd, J=4.5, 6.5 Hz), 4.14 (1H, dd, J=6.8, 10.6 Hz), 4.00 (1H, dd, J=4.5, 10.8 Hz), 3.97 (3H, s), 1.15-1.08 (3H, m), 1.07-1.02 (18H, m).

e) (R)-4-(2-hydroxy-1-phenylethoxy)-3-methoxy-N-(5-(pyridin-4-yl)-1,3,4-thiadiazol-2-yl)benzamide (Compound 1-VII, Scheme 1)

(R)-3-Methoxy-4-(1-phenyl-2-((triisopropylsilyl)oxy) ethoxy)-N-(5-(pyridin-4-yl)-1,3,4-thiadiazo 1-2-yl)benz- amide (0.784 g, 1.29 mmol, 1.0 eq.) was suspended in methanol (15 mL) and the suspension sonicated. Dichloromethane (7 mL) and 2M hydrogen chloride solution in diethyl ether (3.2 mL, 6.45 mmol, 5 eq.) were added and the reaction stirred at ambient temperature for 17 hours. The solvent was removed in vacuo and the resultant solid triturated with ether (10 ether (3.2 mL, 6.45 mmol, 5 eq.) were added and the reaction stirred at ambient temperature for 17 hours. The solvent was removed in vacuo and the resultant solid triturated with ether (10 mL), filtered and washed with ether (3×2 mL). The product was dissolved in methanol (14 mL) and dichloromethane (14 mL), the solution filtered, MP-carbonate (1.0 g, 3 mmol, 2.3 eq.) was added and the mixture stirred for 2.25 hours. The MP-carbonate was removed by filtration, washed with 1:1 methanol:dichloromethane (2×8 mL) and the solvent removed in vacuo. The crude product was dissolved in 1:1 methanol:dichloromethane (6 mL), filtered and the solvent removed in vacuo. The solid was triturated with ether (4 mL) and dried in vacuo to afford (R)-4-(2-hydroxy-1-phenylethoxy)-3-methoxy-N-(5-(pyridin-4-yl)-1,3,4-thiadiazol-2-yl)benzamide (0.18 g, 31% yield). $^1$H NMR (400 MHz, DMSO) 13.21 (1H, s), 8.81-8.78 (2H, m), 8.01-7.98 (2H, m), 7.84(1H, d, J=2.0 Hz), 7.68 (1H, dd, J=2.0, 8.6 Hz), 7.46 (2H, d, J=7.1 Hz), 7.40(2H, dd, J=7.5, 7.5 Hz), 7.32 (1H, dd, J=7.2, 7.2 Hz), 7.07 (1H, d, J=8.8 Hz), 5.56 (1H, dd, J=3.9, 7.5 Hz), 5.26 (1H, dd, J=5.6, 5.6 Hz), 3.99 (3H, s), 3.95-3.82 (1H, m), 3.73-3.66 (1H, m); MS (ESI+)449.

EXAMPLE 8

Formation of (S)-4-(3-hydroxy-1-phenylpropoxy)-3-methoxy-N-(5-(pyridin-4-yl)-1,3,4-thiadiazol-2-yl) benzamide (Compound 1-VII, Scheme 1)

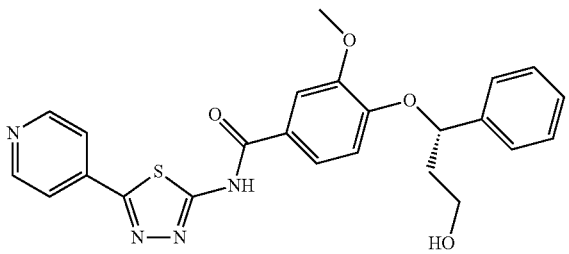

(8)

a) (S)-3-methoxy-4-(1-phenyl-3-((triisopropylsilyl) oxy)propoxy)benzoic acid (Compound of Formula 1-V, Scheme 1)

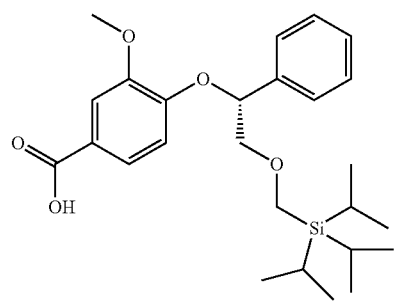 [SMILES: COc1cc(C(=O)O)ccc1O[C@@H](COC[Si](C(C)C)(C(C)C)C(C)C)c1ccccc1]

A solution of lithium hydroxide monohydrate (0.132 g, 1.9 mmol, 1 eq.) in water (2 mL) was added to a solution of (S)-methyl 3-methoxy-4-(1-phenyl-3-((triisopropylsilyl)oxy)propoxy)benzoate (0.744 g, 1.6 mmol, 1 eq., prepared following the general procedure outlined for Example 7, steps a-b, starting from (R)-1-phenylpropane-1,3-diol and methyl 4-hydroxy-3-methoxybenzoate) in tetrahydrofuran (10 mL) and the mixture stirred at 50° C. for 3 hours, at ambient temperature for 48 hours and at 50° C. (R)-1-phenylpropane-1,3-diol and methyl 4-hydroxy-3-methoxybenzoate) in tetrahydrofuran (10 mL) and the mixture stirred at 50° C. for 3 hours, at ambient temperature for 48 hours and at 50° C. for an additional 23 hours. The organic solvents were removed in vacuo and the aqueous phase was acidified to pH 5 with citric acid. The mixture was extracted with dichloromethane then ethyl acetate. The combined extracts were dried with magnesium sulfate and evaporated in vacuo to afford (S)-3-methoxy-4-(1-phenyl-3-((triisopropylsilyl)oxy)propoxy)benzoic acid (0.573 g, 79% yield). $^1$H NMR (400 MHz, DMSO)7.49 (1H, s), 7.43-7.37 (5H, m), 7.35-7.29 (1H, m), 6.83 (1H, d, J=8.3 Hz), 5.54 (1H, dd, J=4.8, 7.8 Hz), 3.93 (1H, ddd, J=5.7, 7.4, 9.9 Hz), 3.87 (3H, s), 3.81-3.74 (1H, m), 2.28-2.19 (1H, m), 2.03-1.97 (1H, m), 1.13-1.06 (3H, m), 1.06-1.04 (18H, m).

b) (S)-4-(3-hydroxy-1-phenylpropoxy)-3-methoxy-N-(5-(pyridin-4-yl)-1,3,4-thiadiazol-2-yl)benzamide (Compound 1-VII, Scheme 1)

A solution of (S)-3-methoxy-4-(1-phenyl-3-((triisopropylsilyl)oxy)propoxy)benzoic acid (0.148 g, 0.27 mmol, 1.05 eq.), 5-(4-pyridyl)-1,3,4-thiadiazol-2-yl amine (0.046 g, 0.25 mmol, 1 eq.), HATU (0.155 g, 0.4 mmol, 1.5 eq.) and diisopropylethylamine (60 µL, 0.32 mmol, 1.2 eq.) in NMP (1.5 mL) was stirred at 70° C. for 16 hours. The cooled reaction mixture was acidified with 2M hydrochloric acid and stirred at ambient temperature for 23 hours. N$^1$,N$^1$-Dimethylethane-1,2-diamine (5 drops) was added and the reaction stirred for 2 hours. The crude mixture was purified by preparative HPLC to afford (S)-4-(3-hydroxy-1-phenylpropoxy)-3-methoxy-N-(5-(pyridin-4-yl)-1,3,4-thiadiazol-2-yl)benzamide as a cream solid (0.05 g, 43%). $^1$H NMR (400 MHz, DMSO) 13.18 (1H, s), 8.80-8.78 (2H, m), 8.00-7.97 (2H, m), 7.84 (1H, d, J=2.0 Hz), 7.67 (1H, dd, J=2.0, 8.6 Hz), 7.47-7.38 (4H, m), 7.32 (1H, dd, J=7.2, 7.2 Hz), 7.01 (1H, d, J=8.6 Hz), 5.64 (1H, dd, J=5.2, 8.2 Hz), 4.68 (1H, dd, J=5.1, 5.1 Hz), 3.98 (3H, s), 3.67-3.49 (2H, m), 2.26-2.16 (1H, m), 2.02-1.93 (1H, m); MS (ESI+) 463.

EXAMPLE 9

Formation of (S)-3-methoxy-4-(1-phenyl-3-(pyrrolidin-1-yl)propoxy)-N-(5-(pyridin-4-yl)-1,3,4-thiadiazol-2-yl)benzamide (Compound 1-VII, Scheme 1)

(9)

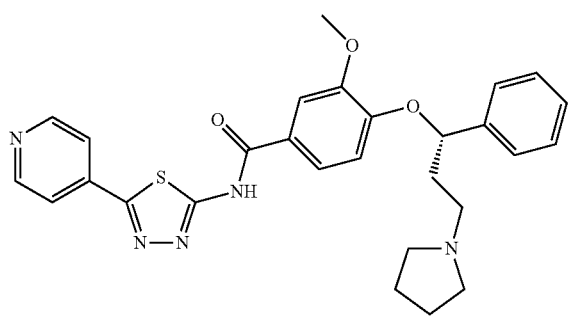

a) (S)-methyl 3-methoxy-4-(1-phenyl-3-(pyrrolidin-1-yl)propoxy)benzoate (Compound of Formula 1-IV, Scheme 1)

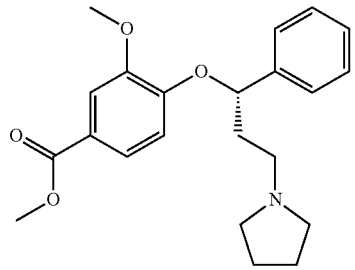 [SMILES: COC(=O)c1ccc(O[C@@H](CCN2CCCC2)c2ccccc2)c(OC)c1]

To a stirred solution of (S)-methyl 4-(3-chloro-1-phenylpropoxy)-3-methoxybenzoate (1.32 g, 4.0 mmol, 1 eq., prepared according to the general procedure outlined for Example 4 step a starting from (R)-3-chloro-1-phenylpropan-1-ol and methyl 4-hydroxy-3-methoxybenzoate) in acetonitrile (9 mL) was added pyrrolidine (350 µL, 4.15 mmol, 1.05 eq.), potassium iodide (0.14 g, 0.84 mmol, 0.2 eq.) and potassium carbonate (1.38 g, 10 mmol, 2.5 eq) and the mixture heated at 75° C. for 17 hours. The cooled reaction was filtered through celite and the solid washed with methanol. The organic solution was loaded onto a Biotage SCX-2 cartridge (20 g). The cartridge was washed through with methanol (120 mL) and the product eluted with ammonia in methanol (3.5M, 100 mL), evaporation in vacuo yielded (S)-methyl 3-methoxy-4-(1-phenyl-3-(pyrrolidin-1-yl)propoxy)benzoate as a brown oil (1.29 g, 86% yield). $^1$H NMR (400 MHz, CDCl$_3$) 7.51 (1H, d, J=2.0 Hz), 7.45 (1H, dd, J=1.9, 8.5 Hz), 7.38-7.29 (4H, m), 7.25-7.22 (1H, m), 6.73 (1H, d, J=8.6 Hz), 5.33 (1H, dd, J=5.8, 7.6 Hz), 3.93 (3H, s), 3.84 (3H, s), 2.61-2.56 (2H, m), 2.53-2.48 (4H, m), 2.39-2.29 (1H, m), 2.12-2.02 (1H, m), 1.79-1.74 (4H, m).

b) (S)-3-methoxy-4-(1-phenyl-3-(pyrrolidin-1-yl)propoxy)-N-(5-(pyridin-4-yl)-1,3,4-thiadiazol-2-yl)benzamide benzoate (Compound of Formula 1-VII, Scheme 1)

To a stirred solution of (S)-methyl 3-methoxy-4-(1-phenyl-3-(pyrrolidin-1-yl)propoxy) benzoate (1.29 g, 3.5 mmol, 1 eq.) in methanol (13 mL) was added 2M aqueous sodium hydroxide solution (3.5 mL, 7.0 mmol, 2 eq.) and the resulting mixture stirred at ambient temperature for 2 days. The pH was adjusted to 6.5-7 with 2N HCl and the solvents removed in vacuo to afford crude (S)-3-methoxy-4-(1-phenyl-3-(pyrrolidin-1-yl)propoxy)benzoic acid which was used in the subsequent step without further purification.

A solution of (S)-3-methoxy-4-(1-phenyl-3-(pyrrolidin-1-yl)propoxy)benzoic acid (3.5 mmol, 1 eq.), 5-(4-pyridyl)-1,3,4-thiadiazol-2-yl amine (0.62 g, 3.5 mmol, 1 eq.), HATU (2.0 g, 5.25 mmol, 1.5 eq.) and diisopropylethylamine (730 µL, 4.2 mmol, 1.2 eq.) in NMP (15 mL) was stirred at 70° C. for 17 hours. The cooled reaction was poured into water and the resultant solid filtered and washed with water. The crude mixture was purified by preparative HPLC to afford (S)-3-methoxy-4-(1-phenyl-3-(pyrrolidin-1-yl)propoxy)-N-(5-(pyridin-4-yl)-1,3,4-thiadiazol-2-yl)benzamide as a tan solid (0.047 g, 3% yield). $^1$H NMR (400 MHz, DMSO) 8.76-8.73 (2H, m), 7.94-7.91 (2H, m), 7.84 (1H, d, J=2.0 Hz), 7.66 (1H, dd, J=2.0, 8.3 Hz), 7.47 (2H, d, J=7.1 Hz), 7.42 (2H, dd, J=7.6, 7.6 Hz), 7.33 (1H, dd, J=7.2, 7.2 Hz), 6.97 (1H, d, J=8.6 Hz), 5.58 (1H, dd, J=5.3, 7.6 Hz), 3.97 (3H, s), 2.78-2.69 (6H, m), 2.32-2.22 (1H, m), 2.13-2.03 (1H, m), 1.81 (4H, dd, J=4.9, 4.9 Hz); MS (ESI+) 516.

EXAMPLE 10

Formation of (R)-3-methoxy-4-(1-phenyl-2-(pyrrolidin-1-yl)ethoxy)-N-(5-(pyridin-4-yl)-1,3,4-thiadiazol-2-yl)benzamide (Compound 1-VII, Scheme 1)

(10)

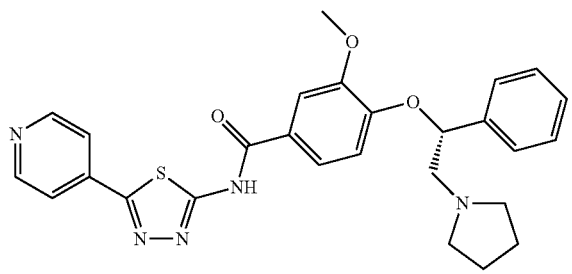

a) (S)-tert-butyl (2-hydroxy-2-phenylethyl)carbamate (Compound 1-III, Scheme 1)

(*Advanced Synthesis & Catalysis,* 350(13), 1991-1995; 2008)

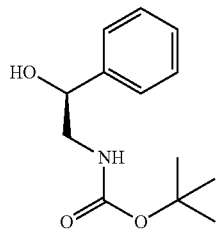 [SMILES: CC(C)(C)OC(=O)NC[C@@H](O)c1ccccc1]

A solution of (S)-2-amino-1-phenylethanol (0.6 g, 4.37 mmol, 1 eq.) and triethylamine (914 µL, 6.57 mmol, 1.5 eq.) in dichloromethane (8 mL) was added to di-tert-butyl dicarbonate (0.946 g, 4.38 mmol, 1.0 eq.) and the resultant mixture stirred at ambient temperature for 2 days. The reaction was quenched with saturated aqueous ammonium chloride solution, the layers were separated and the aqueous layer extracted twice with dichloromethane. The combined organic solution was dried with magnesium sulfate and evaporated in vacuo. The crude product was purified by silica gel column chromatography using a 10-100% ethyl acetate in iso-hexane gradient to afford (S)-tert-butyl (2-hydroxy-2-phenylethyl)carbamate as a clear oil (1.1 g, 100% yield). $^1$H NMR (400 MHz, CDCl$_3$) 7.38-7.32 (4H, m), 7.31-7.27 (1H, m), 4.98 (1H, s), 4.84-4.77 (1H, m), 3.52-3.41 (1H, m), 3.29-3.21 (2H, m), 1.44 (9H, s).

b) (R)-methyl 4-(2-((tert-butoxycarbonyl)amino)-1-phenylethoxy)-3-methoxy benzoate (Compound of Formula 1-IV, Scheme 1)

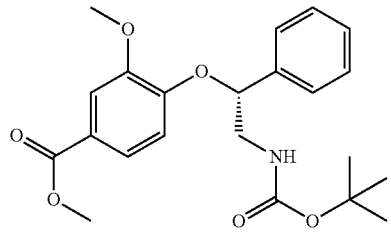 [SMILES: COC(=O)c1ccc(O[C@@H](CNC(=O)OC(C)(C)C)c2ccccc2)c(OC)c1]

Following the general procedure outlined for Example 4 step a starting from (S)-tert-butyl (2-hydroxy-2-phenylethyl)carbamate (0.94 g, 3.98 mmol, 1.1 eq.), methyl 4-hydroxy-3-methoxybenzoate (0.644 g, 3.6 mmol, 1.0 eq.), using dichloromethane (13 mL) as a solvent, (R)-methyl 4-(2-((tert-butoxycarbonyl)amino)-1-phenylethoxy)-3-methoxybenzoate was isolated as a white solid (1.37 g, 95% yield). $^1$H NMR (400 MHz, CDCl$_3$) 7.55 (1H, d, J=2.0 Hz), 7.46 (1H, dd, J=1.9, 8.5 Hz), 7.41-7.32 (4H, m), 7.31-7.27 (1H, m), 6.69 (1H, d, J=8.6 Hz), 5.30 (1H, s), 5.26 (1H, d, J=6.0 Hz), 3.95 (3H, s), 3.85 (3H, s), 3.73-3.65 (1H, m), 3.52-3.41 (1H, m), 1.43 (9H, s).

c) (R)-methyl 4-(2-amino-1-phenylethoxy)-3-methoxybenzoate (Compound of Formula 1-IV, Scheme 1)

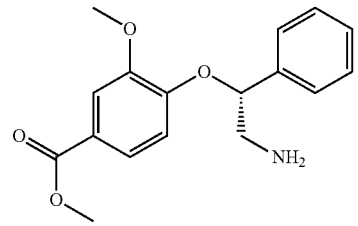 [SMILES: COC(=O)c1ccc(O[C@@H](CN)c2ccccc2)c(OC)c1]

2M Hydrogen chloride in dioxane (2 mL, 7.8 mmol, 3 eq.) was added to a solution of 4-(2-((tert-butoxycarbonyl)amino)-1-phenylethoxy)-3-methoxybenzoate (1.04 g, 2.6 mmol, 1 eq.) in methanol (10 mL) and the reaction stirred at ambient temperature for 19 hours. Sodium carbonate (0.415 g, 3.9 mmol, 1.5 eq.) was added and the solvent removed in vacuo. The crude product was partitioned between dichloromethane and water and the aqueous layer extracted with dichloromethane (×2). The combined organic solution was dried with magnesium sulfate and evaporated in vacuo. The resultant oil was dissolved in methanol and the solution loaded onto a Biotage SCX-2 cartridge (20 g). The cartridge was washed through with methanol and the product eluted with ammonia in methanol (3.5M), evaporation in vacuo yielded (R)-methyl 4-(2-amino-1-phenylethoxy)-3-methoxybenzoate as a clear oil (0.677 g, 86% yield). $^1$H NMR (400 MHz, CDCl$_3$) 7.54 (1H, d, J=1.8 Hz), 7.45 (1H, dd, J=1.9, 8.5 Hz), 7.37-7.31 (4H, m), 7.30-7.27 (1H, m), 6.69 (1H, d, J=8.6 Hz), 5.17 (1H, dd, J=3.9, 7.7 Hz), 3.94 (3H, s), 3.85 (3H, s), 3.22 (1H, dd, J=7.7, 13.5 Hz), 3.09 (1H, dd, J=3.9, 13.5 Hz).

d) (R)-methyl 3-methoxy-4-(1-phenyl-2-(pyrrolidin-1-yl)ethoxy)benzoate (Compound of Formula 1-IV, Scheme 1)

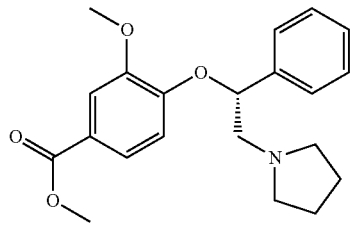 [SMILES: COC(=O)c1ccc(O[C@@H](CN2CCCC2)c2ccccc2)c(OC)c1]

To a stirred solution of (R)-methyl 4-(2-amino-1-phenylethoxy)-3-methoxybenzoate (0.196 g, 0.65 mmol, 1 eq.) in acetonitrile (7 mL) was added 1,4-dibromobutane (85 μL, 0.72 mmol, 1.1 eq.), potassium iodide (0.02 g, 0.12 mmol, 0.18 eq.) and potassium carbonate (0.224 g, 1.63 mmol, 2.5 eq) and the mixture heated at 86° C. for 17 hours. The cooled reaction was filtered through celite and the solvent removed in vacuo. The crude material was purified by silica gel column chromatography using a 0-10% methanol in dichloromethane gradient to afford (R)-methyl 3-methoxy-4-(1-phenyl-2-(pyrrolidin-1-yl)ethoxy)benzoate as a brown glass (0.1 g, 43% yield). $^1$H NMR (400 MHz, CDCl$_3$) 7.53 (1H, d, J=2.0 Hz), 7.46-7.41 (3H, m), 7.35-7.26 (3H, m), 6.72 (1H, d, J=8.3 Hz), 5.84 (1H, dd, J=3.3, 8.1 Hz), 3.94 (3H, s), 3.84 (3H, s), 3.31-3.2 (2H, m), 3.1-2.94 (4H, m), 1.97-1.94 (4H, m).

e) (R)-3-methoxy-4-(1-phenyl-2-(pyrrolidin-1-yl)ethoxy)-N-(5-(pyridin-4-yl)-1,3,4-thiadiazol-2-yl)benzamide (Compound of Formula 1-VII, Scheme 1)

Following the general procedure outlined for Example 9 (step b) starting from (R)-methyl 3-methoxy-4-(1-phenyl-2-(pyrrolidin-1-yl)ethoxy)benzoate (0.1 g, 0.28 mmol, 1 eq.) and 5-(4-pyridyl)-1,3,4-thiadiazol-2-yl amine (0.05 g, 0.28 mmol, 1 eq.), (R)-3-methoxy-4-(1-phenyl-2-(pyrrolidin-1-yl)ethoxy)-N-(5-(pyridin-4-yl)-1,3,4-thiadiazol-2-yl)benzamide was isolated as a cream solid (0.029 g, 21% yield). $^1$H NMR (400 MHz, DMSO) 12.72 (1H, s), 8.77 (2H, d, J=5.3 Hz), 7.96 (2H, d, J=5.1 Hz), 7.84 (1H, s), 7.67 (1H, d, J=8.6 Hz), 7.49 (2H, d, J=7.6 Hz), 7.40 (2H, dd, J=7.3, 7.3 Hz), 7.32 (1H, dd, J=7.1, 7.1 Hz), 7.07 (1H, d, J=8.6 Hz), 5.70 (1H, dd, J=3.8, 7.3 Hz), 3.98 (3H, s), 3.16 (1H, dd, J=8.0, 12.5 Hz), 3.00-2.94 (1H, m), 2.82-2.69 (4H, m), 1.80-1.71 (4H, m); MS (ESI+) 502.

EXAMPLE 11

Formation of (S)-4-(3-(dimethylamino)-1-phenylpropoxy)-3-methoxy-N-(5-(pyridin-4-yl)-1,3,4-thiadiazol-2-yl)benzamide (Compound 1-VII, Scheme 1)

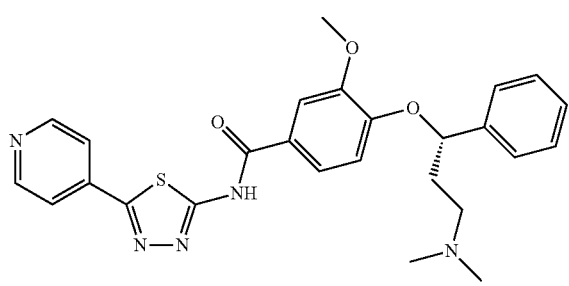

(11)

a) (S)-methyl 4-(3-(dimethylamino)-1-phenylpropoxy)-3-methoxybenzoate (Compound of Formula 1-IV, Scheme 1)

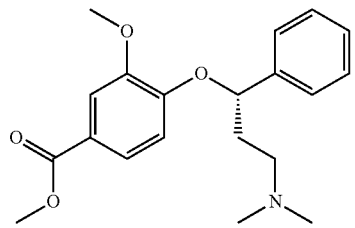 [SMILES: COC(=O)c1ccc(O[C@@H](CCN(C)C)c2ccccc2)c(OC)c1]

Following the general procedure outlined in Example 4 step a starting from (R)-3-(dimethylamino)-1-phenylpropan-1-ol (according to Example 26 step a starting with (R)-3-chloro-1-phenylpropan-1-ol) and methyl 4-hydroxy-3-methoxybenzoate), (S)-methyl 4-(3-(dimethylamino)-1-phenylpropoxy)-3-methoxybenzoate was isolated. $^1$H NMR (400 MHz, CDCl$_3$) 7.52 (1H, d, J=2.0 Hz), 7.45 (1H, dd, J=2.0, 8.3 Hz), 7.39-7.29 (4H, m), 7.26 (1H, s), 7.28-7.24 (1H, m), 6.73 (1H, d, J=8.6 Hz), 5.33 (1H, dd, J=5.5, 7.7 Hz), 3.93 (3H, s), 3.84 (3H, s), 2.49-2.42 (2H, m), 2.35-2.27 (1H, m), 2.25 (6H, s), 2.09-1.97 (1H, m).

b) (S)-4-(3-(dimethylamino)-1-phenylpropoxy)-3-methoxybenzoic acid (Compound of Formula 1-V, Scheme 1)

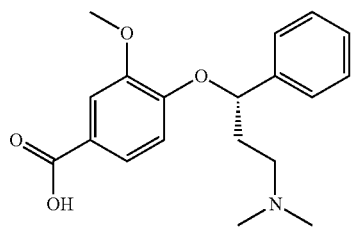 [SMILES: COc1cc(C(=O)O)ccc1O[C@@H](CCN(C)C)c1ccccc1]

To a stirred solution of (S)-methyl 4-(3-(dimethylamino)-1-phenylpropoxy)-3-methoxybenzoate (0.414 g, 1.2 mmol, 1 eq.) in methanol (3 mL) was added 2M aqueous sodium hydroxide solution (600 μL, 1.2 mmol, 1.0 eq.) and the resulting mixture stirred at 50° C. for 5 hours and at ambient temperature for 16 hours. 2M Aqueous sodium hydroxide solution (60 μL, 0.12 mmol, 0.1 eq.) was added and the reaction stirred at 50° C. for 1.75 hours before a further portion of 2M aqueous sodium hydroxide solution (60 μL, 0.12 mmol, 0.1 eq.) was added. After 3 hours at 50° C. the reaction was cooled and the solvent evaporated in vacuo. The crude material was dissolved in methanol and the solution loaded onto a Biotage SCX-2 cartridge (20 g). The cartridge was washed through with methanol and the product eluted with ammonia in methanol (3.5M), evaporation in vacuo yielded crude (S)-4-(3-(dimethylamino)-1-phenylpropoxy)-3-methoxybenzoic acid which was purified by preparative chiral SFC (LUX cellulose 4 column, 50/50 Methanol (0.1% Diethylamine)/carbon dioxide, 70 mL/min, 120 bar 40° C.) to afford (R)-4-(3-(dimethylamino)-1-phenylpropoxy)-3-methoxybenzoic acid as the diethylamine salt (0.194 g, 40% yield) $^1$H NMR (400 MHz, CDCl$_3$) 7.53 (1H, d, J=1.8 Hz), 7.38 (2H, d, J=7.1 Hz), 7.34-7.29 (3H, m), 7.25-7.21 (1H, m), 6.68 (1H, d, J=8.3 Hz), 5.30 (1H, dd, J=5.6, 7.6 Hz), 3.90 (3H, s), 2.84 (4H, q, J=7.2 Hz), 2.62-2.50 (2H, m), 2.32 (6H, s), 2.10-2.00 (1H, m), 1.24 (6H, dd, J=7.2, 7.2 Hz) and (S)-4-(3-(dimethylamino)-1-phenylpropoxy)-3-methoxybenzoic acid as the diethylamine salt (0.082 g, 17% yield) $^1$H NMR (400 MHz, CDCl$_3$) 7.49 (1H, d, J=1.8 Hz), 7.43-7.39 (2H, m), 7.33 (2H, dd, J=7.5, 7.5 Hz), 7.29-7.23 (2H, m), 6.68 (1H, d, J=8.3 Hz), 5.34 (1H, dd, J=5.9, 7.2 Hz), 3.89 (3H, s), 2.81 (4H, q, J=7.2 Hz), 2.73-2.55 (2H, m), 2.38 (6H, s), 2.37-2.25 (1H, m), 2.13-2.02 (1H, m), 1.22 (6H, dd, J=7.2, 7.2 Hz). The material was dissolved in dichloromethane (2 mL) and diisopropylethylamine (200 µL, 1.15 mmol, 5.75 eq.) was added and the solvent removed in vacuo, redissolved in deuterochloroform (1 mL) and acetyl chloride (15 µL, 0.21 mmol, 1.05 eq.) added and the solvent removed in vacuo and the material used in the subsequent step without further purification.

c) (S)-4-(3-(dimethylamino)-1-phenylpropoxy)-3-methoxy-N-(5-(pyridin-4-yl)-1,3,4-thiadiazol-2-yl)benzamide (Compound 1-VII, Scheme 1)

Following the procedure outlined in Example 9 step b starting from (S)-4-(3-(dimethylamino)-1-phenylpropoxy)-3-methoxybenzoic acid and 5-(4-pyridyl)-1,3,4-thiadiazol-2-yl amine, (S)-4-(3-(dimethylamino)-1-phenylpropoxy)-3-methoxy-N-(5-(pyridin-4-yl)-1,3,4-thiadiazol-2-yl)benzamide was isolated. $^1$H NMR (400 MHz, DMSO) 8.76 (2H, d, J=5.8 Hz), 7.94 (2H, d, J=6.1 Hz), 7.83 (1H, d, J=2.0 Hz), 7.66 (1H, dd, J=1.9, 8.5 Hz), 7.47 (2H, d, J=7.3 Hz), 7.41 (2H, dd, J=7.6, 7.6 Hz), 7.33 (1H, dd, J=7.2, 7.2 Hz), 6.98 (1H, d, J=8.6 Hz), 5.56 (1H, dd, J=5.4, 7.7 Hz), 3.97 (3H, s), 2.33 (6H, s), 2.27-2.14 (1H, m), 2.08-1.98 (1H, m) one CH$_2$ is obscured by the residual DMSO signal; MS(ESI+) 490.

EXAMPLE 12

Formation of (S)-3-methoxy-4-(2-(methylamino)-1-phenylethoxy)-N-(5-(pyridin-4-yl)-1,3,4-thiadiazol-2-yl)benzamide (Compound 1-VII, Scheme 1)

(12)

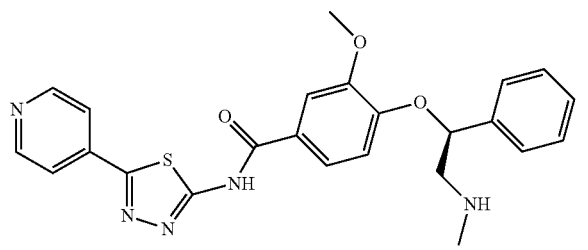

a) (S)-methyl 4-(2-((tert-butoxycarbonyl)(methyl)amino)-1-phenylethoxy)-3-methoxybenzoate (Compound of Formula 1-IV, Scheme 1)

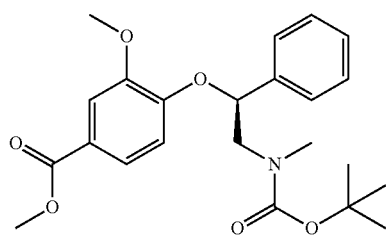 [SMILES: COC(=O)c1ccc(O[C@H](CN(C)C(=O)OC(C)(C)C)c2ccccc2)c(OC)c1]

A mixture of (R)-2-amino-1-phenylethanol (0.627 g, 4.5 mmol, 1 eq), formic acid (4 mL) and formaldehyde (37 wt % in water, 8 mL) was stirred at 95° C. overnight. 2M Hydrochloric acid (5 mL) was added and the reaction washed twice with diethyl ether. The aqueous solution was cooled in an ice bath and basified to pH 14 with sodium hydroxide. The mixture was extracted with dichloromethane (×3), the combined extracts dried with magnesium sulfate and evaporated in vacuo to afford a mixture of (R)-2-(methylamino)-1-phenylethanol and (R)-2-(dimethylamino)-1-phenylethanol.

To a stirred solution of (R)-2-(methylamino)-1-phenylethanol and (R)-2-(dimethylamino)-1-phenylethanol (0.405 g, 2.45 mmol, 1.5 eq.), methyl 4-hydroxy-3-methoxybenzoate (0.3 g, 1.6 mmol, 1.0 eq.) and triphenyl phosphine (0.65 g, 2.45 mmol, 1.5 eq.) in dichloromethane (8 mL) cooled in an ice bath was added diethylazodicarboxylate (400 µL, 2.45 mmol, 1.5 eq.) dropwise over a period of 20 minutes. The organic solution was loaded onto a Biotage SCX-2 cartridge (20 g). The cartridge was washed through with methanol (120 mL) and the product eluted with ammonia in methanol (3.5 M, 100 mL), evaporation in vacuo yielded a mixture of (S)-methyl 3-methoxy-4-(2-(methylamino)-1-phenylethoxy)benzoate and (R)-methyl 4-(2-(dimethylamino)-1-phenylethoxy)-3-methoxybenzoate (0.65 g). The mixture was dissolved in dichloromethane (7 mL) and triethylamine (450 µL, 3.5 mmol, 3 eq.) and cooled in an ice bath. Di-tert-butyl dicarbonate (0.24 g, 1.1 mmol, 1.1 eq.) was added and the ice bath removed and the resultant mixture stirred at ambient temperature for 1 hour. The crude mixture was purified by silica gel column chromatography using 20-100% ethyl acetate in iso-hexane gradient to afford (S)-methyl 4-(2-((tert-butoxycarbonyl)(methyl)amino)-1-phenylethoxy)-3-methoxybenzoate as a clear oil (0.1 g, 23% yield). $^1$H NMR (400 MHz, CDCl$_3$) 7.53 (1H, d, J=2.0 Hz), 7.48-7.38 (2H, m), 7.36-7.27 (4H, m), 6.69 (0.5H, d, J=8.6 Hz), 6.63 (0.5H, d, J=8.6 Hz), 5.52 (0.5H, dd, J=3.4, 8.0 Hz), 5.35 (0.5H, dd, J=4.4, 7.5 Hz), 3.93 (3H, s), 3.85 (3H, s), 3.80-3.76 (1H, m), 3.59-3.43 (1H, m), 1.87-1.83 (3H, m), 1.43 (9H, s) rotameric forms observed in NMR.

b) (S)-4-(2-((tert-butoxycarbonyl)(methyl)amino)-1-phenylethoxy)-3-methoxybenzoic acid (Compound of Formula 1-V, Scheme 1)

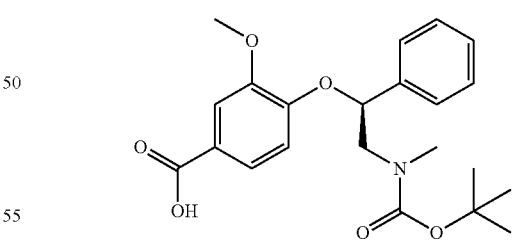

To a stirred solution of (9-methyl 4-(2-((tert-butoxycarbonyl)(methyl)amino)-1-phenylethoxy)-3-methoxybenzoate (0.1 g, 0.24 mmol, 1 eq.) in methanol (3 mL) was added 2M aqueous sodium hydroxide solution (125 µL, 0.25 mmol, 1.04 eq.) and the resulting mixture stirred at ambient for 22 hours. 2M aqueous sodium hydroxide solution (125 µL, 0.25 mmol, 1.04 eq.) was added and the reaction stirred for 4 hours before a further portion of 2M aqueous sodium hydroxide solution (150 µL, 0.3 mmol, 1.25 eq.) was added and the reaction stirred at 50° C. for 2 hours and a further 2 days at ambient temperature. The solvent was evaporated in vacuo, water (3 mL) added and the pH adjusted to 7 with 2M HCl. The mixture was extracted sequentially with dichloromethane and ethyl acetate and the combined extracts dried with magnesium sulfate and evaporated in vacuo to afford (S)-4-(2-((tert-butoxycarbonyl)(methyl)amino)-1-phenylethoxy)-3-methoxybenzoic acid (0.085 g, 88% yield) as a clear glass. $^1$H NMR (400 MHz, CDCl$_3$) 7.57 (1H, d, J=1.8 Hz), 7.53 (1H, d, J=8.3 Hz), 7.41 (1H, d, J=7.3 Hz), 7.37-7.26 (4H, m), 6.71 (0.5H, d, J=8.3 Hz), 6.65 (0.5H, d, J=8.6 Hz), 5.56-5.51 (0.5H, m), 5.40-5.33 (0.5H, m), 3.93 (3H, s), 3.85-3.73 (1H, m), 3.60-3.45 (1H, m), 3.01 (1.5H, s), 2.95 (1.5H, s), 1.43 (9H, s); rotameric forms observed in NMR.

c) (S)-3-methoxy-4-(2-(methylamino)-1-phenylethoxy)-N-(5-(pyridin-4-yl)-1,3,4-thiadiazol-2-yl)benzamide (Compound 1-VII, Scheme 1)

A solution of (S)-4-(2-((tert-butoxycarbonyl)(methyl)amino)-1-phenylethoxy)-3-methoxybenzoic acid (0.085 g, 0.21 mmol, 1 eq.), 5-(4-pyridyl)-1,3,4-thiadiazol-2-yl amine (0.038 g, 0.21 mmol, 1 eq.), HATU (0.12 g, 0.315 mmol, 1.5 eq.) and diisopropylethylamine (45 µL, 0.25 mmol, 1.2 eq.) in NMP (1 mL) was stirred at 70° C. for 17 hours. 5-(4-pyridyl)-1,3,4-thiadiazol-2-yl amine (0.01 g, 0.06 mmol, 0.26 eq.) was added and heating continued for a further 5 hours. The reaction was added to water and the resultant solid filtered and suspended in methanol (6 mL). 4N HCl in dioxane (250 µL, 1 mmol, 4.8 eq.) was added and the mixture stirred for 24 hours at ambient temperature. The solvent was evaporated in vacuo and the crude reaction was purified by preparative HPLC to afford (S)-3-methoxy-4-(2-(methylamino)-1-phenylethoxy)-N-(5-(pyridin-4-yl)-1,3,4-thiadiazol-2-yl)benzamide as a pale yellow solid (0.033 g, 34% yield). $^1$H NMR (400 MHz, DMSO) 8.72 (2H, d, J=6.1 Hz), 7.89 (2H, d, J=6.1 Hz), 7.85 (1H, d, J=1.8 Hz), 7.65 (1H, dd, J=1.6, 8.5 Hz), 7.49 (2H, d, J=7.3 Hz), 7.43 (2H, dd, J=7.6, 7.6 Hz), 7.36 (1H, dd, J=7.2, 7.2 Hz), 6.98 (1H, d, J=8.6 Hz), 5.67 (1H, dd, J=3.3, 8.8 Hz), 3.98 (3H, s), 3.31 (1H, dd, J=9.1, 13.1 Hz), 3.10 (1H, dd, J=3.3, 12.9 Hz), 2.58 (3H, s); MS(ESI+) 462.

EXAMPLE 13

Formation of (S)-3-methoxy-4-(1-(pyridin-3-yl)ethoxy)-N-(5-(pyrimidin-4-yl)-1,3,4-thiadiazol-2-yl)benzamide (Compound 1-VII, Scheme 1)

(13)

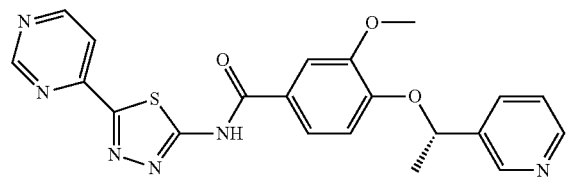

a) 2-(pyrimidin-4-ylmethylene)hydrazinecarbothioamide

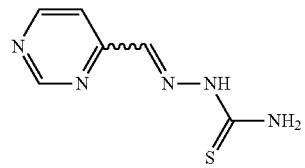 [SMILES: NC(=S)NN=Cc1ccncn1]

To a stirred mixture of pyrimidine-4-carbaldehyde (2 g, 18.5 mmol, 1.0 eq.) and hydrazinecarbothioamide (2.02 g, 22.2 mmol, 1.2 eq.) in ethanol (20 mL) and water (20 mL) was added concentrated hydrochloric acid (100 µL) and the reaction heated at 70° C. for 4 hours. After cooling to room temperature the precipitate was collected by filtration, washed with ethanol and then dried in air to afford 2-(pyrimidin-4-ylmethylene)hydrazinecarbothioamide as a brown solid (2.1 g, 62% yield). $^1$H NMR (400 MHz, DMSO) 11.93 (1H, s), 9.21 (1H, d, J=1.3 Hz), 8.86 (1H, d, J=5.3 Hz), 8.59 (1H, s), 8.43 (1H, s), 8.39 (1H, dd, J=1.3, 5.3 Hz), 8.03 (1H, s).

b) 5-(pyrimidin-4-yl)-1,3,4-thiadiazol-2-amine. (Compound of the Formula 1-VI, Scheme 1)

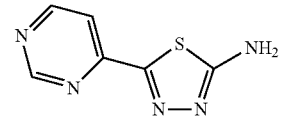 [SMILES: Nc1nnc(-c2ccncn2)s1]

To a stirred suspension of 2-(pyrimidin-4-ylmethylene)hydrazinecarbothioamide (2.3 g, 12.71 mmol, 1.0 eq.) in ethanol (24 mL) was added a solution of iron(III) chloride hexahydrate (6.87 g, 10.72 mmol, 2.0 eq.) in water (24 mL). The reaction was heated at reflux for 6 hours. The reaction was cooled to room temperature and concentrated in vacuo. The residue was dissolved in methanol, acidified with dilute hydrochloric acid and purified using a SCX-2 cartridge (20 g). The crude product obtained following elution with 3.5M ammonia in methanol was further purified by column chromatography using a 0-10% methanol in dichloromethane gradient to afford 5-(pyrimidin-4-yl)-1,3,4-thiadiazol-2-amine as yellow solid (0.928 g, 40% yield). $^1$H NMR (400 MHz, DMSO) 9.25 (1H, d, J=1.5 Hz), 8.93 (1H, d, J=5.3 Hz), 8.11 (1H, dd, J=1.5, 5.3 Hz), 7.95 (2H, s).

c) (S)-3-methoxy-4-(1-(pyridin-3-yl)ethoxy)-N-(5-(pyrimidin-4-yl)-1,3,4-thiadiazol-2-yl) benzamide (Compound of the Formula 1-VII, Scheme 1)

Using the general method outlined for the preparation of Example 4 (steps a-c) starting from methyl 4-hydroxy-3-methoxybenzoate, (R)-1-(3-pyridyl)ethanol and 5-(pyrimidin-4-yl)-1,3,4-thiadiazol-2-amine, following purification by preparative HPLC (S)-3-methoxy-4-(1-(pyridin-3-yl)ethoxy)-N-(5-(pyrimidin-4-yl)-1,3,4-thiadiazol-2-yl)benzamide was isolated. $^1$H NMR (400 MHz, DMSO) 13.29 (1H, s), 9.38 (1H, d, J=1.5 Hz), 9.05 (1H, d, J=5.1 Hz), 8.72 (1H, d, J=2.0 Hz), 8.55 (1H, dd, J=1.6, 4.7 Hz), 8.31 (1H, dd, J=1.5, 5.3 Hz), 7.89-7.85 (2H, m), 7.74 (1H, dd, J=2.1, 8.5

Hz), 7.45 (1H, dd, J=4.9, 8.0 Hz), 7.14 (1H, d, J=8.8 Hz), 5.82 (1H, q, J=6.3 Hz), 3.98 (3H, s), 1.68 (3H, d, J=6.6 Hz); MS (ESI+) 435.

EXAMPLE 14

Formation of (S)-N-(5-(3-fluoropyridin-4-yl)-1,3,4-thiadiazol-2-yl)-3-methoxy-4-(1-(pyridin-3-yl)ethoxy)benzamide (Compound Scheme 1)

(14)

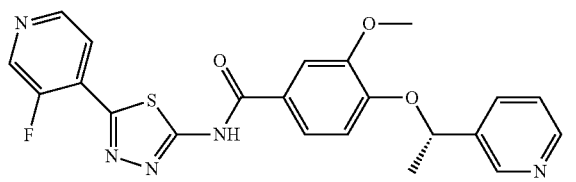

a) 5-(3-fluoropyridin-4-yl)-1,3,4-thiadiazol-2-amine. (Compound of the Formula 1-VI, Scheme 1)

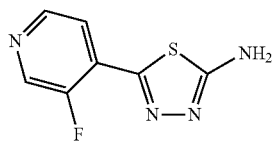 [SMILES: Nc1nnc(-c2ccncc2F)s1]

Following the general procedure outlined for Example 13, steps a and b, starting from 3-fluoroisonicotinaldehyde, 5-(3-fluoropyridin-4-yl)-1,3,4-thiadiazol-2-amine was isolated as a yellow solid (5% yield). ¹H NMR (400 MHz, DMSO) 8.79 (1H, d, J=2.5 Hz), 8.57 (1H, d, J=5.1 Hz), 8.10 (1H, dd, J=5.8, 5.8 Hz), 7.81 (2H, s).

b) (S)-N-(5-(3-fluoropyridin-4-yl)-1,3,4-thiadiazol-2-yl)-3-methoxy-4-(1-(pyridin-3-yl)ethoxy)benzamide (Compound of the Formula 1-VII, Scheme 1)

Using the general method outlined for the preparation of Example 4, starting from methyl 4-hydroxy-3-methoxybenzoate, (R)-1-(3-pyridyl)ethanol and 5-(3-fluoropyridin-4-yl)-1,3,4-thiadiazol-2-amine, following purification by preparative HPLC (S)-N-(5-(3-fluoropyridin-4-yl)-1,3,4-thiadiazol-2-yl)-3-methoxy-4-(1-(pyridin-3-yl)ethoxy)benzamide was isolated. ¹H NMR (400 MHz, DMSO) 13.24 (1H, s), 8.89 (1H, d, J=2.3 Hz), 8.71 (1H, d, J=1.8 Hz), 8.66 (1H, d, J=5.1 Hz), 8.54 (1H, dd, J=1.5, 4.8 Hz), 8.29 (1H, dd, J=5.7, 5.7 Hz), 7.90-7.85 (2H, m), 7.73 (1H, dd, J=2.0, 8.6 Hz), 7.45 (1H, dd, J=4.8, 7.6 Hz), 7.13 (1H, d, J=8.8 Hz), 5.81 (1H, q, J=6.4 Hz), 3.97 (3H, s), 1.68 (3H, d, J=6.3 Hz); MS (ESI+) 452.

EXAMPLE 15

Formation of (S)-3-methoxy-N-(5-(3-methylpyridin-4-yl)-1,3,4-thiadiazol-2-yl)-4-(1-phenylethoxy)benzamide (Compound 1-VII, Scheme 1)

(15)

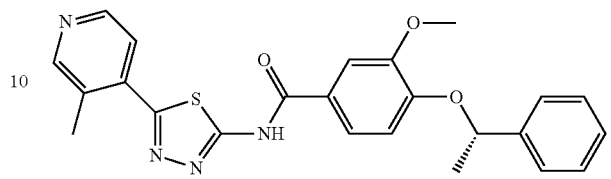

a) 5-(3-methylpyridin-4-yl)-1,3,4-thiadiazol-2-amine. (Compound of the Formula 1-VI, Scheme 1)

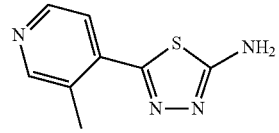

Following the general procedure outlined for Example 13, steps a and b, starting from 3-methylisonicotinaldehyde, 5-(3-methylpyridin-4-yl)-1,3,4-thiadiazol-2-amine was isolated as a yellow solid (72% yield). ¹H NMR (400 MHz, CDCl₃) 8.58 (1H, s), 8.52 (1H, d, J=5.3 Hz), 7.49 (1H, d, J=5.1 Hz), 5.33 (2H, s), 2.60 (3H, s).

b) (S)-3-methoxy-N-(5-(3-methylpyridin-4-yl)-1,3,4-thiadiazol-2-yl)-4-(1-phenylethoxy) benzamide (Compound of the Formula 1-VII, Scheme 1)

Following the general method outlined for the preparation of Example 4 steps a-c, starting from methyl 4-hydroxy-3-methoxybenzoate, (R)-1-phenylethanol and 5-(3-methylpyridin-4-yl)-1,3,4-thiadiazol-2-amine, (S)-3-methoxy-N-(5-(3-methypyridin-4-yl)-1,3,4-thiadiazol-2-yl)-4-(1-phenylethoxy)benzamide was isolated. ¹H NMR (400 MHz, DMSO) 13.14 (1H, s), 8.70 (1H, s), 8.61 (1H, d, J=5.1 Hz), 7.86-7.80 (2H, m), 7.70 (1H, dd, J=1.9, 8.5 Hz), 7.48 (2H, d, J=7.3 Hz), 7.41 (2H, dd, J=7.5, 7.5 Hz), 7.32 (1H, dd, J=7.2, 7.2 Hz), 7.06 (1H, d, J=8.6 Hz), 5.75-5.68 (1H, m), 3.98 (3H, s), 2.62 (3H, s), 1.65 (3H, d, J=6.3 Hz); MS (ESI+) 447.

EXAMPLE 16

Formation of (S)-3-methoxy-N-(5-(2-methylpyridin-4-yl)-1,3,4-thiadiazol-2-yl)-4-(1-phenylethoxy)benzamide (Compound 1-VII, Scheme 1)

(16)

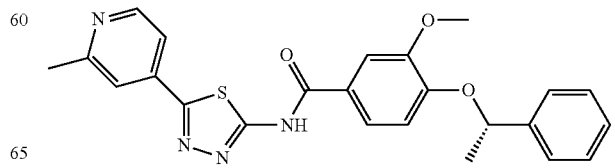

a) 2-((2-methylpyridin-4-yl)methylene)hydrazinecarbothioamide

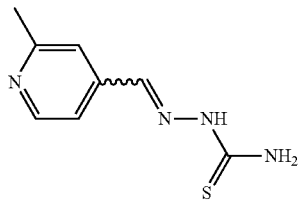

To a suspension of 2-methylisonicotinic acid (0.597 g, 4.36 mmol, 1.0 eq.) in dichloromethane (6 mL) was added oxalyl chloride (550 µL, 6.5 mmol, 1.5 eq.) followed by N,N-dimethylformamide (2 drops) and the resulting reaction stirred overnight at room temperature. The reaction was concentrated in vacuo to afford 2-methylisonicotinoyl chloride hydrochloride which was used without further purification. A suspension of hydrazinecarbothioamide (0.37 g, 4.07 mmol, 1.0 eq.) in pyridine (20 mL) was added to the crude 2-methylisonicotinoyl chloride hydrochloride (0.78 g, 4.07 mmol, 1.0 eq.) and the resulting mixture stirred at room temperature overnight. The reaction was concentrated, water was added and the resulting solid collected by filtration, washed with water and dried in vacuo to afford 2-((2-methylpyridin-4-yl)methylene)hydrazinecarbothioamide as a cream solid (0.66 g, 83% yield). $^1$H NMR (400 MHz, DMSO) 10.62 (1H, s), 9.43 (1H, s), 8.60 (1H, d, J=5.1 Hz), 7.94-7.88 (1H, m), 7.70 (2H, s), 7.61 (1H, d, J=5.1 Hz), 2.55 (3H, s).

b) 5-(2-methylpyridin-4-yl)-1,3,4-thiadiazol-2-amine. (Compound of the Formula 1-VI, Scheme 1)

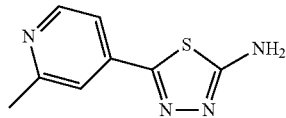

Following the general method outlined for the preparation of Example 13 step b, starting from 2-((2-methylpyridin-4-yl)methylene)hydrazinecarbothioamide (0.66 g, 3.4 mmol), 5-(2-methylpyridin-4-yl)-1,3,4-thiadiazol-2-amine was isolated as a white solid (0.366 g, 83% yield). $^1$H NMR (400 MHz, DMSO) 8.51 (1H, d, J=5.1 Hz), 7.67 (2H, s), 7.58 (1H, s), 7.53 (1H, d, J=5.1 Hz), 2.53 (3H, s).

c) (S)-3-methoxy-N-(5-(2-methylpyridin-4-yl)-1,3,4-thiadiazol-2-yl)-4-(1-(pyridin-3-yl)ethoxy)benzamide (Compound of the Formula 1-VII, Scheme 1)

Following the general method outlined for the preparation of Example 4 steps a to c, starting from methyl 4-hydroxy-3-methoxybenzoate, (R)-1-phenylethanol and 5-(2-methylpyridin-4-yl)-1,3,4-thiadiazol-2-amine, (S)-3-methoxy-N-(5-(2-methylpyridin-4-yl)-1,3,4-thiadiazol-2-yl)-4-(1-(pyridin-3-yl)ethoxy)benzamide was isolated. $^1$H NMR (400 MHz, DMSO) 13.25 (1H, s), 8.75 (1H, d, J=5.3 Hz), 8.10 (1H, s), 8.00 (1H, d, J=4.8 Hz), 7.85 (1H, d, J=1.8 Hz), 7.70 (1H, dd, J=1.9, 8.5 Hz), 7.47 (2H, d, J=7.1 Hz), 7.41 (2H, dd, J=7.5, 7.5 Hz), 7.32 (1H, dd, J=7.2, 7.2 Hz), 7.07 (1H, d, J=8.8 Hz), 5.72 (1H, q, J=6.2 Hz), 3.98 (3H, s), 2.69 (3H, s), 1.65 (3H, d, J=6.3 Hz); MS (ESI$^+$) 447.

EXAMPLE 17

Formation of 4-((1H-imidazol-4-yl)methoxy)-3-methoxy-N-(5-(pyridin-4-yl)-1,3,4-thiadiazol-2-yl)benzamide (Compound 1-VII, Scheme 1)

(17)

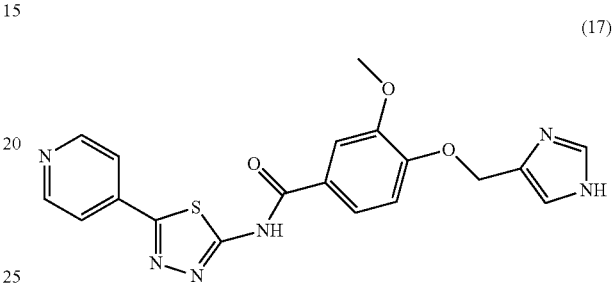

A suspension of 3-methoxy-N-(5-(pyridin-4-yl)-1,3,4-thiadiazol-2-yl)-4-((1-trityl-1H-imidazol-4-yl)methoxy)benzamide (38 mg, 0.058 mmol, 1 eq., prepared following the general procedure outlined for Example 4 steps a-c, starting from methyl 4-hydroxy-3-methoxybenzoate, (1-trityl-1H-imidazol-4-yl)methanol and 5-(4-pyridyl)-1,3,4-thiadiazol-2-ylamine) in methanol (1 mL) and 4N hydrogen chloride in dioxane (3.0 mL) was stirred at 70° C. for 2 hours. The reaction was cooled to room temperature, concentrated to dryness and the residue triturated with diethyl ether to afford 4-((1H-imidazol-4-yl)methoxy)-3-methoxy-N-(5-(pyridin-4-yl)-1,3,4-thiadiazol-2-yl)benzamide as a pale yellow solid (22 mg, 85% yield). $^1$H NMR (400 MHz, DMSO) 14.73 (1H, s), 13.45 (1H, s), 9.23 (1H, s), 8.93 (2H, d, J=2.3 Hz), 8.31 (2H, d, J=4.8 Hz), 7.91 (3H, dd, J=6.6, 6.6 Hz), 7.43 (1H, d, J=8.8 Hz), 5.33 (2H, s), 3.94 (3H, s); MS (ESI$^+$) 409.

EXAMPLE 18

Formation of 3-methoxy-N-(5-(pyridin-4-yl)-1,3,4-thiadiazol-2-yl)-4-(pyrimidin-2-ylmethoxy)benzamide (Compound 1-VII, Scheme 1)

(18)

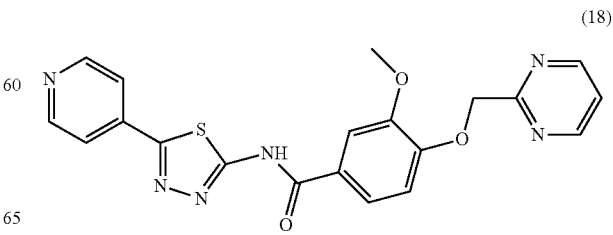

a) methyl 3-methoxy-4-(pyrimidin-2-ylmethoxy) benzoate (Compound of Formula 1-IV, Scheme 1)

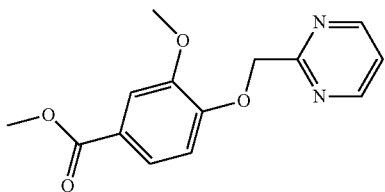 [SMILES: COC(=O)c1ccc(OCc2ncccn2)c(OC)c1]

A solution of methyl 4-hydroxy-3-methoxybenzoate (0.778 g, 4.3 mmol, 1 eq.), 2-chloromethylpyrimidine hydrochloride (0.775 g, 4.7 mmol, 1.1 eq.) and potassium carbonate (1.77 g, 12.8 mmol, 3 eq.) in N,N-dimethylformamide (8 mL) was stirred at 100° C. overnight. The reaction was cooled to room temperature and partitioned between ethyl acetate and water. The organic phase was washed with water, 2M aqueous sodium hydroxide and brine. The solvent was removed in vacuo to afford methyl 3-methoxy-4-(pyrimidin-2-ylmethoxy)benzoate (0.295 g, 25% yield). $^1$H NMR (400 MHz, CDCl$_3$) 8.78 (2H, d, J=4.9 Hz), 7.62-7.57 (2H, m), 7.24 (1H, t, J=4.9 Hz), 6.88 (1H, d, J=8.3 Hz), 5.42 (2H, s), 3.95 (3H, s), 3.88 (3H, s).

b) 3-methoxy-4-(pyrimidin-2-ylmethoxy)benzoic acid (Compound of Formula 1-V, Scheme 1)

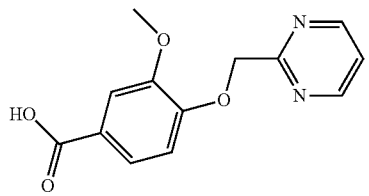 [SMILES: COc1cc(C(=O)O)ccc1OCc1ncccn1]

To a solution of methyl 4-hydroxy-3-methoxybenzoate (0.29 g, 1.1 mmol, 1 eq.) in methanol (3 mL) was added 2M aqueous sodium hydroxide (1.1 mL, 2.2 mmol, 2 eq.) and the reaction stirred at 60° C. for 4.5 hours. The methanol was removed in vacuo, the resulting suspension diluted with water (5 mL) and then washed with ethyl acetate. The aqueous phase was acidified to pH 4 with 2M aqueous hydrochloric acid and the resulting precipitate collected by filtration and washed with water to afford 3-methoxy-4-(pyrimidin-2-ylmethoxy)benzoic acid (0.077 g, 28% yield). $^1$H NMR (400 MHz, DMSO) 12.70 (1H, s), 8.85 (2H, d, J=4.9 Hz), 7.51-7.47 (3H, m), 7.00 (1H, d, J=8.2 Hz), 5.35 (2H, s), 3.83 (3H, s).

c) 3-methoxy-N-(5-(pyridin-4-yl)-1,3,4-thiadiazol-2-yl)-4-(pyrimidin-2-ylmethoxy)benzamide (Compound 1-VII, Scheme 1)

To a solution of 5-(4-pyridyl)-1,3,4-thiadiazol-2-yl amine (0.054 g, 0.30 mmol, 1 eq.) in anhydrous N,N-dimethylformamide (5 mL) was added HATU (0.171 g, 0.45 mmol, 1.5 eq.), 3-methoxy-4-(pyrimidin-2-ylmethoxy)benzoic acid (0.077 g, 0.30 mmol, 1 eq.) and diisopropylethylamine (0.1 mL, 0.39 mmol, 1.3 eq.) and the resulting mixture stirred at 70° C. for 20 hours. The reaction was cooled to room temperature and diluted with saturated aqueous sodium carbonate solution. The resultant precipitate was collected by filtration and washed with warm water and diethyl ether to afford 3-methoxy-N-(5-(pyridin-4-yl)-1,3,4-thiadiazol-2-yl)-4-(pyrimidin-2-ylmethoxy)benzamide (0.067 g, 53% yield). $^1$H NMR (400 MHz, d-6 DMSO) 13.30 (1H, s), 8.86 (2H, d, J=5 Hz), 8.75 (2H, dd, J=4.5, 1.6 Hz), 7.95 (2H, dd, J=4.5, 1.6), 7.83 (1H, d, J=2.0 Hz), 7.75 (1H, dd, J=8.5, 2.1 Hz), 7.50 (1H, t, J=4.9 Hz), 7.11 (1H, d, J=8.6 Hz), 5.41 (2H, s), 3.91 (3H, s); MS (ESI$^+$) 421.

EXAMPLE 19

3-methoxy-4-((1-methyl-1H-imidazol-2-yl)methoxy)-N-(5-(pyridin-4-yl)-1,3,4-thiadiazol-2-yl)benzamide (Compound 1-VII, Scheme 1)

(19)

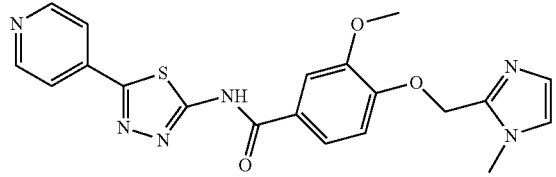

To a suspension of 3-methoxy-4-((1-methyl-1H-imidazol-2-yl)methoxy)benzoic acid (0.100 g, 0.38 mmol, 1 eq., prepared according to Example 4 steps a and b, from methyl 4-hydroxy-3-methoxybenzoate and (1-methyl-1H-imidazol-2-yl)methanol) in anhydrous dichloromethane (5 mL) under a nitrogen atmosphere was added oxalyl chloride (0.1 mL, 1.18 mmol, 3.1 eq.) followed by anhydrous N,N-dimethylformamide (2 drops) and the reaction stirred at room temperature for 2 hours. N,N-Dimethyformamide (2 drops) was added and the reaction stirred at room temperature for 4 days. The solvent was removed in vacuo. The residue was dissolved in anhydrous pyridine (2 mL) and 5-(4-pyridyl)-1,3,4-thiadiazol-2-yl amine (0.061 g, 0.34 mmol, 0.9 eq.) was added. The resultant mixture was stirred at room temperature overnight. The precipitate was collected by filtration and washed with saturated sodium hydrogen carbonate solution, water and diethyl ether to afford 3-methoxy-4-((1-methyl-1H-imidazol-2-yl)methoxy)-N-(5-(pyridin-4-yl)-1,3,4-thiadiazol-2-yl)benzamide (0.082 g, 57% yield). $^1$H NMR (400 MHz, DMSO) 8.62-8.59 (2H, m), 7.80 (1H, d, J=1.8 Hz), 7.78-7.73 (3H, m), 7.20-7.17 (2H, m), 6.89 (1H, d, J=1.1 Hz), 5.15 (2H, s), 3.84 (3H, s), 3.71 (3H, s); MS (ESI$^+$) 423.

EXAMPLE 20

Formation of (S)-5-methyl-6-(1-phenylethoxy)-N-(5-(pyridin-4-yl)-1,3,4-thiadiazol-2-yl)nicotinamide (Compound 2-V, Scheme 2)

(20)

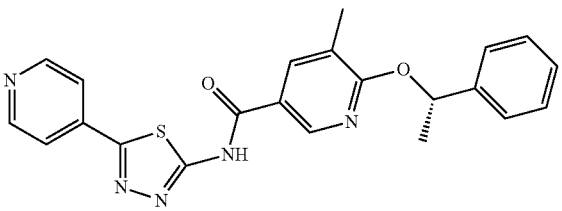

a) 6-chloro-5-methyl-N-(5-(pyridin-4-yl)-1,3,4-thiadiazol-2-yl)nicotinamide (Compound of Formula 2-III, Scheme 2)

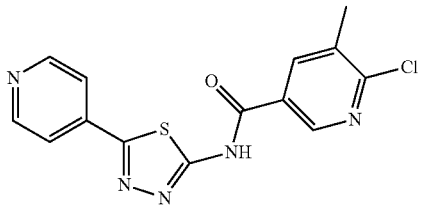 [SMILES: Cc1cc(C(=O)Nc2nnc(-c3ccncc3)s2)cnc1Cl]

To a stirred suspension of 6-chloro-5-methylnicotinic acid (0.50 g, 2.9 mmol, 1 eq.) in anhydrous acetonitrile (4.5 mL) under a nitrogen atmosphere was added thionyl chloride (4.25 mL, 58.3 mmol, 20 eq.). The resulting mixture was stirred at 70° C. for 1.5 hours. The reaction was then cooled to room temperature and the volatiles removed in vacuo. The residue was placed under a nitrogen atmosphere and dissolved in anhydrous pyridine (8 mL). 5-(4-Pyridyl)-1,3,4-thiadiazol-2-yl amine (0.52 g, 2.9 mmol, 1 eq.) was then added and the resultant mixture stirred at room temperature overnight. The precipitate was collected by filtration, washed with water and dried in vacuo to afford 6-chloro-5-methyl-N-(5-(pyridin-4-yl)-1,3,4-thiadiazol-2-yl)nicotinamide (0.76 g, 79% yield). $^1$H NMR (400 MHz, DMSO) 13.65 (1H, s), 8.94 (1H, d, J=2.3 Hz), 8.76 (2H, d, J=6.1 Hz), 8.47 (1H, d, J=1.8 Hz), 7.98 (2H, d, J=6.1 Hz), 2.44 (3H, s).

b) (S)-5-methyl-6-(1-phenylethoxy)-N-(5-(pyridin-4-yl)-1,3,4-thiadiazol-2-yl)nicotinamide (Compound of Formula 2-V, Scheme 2)

To a stirred suspension of 6-chloro-5-methyl-N-(5-(pyridin-4-yl)-1,3,4-thiadiazol-2-yl)nicotinamide (0.12 g, 0.36 mmol, 1 eq.) in anhydrous dimethyl sulfoxide (2.4 mL) under a nitrogen atmosphere were added (S)-1-phenylethanol (82 µL, 0.79 mmol, 2.2 eq.) and sodium hydride (0.031 g, 0.79 mmol, 2.2 eq., 60% dispersion in mineral oil). The resulting mixture was stirred at room temperature for 10 minutes and then at 90° C. for 3 hours. (S)-1-phenylethanol (8 µL, 0.07 mmol, 0.2 eq.) and sodium hydride (0.003 g, 0.08 mmol, 0.2 eq., 60% dispersion in mineral oil) were added and the reaction stirred at 90° C. for a further 2 hours. The reaction was cooled to room temperature and 5 drops of water were added. The mixture was filtered through a celite plug and purified by preparative HPLC to afford (S)-5-methyl-6-(1-phenylethoxy)-N-(5-(pyridin-4-yl)-1,3,4-thiadiazol-2-yl)nicotinamide (0.074 g, 50% yield). $^1$H NMR (400 MHz, DMSO) 13.31 (1H, s), 8.80-8.78 (3H, m), 8.32 (1H, d, J=1.5 Hz), 8.00-7.98 (2H, m), 7.51 (2H, d, J=7.1 Hz), 7.42 (2H, dd, J=7.6, 7.6 Hz), 7.33 (1H, dd, J=7.3, 7.3 Hz), 6.40 (1H, q, J=6.6 Hz), 2.35 (3H, s), 1.67 (3H, d, J=6.6 Hz); MS (ESI$^+$) 418.

EXAMPLE 21

Formation of (S)-5-chloro-6-(1-phenylethoxy)-N-(5-(pyridin-4-yl)-1,3,4-thiadiazol-2-yl)nicotinamide (Compound 2-V, Scheme 2)

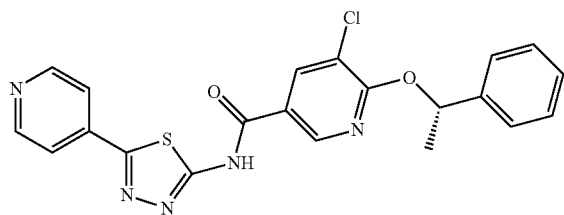

(21)

a) 5,6-dichloro-N-(5-(pyridin-4-yl)-1,3,4-thiadiazol-2-yl)nicotinamide (Compound of Formula 2-III, Scheme 2)

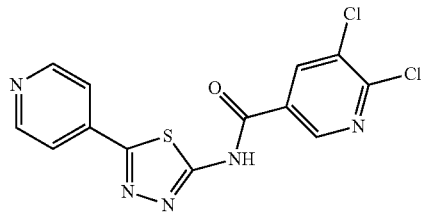 [SMILES: O=C(Nc1nnc(-c2ccncc2)s1)c1cnc(Cl)c(Cl)c1]

Following the general method as outlined in Example 20 step a starting from 5,6-dichloronicotinic acid (5.0 g, 26.0 mmol) and 5-(4-pyridyl)-1,3,4-thiadiazol-2-yl amine (4.64 g, 26.0 mmol), 5,6-dichloro-N-(5-(pyridin-4-yl)-1,3,4-thiadiazol-2-yl)nicotinamide (6.97 g, 76% yield) was isolated. $^1$H NMR (400 MHz, DMSO) 9.09 (1H, d, J=2.3 Hz), 8.84-8.80 (3H, m), 8.04-8.01 (2H, m).

b) (S)-5-chloro-6-(1-phenylethoxy)-N-(5-(pyridin-4-yl)-1,3,4-thiadiazol-2-yl)nicotinamide (Compound of Formula 2-V, Scheme 2)

To a stirred suspension of 5,6-dichloro-N-(5-(pyridin-4-yl)-1,3,4-thiadiazol-2-yl)nicotinamide (1.5 g, 4.3 mmol, 1 eq.) in anhydrous dimethyl sulfoxide (15 mL) under a nitrogen atmosphere was added sodium hydride (0.37 g, 9.3 mmol, 2.2 eq., 60% dispersion in mineral oil) and (S)-1-phenylethanol (0.62 mL, 5.1 mmol, 1.2 eq.). The resulting mixture was stirred at room temperature for 10 minutes and then at 90° C. for 20 hours. (S)-1-phenylethanol (31 µL, 0.3 mmol, 0.07 eq.) and sodium hydride (0.02 g, 0.5 mmol, 0.12 eq., 60% dispersion in mineral oil) were added and the reaction stirred at 90° C. for a further 3 hours. The reaction was cooled to room temperature, diluted with water and extracted with dichloromethane (×3). The combined organic phase was washed with water (×2), dried over magnesium sulfate and the solvent removed in vacuo. The solid was triturated with diethyl ether to afford (S)-5-chloro-6-(1-phenylethoxy)-N-(5-(pyridin-4-yl)-1,3,4-thiadiazol-2-yl)nicotinamide (1.091 g, 58% yield). $^1$H NMR (400 MHz, DMSO) 13.49 (1H, s), 8.87 (1H, d, J=2.0 Hz), 8.81-8.79 (2H, m), 8.64 (1H, d, J=2.3 Hz), 8.02-7.99 (2H, m), 7.52 (2H, d, J=7.3 Hz), 7.44 (2H, dd, J=7.5, 7.5 Hz), 7.37-7.33 (1H, m), 6.43 (1H, q, J=6.5 Hz), 1.71 (3H, d, J=6.3 Hz); MS (ESI$^+$) 438/440 [ME]$^+$.

EXAMPLE 22

Formation of (S)-5-((2-methoxyethyl)amino)-6-(1-phenylethoxy)-N-(5-(pyridin-4-yl)-1,3,4-thiadiazol-2-yl)nicotinamide (Compound 2-VII, Scheme 2)

(22)

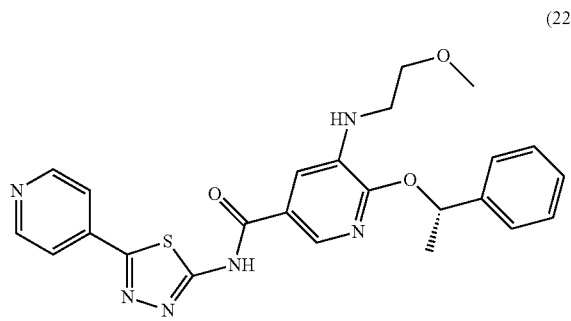

To a mixture of (S)-5-chloro-6-(1-phenylethoxy)-N-(5-(pyridin-4-yl)-1,3,4-thiadiazol-2-yl)nicotinamide (0.125 g, 0.29 mmol, Example 21), BrettPhos Pd G1 methyl t-butyl ether adduct (0.011 g, 0.014 mmol, 0.05 eq.), BrettPhos (0.008 g, 0.015 mmol, 0.05 eq.) and sodium tert-butoxide (0.057 g, 0.59 mmol, 2.0 eq.) under a nitrogen atmosphere were added anhydrous 1,4-dioxane (4.0 mL) and anhydrous NMP (0.8 mL) and the resulting solution was degassed. 2-Methoxyethanamine (0.10 mL, 1.14 mmol, 4.0 eq.) was added and the resultant solution stirred at 90° C. for 24 hours. The reaction was cooled to room temperature and the 1,4-dioxane removed in vacuo. The remaining mixture was filtered through a celite plug and purified by preparative HPLC to afford (S)-5-((2-methoxyethyl)amino)-6-(1-phenylethoxy)-N-(5-(pyridin-4-yl)-1,3,4-thiadiazol-2-yl)nicotinamide (0.102 g, 72% yield). $^1$H NMR (400 MHz, CDCl$_3$) 8.75-8.72 (2H, m), 8.44 (1H, d, mmol, 4.0 eq.) was added and the resultant solution stirred at 90° C. for 24 hours. The reaction was cooled to room temperature and the 1,4-dioxane removed in vacuo. The remaining mixture was filtered through a celite plug and purified by preparative HPLC to afford (S)-5-((2-methoxyethyl)amino)-6-(1-phenylethoxy)-N-(5-(pyridin-4-yl)-1,3,4-thiadiazol-2-yl)nicotinamide (0.102 g, 72% yield). $^1$H NMR (400 MHz, CDCl$_3$) 8.75-8.72 (2H, m), 8.44 (1H, d, J=2.3 Hz), 7.89-7.86 (2H, m), 7.47-7.43 (2H, m), 7.38-7.33 (3H, m), 7.31-7.27 (1H, m), 6.47 (1H, q, J=6.6 Hz), 4.80 (1H, dd, J=5.6, 5.6 Hz), 3.65-3.60 (2H, m), 3.40 (3H, s), 3.39-3.35 (2H, m), 1.74 (3H, d, J=6.6 Hz); MS(ESI$^+$) 477.

EXAMPLE 23

Formation of 6-(benzyloxy)-5-chloro-N-(5-(pyridin-4-yl)-1,3,4-thiadiazol-2-yl)nicotinamide (Compound 2-V, Scheme 2)

(23)

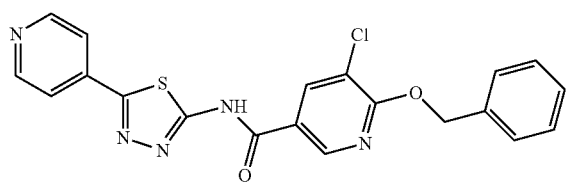

To a stirred suspension of 5,6-dichloro-N-(5-(pyridin-4-yl)-1,3,4-thiadiazol-2-yl) nicotinamide (0.996 g, 2.8 mmol, 1 eq. Example 21 step a) in anhydrous dimethyl sulfoxide (20 mL) under a nitrogen atmosphere was added sodium hydride (0.25 g, 6.3 mmol, 2.2 eq., 60% dispersion in mineral oil) and benzyl alcohol (0.35 mL, 3.4 mmol, 1.2 eq.). The resulting mixture was stirred at 90° C. for 3 hours. The reaction was cooled to room temperature, diluted with water and dichloromethane. The resulting precipitate was collected by filtration to afford 6-(benzyloxy)-5-chloro-N-(5-(pyridin-4-yl)-1,3,4-thiadiazol-2-yl)nicotinamide (0.970 g, 82% yield). $^1$H NMR (400 MHz, DMSO) 8.89 (1H, d, J=1.8 Hz), 8.69 (2H, d, J=5.8 Hz), 8.52 (1H, d, J=2.0 Hz), 7.86 (2H, d, J=6.1 Hz), 7.56 (2H, d, J=7.1 Hz), 7.47 (2H, dd, J=7.3, 7.3 Hz), 7.43-7.38 (1H, m), 5.57 (2H, s); MS (ESI$^+$) 424/426.

EXAMPLE 24

Formation of 6-(benzyloxy)-5-(4-methylpiperazin-1-yl)-N-(5-(pyridin-4-yl)-1,3,4-thiadiazol-2-yl)nicotinamide (Compound 2-VII, Scheme 2)

(24)

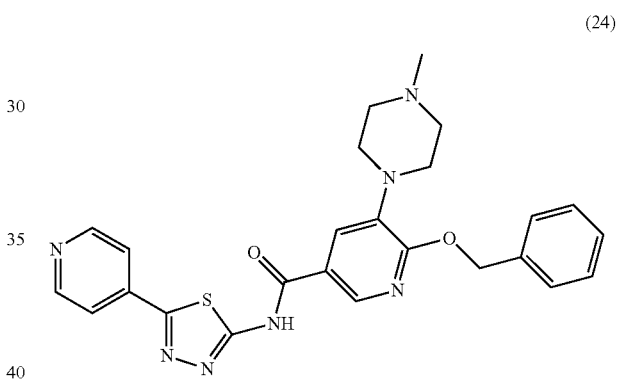

A mixture of 6-(benzyloxy)-5-chloro-N-(5-(pyridin-4-yl)-1,3,4-thiadiazol-2-yl) nicotinamide (0.120 g, 0.28 mmol, 1 eq., Example 23), BrettPhos Pd G1 methyl t-butyl ether adduct (0.011 g, 0.014 mmol, 0.05 eq.), RuPhos (0.007 g, 0.015 mmol, 0.05 eq.) and sodium tert-butoxide (0.057 g, 0.59 mmol, 2.1 eq.) under a nitrogen atmosphere was added anhydrous 1,4-dioxane (4.0 mL) and anhydrous NMP (0.8 mL) and the resulting solution was degassed. N-Methylpiperazine (126 μL, 1.1 mmol, 4 eq.) was added and the reaction stirred at 90° C. overnight. Further BrettPhos Pd G1 methyl t-butyl ether adduct (0.011 g, 0.014 mmol, 0.05 eq.), RuPhos (0.007 g, 0.015 mmol, 0.05 eq.) and sodium tert-butoxide (0.057 g, 0.59 mmol, 2.1 eq.) and N-methylpiperazine (120 μL, 1.1 mmol, 4 eq.) were added and the reaction stirred at 90° C. for 18 hours. The reaction was cooled to room temperature and the volatile solvents removed in vacuo. The remaining mixture was filtered through a celite plug and purified by preparative HPLC to afford 6-(benzyloxy)-5-(4-methylpiperazin-1-yl)-N-(5-(pyridin-4-yl)-1,3,4-thiadiazol-2-yl)nicotinamide (0.047 g, 34% yield). $^1$H NMR (400 MHz, DMSO) 8.81-8.78 (2H, m), 8.63 (1H, d, J=2.0 Hz), 7.99 (3H, dd, J=1.6, 4.4 Hz), 7.55 (2H, d, J=7.3 Hz), 7.47 (2H, dd, J=7.3, 7.3 Hz), 7.40 (1H, dd, J=7.2, 7.2 Hz), 5.56 (2H, s), 3.28 (4H, s), 2.77 (4H, s), 2.45 (3H, s); MS (ESI$^+$) 488.

EXAMPLE 25

Formation of (S)-5-methoxy-6-((1-phenylethyl)amino)-N-(5-(pyridin-4-yl)-1,3,4-thiadiazol-2-yl)nicotinamide (Compound 3-V, Scheme 3)

(25)

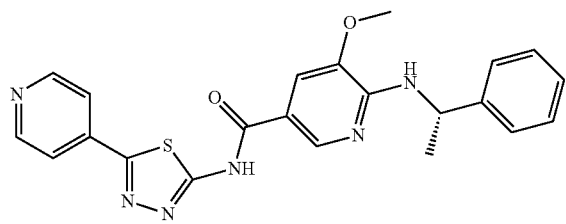

a) 6-chloro-5-methoxy-N-(5-(pyridin-4-yl)-1,3,4-thiadiazol-2-yl)nicotinamide (Compound of Formula 3-III, Scheme 3)

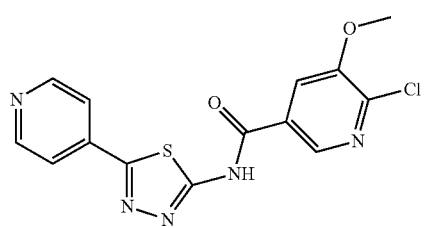 [SMILES: COc1cc(C(=O)Nc2nnc(-c3ccncc3)s2)cnc1Cl]

Following the general method as outlined in Example 20 step a starting from 6-chloro-5-methoxynicotinic acid (1.50 g, 8.0 mmol) and 5-(4-pyridyl)-1,3,4-thiadiazol-2-yl amine (1.42 g, 8.0 mmol), 6-chloro-5-methoxy-N-(5-(pyridin-4-yl)-1,3,4-thiadiazol-2-yl)nicotinamide (1.98 g, 71% yield) was isolated. $^1$H NMR (400 MHz, DMSO) 13.72 (1H, s), 8.82 (2H, d, J=5.6 Hz), 8.73 (1H, d, J=1.8 Hz), 8.30 (1H, d, J=1.8 Hz), 8.02 (2H, d, J=6.1 Hz), 4.08 (3H, s).

b) (S)-5-methoxy-6-(1-phenylethyl)amino)-N-(5-(pyridin-4-yl)-1,3,4-thiadiazol-2-yl)nicotinamide (Compound of Formula 3-V, Scheme 3)

To a mixture of 6-chloro-5-methoxy-N-(5-(pyridin-4-yl)-1,3,4-thiadiazol-2-yl)nicotinamide (0.12 g, 0.35 mmol, 1 eq.), BrettPhos Pd G1 methyl t-butyl ether adduct (0.010 g, 0.013 mmol, 0.04 eq.), BrettPhos (0.007 g, 0.013 mmol, 0.04 eq.) and sodium tert-butoxide (0.070 g, 0.73 mmol, 2.1 eq.) under a nitrogen atmosphere was added anhydrous 1,4-dioxane (4.8 mL) and anhydrous NMP (0.9 mL) and the resulting solution was degassed. (S)-α-Methylbenzylamine (176 μL, 1.4 mmol, 4 eq.) was added and the reaction mixture stirred at 90° C. overnight. Further portions of BrettPhos Pd G1 methyl t-butyl ether adduct (0.010 g, 0.013 mmol, 0.04 eq.), BrettPhos (0.007 g, 0.013 mmol, 0.04 eq.), sodium tert-butoxide (0.070 g, 0.73 mmol, 3.1 eq.) and (S)-α-Methylbenzylamine (180 μL, 1.4 mmol, 4 eq.) were added and the resultant mixture stirred at 90° C. for 6.5 hours. The reaction was cooled to room temperature and concentrated in vacuo. The residue was filtered through a celite plug. The plug was washed with dimethyl sulfoxide and the combined filtrates submitted for purification by preparative HPLC to afford (S)-5-methoxy-6-((1-phenylethyl)amino)-N-(5-(pyridin-4-yl)-1,3,4-thiadiazol-2-yl)nicotinamide (0.097 g, 63% yield). $^1$H NMR (400 MHz, DMSO) 13.02 (1H, s), 8.80-8.78 (2H, m), 8.49 (1H, d, J=1.8 Hz), 7.99-7.97 (2H, m), 7.75 (1H, d, J=1.8 Hz), 7.46 (2H, d, J=7.8 Hz), 7.35 (2H, dd, J=7.6, 7.6 Hz), 7.31-7.22 (2H, m), 5.49-5.42 (1H, m), 3.99 (3H, s), 1.58 (3H, d, J=7.1 Hz); MS (ESI$^+$) 433.

EXAMPLE 26

Formation of (S)-6-(3-(dimethylamino)-1-phenylpropoxy)-5-methoxy-N-(5-(pyridin-4-yl)-1,3,4-thiadiazol-2-yl)nicotinamide (Compound 2-V, Scheme 2)

(26)

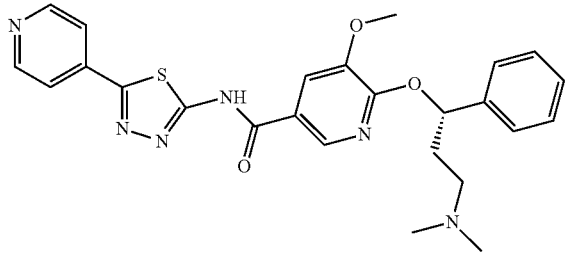

a) (S)-3-(dimethylamino)-1-phenylpropan-1-ol oxalate (Compound of Formula 2-IV, Scheme 2) (as Described in WO 2011/027359)

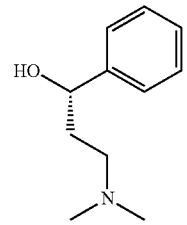

To a stirred solution of (S)-3-chloro-1-phenylpropan-1-ol (1.2 g, 7 mmol, 1 eq.) and potassium iodide (0.12 g, 0.72 mmol, 0.1 eq.) in ethanol (6 mL) was added dimethylamine (40 wt % solution in water, 6 mL, 47 mmol, 6.7 eq.) and the mixture heated at 64° C. for 7 hours. 2M sodium hydroxide (3 mL, 6 mmol) was added to the reaction and the mixture extracted with toluene (22 mL then 10 mL). The combined extracts were washed with brine and evaporated in vacuo to afford (S)-3-(dimethylamino)-1-phenylpropan-1-ol oxalate. This was dissolved in a mixture of ethyl acetate (3 mL) and acetone (3 mL) and a solution of oxalic acid (0.630 g, 7 mmol, 1 eq.) in a mixture of ethyl acetate (3 mL) and acetone (3 mL) was added with stirring. The resultant solid was collected by filtration, washed with ethyl acetate (3×4 mL) and dried in vacuo to afford (S)-3-(dimethylamino)-1-phenylpropan-1-ol oxalate as a white solid (1.71 g, 90% yield). $^1$H NMR (400 MHz, DMSO) 7.37-7.35 (4H, m), 7.29-7.24

(1H, m), 4.64 (1H, dd, J=5.3, 7.6 Hz), 3.18-3.03 (2H, m), 2.74 (6H, s), 1.98-1.91 (2H, m).

b) (S)-6-(3-(dimethylamino)-1-phenylpropoxy)-5-methoxy-N-(5-(pyridin-4-yl)-1,3,4-thiadiazol-2-yl)nicotinamide (Compound 2-V, Scheme 2)

To a stirred suspension of 6-chloro-5-methoxy-N-(5-(pyridin-4-yl)-1,3,4-thiadiazol-2-yl)nicotinamide (0.09 g, 0.26 mmol, 1 eq., Example 25 step a) in anhydrous dimethyl sulfoxide (1.8 mL) under a nitrogen atmosphere was added (S)-3-(dimethylamino)-1-phenylpropan-1-ol oxalate (0.153 g, 0.57 mmol, 2.2 eq.) and sodium hydride (0.079 g, 1.98 mmol, 7.6 eq., 60% dispersion in mineral oil). The resulting mixture was stirred at room temperature for 10 minutes and then at 90° C. for 16 hours. The reaction was cooled to room temperature and 5 drops of water were added. The mixture was filtered through a celite plug and purified by preparative HPLC to afford (S)-6-(3-(dimethylamino)-1-phenylpropoxy)-5-methoxy-N-(5-(pyridin-4-yl)-1,3,4-thiadiazol-2-yl)nicotinamide (0.071 g, 53% yield). $^1$H NMR (400 MHz, DMSO) 8.74-8.72 (2H, m), 8.43 (1H, d, J=1.8 Hz), 8.01 (1H, d, J=1.8 Hz), 7.92-7.89 (2H, m), 7.49 (2H, d, J=7.1 Hz), 7.42 (2H, dd, J=7.5, 7.5 Hz), 7.35-7.31 (1H, m), 6.36 (1H, dd, J=5.6, 7.8 Hz), 3.98 (3H, s), 2.75-2.71 (2H, m), 2.48 (6H, s), 2.41-2.28 (1H, m), 2.20-2.11 (1H, m); MS (ESI$^+$) 491.

EXAMPLE 27

(R)-6-(2-hydroxy-1-phenylethoxy)-5-methoxy-N-(5-(pyridin-4-yl)-1,3,4-thiadiazol-2-yl)nicotinamide (Compound 2-V, Scheme 2)

EXAMPLE 28

(R)-6-(2-hydroxy-2-phenylethoxy)-5-methoxy-N-(5-(pyridin-4-yl)-1,3,4-thiadiazol-2-yl)nicotinamide (Compound 2-V, Scheme 2)

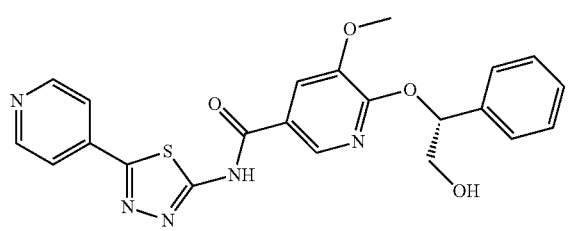

(27)

(28)

a) (1R)-1-phenyl-2-((tetrahydro-2H-pyran-2-yl)oxy)ethanol (Compound of Formula 2-IV, Scheme 2)

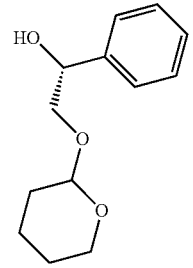

To a stirred solution of (R)-1-phenylethane-1,2-diol (0.984 g, 7.12 mmol, 1 eq.) and pyridinium p-toluene sulfonate (0.180 g, 0.71 mmol, 0.1 eq.) in anhydrous dichloromethane (7 mL) at 0° C. under a nitrogen atmosphere was added 3,4-dihydropyran (0.715 µL, 7.83 mmol, 1.1 eq.) and the resulting mixture stirred at 0° C. for 6 hours and then at room temperature overnight. The reaction was diluted with dichloromethane and washed with saturated sodium bicarbonate (×2). The organic phase was dried with magnesium sulfate and the solvent removed in vacuo. The residue was purified by silica gel column chromatography using a 0 to 30% ethyl acetate in iso-hexane gradient to afford (1R)-1-phenyl-2-((tetrahydro-2H-pyran-2-yl)oxy)ethanol (0.33 g, 21% yield). $^1$H NMR (400 MHz, DMSO) 7.43-7.34 (4H, m), 7.32-7.27 (1H, m), 5.39-5.34 (1H, m), 4.79-4.73 (1H, m), 4.68-4.57 (1H, m), 3.79-3.62 (2H, m), 3.52-3.40 (2H, m), 1.80-1.60 (2H, m), 1.53-1.43 (4H, m).

b) 5-methoxy-6-((1R)-1-phenyl-2-((tetrahydro-2H-pyran-2-yl)oxy)ethoxy)-N-(5-(pyridin-4-yl)-1,3,4-thiadiazol-2-yl)nicotinamide (Compound of Formula 2-V, Scheme 2)

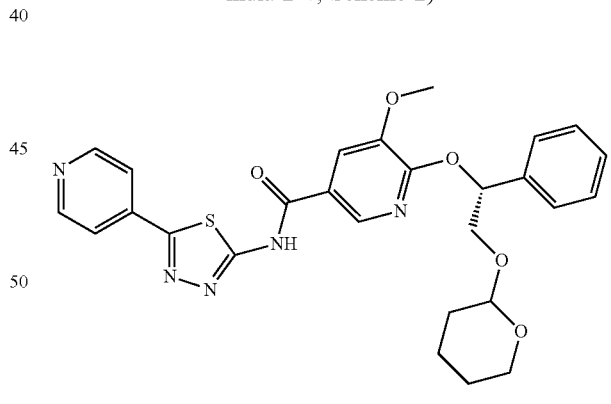

To a stirred suspension of 6-chloro-5-methoxy-N-(5-(pyridin-4-yl)-1,3,4-thiadiazol-2-yl)nicotinamide (0.192 g, 0.55 mmol, 1 eq., Example 25 step a) in anhydrous dimethyl sulfoxide (2.5 mL) under a nitrogen atmosphere was added (1R)-1-phenyl-2-((tetrahydro-2H-pyran-2-yl)oxy)ethanol (0.135 g, 0.61 mmol, 1.1 eq.) and sodium hydride (0.055 g, 1.38 mmol, 2.5 eq., 60% dispersion in mineral oil) and the resulting mixture stirred at room temperature for 30 minutes and then at 90° C. for 2 hours. Further portions of (1R)-1-phenyl-2-((tetrahydro-2H-pyran-2-yl)oxy)ethanol (0.025 g, 0.11 mmol, 0.2 eq.) and sodium hydride (0.011 g, 0.28 mmol, 0.5 eq., 60% dispersion in mineral oil) were added and the reaction stirred at 90° C. for a further 1 hour. The reaction was cooled to room temperature, poured into water (30 mL) and the pH adjusted to 8 by the addition of 2M hydrochloric acid. The resulting precipitate was collected by filtration, washed with water and diethyl ether to afford 5-methoxy-6-((1R)-1-phenyl-2-((tetrahydro-2H-pyran-2-yl)oxy)ethoxy)-N-(5-(pyridin-4-yl)-1,3,4-thiadiazol-2-yl)nicotinamide (0.209 g, 71% yield). ¹H NMR (400 MHz, DMSO) 13.37 (1H, s), 8.81 (2H, d, J=5.1 Hz), 8.48-8.46 (1H, m), 8.06 (1H, s), 8.00 (2H, d, J=5.6 Hz), 7.51 (2H, dd, J=6.8, 6.8 Hz), 7.42 (2H, dd, J=7.2, 7.2 Hz), 7.38-7.32 (1H, m), 6.53-6.44 (1H, m), 4.75 (1H, s), 4.09 (1H, dd, J=7.5, 11.0 Hz), 4.01 (3H, s), 3.97-3.81 (1H, m), 3.74-3.69 (1H, m), 3.49-3.42 (1H, m), 1.68-1.61 (2H, m), 1.52-1.41 (4H, m).

c) (R)-6-(2-hydroxy-1-phenylethoxy)-5-methoxy-N-(5-(pyridin-4-yl)-1,3,4-thiadiazol-2-yl)nicotinamide (Compound 2-V, Scheme 2) and (R)-6-(2-hydroxy-2-phenylethoxy)-5-methoxy-N-(5-(pyridin-4-yl)-1,3,4-thiadiazol-2-yl)nicotinamide (Compound 2-V, Scheme 2)

To a solution of 5-methoxy-6-((1R)-1-phenyl-2-((tetrahydro-2H-pyran-2-yl)oxy)ethoxy)-N-(5-(pyridin-4-yl)-1,3,4-thiadiazol-2-yl)nicotinamide (0.120 g, 0.23 mmol, 1 eq.) in anhydrous dimethylsulfoxide (1.2 mL) was added lithium chloride (0.049 g, 1.16 mmol, 5 eq.) and water (0.042 μL, 2.33 mmol, 10 eq.) and the resulting solution stirred at 90° C. overnight. The reaction was cooled to room temperature and filtered through a celite plug. The filtrate was submitted for purification by preparative HPLC to afford (R)-6-(2-hydroxy-1-phenylethoxy)-5-methoxy-N-(5-(pyridin-4-yl)-1,3,4-thiadiazol-2-yl) nicotinamide (0.022 g, 21% yield). ¹H NMR (400 MHz, DMSO) 13.36 (1H, s), 8.81-8.78 (2H, m), 8.46 (1H, d, J=2.0 Hz), 8.04 (1H, d, J=2.0 Hz), 8.00-7.98 (2H, m), 7.48-7.44 (2H, m), 7.40 (2H, dd, J=7.5, 7.5 Hz), 7.34-7.30 (1H, m), 6.31 (1H, dd, J=4.0, 7.6 Hz), 5.16 (1H, dd, J=5.7, 5.7 Hz), 4.01 (3H, s), 3.97-3.86 (1H, m), 3.81-3.74 (1H, m); MS (ESI⁺) 450. Also isolated from the preparative HPLC was (R)-6-(2-hydroxy-2-phenylethoxy)-5-methoxy-N-(5-(pyridin-4-yl)-1,3,4-thiadiazol-2-yl)nicotinamide (0.007 g, 7% yield). ¹H NMR (400 MHz, DMSO) 13.40 (1H, s), 8.81-8.78 (2H, m), 8.57 (1H, d, J=1.9 Hz), 8.04 (1H, d, J=2.0 Hz), 8.01-7.99 (2H, m), 7.51 (2H, d, J=7.1 Hz), 7.42 (2H, dd, J=7.5, 7.5 Hz), 7.37-7.32 (1H, m), 5.70 (1H, d, J=5.3 Hz), 5.05 (1H, q, J=5.3 Hz), 4.50-4.46 (2H, m), 3.96 (3H, s); MS (ESI⁺) 450.

EXAMPLE 29

(R)-5-chloro-6-(2-hydroxy-2-methyl-1-phenylpropoxy)-N-(5-(pyridin-4-yl)-1,3,4-thiadiazol-2-yl) nicotinamide (Compound 2-V, Scheme 2)

(29)

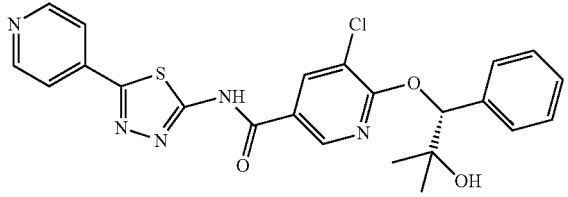

a) (R)-2-methyl-1-phenylpropane-1,2-diol (Compound of Formula 2-IV, Scheme 2)

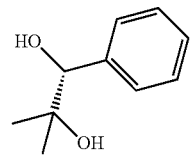

To a stirred solution of (R)-methyl 2-hydroxy-2-phenylacetate (2.0 g, 12.0 mmol, 1 eq.) in anhydrous tetrahydrofuran (100 mL) under a nitrogen atmosphere at 0° C. was added methylmagnesium chloride (8 mL, 24.0 mmol, 2 eq., 3M in tetrahydrofuran) dropwise maintaining the internal reaction temperature below 5° C. The reaction was stirred at 0° C. for 30 minutes and methylmagnesium chloride (8 mL, 24.0 mmol, 2 eq., 3M in tetrahydrofuran) was added. The reaction was allowed to warm to room temperature and stirred overnight. The reaction was quenched with 2M hydrochloric acid to pH 1 and diluted with water. The tetrahydrofuran was removed in vacuo and the aqueous residue extracted with ethyl acetate (×4). The combined organic phase was washed with water and brine, dried with magnesium sulfate and the solvent removed in vacuo. The resulting oil was dissolved in ethyl acetate, washed with 2M sodium hydroxide, water and brine and the solvent removed in vacuo to afford (R)-2-methyl-1-phenylpropane-1,2-diol as a pale oil (1.95 g, 98% yield). ¹H NMR (400 MHz, DMSO) 7.42-7.38 (2H, m), 7.34-7.25 (3H, m), 5.20 (1H, d, J=4.3 Hz), 4.36 (1H, d, J=4.0 Hz), 4.26 (1H, s), 1.10 (3H, s), 1.01 (3H, s).

b) (R)-5-chloro-6-(2-hydroxy-2-methyl-1-phenylpropoxy)-N-(5-(pyridin-4-yl)-1,3,4-thiadiazol-2-yl) nicotinamide (Compound 2-V, Scheme 2)

To a stirred solution of (R)-2-methyl-1-phenylpropane-1,2-diol (0.071 g, 0.43 mmol, 1 eq.) in anhydrous dimethyl sulfoxide (1 mL) under a nitrogen atmosphere was added sodium hydride (0.051 g, 1.28 mmol, 3 eq., 60% dispersion in mineral oil) followed by 5,6-dichloro-N-(5-(pyridin-4-yl)-1,3,4-thiadiazol-2-yl)nicotinamide (0.150 g, 0.43 mmol, 1 eq. Example 21 step a) and the resulting mixture stirred at 70° C. for 90 minutes. The reaction was cooled to room temperature, quenched by the addition of 5 drops of water, filtered through a celite plug and submitted to preparative HPLC for purification to afford (R)-5-chloro-6-(2-hydroxy-2-methyl-1-phenylpropoxy)-N-(5-(pyridin-4-yl)-1,3,4-thiadiazol-2-yl) nicotinamide (0.043 g, 21% yield). ¹H NMR (400 MHz, DMSO) 13.43 (1H, s), 8.79 (2H, dd, J=1.4, 4.6 Hz), 8.77 (1H, d, J=2.2 Hz), 8.62 (1H, d, J=2.3 Hz), 7.99 (2H, dd, J=1.8, 4.5 Hz), 7.47 (2H, d, J=7.1 Hz), 7.38 (2H, dd, J=7.5, 7.5 Hz), 7.31 (1H, t, J=7.2 Hz), 6.13 (1H, s), 4.84 (1H, s), 1.32 (3H, s), 1.17 (3H, s); MS (ESI⁺) 482/484.

EXAMPLE 30

5-chloro-6-(2-(dimethylamino)-1-(pyridin-2-yl)
ethoxy)-N-(5-(pyridin-4-yl)-1,3,4-thiadiazol-2-yl)
nicotinamide (Compound 2-V, Scheme 2)

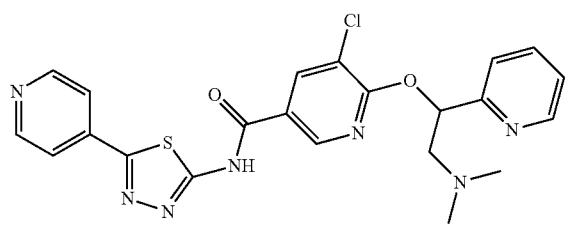

(30)

a) 2-(dimethylamino)-1-(pyridin-2-yl)ethanol (Compound of Formula 2-IV, Scheme 2)

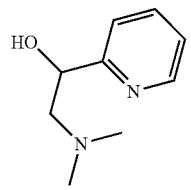

A solution of 2-amino-1-(pyridin-2-yl)ethanol dihydrochloride (1.0 g, 4.7 mmol) in 2M sodium hydroxide solution at pH 12 was extracted with dichloromethane (×3). The combined organic phase was dried with magnesium sulfate and the solvent removed in vacuo to afford 2-amino-1-(pyridin-2-yl)ethanol (0.31 g, 2.2 mmol). The 2-amino-1-(pyridin-2-yl)ethanol (0.31 g, 2.2 mmol, 1 eq.) was dissolved in formic acid (0.7 mL) and aqueous formaldehyde solution (1.4 mL, 37%) and the resultant solution heated at 85° C. for 2 hours. The reaction mixture was cooled to room temperature and washed with diethyl ether. The aqueous phase was basified with 2M sodium hydroxide solution and extracted with dichloromethane (×2). The combined organic phase was dried with magnesium sulfate and the solvent removed in vacuo to afford 2-(dimethylamino)-1-(pyridin-2-yl)ethanol (0.135 g, 37% yield) which was used without further purification. $^1$H NMR (400 MHz, CDCl$_3$) 8.54-8.53 (1H, m), 7.73-7.67 (1H, m), 7.53 (1H, d, J=8.3 Hz), 7.20-7.16 (1H, m), 4.82-4.77 (1H, m), 2.65 (1H, dd, J=3.8, 12.1 Hz), 2.52 (1H, dd, J=10.0, 12.1 Hz), 2.36 (6H, s).

b) 5-chloro-6-(2-(dimethylamino)-1-(pyridin-2-yl)
ethoxy)-N-(5-(pyridin-4-yl)-1,3,4-thiadiazol-2-yl)
nicotinamide (Compound 2-V, Scheme 2)

To a solution of 5,6-dichloro-N-(5-(pyridin-4-yl)-1,3,4-thiadiazol-2-yl)nicotinamide (0.100 g, 0.28 mmol, 1 eq. Example 21 step a) in anhydrous dimethyl sulfoxide (1 mL) under a nitrogen atmosphere was added a solution of 2-(dimethylamino)-1-(pyridin-2-yl)ethanol (0.061 g, 0.37 mmol, 1.3 eq.) in anhydrous dimethyl sulfoxide (1 mL) followed by sodium hydride (0.025 g, 0.62 mmol, 2.2 eq., 60% dispersion in mineral oil). The resulting solution was stirred at room temperature for 10 minutes and then at 90° C. for 16 hours. The reaction was cooled to room temperature and quenched with 5 drops of water, filtered through a celite plug and purified by preparative HPLC to afford 5-chloro-6-(2-(dimethylamino)-1-(pyridin-2-yl)ethoxy)-N-(5-(pyridin-4-yl)-1,3,4-thiadiazol-2-yl)nicotinamide (0.045 g, 33% yield). $^1$H NMR (400 MHz, CDCl$_3$) 8.85 (1H, d, J=1.8 Hz), 8.80-8.77 (2H, m), 8.60 (1H, d, J=4.8 Hz), 8.39 (1H, d, J=2.0 Hz), 7.85-7.82 (2H, m), 7.68-7.62 (1H, m), 7.44 (1H, d, J=7.8 Hz), 7.19 (1H, dd, J=5.4, 6.9 Hz), 6.73 (1H, dd, J=2.8, 9.3 Hz), 3.29 (1H, dd, J=9.3, 13.6 Hz), 3.04 (1H, dd, J=2.9, 13.5 Hz), 2.52 (6H, s); MS (ESI$^+$) 482/484.

EXAMPLE 31

Formation of (R)-6-(2-(dimethylamino)-1-phenylethoxy)-N-(5-(pyridin-4-yl)-1,3,4-thiadiazol-2-yl)
nicotinamide (Compound of Formula 2-V, Scheme 2)

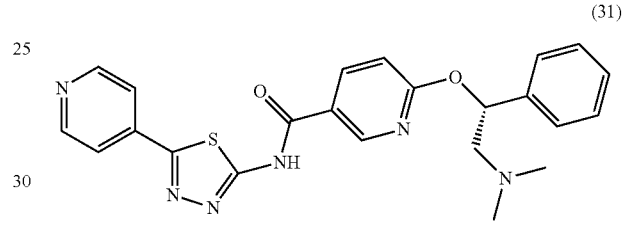

(31)

a) 6-fluoro-N-(5-(pyridin-4-yl)-1,3,4-thiadiazol-2-yl)
nicotinamide (Compound of Formula 2-III, Scheme 2)

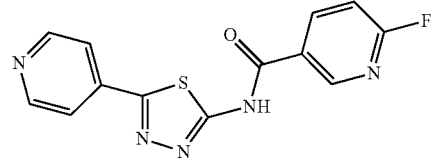 [SMILES: O=C(Nc1nnc(-c2ccncc2)s1)c1ccc(F)nc1]

A solution of 5-(pyridin-4-yl)-1,3,4-thiadiazol-2-amine (1.2 g, 6.7 mmol, 1 eq), 6-fluoronicotinic acid (1 g, 6.7 mmol, 1.05 eq), HATU (3.8 g, 10 mmol, 1.5 eq) and diisopropylethylamine (1.4 mL, 8.0 mmol, 1.2 eq) in NMP (14 mL) was heated to 70° C. for 18 hours. The reaction was cooled and poured into water (100 mL). The resultant solid was filtered, washed with water and dried in vacuo to give 6-fluoro-N-(5-(pyridin-4-yl)-1,3,4-thiadiazol-2-yl)nicotinamide as a white solid (1.87 g, 93% yield). $^1$H NMR (400 MHz, DMSO) 13.69 (1H, s), 9.04 (1H, d, J=2.5 Hz), 8.83-8.80 (2H, m), 8.75-8.69 (1H, m), 8.04-8.01 (2H, m), 7.49 (1H, dd, J=2.3, 8.6 Hz).

b) (R)-6-(2-(dimethylamino)-1-phenylethoxy)-N-(5-(pyridin-4-yl)-1,3,4-thiadiazol-2-yl)nicotinamide
(Compound of Formula 2-V, Scheme 2)

Sodium hydride (0.07 g, 1.65 mmol, 5 eq., 60% dispersion in mineral oil) was added to a solution of (R)-2-(dimethylamino)-1-phenylethanol (0.19 g, 1.15 mmol, 3.5 eq, Example 6 step a) in dimethyl sulfoxide (2 mL) and the resulting suspension stirred at ambient temperature for 15 minutes. 6-Fluoro-N-(5-(pyridin-4-yl)-1,3,4-thiadiazol-2-yl) nicotinamide (0.1 g, 0.33 mmol, 1 eq) and dimethyl sulfoxide (1 mL) were added and the reaction heated to 50° C. for 90 minutes. The reaction was cooled to room temperature and 5 drops of water were added. The mixture was filtered through a celite plug and purified by preparative HPLC to afford (R)-6-(2-(dimethylamino)-1-phenylethoxy)-N-(5-(pyridin-4-yl)-1,3,4-thiadiazol-2-yl) nicotinamide (0.064 g, 44% yield). $^1$H NMR (400 MHz, DMSO) 12.6 (1H, s), 8.89 (1H, d, J=2.5 Hz), 8.78-8.75 (2H, m), 8.43 (1H, dd, J=2.4, 8.7 Hz), 7.97-7.94 (2H, m), 7.51 (2H, d, J=7.1 Hz), 7.42 (2H, dd, J=7.5, 7.5 Hz), 7.37-7.31 (1H, m), 7.09 (1H, d, J=8.8 Hz), 6.47 (1H, dd, J=3.8, 9.1 Hz), 3.16 (1H, dd, J=9.1, 13.1 Hz), 2.84 (1H, dd, J=3.7, 13.3 Hz), 2.45 (6H, s); MS (ESI$^+$) 447.

EXAMPLE 32

6-(((1S,2R)-1-(dimethylamino)-2,3-dihydro-1H-inden-2-yl)oxy)-N-(5-(pyridin-4-yl)-1,3,4-thiadiazol-2-yl)nicotinamide (Compound of Formula 2-V, Scheme 2)

(32)

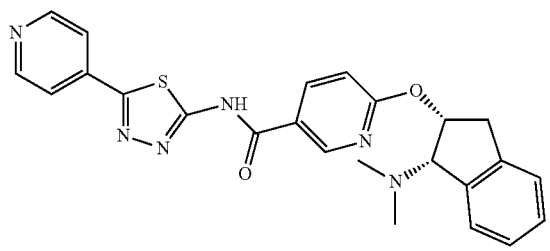

a) (1S,2R)-1-(dimethylamino)-2,3-dihydro-1H-inden-2-ol (Compound of Formula 2-IV, Scheme 2) (*Org. Lett.* 2012, 14, 812)

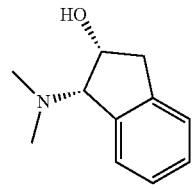

A mixture of (1S,2R)-1-amino-2,3-dihydro-1H-inden-2-ol (1.0 g, 6.7 mmol, 1 eq), formic acid (3.5 mL) and formaldehyde (37 wt % in water 4.5 mL) was stirred at 115° C. for 17.5 hours. The cooled reaction was evaporated, water (5 mL) was added and the resultant residue, cooled in an ice bath and basified to pH 14 using concentrated sodium hydroxide (3 mL). The reaction was extracted with dichloromethane (3×25 mL). The combined extracts were dried with magnesium sulfate and evaporated in vacuo to yield (1S,2R)-1-(dimethylamino)-2,3-dihydro-1H-inden-2-ol as a pale yellow liquid (1.4 g, 100% yield). $^1$H NMR (400 MHz, CDCl$_3$) 7.34-7.18 (4H, m), 4.48-4.41 (1H, m), 4.07 (1H, d, J=7.8 Hz), 3.26 (1H, dd, J=8.1, 16.4 Hz), 2.80 (1H, dd, J=7.7, 16.3 Hz), 2.28 (6H, s).

b) 6-(((1S,2R)-1-(dimethylamino)-2,3-dihydro-1H-inden-2-yl)oxy)-N-(5-(pyridin-4-yl)-1,3,4-thiadiazol-2-yl)nicotinamide (Compound of Formula 2-V, Scheme 2)

Following the general method outlined for the preparation of Example 31 step b starting from 6-fluoro-N-(5-(pyridin-4-yl)-1,3,4-thiadiazol-2-yl)nicotinamide (Example 31 step a) and (1S,2R)-1-(dimethylamino)-2,3-dihydro-1H-inden-2-ol, 6-(((1S,2R)-1-(dimethylamino)-2,3-dihydro-1H-inden-2-yl)oxy)-N-(5-(pyridin-4-yl)-1,3,4-thiadiazol-2-yl)nicotinamide was isolated. $^1$H NMR (400 MHz, DMSO) 13.10 (1H, s), 9.05 (1H, d, J=2.5 Hz), 8.79 (2H, d, J=5.8 Hz), 8.45 (1H, dd, J=2.4, 8.7 Hz), 7.99 (2H, d, J=6.1 Hz), 7.45-7.40 (1H, m), 7.37-7.31 (3H, m), 7.01 (1H, d, J=8.8 Hz), 6.03 (1H, q, J=6.1 Hz), 4.59 (1H, d, J=6.3 Hz), 3.40-3.34 (1H, m), 3.13 (1H, dd, J=5.2, 16.5 Hz), 2.41 (6H, s); MS (ESI$^+$) 459.

EXAMPLE 33

Formation of (S)-6-((1-(dimethylamino)-3-phenylpropan-2-yl)oxy)-N-(5-(pyridin-4-yl)-1,3,4-thiadiazol-2-yl)nicotinamide (Compound of Formula 2-V, Scheme 2)

(33)

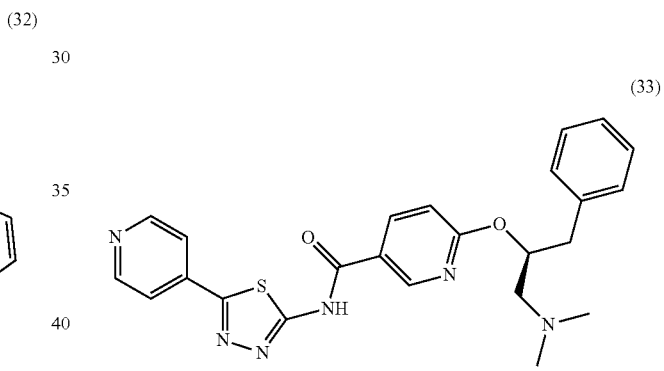

a) (S)-2-hydroxy-N,N-dimethyl-3-phenylpropanamide (Compound of Formula 2-V, Scheme 2)

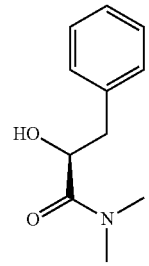

To a solution of (S)-2-hydroxy-3-phenylpropanoic acid (5.3 g, 31.9 mmol, 1 eq.), dimethylamine (40 wt % solution in water, 24 mL, 47.8 mmol, 1.5 eq.) and diisopropylethylamine (8.3 mL, 47.8 mmol, 1.5 eq.) was added HATU (18 g, 47.8 mmol, 1.5 eq.) in portions over 30 minutes in tetrahydrofuran (100 mL) cooled in an ice bath. The bath was removed and the reaction stirred at ambient temperature for 18 hours. The reaction was concentrated in vacuo to ca 20 mL volume and partitioned between ethyl acetate (100 mL) and 1M hydrochloric acid (100 mL). The layers were separated and the aqueous extracted with ethyl acetate (5 mL). The combined organic solutions were washed successively with 1M NaOH (100 mL) and water (30 mL) then dried with magnesium sulfate and evaporated in vacuo. The crude reaction was purified by silica gel column chromatography using 20-100% ethyl acetate in iso-hexane gradient to afford (S)-2-hydroxy-N,N-dimethyl-3-phenylpropanamide as a colourless solid (2.27 g, 37% yield). $^1$H NMR (400 MHz, CDCl$_3$) 7.33-7.20 (5H, m), 4.62-4.56 (1H, m), 3.69 (1H, d, J=8.3 Hz), 2.97 (3H, s), 2.96-2.84 (2H, m), 2.79 (3H, s).

b) (S)-1-(dimethylamino)-3-phenylpropan-2-ol (Compound of Formula 2-IV, Scheme 2) (WO2007072153)

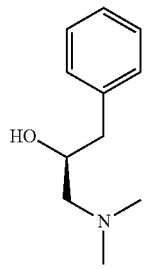

A solution of (S)-2-hydroxy-N,N-dimethyl-3-phenylpropanamide (1.0 g, 5.2 mmol. 1 eq.) in tetrahydrofuran (10 mL) was cooled in an ice bath. Lithium aluminium hydride 2N in tetrahydrofuran (10 mL, 20 mmol, 4 eq.) was added over a period of 10 minutes, the cooling was removed and the reaction was stirred at ambient for 20 hours. The reaction was cooled in an ice bath and quenched with saturated aqueous sodium hydrogen carbonate (1 mL) and water (3 mL). The mixture was extracted twice with ether and the combined organic solution extracted with 1M HCl (20 mL and 10 mL). The combined aqueous solution was basified with concentrated sodium hydroxide (3 mL) and extracted with ether (3×25 mL). The combined extracts were dried with magnesium sulphate and evaporated in vacuo to afford (S)-1-(dimethylamino)-3-phenylpropan-2-ol as a clear oil (0.883 g, 95% yield). $^1$H NMR (400 MHz, CDCl$_3$) 7.31-7.19 (5H, m), 3.91-3.84 (1H, m), 2.81 (1H, dd, J=7.1, 13.6 Hz), 2.67 (1H, dd, J=5.6, 13.6 Hz), 2.33 (1H, dd, J=10.4, 12.1 Hz), 2.24 (6H, s), 2.19 (1H, dd, J=3.2, 12.1 Hz).

c) (S)-6-((1-(dimethylamino)-3-phenylpropan-2-yl)oxy)-N-(5-(pyridin-4-yl)-1,3,4-thiadiazol-2-yl)nicotinamide (Compound of Formula 2-V, Scheme 2)

Following the general method outlined for the preparation of Example 31 step b starting from 6-fluoro-N-(5-(pyridin-4-yl)-1,3,4-thiadiazol-2-yl)nicotinamide (Example 31 step a) (0.08 g, 0.26 mmol) and (S)-1-(dimethylamino)-3-phenylpropan-2-ol (0.064 g, 0.35 mmol), (S)-6-((1-(dimethylamino)-3-phenylpropan-2-yl)oxy)-N-(5-(pyridin-4-yl)-1,3,4-thiadiazol-2-yl)nicotinamide was isolated (0.03 g, 25% yield). $^1$H NMR (400 MHz, DMSO) 8.99-8.94 (2H, m), 8.80 (1H, s), 8.41 (1H, d, J=8.3 Hz), 8.06-7.92 (2H, m), 7.32 (4H, d, J=6.3 Hz), 7.26-7.21 (1H, m), 6.93 (1H, d, J=8.3 Hz), 5.78-5.70 (1H, m), 3.15-2.99 (2H, m), 2.78-2.65 (2H, m), 2.36 (6H, s); MS (ESI$^+$) 461.

EXAMPLE 34

Formation of 6-((1-phenylpropan-2-yl)oxy)-N-(5-(pyridin-4-yl)-1,3,4-thiadiazol-2-yl)nicotinamide (Compound of Formula 2-V, Scheme 2)

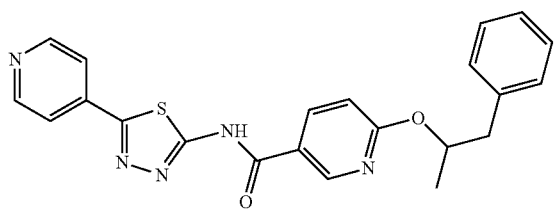

(34)

A mixture of 1-phenylpropan-2-ol (0.115 g, 0.85 mmol, 3 eq.), 6-fluoro-N-(5-(pyridin-4-yl)-1,3,4-thiadiazol-2-yl)nicotinamide (Example 31 step a) (0.085 g, 0.28 mmol, 1 eq) and cesium carbonate (0.275 g, 0.85 mmol, 3 eq) in dimethyl sulfoxide (1 mL) was heated to 160° C. for 2.75 hours. The mixture was cooled to ambient temperature, filtered through a celite plug and purified by preparative HPLC to afford 6-((1-phenylpropan-2-yl)oxy)-N-(5-(pyridin-4-yl)-1,3,4-thiadiazol-2-yl)nicotinamide as a mustard coloured solid (0.025 g, 21% yield). $^1$H NMR (400 MHz, DMSO) 13.39 (1H, s), 9.00 (1H, d, J=2.5 Hz), 8.82-8.79 (2H, m), 8.41 (1H, dd, J=2.5, 8.8 Hz), 8.02-7.99 (2H, m), 7.36-7.33 (4H, m), 7.28-7.22 (1H, m), 6.97 (1H, d, J=8.8 Hz), 5.59-5.52 (1H, m), 3.10 (1H, dd, J=6.8, 13.6 Hz), 2.99 (1H, dd, J=6.1, 13.6 Hz), 1.36 (3H, d, J=6.1 Hz); MS (ESI$^+$) 418.

EXAMPLE 35

Formation of (S)-6-(1-(pyridin-3-yl)ethoxy)-N-(5-(pyridin-4-yl)-1,3,4-thiadiazol-2-yl)nicotinamide (Compound of Formula 2-V, Scheme 2)

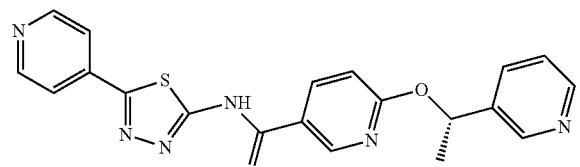

(35)

a) 6-chloro-N-(5-(pyridin-4-yl)-1,3,4-thiadiazol-2-yl)nicotinamide (Compound of Formula 2-III, Scheme 2)

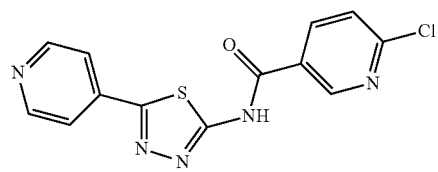 [SMILES: O=C(Nc1nnc(-c2ccncc2)s1)c1ccc(Cl)nc1]

To a suspension of 6-chloronicotinoyl chloride hydrochloride (0.985 g, 5.6 mmol, 1 eq.) in pyridine (10 mL), cooled in an ice bath was added 5-(pyridin-4-yl)-1,3,4-thiadiazol-2-amine (1.0 g, 5.6 mmol, 1 eq.). The mixture was allowed to warm to ambient temperature and stirred for 16 hours. The resultant solid was filtered and washed successively with saturated aqueous sodium hydrogen carbonate and water before being dried in vacuo to give 6-chloro-N-(5-(pyridin-4-yl)-1,3,4-thiadiazol-2-yl)nicotinamide as a white solid (1.61 g, 91% yield). $^1$H NMR (400 MHz, DMSO) 13.72 (1H, s), 9.10 (1H, d, J=2.3 Hz), 8.77-8.75 (2H, m), 8.50 (1H, dd, J=2.5, 8.6 Hz), 7.98-7.96 (2H, m), 7.77 (1H, d, J=8.6 Hz).

b) (R)-6-(2-(dimethylamino)-1-phenylethoxy)-N-(5-(pyridin-4-yl)-1,3,4-thiadiazol-2-yl)nicotinamide) Compound of Formula 2-V, Scheme 2)

A mixture of sodium hydride (0.032 g, 0.8 mmol, 2.5 eq., 60% dispersion in mineral oil), (S)-1-(pyridin-3-yl)ethanol (0.045 g, 0.37 mmol, 1.2 eq.) and 6-chloro-N-(5-(pyridin-4-yl)-1,3,4-thiadiazol-2-yl)nicotinamide (0.1 g, 0.31 mmol, 1 eq) in dimethyl sulfoxide (1.5 mL) was heated to 70° C. for 2 hours. (S)-1-(Pyridin-3-yl)ethanol (0.01 g, 0.08 mmol, 0.26 eq) and sodium hydride (0.02 g, 0.5 mmol, 1.6 eq., 60% dispersion in mineral oil) were added and heating continued at 70° C. for a further 3 hours and at ambient for 16 hours. The mixture was filtered through a celite plug and purified by preparative HPLC to afford (S)-6-(1-(pyridin-3-yl)ethoxy)-N-(5-(pyridin-4-yl)-1,3,4-thiadiazol-2-yl)nicotinamide as a yellow solid (0.017 g, 14% yield). $^1$H NMR (400 MHz, DMSO) 13.40 (1H, s), 8.95 (1H, d, J=2.5 Hz), 8.81 (2H, dd, J=3.9, 3.9 Hz), 8.77-8.74 (1H, m), 8.56 (1H, d, J=4.3 Hz), 8.45 (1H, dd, J=2.4, 8.7 Hz), 8.02-7.98 (2H, m), 7.96-7.92 (1H, m), 7.45 (1H, dd, J=4.8, 7.8 Hz), 7.11 (1H, d, J=8.8 Hz), 6.40 (1H, q, J=6.6 Hz), 1.72 (3H, d, J=6.6 Hz); MS (ESI$^+$) 405.

EXAMPLE 36

Formation of 6-((1-(pyridin-3-yl)ethyl)amino)-N-(5-(pyridin-4-yl)-1,3,4-thiadiazol-2-yl)nicotinamide (Compound of Formula 3-V, Scheme 3)

(36)

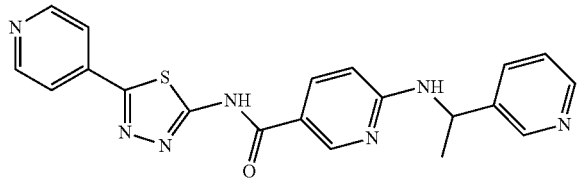

A mixture of 1-(pyridin-3-yl)ethanamine (0.142 g, 1.16 mmol, 5 eq.) and 6-fluoro-N-(5-(pyridin-4-yl)-1,3,4-thiadiazol-2-yl)nicotinamide (Example 31 step a) (0.07 g, 0.23 mmol, 1 eq., Example 31 step a) in NMP (1 mL) was heated to 150° C. for 1 hour. The mixture was purified by preparative HPLC to afford 6-((1-(pyridin-3-yl)ethyl)amino)-N-(5-(pyridin-4-yl)-1,3,4-thiadiazol-2-yl)nicotinamide as an orange solid (0.069 g, 74% yield). $^1$H NMR (400 MHz, DMSO) 12.59 (1H, s), 8.82 (1H, d, J=2.3 Hz), 8.79-8.77 (2H, m), 8.68 (1H, d, J=2.0 Hz), 8.49 (1H, dd, J=1.8, 4.8 Hz), 8.13 (1H, dd, J=2.4, 9.0 Hz), 8.04 (1H, d, J=7.8 Hz), 7.98-7.96 (2H, m), 7.85-7.81 (1H, m), 7.40 (1H, dd, J=4.8, 7.8 Hz), 6.67 (1H, d, J=8.8 Hz), 5.31-5.26 (1H, m), 1.56 (3H, d, J=6.8 Hz); MS (ESI$^+$) 404.

EXAMPLE 37

Formation of (S)-6-(1-phenylethoxy)-N-(5-(pyridin-4-yl)-1,3,4-thiadiazol-2-yl)-5-((tetrahydro-2H-pyran-4-yl)methoxy)nicotinamide (Compound 2-V, Scheme 2)

(37)

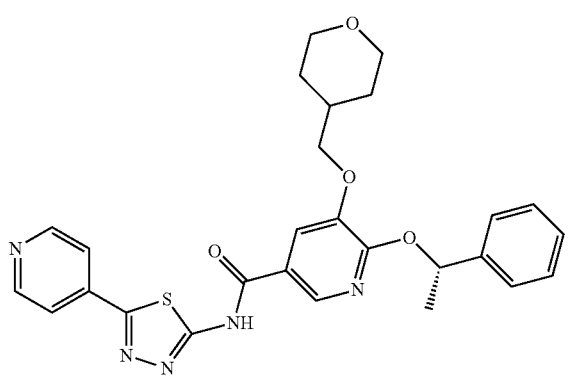

a) Chloro-5-((tetrahydro-2H-pyran-4-yl)methoxy) nicotinic acid (Compound of Formula 2-I, Scheme 2)

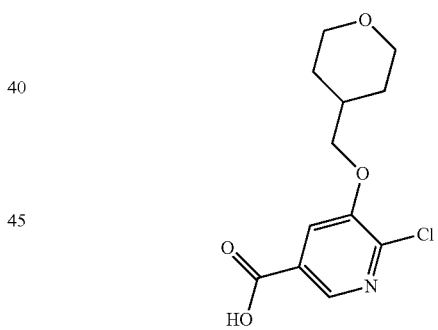

Following the general method outlined for the preparation of Example 4 (steps a-b) using methyl 6-chloro-5-hydroxynicotinate and (tetrahydro-2H-pyran-4-yl)methanol, chloro-5-((tetrahydro-2H-pyran-4-yl)methoxy)nicotinic acid was isolated, as a cream solid. $^1$H NMR (400 MHz, DMSO) 13.67 (1H, s), 8.51 (1H, s), 7.92 (1H, d, J=1.8 Hz), 4.12 (2H, d, J=6.2 Hz), 3.94 (2H, dd, J=2.9, 11.2 Hz), 3.45-3.36 (2H, m), 2.15-2.07 (1H, m), 1.75 (2H, dd, J=1.5, 12.9 Hz), 1.50-1.38 (2H, m).

b) (S)-6-(1-phenylethoxy)-N-(5-(pyridin-4-yl)-1,3,4-thiadiazol-2-yl)-5-((tetrahydro-2H-pyran-4-yl)methoxy)nicotinamide (Compound of Formula 2-V, Scheme 2)

Following the general procedure outlined for Example 20 (steps a-b) using 6-chloro-5-methylnicotinic acid, 5-(4- pyridyl)-1,3,4-thiadiazol-2-yl amine and (S)-1-phenylethanol, (S)-6-(1-phenylethoxy)-N-(5-(pyridin-4-yl)-1,3,4-thiadiazol-2-yl)-5-((tetrahydro-2H-pyran-4-yl)methoxy) nicotinamide was isolated (17% yield). $^1$H NMR (400 MHz, DMSO) 13.38 (1H, s), 8.85-8.82 (2H, m), 8.55 (1H, d, J=2.0 Hz), 8.10 (1H, d, J=1.8 Hz), 8.05-8.02 (2H, m), 7.54 (2H, d, J=7.3 Hz), 7.45 (2H, dd, J=7.6, 7.6 Hz), 7.37 (1H, dd, J=7.3, 7.3 Hz), 6.44 (1H, q, J=6.5 Hz), 4.14-3.98 (4H, m), 3.51-3.44 (2H, m), 2.25-2.17 (1H, m), 1.86-1.79 (2H, m), 1.71 (3H, d, J=6.6 Hz), 1.56-1.45 (2H, m); MS (ESI$^+$) 518.

EXAMPLE 38

Formation of (S)-6-(3-morpholino-1-phenylpropoxy)-N-(5-(pyridin-4-yl)-1,3,4-thiadiazol-2-yl) nicotinamide (Compound 2-V, Scheme 2)

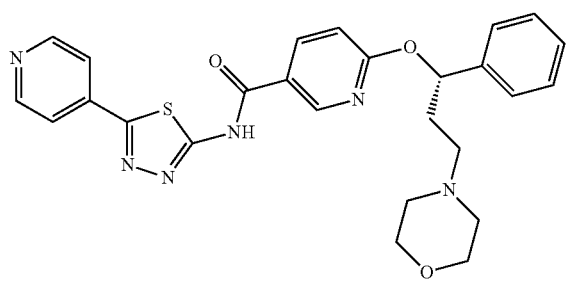

(38)

a) (S)-3-morpholino-1-phenylpropan-1-ol (Compound of Formula 2-IV, Scheme 2)

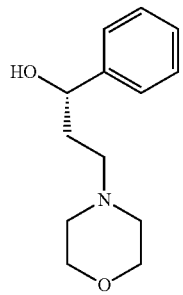 [SMILES: O[C@@H](CCN1CCOCC1)c1ccccc1]

A solution of (S)-3-iodo-1-phenylpropan-1-ol (0.326 g, 1.24 mmol, 1.0 eq.) (Biological and Pharmaceutical Bulletin, 34(4), 538-544, 2011) and morpholine (0.544 mL, 6.22 mmol, 5.0 eq.) in tetrahydrofuran (3 mL) was stirred at reflux for 3 hours. The reaction was cooled to room temperature, brine was added and the mixture extracted with dichloromethane (×2). The combined organic layers were concentrated in vacuo and the residue purified by silica gel column chromatography using a 0-10% methanol in dichloromethane gradient to afford (S)-3-morpholino-1-phenylpropan-1-ol as a colourless gum (0.25 g, 91% yield). $^1$H NMR (400 MHz, CDCl$_3$) 7.38 (1H, dd, J=3.0, 3.0 Hz), 7.37-7.34 (4H, m), 6.37 (1H, s), 4.95 (1H, dd, J=5.7, 5.7 Hz), 3.76 (4H, dd, J=4.7, 4.7 Hz), 2.65 (4H, s), 2.52 (2H, s), 1.90-1.85 (2H, m).

b) (S)-6-(3-morpholino-1-phenylpropoxy)-N-(5-(pyridin-4-yl)-1,3,4-thiadiazol-2-yl) nicotinamide (Compound of Formula 2-V, Scheme 2)

Following the general method outlined for the preparation of Example 31 step b starting from (S)-3-morpholino-1-phenylpropan-1-ol (0.104 g, 0.47 mmol) and 6-Fluoro-N-(5-(pyridin-4-yl)-1,3,4-thiadiazol-2-yl)nicotinamide (Example 31 step a) (0.129 g, 0.427 mmol, 1 eq, (Example 31 step a)) (S)-6-(3-morpholino-1-phenylpropoxy)-N-(5-(pyridin-4-yl)-1,3,4-thiadiazol-2-yl) nicotinamide (0.108 g, 50% yield) was isolated. $^1$H NMR (400 MHz, DMSO) 13.14 (1H, s), 8.91 (1H, d, J=2.3 Hz), 8.79 (2H, d, J=4.0 Hz), 8.42 (1H, dd, J=2.5, 8.6 Hz), 7.98 (2H, d, J=6.1 Hz), 7.49 (2H, d, J=7.1 Hz), 7.41 (2H, dd, J=7.5, 7.5 Hz), 7.35-7.30 (1H, m), 7.08 (1H, d, J=8.8 Hz), 6.34-6.29 (1H, m), 3.62 (4H, dd, J=4.5, 4.5 Hz), 2.48-2.40 (6H, m), 2.31-2.21 (1H, m), 2.13-2.03 (1H, m); MS (ESI$^+$) 503.

EXAMPLE 39

Formation of (R)-6-(2-morpholino-1-phenylethoxy)-N-(5-(pyridin-4-yl)-1,3,4-thiadiazol-2-yl)nicotinamide (Compound 2-V, Scheme 2)

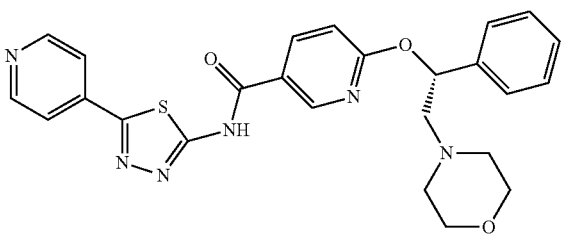

(39)

a) (R)-2-hydroxy-2-phenylethyl 4-methylbenzenesulfonate (Compound of Formula 2-IV, Scheme 2)

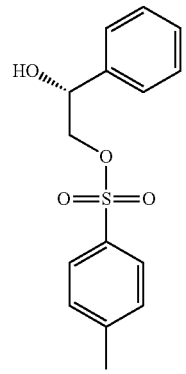 [SMILES: Cc1ccc(S(=O)(=O)OC[C@H](O)c2ccccc2)cc1]

To a stirred solution of (R)-1-phenylethane-1,2-diol (0.5 g, 3.6 mmol, 1.0 eq.) in anhydrous pyridine (2 mL) under a nitrogen atmosphere at 0° C. was added 4-methylbenzene-1-sulfonyl chloride (0.76 g, 4.0 mmol, 1.1 eq.) portionwise over 20 minutes maintaining the temperature at 0° C. The reaction was allowed to warm to room temperature and stirred overnight. Brine was added and the mixture extracted with dichloromethane (×2). The combined organic layers were washed with 1 M hydrochloric acid (×2) and water and the solvent removed in vacuo to afford (R)-2-hydroxy-2-phenylethyl 4-methylbenzenesulfonate as a white solid (0.817 g, 78% yield). $^1$H NMR (400 MHz, DMSO) 7.76 (2H, d, J=8.3 Hz), 7.49 (2H, d, J=7.8 Hz), 7.37-7.32 (5H, m), 5.81 (1H, d, J=4.6 Hz), 4.81 (1H, dd, J=4.9, 11.3 Hz), 4.07-4.04 (1H, m), 2.47 (3H, s).

b) (R)-2-morpholino-1-phenylethanol (Compound of Formula 2-IV, Scheme 2)

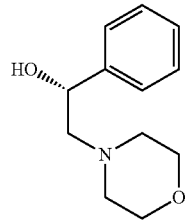

A solution of (R)-2-hydroxy-2-phenylethyl 4-methylbenzenesulfonate (0.219 g, 0.75 mmol, 1.0 eq.) and morpholine (0.328 mL, 3.75 mmol, 5.0 eq) in tetrahydrofuran (2 mL) was stirred at 60° C. for 18 hours. The reaction was cooled to room temperature, brine was added and the mixture extracted with dichloromethane (×2). The combined organic layers were concentrated in vacuo and the residue purified by silica gel column chromatography using a 0-10% methanol in dichloromethane gradient to afford (R)-2-morpholino-1-phenylethanol as a cream solid (0.095 g., 61% yield $^1$H NMR (400 MHz, CDCl$_3$) 7.37-7.34 (4H, m), 7.30-7.26 (1H, m), 4.76 (1H, dd, J=3.5, 10.4 Hz), 3.78-3.73 (4H, m), 2.79-2.71 (2H, m), 2.58-2.43 (4H, m).

c) (R)-6-(2-morpholino-1-phenylethoxy)-N-(5-(pyridin-4-yl)-1,3,4-thiadiazol-2-yl)nicotinamide (Compound of Formula 2-V, Scheme 2)

Following the general method outlined for the preparation of Example 31 step b starting from (R)-2-morpholino-1-phenylethanol (0.050 g, 0.241 mmol) and 6-Fluoro-N-(5-(pyridin-4-yl)-1,3,4-thiadiazol-2-yl)nicotinamide (Example 31 step a) (0.066 g, 0.219 mmol, (Example 31 step a)) (R)-6-(2-morpholino-1-phenylethoxy)-N-(5-(pyridin-4-yl)-1,3,4-thiadiazol-2-yl)nicotinamide (0.048 g, 45% yield) was isolated. $^1$H NMR (400 MHz, CDCl$_3$) 9.05 (1H, d, J=2.3 Hz), 8.79-8.76 (2H, m), 8.42 (1H, dd, J=2.5, 8.8 Hz), 7.86-7.84 (2H, m), 7.44 (2H, d, J=7.1 Hz), 7.36-7.27 (3H, m), 6.98 (1H, d, J=8.6 Hz), 6.53 (1H, dd, J=3.8, 8.8 Hz), 3.68-3.58 (4H, m), 3.07 (1H, dd, J=8.7, 13.5 Hz), 2.73 (1H, dd, J=3.9, 13.5 Hz), 2.65-2.52 (4H, m); MS (ESI$^+$) 489.

EXAMPLE 40

Formation of 4-(isoindolin-2-ylmethyl)-3-methoxy-N-(5-(pyridin-4-yl)-1,3,4-thiadiazol-2-yl)benzamide (Compound 4-VII, Scheme 4)

(40)

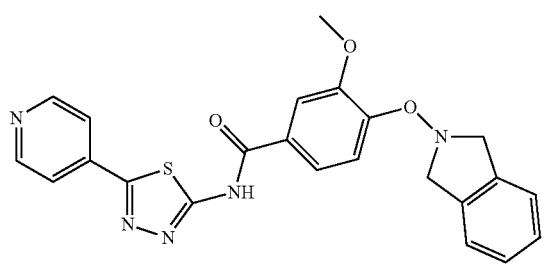

a) Methyl 4-(isoindolin-2-ylmethyl)-3-methoxybenzoate (Compound of Formula 4-IV, Scheme 4)

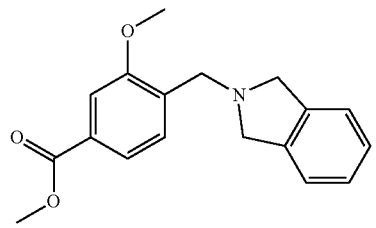 [SMILES: COC(=O)c1ccc(CN2Cc3ccccc3C2)c(OC)c1]

To a stirred suspension of methyl 4-(bromomethyl)-3-methoxybenzoate (0.53 g, 2.04 mmol, 1 eq.) and potassium carbonate (0.56 g, 4 mmol, 2 eq.) in N,N-dimethylformamide (5 mL) was added isoindoline (280 µL, 2.45 mmol, 1.2 eq.). The resulting mixture was then stirred at room temperature for 17 hours. The solvent was removed in vacuo and the crude product was partitioned between water and dichloromethane, the layers were separated and the aqueous phase extracted with dichloromethane. The combined extracts were dried with magnesium sulfate and evaporated in vacuo. The residue was purified by silica gel column chromatography using a 10-100% ethyl acetate in iso-hexane gradient to afford methyl 4-(isoindolin-2-ylmethyl)-3-methoxybenzoate as a red liquid (0.417 g, 70% yield). $^1$H NMR (400 MHz, CDCl$_3$) 7.66 (1H, d, J=7.8 Hz), 7.55-7.53 (2H, m), 7.18 (4H, s), 4.0-3.98 (6H, m), 3.92-3.91 (6H, m).

b) 4-(isoindolin-2-ylmethyl)-3-methoxybenzoic acid (Compound of Formula 4-V, Scheme 4)

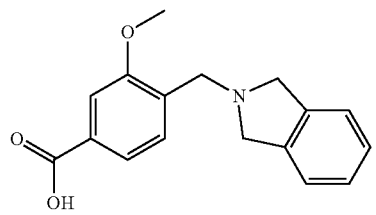 [SMILES: COc1cc(C(=O)O)ccc1CN1Cc2ccccc2C1]

To a stirred solution of methyl 4-(isoindolin-2-ylmethyl)-3-methoxybenzoate (0.417 g, 1.4 mmol, 1 eq.) in methanol (12 mL) was added 2M aqueous sodium hydroxide solution (3 mL, 6 mmol, 4 eq.) and the resulting mixture stirred at ambient temperature for 3 days. The solvent was removed in vacuo and water was added. The pH was adjusted to 5 using 2M hydrochloric acid and the volume reduced in vacuo. The resultant solid was collected by filtration, washed with water and dried in vacuo to afford 4-(isoindolin-2-ylmethyl)-3-methoxybenzoic acid as a green solid (0.258 g, 65% yield). $^1$H NMR (400 MHz, DMSO) 13.0 (1H, s), 7.6-7.56 (1H, m), 7.54-7.49 (2H, m), 7.25-7.17 (4H, m), 3.92 (2H, s), 3.9 (4H, s), 3.86 (3H, s).

c) 4-(isoindolin-2-ylmethyl)-3-methoxy-N-(5-(pyridin-4-yl)-1,3,4-thiadiazol-2-yl) benzamide (Compound 4-VII, Scheme 4)

A solution of 4-(isoindolin-2-ylmethyl)-3-methoxybenzoic acid (0.114 g, 0.4 mmol, 1 eq.), 5-(4-pyridyl)-1,3,4-thiadiazol-2-yl amine (0.071 g, 0.4 mmol, 1 eq.), HATU, 0.23 g, 0.6 mmol, 1.5 eq.) and diisopropylethylamine (100 µL, 0.58 mmol, 1.45 eq.) in NMP (2 mL) was stirred at 70° C. overnight. The cooled reaction was quenched into water and the resultant solid filtered and dried in vacuo. The crude material was triturated in hot ethanol (×2), purified by preparative HPLC then triturated successively hot water and hot ethanol (×2) before being dried in vacuo to afford 4-(isoindolin-2-ylmethyl)-3-methoxy-N-(5-(pyridin-4-yl)-1,3,4-thiadiazol-2-yl)benzamide (0.022 g, 12% yield). $^1$H NMR (400 MHz, DMSO) 8.83-8.81 (2H, m), 8.04-8.01 (2H, m), 7.95 (1H, s), 7.88 (1H, dd, J=1.5, 7.8 Hz), 7.74 (1H, d, J=7.8 Hz), 7.43-7.34 (4H, m), 4.46-4.46 (6H, m), 4.04 (3H, s); MS (ESI$^+$) 444.

The structures of further compounds of the invention (Ex.) are listed in the following Table 1:

TABLE 1

| Ex. | Structure and Name | Data | Method |
|---|---|---|---|
| 41 | 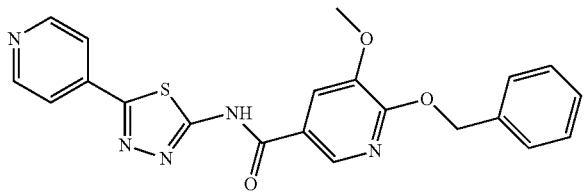<br>6-(benzyloxy)-5-methoxy-N-(5-(pyridin-4-yl)-1,3,4-thiadiazol-3-yl)nicotinamide | $^1$H NMR (400 MHz, DMSO) 13.44 (1H, s), 8.80 (2H, d, J = 4.8 Hz), 8.60 (1H, d, J = 2.0 Hz), 8.06 (1H, d, J = 1.8 Hz), 8.02-7.98 (2H, m), 7.56-7.51 (2H, m), 7.49-7.40 (3H, m), 5.52 (2H, s), 3.96 (3H, s); MS (ESI$^+$) 420 | Ex. 20 (Scheme 2) from 6-chloro-5-methoxynicotinic acid, 5-(4-pyridyl)-1,3,4-thiadiazol-2-yl amine and benzyl alcohol |
| 42 | 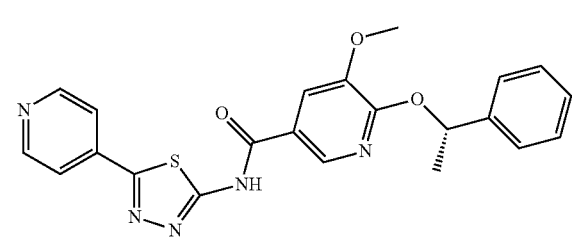<br>(S)-5-methoxy-6-(1-phenyl ethoxy)-N-(5-(pyridin-4-yl)-1,3,4-thiadiazol-2-yl)nicotinamide | $^1$H NMR (400 MHz, DMSO) 13.39 (1H, s), 8.80 (2H, d, J = 6.1 Hz), 8.50 (1H, d, J = 2.0 Hz), 8.04 (1H, d, J = 2.0 Hz), 8.01-7.99 (2H, m), 7.51-7.48 (2H, m), 7.41 (2H, dd, J = 7.5, 7.5 Hz), 7.35-7.31 (1H, m), 6.39 (1H, q, J = 6.5 Hz), 3.98 (3H, s), 1.67 (3H, d, J = 6.6 Hz); MS (ESI$^+$) 434 | Ex 20 (Scheme 2) from 6-chloro-5-methoxy nicotinic acid, 5-(4-pyridyl)-1,3,4-thiadiazol-2-yl amine and (S)-1-phenylethanol |
| 43 | 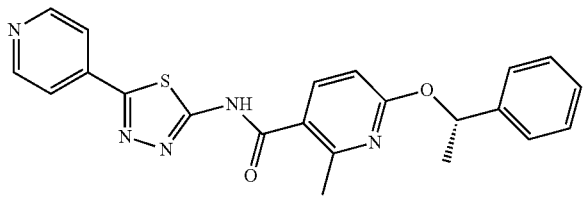<br>(S)-2-methyl-6-(1-phenylethoxy)-N-(5-(pyridin-4-yl)-1,3,4-thiadiazol-2-yl)nicotinamide | $^1$H NMR (400 MHz, DMSO) 13.26 (1H, s), 8.81-8.78 (2H, m), 8.08 (1H, d, J = 8.3 Hz), 8.02-7.99 (2H, m), 7.52 (2H, d, J = 7.3 Hz), 7.42 (2H, dd, J = 7.6, 7.6 Hz), 7.35-7.31 (1H, m), 6.85 (1H, d, J = 8.6 Hz), 6.32 (1H, q, J = 6.6 Hz), 2.59 (3H, s), 1.66 (3H, d, J = 6.6 Hz); MS (ESI$^+$) 418 | Ex 20 (Scheme 2) from 6-chloro-2-methylnicotinic acid, 5-(4-pyridyl)-1,3,4-thiadiazol-2-yl amine and (S)-1-phenylethanol |
| 44 | 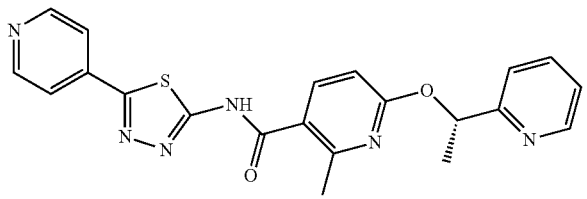<br>(S)-2-methyl-6-(1-(pyridin-2-yl)ethoxy)-N-(5-(pyridin-4-yl)-1,3,4-thiadiazol-2-yl)nicotinamide | $^1$H NMR (400 MHz, DMSO) 13.28 (1H, s), 8.80-8.77 (2H, m), 8.61 (1H, d, J = 3.8 Hz), 8.13 (1H, d, J = 8.6 Hz), 8.00-7.98 (2H, m), 7.87-7.82 (1H, m), 7.52 (1H, d, J = 7.8 Hz), 7.37-7.33 (1H, m), 6.89 (1H, d, J = 8.6 Hz), 6.31 (1H, q, J = 6.6 Hz), 2.57 (3H, s), 1.69 (3H, d, J = 6.6 Hz); MS (ESI$^+$) 419 | Ex 20 (Scheme 2) from 6-chloro-2-methylnicotinic acid, 5-(4-pyridyl)-1,3,4-thiadiazol-2-yl amine and (S)-1-(pyridin-2-yl)ethanol |

TABLE 1-continued

| Ex. | Structure and Name | Data | Method |
|---|---|---|---|
| 45 | 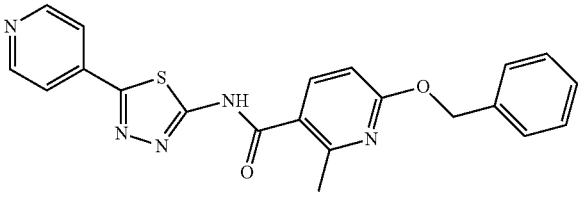<br>6-(benzyloxy)-2-methyl-N-(5-(pyridin-4-yl)-1,3,4-thiadiazol-2-yl)nicotinamide | $^1$H NMR (400 MHz, DMSO) 13.31 (1H, s), 8.80 (2H, d, J = 4.5 Hz), 8.13 (1H, d, J = 8.6 Hz), 8.01 (2H, d, J = 4.5 Hz), 7.54 (2H, d, J = 7.6 Hz), 7.48-7.38 (3H, m), 6.89 (1H, d, J = 8.6 Hz), 5.48 (2H, s), 2.66 (3H, s); MS (ESI$^+$) 404 | Ex 20 (Scheme 2) from 6-chloro-2-methylnicotinic acid, 5-(4-pyridyl)-1,3,4-thiadiazol-2-yl amine and benzyl alcohol |
| 46 | 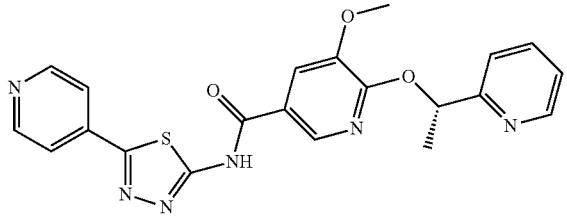<br>(S)-5-methoxy-6-(1-(pyridin-2-yl)ethoxy)-N-(5-(pyridin-4-yl)-1,3,4-thiadiazol-2-yl)nicotinamide | $^1$H NMR (400 MHz, DMSO) 13.42-13.33 (1H, m), 8.82-8.79 (2H, m), 8.61 (1H, d, J = 4.0 Hz), 8.48 (1H, d, J = 2.0 Hz), 8.06 (1H, d, J = 2.0 Hz), 8.01-7.99 (2H, m), 7.87-7.81 (1H, m), 7.46 (1H, d, J = 7.8 Hz), 7.38-7.33 (1H, m), 6.35 (1H, q, J = 6.6 Hz), 4.01-4.00 (3H, m), 1.71 (3H, d, J = 6.6 Hz); MS (ES$^+$) 435 | Ex 20 (Scheme 2) from 6-chloro-5-methoxynicotinic acid, 5-(4-pyridyl)-1,3,4-thiadiazol-2-yl amine and (S)-1-(pyridin-2-yl)ethanol |
| 47 | 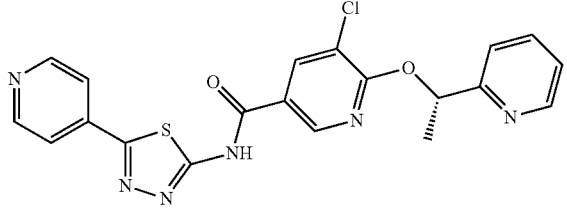<br>(S)-5-chloro-6-(1-(pyridin-2-yl)ethoxy)-N-(5-(pyridin-4-yl)-1,3,4-thiadiazol-2-yl)nicotinamide | $^1$H NMR (400 MHz, DMSO) 13.48 (1H, s), 8.84 (1H, d, J = 2.0 Hz), 8.81-8.78 (2H, m), 8.66 (1H, d, J = 2.3 Hz), 8.62 (1H, d, J = 4.8 Hz), 8.01-7.98 (2H, m), 7.90-7.85 (1H, m), 7.52 (1H, d, J = 7.8 Hz), 7.39-7.36 (1H, m), 6.38 (1H, q, J = 6.6 Hz), 1.75 (3H, d, J = 6.6 Hz); MS (ESI$^+$) 439/441 | Ex 30 step b (Scheme 2) 5,6-dichloro-N-(5-(pyridin-4-yl)-1,3,4-thiadiazol-2-yl)nicotinamide (Ex 21 step a) and (S)-1-(pyridin-2-yl)ethanol |
| 48 | 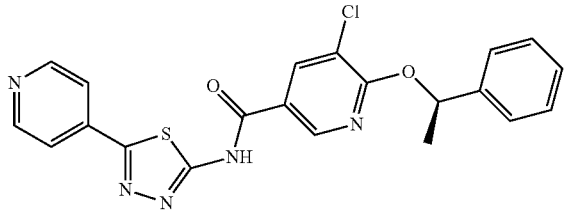<br>(R)-5-chloro-6-(1-phenylethoxy)-N-(5-(pyridin-4-yl)-1,3,4-thiadiazol-2-yl)nicotinamide | $^1$H NMR (400 MHz, DMSO) 13.43 (1H, s), 8.87 (1H, d, J = 2.3 Hz), 8.80 (2H, d, J = 6.1 Hz), 8.64 (1H, d, J = 2.3 Hz), 8.01-7.98 (2H, m), 7.52 (2H, d, J = 7.3 Hz), 7.44 (2H, dd, J = 7.5, 7.5 Hz), 7.36 (1H, dd, J = 7.3, 7.3 Hz), 6.43 (1H, q, J = 6.5 Hz), 1.71 (3H, d, J = 6.6 Hz); MS (ESI$^+$) 438/440 | Ex 21(Scheme 2) from 5,6-dichloronicotinic acid, 5-(4-pyridyl)-1,3,4-thiadiazol-2-yl amine and (R)-1-phenylethanol |

TABLE 1-continued

| Ex. | Structure and Name | Data | Method |
|---|---|---|---|
| 49 | 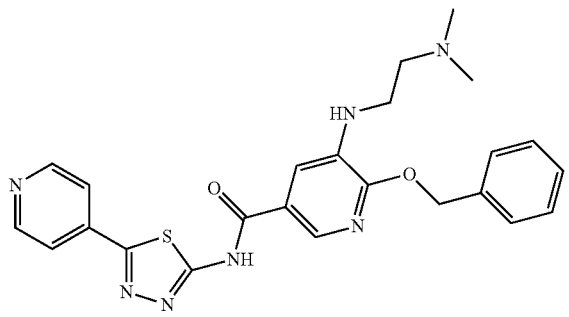<br>6-(benzyloxy)-5-((2-(dimethylamino)ethyl)amino)-N-(5-(pyridin-4-yl)-1,3,4-thiadiazol-2-yl)nicotinamide | $^{1}$H NMR (400 MHz, DMSO) 8.79-8.77 (2H, m), 8.29 (1H, d, J = 1.8 Hz), 7.98-7.96 (2H, m), 7.59 (1H, d, J = 2.0 Hz), 7.55 (2H, d, J = 7.3 Hz), 7.45 (2H, dd, J = 7.3, 7.3 Hz), 7.42-7.36 (1H, m), 5.57 (2H, s), 5.46 (1H, dd, J = 4.7, 4.7 Hz), 3.40 (2H, dd, J = 5.6, 11.1 Hz), 2.82 (2H, dd, J = 6.1, 6.1 Hz), 2.45 (6H, s); MS (ESI$^{+}$) 476 | Ex 22 (Scheme 2) from 6-(benzyloxy)-5-chloro-N-(5-(pyridin-4-yl)-1,3,4-thiadiazol-2-yl)nicotinamide (Ex23) and N,N-dimethylethylene diamine |
| 50 | 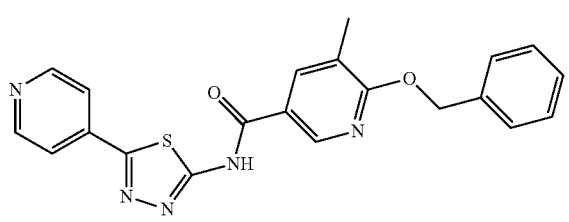<br>6-(benzyloxy)-5-methyl-N-(5-(pyridin-4-yl)-1,3,4-thiadiazol-2-yl)nicotinamide | $^{1}$H NMR (400 MHz, DMSO) 13.37 (1H, s), 8.89 (1H, d, J = 2.3 Hz), 8.82-8.79 (2H, m), 8.35 (1H, d, J = 1.5 Hz), 8.02-8.00 (2H, m), 7.54 (2H, d, J = 7.1 Hz), 7.46 (2H, dd, J = 7.2, 7.2 Hz), 7.42-7.37 (1H, m), 5.55 (2H, s), 2.32 (3H, s); MS (ESI$^{+}$) 404 | Ex 20 (Scheme 2) from 6-chloro-5-methylnicotinic acid. 5-(4-pyridyl)-1,3,4-thiadiazol-2-yl amine and benzyl alcohol |
| 51 | 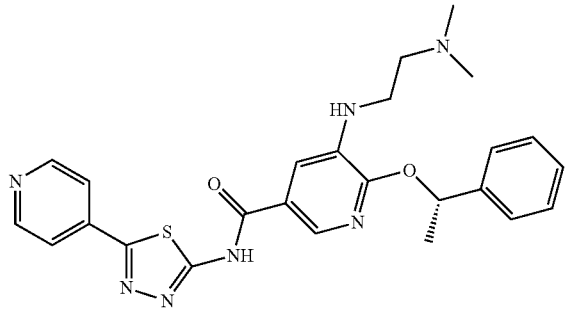<br>(S)-5-((2-(dimethylamino)ethyl)amino)-6-(1-phenylethoxy)-N-(5-(pyridin-4-yl)-1,3,4-thiadiazol-2-yl) nicotinamide | $^{1}$H NMR (400 MHz, DMSO) 8.79-8.76 (2H, m), 8.20 (1H, d, J = 2.0 Hz), 7.97-7.95 (2H, m), 7.56-7.51 (3H, m), 7.41 (2H, dd, J = 7.5, 7.5 Hz), 7.32 (1H, dd, J = 7.3, 7.3 Hz), 6.40 (1H, q, J = 6.6 Hz), 5.53 (1H, dd, J = 4.9, 4.9 Hz), 3.44-3.35 (2H, m), 2.83-2.76 (2H, m), 2.44 (6H, s), 1.67 (3H, d, J = 6.6 Hz); MS (ESI$^{+}$) 490 | Ex22 (Scheme 2) from (S)-5-chloro-6-(1-phenylethoxy)-N-(5-(pyridin-4-yl)-1,3,4-thiadiazol-2-yl)nicotinamide (Ex 21) and N,N-dimethylethylene diamine |
| 52 | 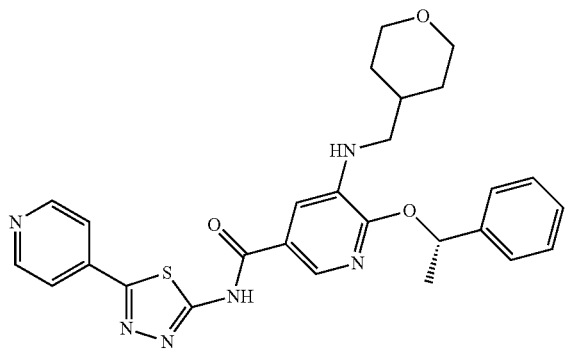<br>(S)-6-(1-phenylethoxy)-N-(5-(pyridin-4-yl)-1,3,4-thiadiazol-2-yl)-5-(((tetrahydro-2H-pyran-4-yl)methyl)amino)nicotinamide | $^{1}$H NMR (400 MHz, CDCl$_{3}$) 8.75-8.73 (2H, m), 8.42 (1H, d, J = 2.3 Hz), 7.89-7.87 (2H, m), 7.46-7.42 (2H, m), 7.39-7.30 (4H, m), 6.49 (1H, q, J = 6.6 Hz), 4.54 (1H, dd, J = 5.9, 5.9 Hz), 4.00 (2H, dd, J = 3.7, 11.2 Hz), 3.40 (2H, dd, J = 11.7, 11.7 Hz), 3.12 (2H, dd, J = 6.4, 6.4 Hz), 1.96-1.86 (1H, m), 1.75 (3H, d, J = 6.6 Hz), 1.69 (2H, td, J = 2.0, 13.2 Hz), 1.44-1.32 (2H, m); MS (ESI$^{+}$) 517 | Ex 22 (Scheme 2) from (S)-5-chloro-6-(1-phenylethoxy)-N-(5-(pyridin-4-yl)-1,3,4-thiadiazol-2-yl)nicotinamide (Ex 21) and (tetrahydro-2H-pyran-4-yl)methanamine |

TABLE 1-continued

| Ex. | Structure and Name | Data | Method |
|---|---|---|---|
| 53 | 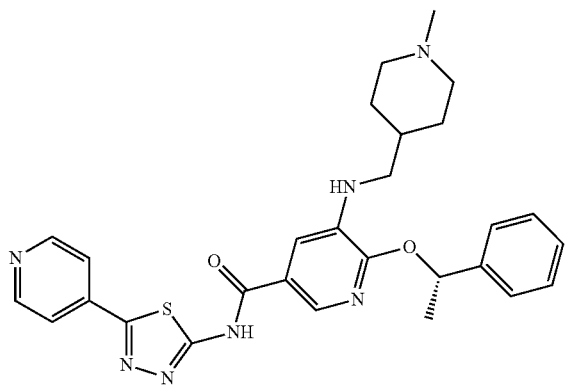<br>(S)-5-(((1-methylpiperidin-4-yl)methyl)amino)-6-(1-phenylethoxy)-N-(5-(pyridin-4-yl)-1,3,4-thiadiazol-2-yl)nicotinamide | $^1$H NMR (400 MHz, CDCl$_3$) 8.75-8.72 (2H, m), 8.38 (1H, d, J = 2.0 Hz), 7.89-7.86 (2H, m), 7.46-7.42 (2H, m), 7.36 (2H, dd, J = 7.3, 7.3 Hz), 7.32-7.28 (2H, m), 6.48 (1H, q, J = 6.6 Hz), 4.52 (1H, dd, J = 5.8, 5.8 Hz), 3.10 (2H, dd, J = 6.3, 6.3 Hz), 2.92-2.83 (2H, m), 2.28 (3H, s), 1.97-1.88 (2H, m), 1.78-1.73 (5H, m), 1.66-1.58 (1H, m), 1.41-1.30 (2H, m); MS (ESI$^+$) 530 | Ex 53 (Scheme 2) from (S)-5-chloro-6-(1-phenylethoxy)-N-(5-(pyridin-4-yl)-1,3,4-thiadiazol-2-yl)nicotinamide (Ex 21) and (1-methylpiperidin-4-yl)methanamine |
| 54 | 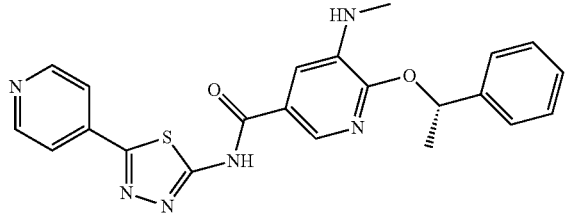<br>(S)-5-(methylamino)-6-(1-phenylethoxy)-N-(5-(pyridin-4-yl)-1,3,4-thiadiazol-2-yl)nicotinamide | $^1$H NMR (400 MHz, DMSO) 13.22 (1H, s), 8.81-8.78 (2H, m), 8.17 (1H, d, J = 2.0 Hz), 8.00-7.98 (2H, m), 7.55 (2H, d, J = 7.3 Hz), 7.44-7.38 (3H, m), 7.32 (1H, dd, J = 7.3, 7.3 Hz), 6.41 (1H, q, J = 6.5 Hz), 5.81 (1H, q, J = 4.8 Hz), 2.89 (3H, d, J = 5.1 Hz), 1.66 (3H, d, J = 6.6 Hz); MS (ESI$^+$) 433 | Ex 22 (Scheme 2) from (S)-5-chloro-6-(1-phenylethoxy)-N-(5-(pyridin-4-yl)-1,3,4-thiadiazol-2-yl)nicotinamide (Example 21) |
| 55 | 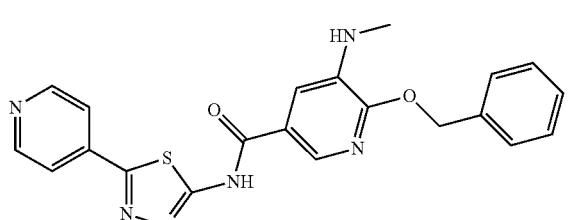<br>6-(benzyloxy)-5-(methylamino)-N-(5-(pyridin-4-yl)-1,3,4-thiadiazol-2-yl)nicotinamide | $^1$H NMR (400 MHz, DMSO) 13.28 (1H, s), 8.81-8.79 (2H, m), 8.27 (1H, d, J = 2.3 Hz), 8.01-7.99 (2H, m), 7.57 (2H, d, J = 7.1 Hz), 7.48-7.43 (3H, m), 7.41-7.36 (1H, m), 5.76-5.70 (1H, m), 5.56 (2H, s), 2.87 (3H, d, J = 4.8 Hz); MS (ESI$^+$) 419 | Ex 22 (Scheme 2) from 6-(benzyloxy)-5-chloro-N-(5-(pyridin-4-yl)-1,3,4-thiadiazol-2-yl)nicotinamide (Example 23) |
| 56 | 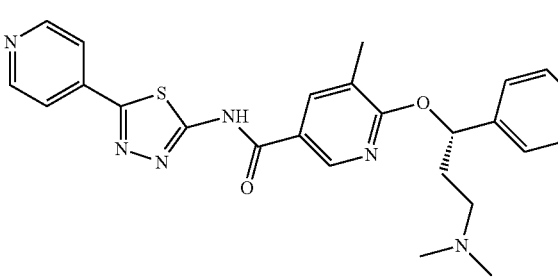<br>(S)-6-(3-(dimethylamino)-1-phenylpropoxy)-5-methyl-N-(5-(pyridin-4-yl)-1,3,4-thiadiazol-2-yl)nicotinamide | $^1$H NMR (400 MHz, DMSO) 8.74-8.69 (3H, m), 8.29 (1H, d, J = 1.5 Hz), 7.92-7.90 (2H, m), 7.49 (2H, d, J = 7.3 Hz), 7.42 (2H, dd, J = 7.6, 7.6 Hz), 7.33 (1H, dd, J = 7.2, 7.2 Hz), 6.35 (1H, dd, J = 5.2, 8.0 Hz), 2.73 (2H, dd, J = 7.5, 7.5 Hz), 2.47 (6H, s), 2.37 (3H, s), 2.35-2.25 (1H, m), 2.20-2.10 (1H, m); MS (ESI$^+$) 475 | Ex 26 step b (Scheme 2) from 6-chloro-5-methyl-N-(5-(pyridin-4-yl)-1,3,4-thiadiazol-2-yl)nicotinamide (Ex 20 step a) and (S)-3-(dimethylamino)-1-phenylpropan-1-ol oxalate (Ex 26 step a) |

TABLE 1-continued

| Ex. | Structure and Name | Data | Method |
|---|---|---|---|
| 57 | 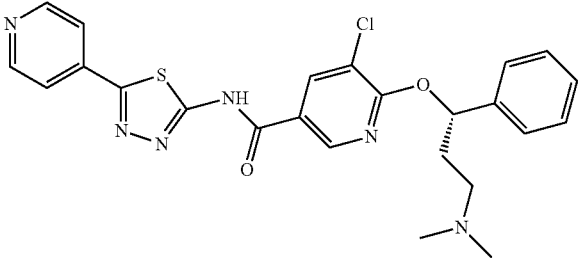<br>(S)-5-chloro-6-(3-(dimethylamino)-1-phenylpropoxy)-N-(5-(pyridin-4-yl)-1,3,4-thiadiazol-2-yl)nicotinamide | $^1$H NMR (400 MHz, DMSO) 8.78 (1H, d, J = 2.0 Hz), 8.72-8.69 (2H, m), 8.53 (1H, d, J = 2.0 Hz), 7.89-7.86 (2H, m), 7.52 (2H, d, J = 7.1 Hz), 7.45 (2H, dd, J = 7.6, 7.6 Hz), 7.36 (1H, dd, J = 7.3, 7.3 Hz), 6.39 (1H, dd, J = 5.2, 8.0 Hz), 2.97-2.90 (2H, m), 2.63 (6H, s), 2.45-2.35 (1H, m), 2.31-2.22 (1H, m); MS (ESI$^+$) 495/497 | Ex 21 (Scheme 2) from 5,6-dichloronicotinic acid, 5-(4-pyridyl)-1,3,4-thiadiazol-2-yl amine & (S)-3 (dimethylamino)-1-phenylpropan-1-ol (Ex 26 step a) |
| 58 | 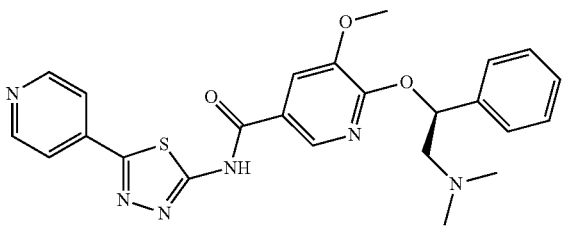<br>(S)-6-(2-(dimethylamino)-1-phenylethoxy)-5-methoxy-N-(5-(pyridin-4-yl)-1,3,4-thiadiazol-2-yl)nicotinamide | $^1$H NMR (400 MHz, DMSO) 8.78-8.76 (2H, m), 8.45 (1H, d, J = 2.0 Hz), 8.03 (1H, d, J = 2.0 Hz), 7.97-7.95 (2H, m), 7.49 (2H, d, J = 7.3 Hz), 7.41 (2H, dd, J = 7.5, 7.5 Hz), 7.36-7.31 (1H, m), 6.52 (1H, dd, J = 3.8, 8.8 Hz), 4.00 (3H, s), 3.14 (1H, dd, J = 9.2, 12.8 Hz), 2.87-2.80 (1H, m), 2.43 (6H, s); MS (ESI$^+$) 475 | Ex 20 (Scheme 2) From 6-chloro-5-methoxynicotinic acid, 5-(4-pyridyl)-1,3,4-thiadiazol-2-yl amine & (S)-2-(dimethylamino)-1-phenylethanol (according to Example 6 step a starting from (S)-2-amino-1-phenylethanol) |
| 59 | 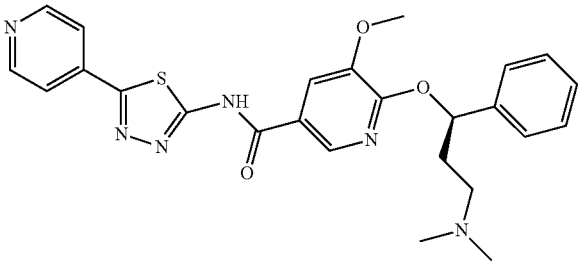<br>(R)-6-(3-(dimethylamino)-1-phenylpropoxy)-5-methyl-N-(5-(pyridin-4-yl)-1,3,4-thiadiazol-2-yl)nicotinamide | $^1$H NMR (400 MHz, CDCl$_3$) 8.77-8.74 (2H, m), 8.64 (1H, d, J = 2.0 Hz), 7.85-7.82 (2H, m), 7.73 (1H, d, J = 2.0 Hz), 7.45 (2H, d, J = 7.3 Hz), 7.31 (2H, dd, J = 7.3, 7.3 Hz), 7.28-7.23 (1H, m), 6.44 (1H, dd, J = 6.7, 6.7 Hz), 3.93 (3H, s), 2.54-2.52 (2H, m), 2.47-2.37 (1H, m), 2.34 (6H, s), 2.24-2.18 (1H, m); MS (ESI$^+$) 491 | Ex 26 (Scheme 2) from 6-chloro-5-methoxy-N-(5-pyridin-4-yl)-1,3,4-thiadiazol-2-yl)nicotinamide (Example 25 step a) and (R)-3-choro-1-phenylpropan-1-ol) |
| 60 | 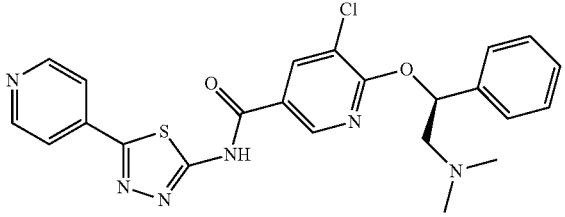<br>(S)-5-chloro-6-(2-(dimethylamino)-1-phenylethoxy)-N-(5-(pyridin-4-yl)-1,3,4-thiadiazol-2-yl)nicotinamide | $^1$H NMR (400 MHz, CDCl$_3$) 8.79-8.75 (3H, m), 8.34 (1H, d, J = 2.0 Hz), 7.84-7.82 (2H, m), 7.48-7.44 (2H, m), 7.34 (2H, dd, J = 7.3, 7.3 Hz), 7.30-7.27 (1H, m), 6.63 (1H, dd, J = 2.9, 9.2 Hz), 3.24 (1H, dd, J = 9.5, 13.5 Hz), 2.71 (1H, dd, J = 3.3, 13.6 Hz), 2.48 (6H, s); MS: (ESI$^+$) 479/481 | Ex 30 step b (Scheme 2) 5,6-dichloro-N-(5-(pyridin-4-yl)-1,3,4-thiadiazol-2-yl)nicotinamide (Example 21 step a) & (S)-2-(dimethylamino)-1-phenylethanol (Ex 6 step a starting from (S)-2-amino-1-phenylethanol) |

TABLE 1-continued

| Ex. | Structure and Name | Data | Method |
|---|---|---|---|
| 61 | 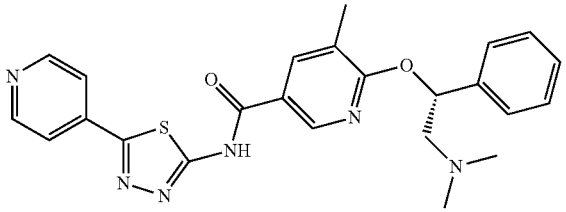<br>(R)-6-(2-(dimethylamino)-1-phenylethoxy)-5-methyl-N-(5-(pyridin-4-yl)-1,3,4-thiadiazol-2-yl)nicotinamide | $^1$H NMR (400 MHz, DMSO) 8.78-8.75 (2H, m), 8.73 (1H, d, J = 2.0 Hz), 8.31 (1H, d, J = 1.5 Hz), 7.97-7.94 (2H, m), 7.50 (2H, d, J = 7.1 Hz), 7.41 (2H, dd, J = 7.5, 7.5 Hz), 7.35-7.31 (1H, m), 6.51 (1H, dd, J = 3.9, 8.7 Hz), 3.13 (1H, dd, J = 8.7, 13.5 Hz), 2.86 (1H, dd, J = 3.5, 13.1 Hz), 2.44 (6H, s), 2.38 (3H, s); MS (ESI$^+$) 461 | Ex 20 (Scheme 2) From 6-chloro-5-methylnicotinic acid, 5-(4-pyridyl)-1,3,4-thiadiazol-2-yl amine and (R)-2-(dimethylamino)-1-phenylethanol (Ex 6 step a) |
| 62 | 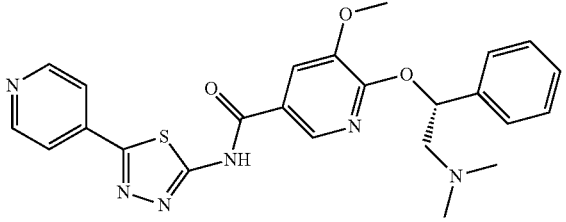<br>(R)-6-(2-(dimethylamino)-1-phenylethoxy)-5-methoxy-N-(5-(pyridin-4-yl)-1,3,4-thiadiazol-2-yl)nicotinamide | $^1$H NMR (400 MHz, DMSO) 8.78-8.76 (2H, m), 8.46 (1H, d, J = 2.0 Hz), 8.03 (1H, d, J = 2.0 Hz), 7.97-7.95 (2H, m), 7.49 (2H, d, J = 7.1 Hz), 7.41 (2H, dd, J = 7.3, 7.3 Hz), 7.35-7.31 (1H, m), 6.52 (1H, dd, J = 3.8, 8.8 Hz), 4.00 (3H, s), 3.14 (1H, dd, J = 9.1, 13.1 Hz), 2.83 (1H, dd, J = 4.0, 13.3 Hz), 2.43 (6H, s); MS (ESI$^+$) 477 | Ex 20 (Scheme 2) from 6-chloro-5-methoxynicotinic acid, 5-(4-pyridyl)-1,3,4-thiadiazol-2-yl amine & (R)-2-(dimethylamino)-1-phenylethanol (Ex 6 step a) |
| 63 | 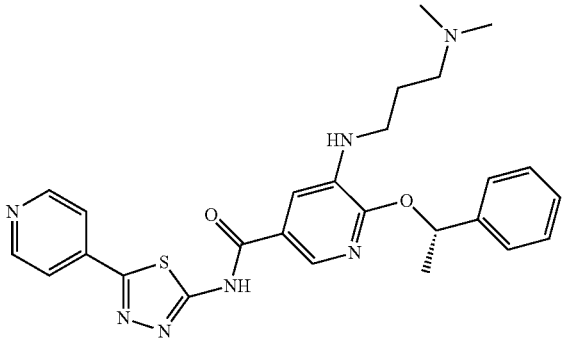<br>(S)-5-((3-(dimethylamino)propyl)amino)-6-(1-phenylethoxy)-N-(5-(pyridin-4-yl)-1,3,4-thiadiazol-2-yl)nicotinamide | $^1$H NMR (400 MHz, DMSO) 8.77-8.74 (2H, m), 8.16 (1H, d, J = 2.0 Hz), 7.95-7.92 (2H, m), 7.54 (2H, d, J = 7.3 Hz), 7.50 (1H, d, J = 2.0 Hz), 7.41 (2H, dd, J = 7.6, 7.6 Hz), 7.32 (1H, dd, J = 7.2, 7.2 Hz), 6.39 (1H, q, J = 6.5 Hz), 5.93 (1H, s), 3.30 (2H, dd, J = 6.3, 6.3 Hz), 2.66 (2H, dd, J = 6.8, 6.8 Hz), 2.42 (6H, s), 1.95-1.86 (2H, m), 1.66 (3H, d, J = 6.6 Hz); MS (ESI$^+$) 504 | Ex 22 (Scheme 2) from (S)-5-chloro-6-(1-phenylethoxy)-N-(5-(pyridin-4-yl)-1,3,4-thiadiazol-2-yl)nicotinamide (Ex 21) & N,N-dimethylpropylene diamine |
| 64 | 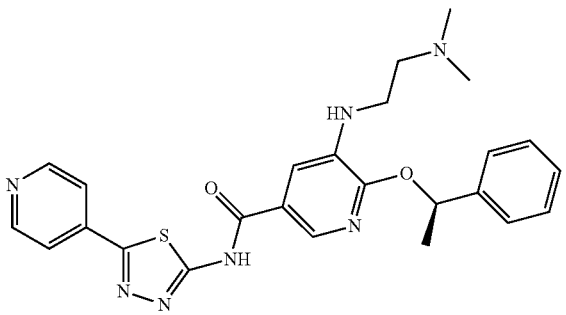<br>(R)-5-((2-(dimethylamino)ethyl)amino)-6-(1-phenylethoxy)-N-(5-(pyridin-4-yl)-1,3,4-thiadiazol-2-yl)nicotinamide | $^1$H NMR (400 MHz, DMSO) 8.82-8.79 (2H, m), 8.23 (1H, d, J = 2.0 Hz), 8.00-7.98 (2H, m), 7.60-7.54 (3H, m), 7.44 (2H, dd, J = 7.5, 7.5 Hz), 7.36 (1H, dd, J = 7.3, 7.3 Hz), 6.44 (1H, q, J = 6.5 Hz), 5.53 (1H, dd, J = 5.4, 5.4 Hz), 3.45-3.37 (2H, m), 2.83-2.76 (2H, m), 2.46 (6H, s), 1.70 (3H, d, J = 6.3 Hz); MS (ESI$^+$) 490 | Ex 22 (Scheme 2) from (R)-5-chloro-6-(1-phenylethoxy)-N-(5-(pyridin-4-yl)-1,3,4-thiadiazol-2-yl)nicotinamide (Ex 48) & N,N-dimethylethylene diamine |

TABLE 1-continued

| Ex. | Structure and Name | Data | Method |
|---|---|---|---|
| 65 | 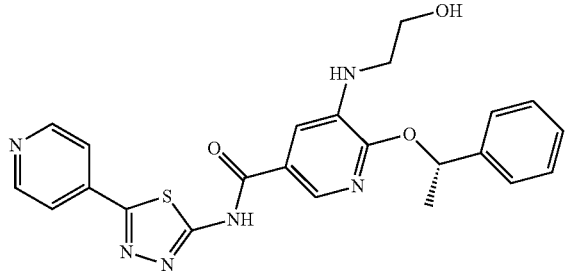<br>(S)-5-((2-hydroxyethyl)amino)-6-(1-phenylethoxy)-N-(5-(pyridin-4-yl)-1,3,4-thiadiazol-2-yl)nicotinamide | $^1$H NMR (400 MHz, DMSO) 13.23 (1H, s), 8.79 (2H, d, J = 6.1 Hz), 8.18 (1H, d, J = 2.0 Hz), 8.00-7.97 (2H, m), 7.57-7.52 (3H, m), 7.41 (2H, dd, J = 7.5, 7.5 Hz), 7.33 (1H, dd, J = 7.3, 7.3 Hz), 6.41 (1H, q, J = 6.6 Hz), 5.48 (1H, dd, J = 5.7, 5.7 Hz), 4.92 (1H, dd, J = 5.4, 5.4 Hz), 3.72 (2H, q, J = 5.6 Hz), 3.35-3.32 (2H, m), 1.68 (3H, d, J = 6.6 Hz); MS (ESI$^+$) 463 | Ex 22 (Scheme 2) from (S)-5-chloro-6-(1-phenylethoxy)-N-(5-(pyridin-4-yl)-1,3,4-thiadiazol-2-yl)nicotinamide (Example 21) and 2-aminoethanol |
| 66 | 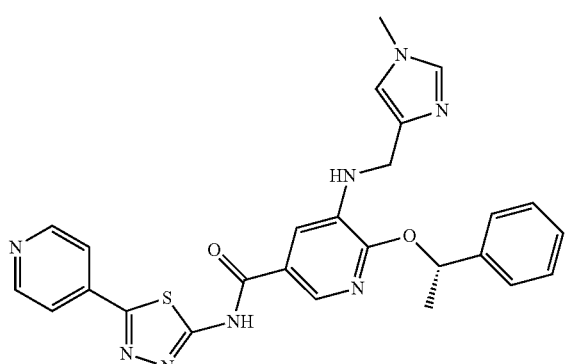<br>(S)-6-(((1-methyl-1H-imidazol-4-yl)methyl)amino)-6-(1-phenylethoxy)-N-(5-(pyridin-4-yl)-1,3,4-thiadiazol-2-yl)nicotinamide | $^1$H NMR (400 MHz, DMSO) 8.80-8.78 (2H, m), 8.19 (1H, d, J = 2.0 Hz), 7.99-7.97 (2H, m), 7.60-7.58 (2H, m), 7.54 (2H, d, J = 7.1 Hz), 7.41 (2H, dd, J = 7.5,7.5 Hz), 7.35-7.30 (1H, m), 7.03 (1H, s), 6.41 (1H, q, J = 6.4 Hz), 5.82 (1H, dd, J = 5.7, 5.7 Hz), 4.35 (2H, d, J = 5.8 Hz), 3.65 (3H, s), 1.68 (3H, d, J = 6.6 Hz); MS (ESI$^+$) 513 | Ex 22 (Scheme 2) from (S)-5-chloro-6-(1-phenylethoxy)-N-(5-(pyridin-4-yl)-1,3,4-thiadiazol-2-yl)nicotinamide (Ex 21) and (1-methyl-1H-imidazol-4-yl)methanamine hydrochloride |
| 67 | 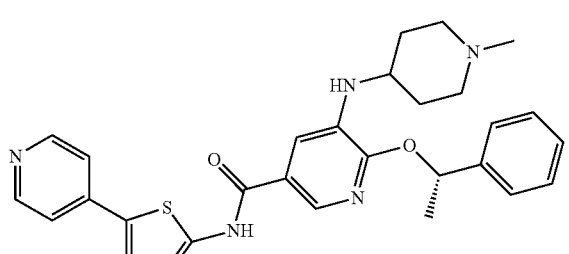<br>(S)-5-((1-methylpiperidin-4-yl)amino)-6-(1-phenylethoxy)-N-(5-(pyridin-4-yl)-1,3,4-thiadiazol-2-yl)nicotinamide | $^1$H NMR (400 MHz, CDCl$_3$) 8.75-8.73 (2H, m), 8.39 (1H, d, J = 2.3 Hz), 7.89-7.87 (2H, m), 7.45-7.41 (2H, m), 7.38-7.34 (2H, m), 7.32-7.29 (2H, m), 6.46 (1H, q, J = 6.6 Hz), 4.37 (1H, d, J = 7.8 Hz), 3.41-3.32 (1H, m), 2.82-2.76 (2H, m), 2.31 (3H, s), 2.19-2.00 (4H, m), 1.74 (3H, d, J = 6.6 Hz), 1.65-1.52 (2H, m); MS (ESI$^+$) 516 | Ex 22 (Scheme 2) from (S)-5-chloro-6-(1-phenylethoxy)-N-(5-(pyridin-4-yl)-1,3,4-thiadiazol-2-yl)nicotinamide (Ex 21) and 1-methylpiperidin-4-amine |

TABLE 1-continued

| Ex. | Structure and Name | Data | Method |
|---|---|---|---|
| 68 | 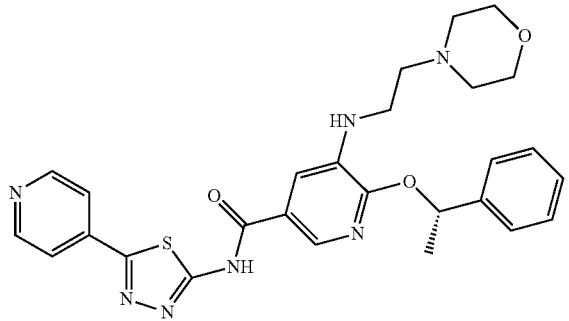<br>(S)-5-((2-morpholinoethyl)amino)-6-(1-phenylethoxy)-N-(5-(pyridin-4-yl)-1,3,4-thiadiazol-2-yl)nicotinamide | $^1$H NMR (400 MHz, CDCl$_3$) 11.67 (1H, s), 8.74 (2H, d, J = 6.1 Hz), 8.41 (1H, d, J = 2.3 Hz), 7.89-7.86 (2H, m), 7.48 (2H, d, J = 7.6 Hz), 7.38 (2H, dd, J = 7.5, 7.5 Hz), 7.34-7.30 (2H, m), 6.45 (1H, q, J = 6.5 Hz), 5.24 (1H, dd, J = 4.7, 4.7 Hz), 3.70 (4H, d, J = 2.8 Hz), 3.27-3.19 (2H, m), 2.74-2.61 (2H, m), 2.48 (4H, dd, J = 4.3, 4.3 Hz), 1.75 (3H, d, J = 6.3 Hz); MS (ESI$^+$) 532 | Ex 22 (Scheme 2) from (S)-5-chloro-6-(1-phenylethoxy (5-(pyridin-4-yl)-1,3,4-thiadiazol-2-yl)nicotinamide (Ex 21) and 2-morpholino ethanamine |
| 69 | 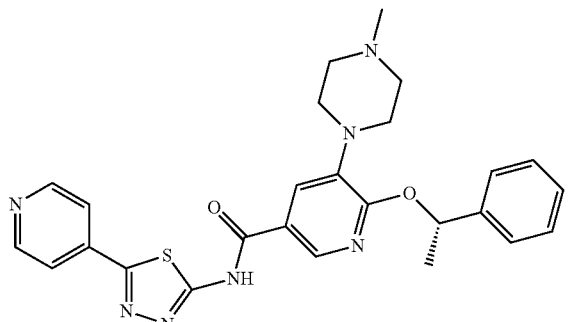<br>(S)-5-(4-methylpiperazin-1-yl)-6-(1-phenylethoxy)-N-(5-(pyridin-4-yl)-1,3,4-thiadiazol-2-yl)nicotinamide | $^1$H NMR (400 MHz, DMSO) 8.75-8.72 (2H, m), 8.51 (1H, d, J = 2.0 Hz), 7.94-7.91 (3H, m), 7.50 (2H, d, J = 7.1 Hz), 7.41 (2H, dd, J = 7.6, 7.6 Hz), 7.35-7.31 (1H, m), 6.34 (1H, q, J = 6.4 Hz), 3.27-3.23 (4H, m), 2.90-2.86 (4H, m), 2.50 (3H, s), 1.65 (3H, d, J = 6.6 Hz); MS (ESI$^+$) 502 | Ex24 (Scheme 2) from (S)-5-chloro-6-(1-phenylethoxy)-N-(5-(pyridin-4-yl)-1,3,4-thiadiazol-2-yl)nicotinamide (Ex 21) |
| 70 | 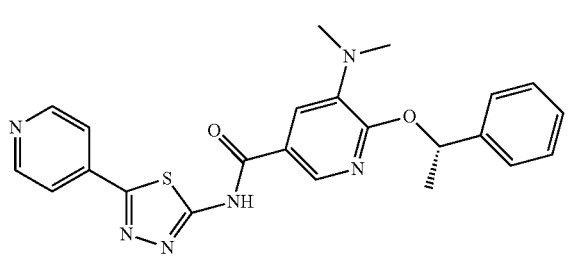<br>(S)-5-(dimethylamino)-6-(1-phenylethoxy)-N-(5-(pyridin-4-yl)-1,3,4-thiadiazol-2-yl)nicotinamide | $^1$H NMR (400 MHz, DMSO) 13.36 (1H, s), 8.81-8.78 (2H, m), 8.47 (1H, d, J = 2.3 Hz), 8.00-7.98 (2H, m), 7.85 (1H, d, J = 2.0 Hz), 7.53 (2H, d, J = 7.3 Hz), 7.43 (2H, dd, J = 7.6, 7.6 Hz), 7.34 (1H, dd, J = 7.3, 7.3 Hz), 6.42 (1H, q, J = 6.6 Hz), 2.93 (6H, s), 1.70 (3H, d, J = 6.6 Hz); MS (ESI$^+$) 447 | Ex 24 (Scheme 2) from (S)-5-chloro-6-(1-phenylethoxy)-N-(5-(pyridin-4-yl)-1,3,4-thiadiazol-2-yl)nicotinamide (Ex 21) |
| 71 | 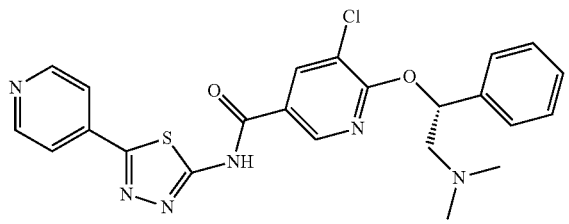<br>(R)-5-chloro-6-(2-(dimethylamino)-1-phenylethoxy)-N-(5-(pyridin-4-yl)-1,3,4-thiadiazol-2-yl)nicotinamide | $^1$H NMR (400 MHz, DMSO) 8.77 (1H, d, J = 2.0 Hz), 8.71 (2H, d, J = 5.8 Hz), 8.54 (1H, d, J = 2.0 Hz), 7.89 (2H, d, J = 6.1 Hz), 7.52 (2H, d, J = 7.3 Hz), 7.44 (2H, dd, J = 7.5, 7.5 Hz), 7.37 (1H, dd, J = 7.2, 7.2 Hz), 6.61 (1H, dd, J = 2.9, 9.7 Hz), 3.53-3.45 (1H, m), 3.23-3.19 (1H, m), 2.69 (6H, s); MS (ESI$^+$) 481/483 | Ex 30 step b (Scheme 2) 5,6-dichloro-N-(5-(pyridin-4-yl)-1,3,4-thiadiazol-2-yl)nicotinamide (Ex 21 step a) and (R)-2-(dimethylamino)-1-phenylethanol (Ex 26 step a) |

TABLE 1-continued

| Ex. | Structure and Name | Data | Method |
|---|---|---|---|
| 72 | 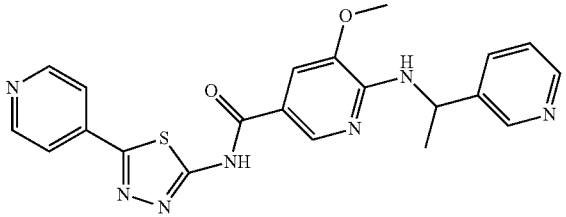<br>5-methoxy-6-((1-(pyridin-3-yl)ethyl)amino)-N-(5-(pyridin-4-yl)-1,3,4-thiadiazol-2-yl)nicotinamide | $^1$H NMR (400 MHz, DMSO) 13.02 (1H, s), 8.79 (2H, d, J = 6.1 Hz), 8.68 (1H, d, J = 2.0 Hz), 8.50-8.45 (2H, m), 7.99-7.97 (2H, m), 7.88-7.86 (1H, m), 7.76 (1H, d, J = 1.8 Hz), 7.45 (1H, d, J = 8.1 Hz), 7.38 (1H, dd, J = 4.8, 7.8 Hz), 5.51-5.46 (1H, m), 4.00 (3H, s), 1.61 (3H, d, J = 7.1 Hz); MS (ESI$^+$) 434 | Ex 25 (Scheme 3) from 6-chloro-5-methoxy-N-(5-(pyridin-4-yl)-1,3,4-thiadiazol-2-yl)nicotinamide and 1-(pyridin-3-yl)ethanamine |
| 73 | 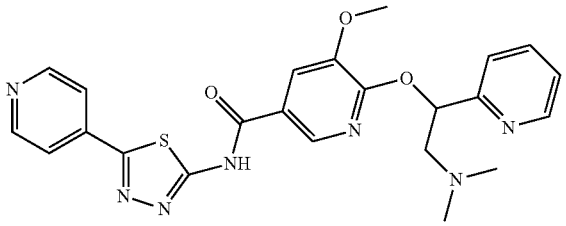<br>6-(2-(dimethylamino)-1-(pyridin-2-yl)ethoxy)-5-methoxy-N-(5-(pyridin-4-yl)-1,3,4-thiadiazol-2-yl)nicotinamide | $^1$H NMR (400 MHz, CDCl$_3$) 8.80-8.77 (2H, m), 8.59-8.54 (2H, m), 7.85-7.82 (2H, m), 7.67 (1H, d, J = 1.8 Hz), 7.64-7.59 (1H, m), 7.42 (1H, d, J = 7.8 Hz), 7.18-7.14 (1H, m), 6.66 (1H, dd, J = 3.0, 9.3 Hz), 3.87 (3H, s), 3.26 (1H, dd, J = 9.4, 13.4 Hz), 2.97 (1H, dd, J = 3.3, 13.4 Hz), 2.46 (6H, s); MS (ESI$^+$) 478 | Ex 30 (Scheme 2) from 6-chloro-5-methoxynicotinic acid (Example 25 step a) and 2-(dimethylamino)-1-(pyridin-2-yl)ethanol |
| 74 | 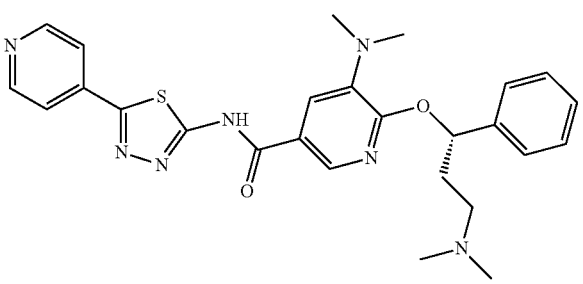<br>(S)-5-(dimethylamino)-6-(3-(dimethylamino)-1-phenylpropoxy)-N-(5-(pyridin-4-yl)-1,3,4-thiadiazol-2-yl)nicotinamide | $^1$H NMR (400 MHz, DMSO) 8.75-8.73 (2H, m), 8.41 (1H, d, J = 2.0 Hz), 7.94-7.91 (2H, m), 7.87 (1H, d, J = 2.0 Hz), 7.50 (2H, d, J = 7.3 Hz), 7.42 (2H, dd, J = 7.6, 7.6 Hz), 7.33 (1H, dd, J = 7.2, 7.2 Hz), 6.41-6.36 (1H, m), 2.92 (6H, s), 2.66 (2H, t, J = 7.0 Hz), 2.44 (6H, s), 2.41-2.31 (1H, m), 2.22-2.12 (1H, m); MS (ESI$^+$) 504 | Ex 24 (Scheme 2) from (S)-5-chloro-6-(3-(dimethylamino)-1-phenylpropoxy)-N-(5-(pyridin-4-yl)-1,3,4-thiadiazol-2-yl)nicotinamide (Ex 57) |
| 75 | 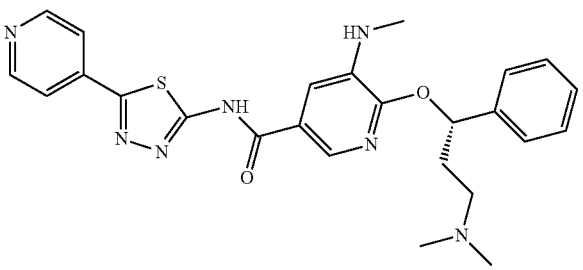<br>(S)-6-(3-(dimethylamino)-1-phenylpropoxy)-5-(methylamino)-N-(5-(pyridin-4-yl)-1,3,4-thiadiazol-2-yl)nicotinamide | $^1$H NMR (400 MHz, DMSO) 8.76-8.74 (2H, m), 8.11 (1H, d, J = 2.0 Hz), 7.95-7.92 (2H, m), 7.52 (2H, d, J = 7.3 Hz), 7.44-7.37 (3H, m), 7.31 (1H, dd, J = 7.3, 7.3 Hz), 6.34 (1H, dd, J = 5.2, 8.0 Hz), 5.86-5.80 (1H, m), 2.90 (3H, d, J = 4.8 Hz), 2.65-2.58 (2H, m), 2.38 (6H, s), 2.32-2.22 (1H, m), 2.13-2.03 (1H, m); MS (ESI$^+$) 490 | Ex 22 (Scheme 2) from (S)-5-chloro-6-(3-(dimethylamino)-1-phenylpropoxy)-N-(5-(pyridin-4-yl)-1,3,4-thiadiazol-2-yl)nicotinamide (Ex 57) |

TABLE 1-continued

| Ex. | Structure and Name | Data | Method |
|---|---|---|---|
| 76 | 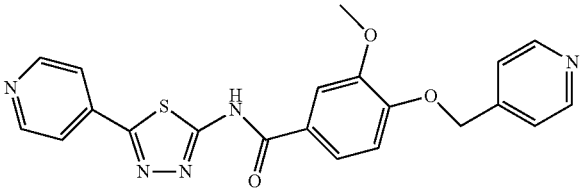<br>3-methoxy-N-(5-(pyridin-4-yl)-1,3,4-thiadiazol-2-yl)-4-(pyridin-4-ylmethoxy)benzamide | $^1$H NMR (400 MHz, DMSO) 8.74 (2H, dd, J = 1.6, 4.4 Hz), 8.61 (2H, dd, J = 1.5, 4.5 Hz), 7.94 (2H, dd, J = 1.5, 4.5 Hz), 7.85 (1H, d, J = 2.0 Hz), 7.80 (1H, dd, J = 2.0, 8.6 Hz), 7.45 (2H, d, J = 5.8 Hz), 7.19 (1H, d, J = 8.6 Hz), 5.31 (2H, s), 3.93 (3H, s); MS (ESI$^+$) 420 | Ex 4 (Scheme 1) from methyl 4-hydroxy-3-methoxybenzoate, pyridin-4-ylmethanol and 5-(4-pyridyl)-1,3,4-thiadiazol-2-yl amine |
| 77 | 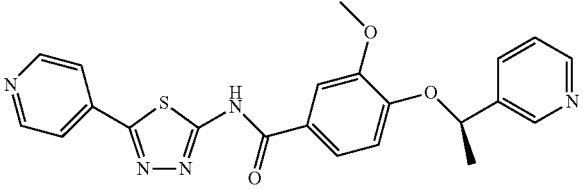<br>(R)-3-methoxy-4-(1-(pyridin-3-yl)ethoxy)-N-(5-(pyridin-4-yl)-1,3,4-thiadiazol-2-yl)benzamide | $^1$H NMR (400 MHz, DMSO) 8.75 (2H, dd, J = 1.2, 4.7 Hz), 8.71 (1H, d, J = 1.8 Hz), 8.54 (1H, dd, J = 1.3, 4.8 Hz), 7.93 (2H, dd, J = 1.2, 4.8 Hz), 7.88 (1H, ddd, J = 1.6, 1.6, 7.9 Hz), 7.84 (1H, d, J = 1.7 Hz), 7.70 (1H, dd, J = 1.9, 8.5 Hz), 7.44 (1H, dd, J = 4.8, 7.6 Hz), 7.08 (1H, d, J = 8.6 Hz), 5.77 (1H, q, J = 6.3 Hz), 3.96 (3H, s), 1.67 (3H, d, J = 6.3 Hz); MS (ESI$^+$) 434 | Ex 4 (Scheme 1) from methyl 4-hydroxy-3-methoxybenzoate, (R)-1-(pyridin-3-yl)ethanol and 5-(4-pyridyl)-1,3,4-thiadiazol-2-yl amine |
| 78 | 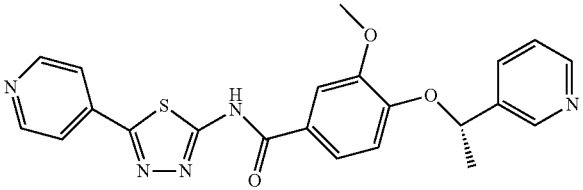<br>(S)-3-methoxy-4-(1-(pyridin-3-yl)ethoxy)-N-(5-(pyridin-4-yl)-1,3,4-thiadiazol-2-yl)benzamide | $^1$H NMR (400 MHz, DMSO) 13.24 (1H, s), 8.79 (2H, d, J = 5.1 Hz), 8.72 (1H, s), 8.55 (1H, d, J = 4.3 Hz), 7.99 (2H, d, J = 5.3 Hz), 7.91-7.84 (2H, m), 7.73 (1H, d, J = 8.3 Hz), 7.45 (1H, dd, J = 4.8, 7.6 Hz), 7.14 (1H, d, J = 8.6 Hz), 5.82 (1H, q, J = 6.0 Hz), 3.98 (3H, s), 1.69 (3H, d, J = 6.1 Hz); MS (ESI$^+$) 434 | Ex 4 (Scheme 1) from methyl 4-hydroxy-3-methoxybenzoate, (S)-1-(pyridin-3-yl)ethanol and 5-(4-pyridyl)-1,3,4-thiadiazol-2-yl amine |
| 79 | 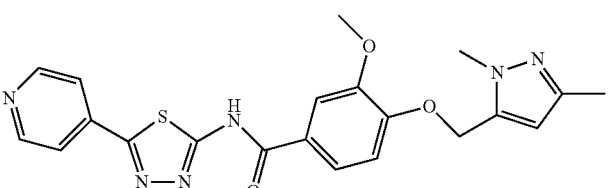<br>4-((1,3-dimethyl-1H-pyrazol-5-yl)methoxy)-3-methoxy-N-(5-(pyridin-4-yl)-1,3,4-thiadiazol-2-yl)benzamide | $^1$H NMR (400 MHz, DMSO) 8.66 (2H, d, J = 5.1 Hz), 7.87-7 77 (4H, m), 7.18 (1H, d, J = 8.3 Hz), 6.20 (1H, s), 5.17 (2H, s), 3.88 (3H, s), 3.82 (3H, s), 2.18 (3H, s); MS (ESI$^+$) 437 | Ex 4 (Scheme 1) from methyl 4-hydroxy-3-methoxybenzoate, (1,3-dimethyl-1H-pyrazol-5-yl)methanol and 5-(4-pyridyl)-1,3,4-thiadiazol-2-yl amine |
| 80 | 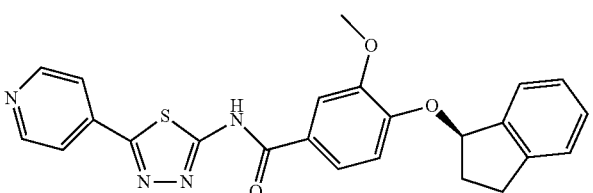<br>(R)-4-((2,3-dihydro-1H-inden-1-yl)oxy)-3-methoxy-N-(5-(pyridin-4-yl)-1,3,4-thiadiazol-2-yl)benzamide | $^1$H NMR (400 MHz, DMSO) δ 13.28 (1H, s), 8.81 (2H, dd, J = 1.6, 4.4 Hz), 8.01 (2H, dd, J = 1.6, 4.4 Hz), 7.91 (1H, dd, J = 2.1, 8.4 Hz), 7.88 (1H, d, J = 2.0 Hz), 7.49-7.40 (4H, m), 7.34-7.28 (1H, m), 6.04 (1H, dd, J = 3.5, 6.6 Hz), 3.89 (3H, s), 3.12 (1H, ddd, J = 6.7, 8.7, 15.8 Hz), 2.96 (1H, ddd, J = 4.8, 8.6, 16.2 Hz), 2.70-2.59 (1H, m), 2.17-2.07 (1H, m); MS (ESI$^+$) 445 | Ex 4 (Scheme 1) from methyl 4-hydroxy-3-methoxybenzoate, (R)-2,3-dihydro-1H-inden-1-ol and 5-(4-pyridyl)-1,3,4-thiadiazol-2-yl amine |

TABLE 1-continued

| Ex. | Structure and Name | Data | Method |
|---|---|---|---|
| 81 | 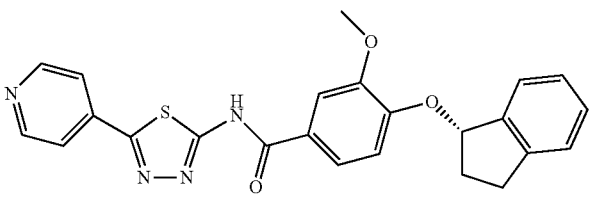<br>(S)-4-((2,3-dihydro-1H-inden-1-yl)oxy)-3-methoxy-N-(5-(pyridin-4-yl)-1,3,4-thiadiazol-2-yl)benzamide | $^1$H NMR (400 MHz, DMSO) δ 13.28 (1H, s), 8.82 (2H, dd, J = 1.5, 4.5 Hz), 8.03 (2H, dd, J = 1.6, 4.5 Hz), 7.91 (1H, dd, J = 2.1, 8.4 Hz), 7.88 (1H, d, J = 2.1 Hz), 7.49-7.40 (4H, m), 7.34-7.28 (1H, m), 6.04 (1H, dd, J = 3.5, 6.6 Hz), 3.89 (3H, s), 3.12 (1H, ddd, J = 6.7, 8.7, 15.8 Hz), 2.96 (1H, ddd, J = 4.8, 8.7, 16.2 Hz), 2.70-2.59 (1H, m), 2.12 (1H, ddd, J = 4.9, 8.6, 17.3 Hz); MS (ESI$^+$) 445 | Ex4 (Scheme 1) from methyl 4-hydroxy-3-methoxybenzoate, (S)-2,3-dihydro-1H-inden-1-ol and 5-(4-pyridyl)-1,3,4-thiadiazol-2-yl amine |
| 82 | 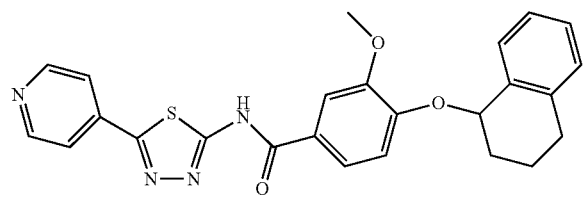<br>3-methoxy-N-(5-(pyridin-4-yl)-1,3,4-thiadiazol-2-yl)-4-((1,2,3,4-tetrahydronaphthalen-1-yl)oxy)benzamide | $^1$H NMR (400 MHz, DMSO) 13.28 (1H, s), 8.81 (2H, d, J = 6.1 Hz), 8.01 (2H, d, J = 6.1 Hz), 7.92-7.87 (2H, m), 7.45 (1H, d, J = 9.1 Hz), 7.38 (1H, d, J = 7.3 Hz), 7.34-7.29 (1H, m), 7.28-7.21 (2H, m), 5.69 (1H, dd, J = 4.2, 4.2 Hz), 3.91 (3H, s), 2.96-2.74 (2H, m), 2.08-1.91 (3H, m), 1.86-1.80 (1H, m); MS (ESI$^+$) 459 | Ex 4 (Scheme 1) from methyl 4-hydroxy-3-methoxybenzoate, 1,2,3,4-tetrahydronaphthalen-1-ol and 5-(4-pyridyl)-1,3,4-thiadiazol-2-yl amine |
| 83 | 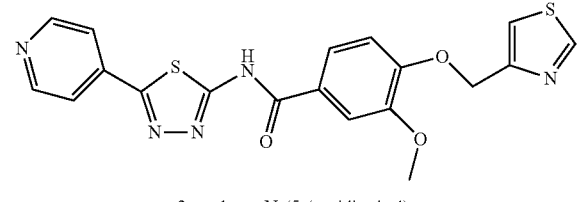<br>3-methoxy-N-(5-(pyridin-4-yl)-1,3,4-thiadiazol-2-yl)-4-(thiazol-4-ylmethoxy)benzamide | $^1$H NMR (400 MHz, DMSO) 13.27 (1H, s), 9.20 (1H, d, J = 1.5 Hz), 8.81 (2H, d, J = 5.6 Hz), 8.01 (2H, d, J = 5.8 Hz), 7.90-7.84 (3H, m), 7.38 (1H, d, J = 9.1 Hz), 5.38 (2H, s), 3.94 (3H, s); MS (ESI$^+$) 426 | Ex 4 (Scheme 1) from methyl 4-hydroxy-3-methoxybenzoate, thiazol-4-ylmethanol and 5-(4-pyridyl)-1,3,4-thiadiazol-2-yl amine |
| 84 | 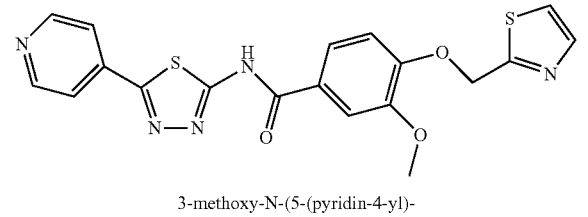<br>3-methoxy-N-(5-(pyridin-4-yl)-1,3,4-thiadiazol-2-yl)-4-(thiazol-2-ylmethoxy)benzamide | $^1$H NMR (400 MHz, DMSO) 13.30 (1H, s), 8.80 (2H, dd, J = 1.5, 4.5 Hz), 8.00 (2H, dd, J = 1.8, 4.5 Hz), 7.93 (1H, d, J = 3.2 Hz), 7.90 (1H, d, J = 2.0 Hz), 7.87-7.84 (2H, m), 7.36 (1H, d, J = 8.6 Hz), 5.61 (2H, s), 3.97 (3H, s); MS (ESI$^+$) 426 | Ex 4 (Scheme 1) from methyl 4-hydroxy-3-methoxybenzoate, thiazol-2-ylmethanol and 5-(4-pyridyl)-1,3,4-thiadiazol-2-yl amine |
| 85 | 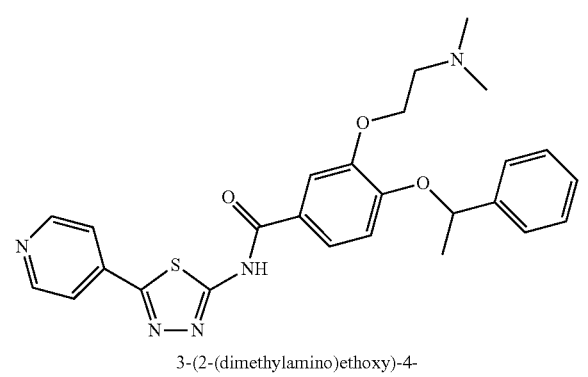<br>3-(2-(dimethylamino)ethoxy)-4-(1-phenylethoxy)-N-(5-(pyridin-4-yl)-1,3,4-thiadiazol-2-yl)benzamide | $^1$H NMR (400 MHz, DMSO) 8.79 (2H, dd, J = 1.6, 4.4 Hz), 7.98 (2H, dd, J = 1.8, 4.5 Hz), 7.89 (1H, d, J = 2.0 Hz), 7.74 (1H, dd, J = 2.0, 8.6 Hz), 7.48 (2H, d, J = 7.1 Hz), 7.41 (2H, dd, J = 7.5, 7.5 Hz), 7.33 (1H, t, J = 7.2 Hz), 7.10 (1H, d, J = 8.6 Hz), 5.72 (1H, q, J = 6.4 Hz), 4.37 (1H, t, J = 5.3 Hz), 3.14 (1H, t, J = 4.9 Hz), 2.63 (6H, s), 1.64 (3H, d, J = 6.3 Hz); MS (ESI$^+$) 490 | Ex 1 (steps a-d) (Scheme 1) from methyl 3-hydroxy-4-(1-phenyl ethoxy)benzoate, 2-(dimethylamino) ethanol and 5-(4-pyridyl)-1,3,4-thiadiazol-2-yl amine |

TABLE 1-continued

| Ex. | Structure and Name | Data | Method |
|---|---|---|---|
| 86 | 3-(2-methoxyethoxy)-4-(1-phenylethoxy)-N-(5-(pyridin-4-yl)-1,3,4-thiadiazol-2-yl)benzamide | $^1$H NMR (400 MHz, DMSO) 13.17 (1H, s), 8.80 (2H, d, J = 6.1 Hz), 7.99 (2H, d, J = 6.1 Hz), 7.87 (1H, d, J = 2.0 Hz), 7.71 (1H, dd, J = 1.9, 8.5 Hz), 7.49 (2H, d, J = 7.1 Hz), 7.41 (2H, dd, J = 7.5, 7.5 Hz), 7.32 (1H, t, J = 7.2 Hz), 7.10 (1H, d, J = 8.6 Hz), 5.72 (1H, q, J = 6.2 Hz), 4.32 (2H, t, J = 4.5 Hz), 3.82 (2H, t, J = 4.5 Hz), 3.46 (3H, s), 1.64 (3H, d, J = 6.3 Hz). MS (ESI$^+$) 477 | Ex1 (steps a-d) (Scheme 1) from methyl 3-hydroxy-4-(1-phenyl ethoxy)benzoate, 2-methoxyethanol and 5-(4-pyridyl)-1,3,4-thiadiazol-2-yl amine |
| 87 | 3-((1-methylpiperidin-4-yl)methoxy)-4-(1-phenylethoxy)-N-(5-(pyridin-4-yl)-1,3,4-thiadiazol-2-yl)benzamide | $^1$H NMR (400 MHz, DMSO) 8.74 (2H, dd, J = 1.4, 4.7 Hz), 7.92 (2H, dd, J = 1.5, 4.5 Hz), 7.85 (1H, d, J = 1.8 Hz), 7.69 (1H, dd, J = 2.0, 8.6 Hz), 7.48 (2H, d, J = 7.1 Hz), 7.41 (2H, dd, J = 7.6, 7.6 Hz), 7.32 (1H, t, J = 7.2 Hz), 7.04 (1H, d, J = 8.8 Hz), 5.65 (1H, q, J = 6.3 Hz), 4.03 (2H, d, J = 6.1 Hz), 3.07 (2H, d, J = 11.1 Hz), 2.42 (3H, s), 2.31 (2H, t, J = 10.9 Hz), 1.97-1.89 (3H, m), 1.63 (3H, d, J = 6.3 Hz), 1.52 (2H, ddd, J = 12.1, 12.1, 12.1 Hz). MS (ESI$^+$) 530 | Ex 1 (steps a-d) (Scheme 1) from methyl 3-hydroxy-4-(1-phenylethoxy) benzoate, (1-methylpiperidin-4-yl)methanol and 5-(4-pyridyl)-1,3,4-thiadiazol-2-yl amine |
| 88 | (R)-3-methoxy-4-(1-(pyridin-2-yl)ethoxy)-N-(5-(pyridin-4-yl)-1,3,4-thiadiazol-2-yl)benzamide | $^1$H NMR (400 MHz, DMSO) 13.15 (1H, s), 8.73 (2H, d, J = 5.1 Hz), 8.58 (1H, d, J = 4.3 Hz), 7.92 (2H, d, J = 4.8 Hz), 7.84-7.79 (2H, m), 7.65 (1H, d, J = 8.6 Hz), 7.45 (1H, d, J = 8.1 Hz), 7.35-7.29 (1H, m), 6.97 (1H, d, J = 8.6 Hz), 5.62-5.57 (1H, m), 3.93 (3H, s), 1.64 (3H, d, J = 6.1 Hz); MS (ESI$^+$) 434. | Ex 4 (Scheme 1) from methyl 4-hydroxy-3-methoxybenzoate, (R)-1-(pyridin-2-yl)ethanol and 5-(4-pyridyl)-1,3,4-thiadiazol-2-yl amine |
| 89 | 3-methoxy-4-((2-methylpyridin-3-yl)methoxy)-N-(5-(pyridin-4-yl)-1,3,4-thiadiazol-2-yl)benzamide | $^1$H NMR (400 MHz, DMSO) 13.25 (1H, s), 8.74 (2H, d, J = 6.0 Hz), 8.44 (1H, d, J = 3.4 Hz), 7.94 (2H, d, J = 6.0 Hz), 7.86-7.79 (3H, m), 7.32-7.25 (2H, m), 5.25 (2H, s), 3.90 (3H, s), 2.54 (3H, s); MS (ESI$^+$) 434. | Ex4 (Scheme 1) from methyl 4-hydroxy-3-methoxybenzoate, (2-methylpyridin-3-yl)methanol and 5-(4-pyridyl)-1,3,4-thiadiazol-2-yl amine |

TABLE 1-continued

| Ex. | Structure and Name | Data | Method |
|---|---|---|---|
| 90 | 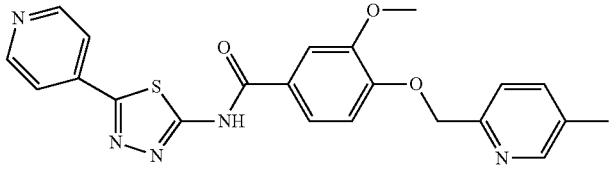<br>3-methoxy-4-((5-methylpyridin-2-yl)methoxy)-N-(5-(pyridin-4-yl)-1,3,4-thiadiazol-2-yl)benzamide | $^1$H NMR (400 MHz, DMSO) 13.23 (1H, s), 8.71 (2H, d, J = 5.4 Hz), 8.44 (1H, s), 7.90 (2H, d, J = 5.3 Hz), 7.82 (1H, s), 7.77 (1H, d, J = 7.7 Hz), 7.67 (1H, d, J = 7.5 Hz), 7.44 (1H, d, J = 8.0 Hz), 7.17 (1H, d, J = 8.5 Hz), 5.22 (2H, s), 3.89 (3H, s), 2.32 (3H, s); MS (ESI$^+$) 434 | Ex 4 (Scheme 1) from methyl 4-hydroxy-3-methoxybenzoate, (5-methylpyridin-2-yl)methanol and 5-(4-pyridyl)-1,3,4-thiadiazol-2-yl amine |
| 91 | 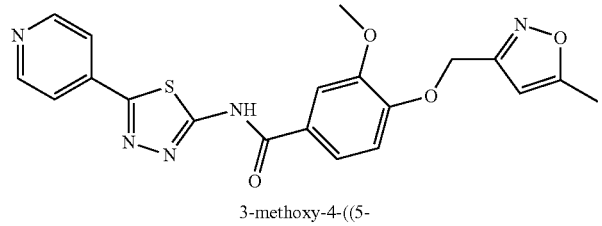<br>3-methoxy-4-((5-methylisoxazol-3-yl)methoxy)-N-(5-(pyridin-4-yl)-1,3,4-thiadiazol-2-yl)benzamide | $^1$H NMR (400MHz, DMSO) 8.61 (2H, dd, J = 1.6, 4.5 Hz), 7.81 (1H, d, J = 1.9 Hz), 7.78 (2H, dd, J = 1.5, 4.5 Hz), 7.44 (1H, dd, J = 1.8, 8.3 Hz), 7.10 (1H, d, J = 8.4 Hz), 6.35 (1H, d, J = 0.8 Hz), 5.17 (2H, s), 3.85 (3H, s), 2.43 (3H, d, J = 0.7 Hz); MS (ESI$^+$) 424 | Ex 18 (Scheme 1) from methyl 4-hydroxy-3-methoxybenzoate, 3-(bromomethyl)-5-methylisoxazole and 5-(4-pyridyl)-1,3,4-thiadiazol-2-yl amine |
| 92 | 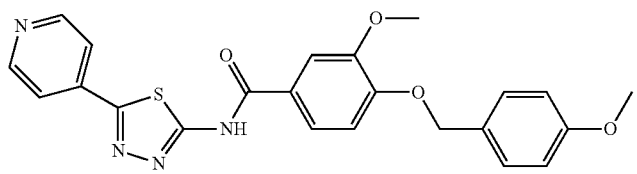<br>3-methoxy-4-((4-methoxybenzyl)oxy)-N-(5-(pyridin-4-yl)-1,3,4-thiadiazol-2-yl)benzamide | $^1$H NMR (400 MHz, DMSO) 13.21 (1H, s), 8.77-8.74 (2H, m), 7.97-7.94 (2H, m), 7.83-7.79 (2H, m), 7.41 (2H, d, J = 8.7 Hz), 7.25 (1H, d, J = 9.2 Hz), 6.97 (2H, d, J = 8.8 Hz), 5.13 (2H, s), 3.88 (3H, s), 3.77 (3H, s); MS (ESI$^+$) 449 | Ex 18 (Scheme 1) from methyl 4-hydroxy-3-methoxybenzoate, 1-(chloromethyl)-4-methoxybenzene and 5-(4-pyridyl)-1,3,4-thiadiazol-2-yl amine |
| 93 | 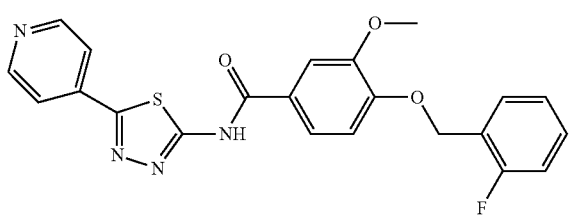<br>4-((2-fluorobenzyl)oxy)-3-methoxy-N-(5-(pyridin-4-yl)-1,3,4-thiadiazol-2-yl)benzamide | $^1$H NMR (400 MHz, DMSO) 13.24 (1H, s), 8.77-8.73 (2H, m), 7.95 (2H, d, J = 5.9 Hz), 7.86-7.81 (2H, m), 7.59 (1H, dd, J = 7.1, 7.1 Hz), 7.49-7.44 (1H, m), 7.33-7.24 (3H, m), 5.25 (2H, s), 3.88 (3H, s); MS (ESI$^+$) 437 | Ex 18 (Scheme 1) from methyl 4-hydroxy-3-methoxybenzoate, 1-(bromomethyl)-2-fluorobenzene and 5-(4-pyridyl)-1,3,4-thiadiazol-2-yl amine |
| 94 | 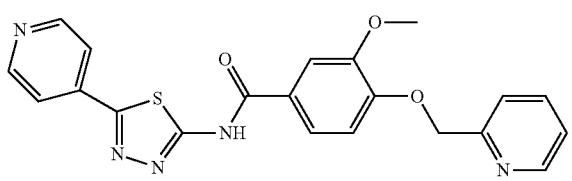<br>3-methoxy-4-(pyridin-2-ylmethoxy)-N-(5-(pyridin-4-yl)-1,3,4-thiadiazol-2-yl)benzamide | $^1$H NMR (400 MHz, DMSO) 13.22 (1H, s), 8.77-8.74 (2H, m), 8.61 (1H, d, J = 4.4 Hz), 7.97-7.94 (2H, m), 7.90-7.83 (2H, m), 7.80 (1H, dd, J = 2.0, 8.5 Hz), 7.55 (1H, d, J = 7.8 Hz), 7.38 (1H, dd, J = 5.1, 7.0 Hz), 7.24 (1H, d, J = 8.5 Hz), 5.30 (2H, s), 3.92 (3H, s); MS (ESI$^+$) 420. | Ex18 (Scheme 1) from methyl 4-hydroxy-3-methoxybenzoate, 2-(bromomethyl)pyridine hydrobromide and 5-(4-pyridyl)-1,3,4-thiadiazol-2-yl amine |

TABLE 1-continued

| Ex. | Structure and Name | Data | Method |
|---|---|---|---|
| 95 | <br>(S)-5-chloro-6-(2-hydroxy-2-methyl-1-phenylpropoxy)-N-(5-(pyridin-4-yl)-1,3,4-thiadiazol-2-yl)nicotinamide | $^1$H NMR (400 MHz, DMSO) 13.43 (1H, s), 8.80 (2H, dd, J = 1.2, 4.7 Hz), 8.77 (1H, d, J = 2.1 Hz), 8.62 (1H, d, J = 2.3 Hz), 7.99 (2H, dd, J = 1.5, 4.5 Hz), 7.47 (2H, d, J = 7.3 Hz), 7.38 (2H, dd, J = 7.3, 7.3 Hz), 7.31 (1H, t, J = 7.2 Hz), 6.13 (1H, s, 1H), 4.84 (1H, s), 1.32 (3H, s), 1.16 (3H, s); MS (ESI$^+$) 482/484 | Ex 29 (Scheme 2) from 5,6-dichloro-N-(5-(pyridin-4-yl)-1,3,4-thiadiazol-2-yl)nicotinamide (Ex 21 step a) and (S)-methyl 2-hydroxy-2-phenylacetate |
| 96 | 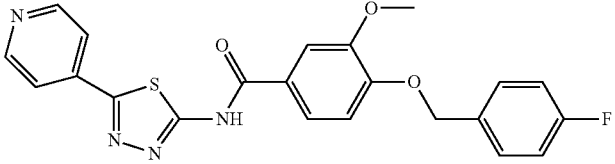<br>4-((4-fluorobenzyl)oxy)-3-methoxy-N-(5-(pyridin-4-yl)-1,3,4-thiadiazol-2-yl)benzamide | $^1$H NMR (400 MHz, DMSO) 13.21 (1H, s), 8.76 (2H, d, J = 5.0 Hz), 7.96 (2H, d, J = 5.0 Hz), 7.85-7.79 (2H, m), 7.53 (1H, dd, J = 5.5, 7.8 Hz), 7.29-7.22 (3H, m), 5.20 (2H, s), 3.89 (3H, s); MS (ESI$^+$) 437 | (Ex 18 step a and b) and Ex 19 (Scheme 1) from methyl 4-hydroxy-3-methoxybenzoate, 1-(bromomethyl)-4-fluorobenzene and 5-(4-pyridyl)-1,3,4-thiadiazol-2-yl amine |
| 97 | 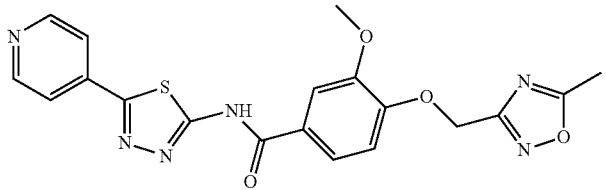<br>3-methoxy-4-((5-methyl-1,2,4-oxadiazol-3-yl)methoxy)-N-(5-(pyridin-4-yl)-1,3,4-thiadiazol-2-yl)benzamide | $^1$H NMR (400 MHz, DMSO) 13.15 (1H, s), 8.67 (2H, d, J = 6.1 Hz), 7.89-7.86 (2H, m), 7.77-7.71 (2H, m), 7.20 (1H, d, J = 8.6 Hz), 5.28 (2H, s), 3.82 (3H, s), 2.56 (3H, s); MS (ESI$^+$) 425 | Ex 4 (Scheme 1) from methyl 4-hydroxy-3-methoxybenzoate, 5-(4-pyridyl)-1,3,4-thiadiazol-2-yl amine and (5-methyl-1,2,4-oxadiazol-3-yl)methanol |
| 98 | 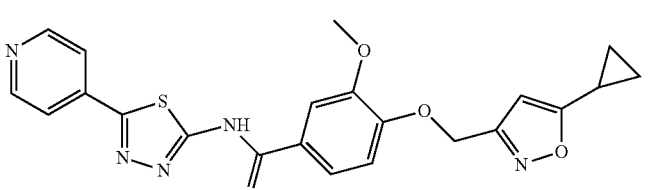<br>4-((5-cyclopropylisoxazol-3-yl)methoxy)-3-methoxy-N-(5-(pyridin-4-yl)-1,3,4-thiadiazol-2-yl)benzamide | $^1$H NMR (400 MHz, DMSO) 13.24 (1H, s), 8.75 (2H, d, J = 6.1 Hz), 7.95 (2H, d, J = 6.1 Hz), 7.84-7.79 (2H, m), 7.26 (1H, d, J = 8.6 Hz), 6.33 (1H, s), 5.23 (2H, s), 3.89 (3H, s), 2.21-2.13 (1H, m), 1.11-1.04 (2H, m), 0.94-0.88 (2H, m); MS (ES$^+$) 450 | Ex 4 (Scheme 1) from methyl 4-hydroxy-3-methoxybenzoate and 5-(4-pyridyl)-1,3,4-thiadiazol-2-yl amine and (5-cyclopropyl-3-isoxazolyl)methanol |
| 99 | 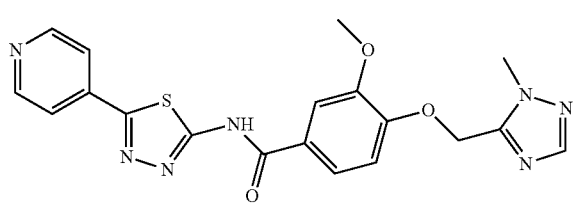<br>3-methoxy-4-((1-methyl-1H-1,2,4-triazol-5-yl)methoxy)-N-(5-(pyridin-4-yl)-1,3,4-thiadiazol-2-yl)benzamide | $^1$H NMR (400 MHz, DMSO) 8.60 (2H, d, J = 5.1 Hz), 7.94 (1H, s), 7.82 (1H, s), 7.79-7.72 (3H, m), 7.15 (1H, d, J = 8.3 Hz), 5.31 (2H, s), 3.93 (3H, s), 3.85 (3H, s); MS (ESI$^+$) 424 | Ex 4 (Scheme 1) from methyl 4-hydroxy-3-methoxybenzoate, 5-(4-pyridyl)-1,3,4-thiadiazol-2-yl amine and (2-methyl-2H-[1,2,4]triazol-3-yl)methanol |

TABLE 1-continued

| Ex. | Structure and Name | Data | Method |
|---|---|---|---|
| 100 | 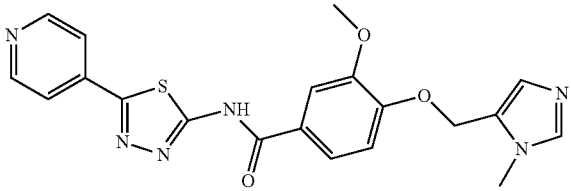<br>3-methoxy-4-((1-methyl-1H-imidazol-5-yl)methoxy)-N-(5-(pyridin-4-yl)-1,3,4-thiadiazol-2-yl)benzamide | $^1$H NMR (400 MHz, DMSO) 13.24 (1H, s), 8.75 (2H, d, J = 28.3 Hz), 7.95 (2H, d, J = 28.0 Hz), 7.83 (2H, d, J = 27.1 Hz), 7.68 (1H, s), 7.37-7.32 (1H, m), 7.07 (1H, s), 5.24-5.19 (2H, m), 3.87 (3H, s), 3.66 (3H, s); MS (ESI$^+$) 423 | Ex 4 (Scheme 1) from methyl 4-hydroxy-3-methoxybenzoate, 5-(4-pyridyl)-1,3,4-thiadiazol-2-yl amine and (1-methyl-1H-imidazol-5-yl)methanol |
| 101 | 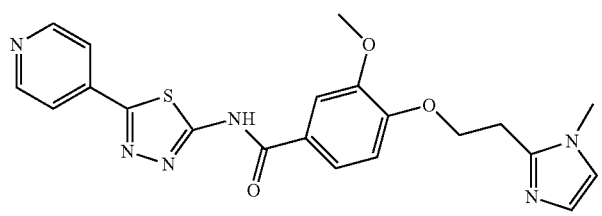<br>3-methoxy-4-(2-(1-methyl-1H-imidazol-2-yl)methoxy)-N-(5-(pyridin-4-yl)-1,3,4-thiadiazol-2-yl)benzamide | $^1$H NMR (400 MHz, DMSO) 13.27 (1H, s), 8.76-8.73 (2H, m), 7.95 (2H, d, J = 5.1 Hz), 7.82-7.79 (2H, m), 7.16 (1H, d, J = 8.6 Hz), 7.07 (1H, s), 6.79 (1H, s), 4.38 (2H, dd, J = 6.7, 6.7 Hz), 3.88 (3H, s), 3.67 (3H, s), 3.16 (2H, dd, J = 6.2, 6.2 Hz); MS (ESI$^+$) 437 | Ex 4 (Scheme 1) from methyl 4-hydroxy-3-methoxybenzoate, 5-(4-pyridyl)-1,3,4-thiadiazol-2-yl amine and 2 (1-methyl-1H-imidazol-2-yl)ethanol |
| 102 | 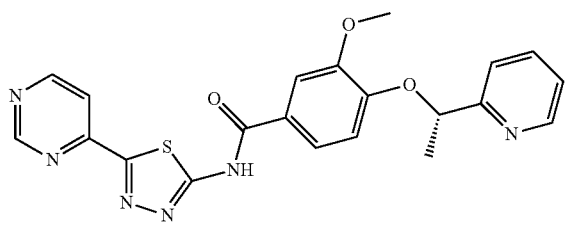<br>(S)-3-methoxy-4-(1-(pyridin-2-yl)ethoxy)-N-(5-(pyridin-4-yl)-1,3,4-thiadiazol-2-yl)benzamide | $^1$H NMR (400 MHz, DMSO) 13.18 (1H, s), 9.24 (1H, s), 8.90 (1H, d, J = 5.3 Hz), 8.57 (1H, d, J = 4.5 Hz), 8.20 (1H, dd, J = 1.3, 5.2 Hz), 7.83-7.77 (2H, m), 7.65 (1H, dd, J = 1.9, 8.5 Hz), 7.46 (1H, d, J = 7.9 Hz), 7.31 (1H, dd, J = 5.2, 7.0 Hz), 6.91 (1H, d, J = 8.7 Hz), 5.56 (1H, q, J = 6.5 Hz), 3.92 (3H, s), 1.63 (3H, d, J = 6.5 Hz); MS (ESI$^+$) 435 | Ex 13 step c (Scheme 1) from methyl 4-hydroxy-3-methoxybenzoate,5-(pyrimidin-4-yl)-1,3,4-thiadiazol-2-yl amine (Ex 13 steps a and b) and (R)-1-(pyridin-2-yl)ethanol |
| 103 | 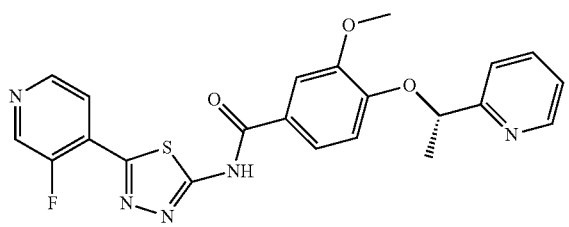<br>(S)-N-(5-(3-fluoropyridin-4-yl)-1,3,4-thiadiazol-2-yl)-3-methoxy-4-(1-(pyridin-2-yl)ethoxy)benzamide | $^1$H NMR (400 MHz, DMSO) 13.27 (1H, s), 8.90 (1H, d, J = 1.8 Hz), 8.64 (2H, dd, J = 4.9, 11.7 Hz), 8.29 (1H, dd, J = 5.7, 5.7 Hz), 7.88-7.83 (2H, m), 7.72 (1H, d, J = 8.3 Hz), 7.49 (1H, d, J = 7.8 Hz), 7.36 (1H, dd, J = 5.1, 6.6 Hz), 7.02 (1H, d, J = 8.6 Hz), 5.66 (1H, q, J = 6.3 Hz), 3.98 (3H, s), 1.69 (3H, d, J = 6.6 Hz); MS (ESI$^+$) 452 | Ex 14 step b (Scheme 1) from methyl 4-hydroxy-3-melhoxybenzoate, 5-(3-fluoropyridin-4-yl)-1,3,4-thiadiazol-2-amine (Example 14 step a) and (R)-1-(pyridin-2-yl)ethanol |

TABLE 1-continued

| Ex. | Structure and Name | Data | Method |
|---|---|---|---|
| 104 | 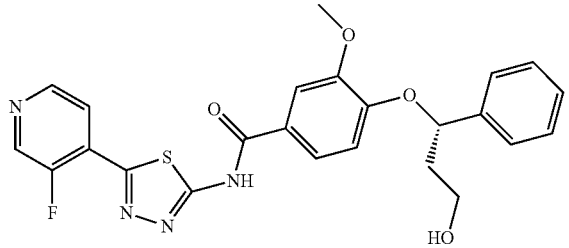<br>(S)-N-(5-(3-fluoropyridin-4-yl)-1,3,4-thiadiazol-2-yl)-4-(3-hydroxy-1-phenylpropoxy)-3-methoxybenzamide | $^1$H NMR (400 MHz, DMSO) 13.25 (1H, s), 8.90 (1H, d, J = 1.8 Hz), 8.66 (1H, d, J = 4.8 Hz), 8.29 (1H, dd, J = 5.6, 5.6 Hz), 7.86-7.83 (1H, m), 7.69 (1H, dd, J = 1.3, 8.6 Hz), 7.48-7.38 (4H, m), 7.33 (1H, dd, J = 7.1, 7.1 Hz), 7.02 (1H, d, J = 8.3 Hz), 5.67-5.62 (1H, m), 4.67 (1H, dd, J = 4.7, 4.7 Hz), 3.98 (3H, s), 3.66-3.50 (2H, m), 2.26-2.19 (1H, m), 2.02-1.93 (1H, m); MS (ESI$^+$) 481 | Example 8 (Scheme 1) Prepared from methyl 4-hydroxy-3-methoxybenzoate, 5-(3-fluoropyridin-4-yl)-1,3,4-thiadiazol-2-amine (Example 14 step a) and (R)-1-phenylpropane-1,3-diol |
| 105 | 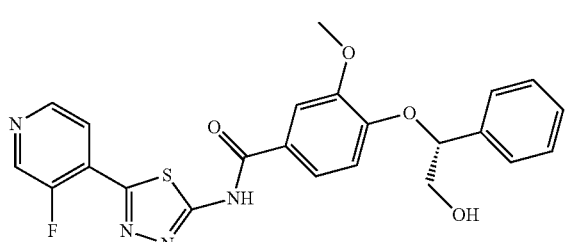<br>(R)-N-(5-(3-fluoropyridin-4-yl)-1,3,4-thiadiazol-2-yl)-4-(2-hydroxy-1-phenylpropoxy)-3-methoxybenzamide | $^1$H NMR (400 MHz, DMSO) 13.22 (1H, s), 8.89 (1H, d, J = 1.8 Hz), 8.65 (1H, d, J = 5.1 Hz), 8.28 (1H, dd, J = 5.7, 5.7 Hz), 7.85 (1H, d, J = 2.0 Hz), 7.69 (1H, dd, J = 2.0, 8.6 Hz), 7.47 (2H, d, J = 7.1 Hz), 7.40 (2H, dd, J = 7.6, 7.6 Hz), 7.33 (1H, dd, J = 7.1, 7.1 Hz), 7.07 (1H, d, J = 8.6 Hz), 5.55 (1H, dd, J = 4.2, 7.2 Hz), 5.19 (1H, dd, J = 5.2, 5.2 Hz), 3.99 (3H, s), 3.91-3.83 (1H, m), 3.74-3.68 (1H, m); MS (ESI$^+$) 467 | Ex 7 (Scheme 1) from methyl 4-hydroxy-3-methoxybenzoate, 5-(3-fluoropyridin-4-yl)-1,3,4-thiadiazol-2-amine (Example 14 step a) and (S)-1-phenylethane-1,2-diol |
| 106 | 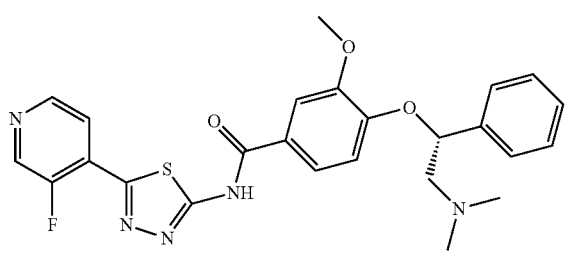<br>(R)-4-(2-(dimethylamino)-1-phenylethoxy)-N-(5-(3-fluoropyridin-4-yl)-1,3,4-thiadiazol-2-yl)-3-methoxybenzamide | $^1$H NMR (400 MHz, DMSO) 12.82 (1H, s), 8.89 (1H, d, J = 2.0 Hz), 8.65 (1H, d, J = 5.1 Hz), 8.28 (1H, dd, J = 5.7, 5.7 Hz), 7.85 (1H, d, J = 2.0 Hz), 7.69 (1H, dd, J = 2.0, 8.6 Hz), 7.49 (2H, d, J = 7.3 Hz), 7.40 (2H, dd, J = 7.6, 7.6 Hz), 7.32 (1H, dd, J = 7.3, 7.3 Hz), 7.10 (1H, d, J = 8.8 Hz), 5.73 (1H, dd, J = 4.2, 8.0 Hz), 3.98 (3H, s), 3.09-3.00 (1H, m), 2.78-2.71 (1H, m), 2.41 (6H, s); MS (ESI$^+$) 494 | Ex 6 (Scheme 1) from methyl 4-hydroxy-3-methoxybenzoate, 5-(3-fluoropyridin-4-yl)-1,3,4-thiadiazol-2-amine (Example 14 step a) and (R)-2-(dimethylamino)-1-phenylethanol (Ex 6 step a) |
| 107 | 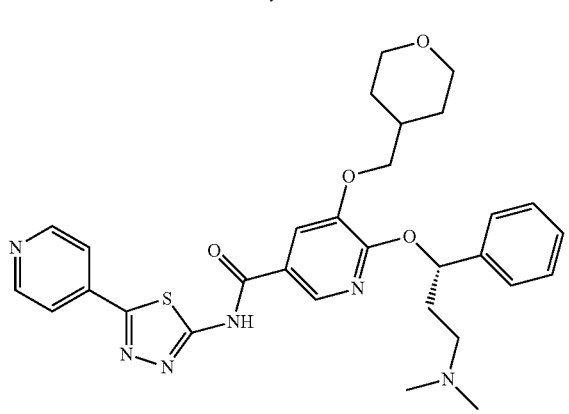<br>(S)-6-(3-(dimethylamino)-1-phenylpropoxy)-N-(5-(pyridin-4-yl)-1,3,4-thiadiazol-2-yl)-5-((tetrahydro-2H-pyran-4-yl)methoxy)nicotinamide | $^1$H NMR (400 MHz, DMSO) 8.76-8.73 (2H, m), 8.44 (1H, d, J = 1.8 Hz), 8.03 (1H, d, J = 1.8 Hz), 7.94-7.91 (2H, m), 7.48 (2H, d, J = 7.3 Hz), 7.41 (2H, dd, J = 7.6, 7.6 Hz), 7.33 (1H, dd, J = 7.2, 7.2 Hz), 6.33 (1H, dd, J = 5.3, 7.8 Hz), 4.07 (2H, d, J = 6.6 Hz), 3.98 (2H, dd, J = 2.9, 11.0 Hz), 3.44 (2H, dd, J = 11.7, 11.7 Hz), 2.77-2.71 (2H, m), 2.51 (6H, s), 2.39-2.28 (1H, m), 2.20-2.14 (2H, m), 1.83-1.77 (2H, m), 1.54-1.43 (2H, m); MS (ESI$^+$) 575 | Ex 37 (Scheme 2) from methyl 6-chloro-5-hydroxynicotinate, (tetrahydro-2H-pyran-4-yl)methanol, 5-(4-pyridyl)-1,3,4-thiadiazol-2-ylamine and (S)-3-(dimethylamino)-1-phenylpropan-1-ol (Ex 26 step a) |

TABLE 1-continued

| Ex. | Structure and Name | Data | Method |
|---|---|---|---|
| 108 | 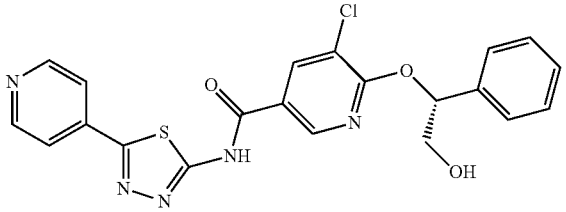<br>(R)-5-chloro-6-(2-hydroxy-1-phenylethoxy)-N-(5-(pyridin-4-yl)-1,3,4-thiadiazol-2-yl)nicotinamide | $^1$H NMR (400 MHz, DMSO) 13.49 (1H, s), 8.84-8.79 (3H, m), 8.64 (1H, d, J = 2.0 Hz), 8.01 (2H, d, J = 6.1 Hz), 7.49 (2H, d, J = 7.3 Hz), 7.42 (2H, dd, J = 7.5, 7.5 Hz), 7.35 (1H, dd, J = 7.2, 7.2 Hz), 6.36 (1H, dd, J = 3.8, 7.6 Hz), 5.26 (1H, s), 3.91 (1H, dd, J = 7.8, 11.9 Hz), 3.80 (1H, dd, J = 3.2, 11.5 Hz); MS (ESI$^+$) 454/465 | Ex 27 (Scheme 2) from 5,6-dichloro-N-(5-(pyridin-4-yl)-1,3,4-thiadiazol-2-yl)nicotinamide (Ex 21 step a) and (R)-1-phenylethane-1,2-diol |
| 109 | 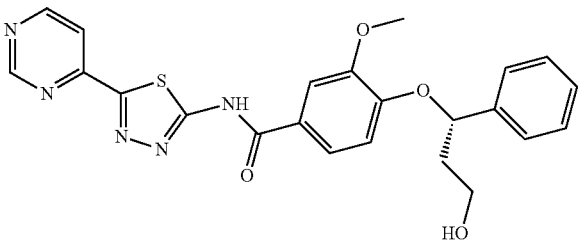<br>(S)-4-(3-hydroxy-1-phenylpropoxy)-3-methoxy-N-(5-(pyrimidin-4-yl)-1,3,4-thiadiazol-2-yl)benzamide | $^1$H NMR (400 MHz, DMSO) 13.26 (1H, s), 9.38 (1H, d, J = 1.5 Hz), 9.05 (1H, d, J = 5.3 Hz), 8.31 (1H, dd, J = 1.3, 5.3 Hz), 7.83 (1H, d, J = 2.0 Hz), 7.69 (1H, dd, J = 2.0, 8.6 Hz), 7.47-7.38 (4H, m), 7.32 (1H, dd, J = 7.1, 7.1 Hz), 7.01 (1H, d, J = 8.8 Hz), 5.64 (1H, dd, J = 5.1, 8.3 Hz), 4.72 (1H, dd, J = 5.1, 5.1 Hz), 3.98 (3H, s), 3.67-3.49 (2H, m), 2.25-2.15 (1H, m), 2.01-1.91 (1H, m); MS (ESI$^+$) 464 | Example 8 (Scheme 1) Prepared from methyl 4-hydroxy-3-methoxybenzoate, 5-(pyrimidin-4-yl)-1,3,4-thiadiazol-2-yl amine (Example 13 steps a-b) and (R)-1-phenylpropane-1,3-diol |
| 110 | 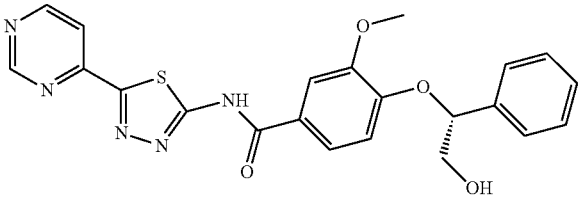<br>(R)-4-(2-hydroxy-1-phenylethoxy)-3-methoxy-N-(5-(pyrimidin-4-yl)-1,3,4-thiadiazol-2-yl)benzamide | $^1$H NMR (400 MHz, DMSO) 13.27 (1H, s), 9.38 (1H, d, J = 1.3 Hz), 9.05 (1H, d, J = 5.3 Hz), 8.31 (1H, dd, J = 1.3, 5.3 Hz), 7.84 (1H, d, J = 2.0 Hz), 7.69 (1H, dd, J = 2.0, 8.6 Hz), 7.46 (2H, d, J = 7.1 Hz), 7.40 (2H, dd, J = 7.6, 7.6 Hz), 7.33 (1H, dd, J = 7.2, 7.2 Hz), 7.07 (1H, d, J = 8.8 Hz), 5.56 (1H, dd, J = 3.9, 7.5 Hz), 5.25 (1H, dd, J = 5.7, 5.7 Hz), 3.99 (3H, s), 3.90-3.82 (1H, m), 3.73-3.66 (1H, m); MS (ESI$^+$) 450 | Ex 21 (Scheme 1) from methyl 4-hydroxy-3-methoxybenzoate, 5-(pyrimidin-4-yl)-1,3,4-thiadiazol-2-yl amine (Ex 13 steps a-b) and (S)-1-phenylethane-1,2-diol |
| 111 | 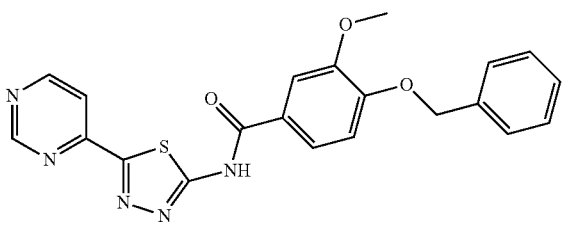<br>4-(benzyloxy)-3-methoxy-N-(5-(pyrimidin-4-yl)-1,3,4-thiadiazol-2-yl)benzamide | $^1$H NMR (400 MHz, DMSO) 13.20 (1H, s), 9.26 (1H, d, J = 1.3 Hz), 8.93 (1H, d, J = 5.3 Hz), 8.19 (1H, dd, J = 1.5, 5.3 Hz), 7.78-7.73 (2H, m), 7.43-7.39 (2H, m), 7.37-7.29 (3H, m), 7.18-7.14 (1H, m), 5.14 (2H, s), 3.82 (3H, s); MS (ESI$^+$) 420 | Ex 13 step c (Scheme 1) from methyl 4-hydroxy-3-methoxybenzoate, 5-(pyrimidin-4-yl)-1,3,4-thiadiazol-2-yl amine (Ex 13 steps a and b) and benzyl alcohol |
| 112 | 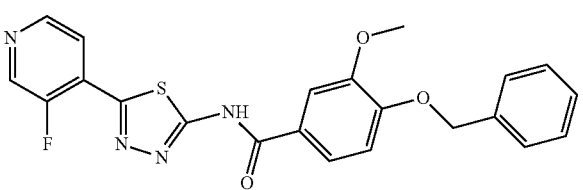<br>4-(benzyloxy)-N-(5-(3-fluoropyridin-4-yl)-1,3,4-thiadiazol-2-yl)-3-methoxybenzamide | $^1$H NMR (400 MHz, DMSO) 13.30 (1H, s), 8.87 (1H, d, J = 2.3 Hz), 8.63 (1H, d, J = 5.1 Hz), 8.26 (1H, dd, J = 5.7, 5.7 Hz), 7.84-7.80 (2H, m), 7.48 (2H, d, J = 6.8 Hz), 7.45-7.36 (3H, m), 7.25 (1H, d, J = 8.3 Hz), 5.22 (2H, s), 3.89 (3H, s); MS (ESI$^+$) 437 | Ex 14 (step b) (Scheme 1) from methyl 4-hydroxy-3-methoxybenzoate, 5-(3-fluoropyridin-4-yl)-1,3,4-thiadiazol-2-amine (Ex 14 step a) and benzyl alcohol |

TABLE 1-continued

| Ex. | Structure and Name | Data | Method |
|---|---|---|---|
| 113 | 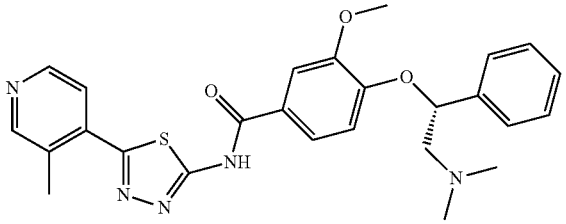<br>(R)-4-(2-(dimethylamino)-1-phenylethoxy)-3-methoxy-N-(5-(3-methylpyridin-4-yl)-1,3,4-thiadiazol-2-yl)benzamide | $^1$H NMR (400 MHz, DMSO) 12.82 (1H, s), 8.70 (1H, s), 8.61 (1H, d, J = 4.8 Hz), 7.84-7.79 (2H, m), 7.68 (1H, d, J = 8.1 Hz), 7.48 (2H, d, J = 7.3 Hz), 7.44-7.37 (2H, m), 7.33 (1H, dd, J = 7.1, 7.1 Hz), 7.10 (1H, d, J = 8.8 Hz), 5.72 (1H, dd, J = 3.9, 7.2 Hz), 3.98 (3H, s), 3.00 (1H, s), 2.74 (1H, d, J = 8.1 Hz), 2.63 (3H, s), 2.39 (6H, s); MS (ESI$^+$) 490 | Ex 6 (Scheme 1) from methyl 4-hydroxy-3-methoxybenzoate, 5-(3-methylpyridin-4-yl)-1,3,4-thiadiazol-2-amine (Ex 15 steps a-b) and (R)-2-(dimethylamino)-1-phenylethanol |
| 114 | 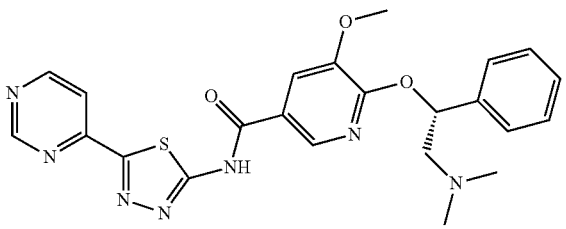<br>(R)-6-(2-(dimethylamino)-1-phenylethoxy)-5-methoxy-N-(5-(pyrimidin-4-yl)-1,3,4-thiadiazol-2-yl)nicotinamide | $^1$H NMR (400 MHz, DMSO), 9.34 (1H, d, J = 1.5 Hz), 9.01 (1H, d, J = 5.3 Hz), 8.47 (1H, d, J = 2.0 Hz), 8.28 (1H, dd, J = 1.5, 5.3 Hz), 8.03 (1H, d, J = 2.0 Hz), 7.50 (2H, d, J = 7.1 Hz), 7.41 (2H, dd, J = 7.5, 7.5 Hz), 7.35-7.31 (1H, m), 6.53 (1H, dd, J = 3.9, 8.7 Hz), 4.00 (3H, s), 3.17-3.09 (1H, m), 2.88-2.81 (1H, m), 2.43 (6H, s); MS (ESI$^+$) 478 | Example 20 (Scheme 2) Prepared from 6-chloro-5-methoxynicotinic acid, 5-(pyrimidin-4-yl)-1,3,4-thiadiazol-2-amine (Example 13 steps a and b) and (R)-2-(dimethylamino)-1-phenylethanol (Example 6 step a) |
| 115 | 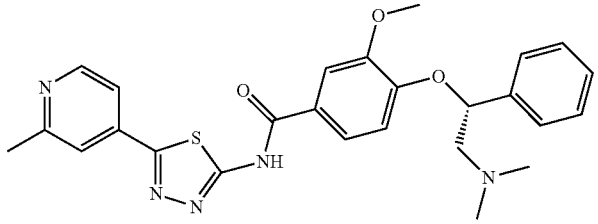<br>(R)-4-(2-(dimethylamino)-1-phenylethoxy)-3-methoxy-N-(5-(2-methylpyridin-4-yl)-1,3,4-thiadiazol-2-yl)benzamide | $^1$H NMR (400 MHz, DMSO) 12.91 (1H, s), 8.64 (1H, d, J = 5.3 Hz), 7.86-7.82 (2H, m), 7.76 (1H, dd, J = 1.3, 5.3 Hz), 7.67 (1H, dd, J = 2.1, 8.5 Hz), 7.48 (2H, d, J = 7.1 Hz), 7.40 (2H, dd, J = 7.5, 7.5 Hz), 7.34-7.30 (1H, m), 7.09 (1H, d, J = 8.8 Hz), 5.70 (1H, dd, J = 4.3, 7.8 Hz), 3.98 (3H, s), 3.02-2.94 (1H, m), 2.73-2.66 (1H, m), 2.61 (3H, s), 2.37 (6H, s); MS (ESI$^+$) 490 | Ex (Scheme 1) from methyl 4-hydroxy-3-methoxybenzoate, 5-(2-methylpyridin-4-yl)-1,3,4-thiadiazol-2-amine (Ex 16 steps a and b) and (R)-2-(dimethylamino)-1-phenylethanol |
| 116 | 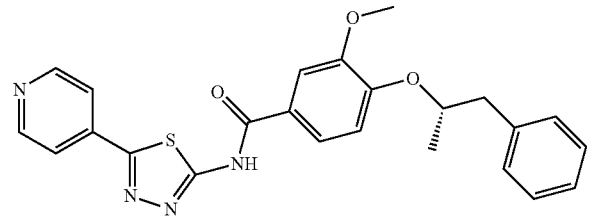<br>(S)-3-methoxy-4-((1-phenylpropan-2-yl)oxy)-N-(5-(pyridin-4-yl)-1,3,4-thiadiazol-2-yl)benzamide | $^1$H NMR (400 MHz, DMSO) 13.23 (1H, s), 8.81-8.78 (2H, m), 8.01-7.98 (2H, m), 7.87-7.81 (2H, m), 7.37-7.34 (4H, m), 7.28-7.22 (2H, m), 4.90 (1H, q, J = 6.2 Hz), 3.93 (3H, s), 3.10 (1H, dd, J = 6.3, 13.6 Hz), 2.94 (1H, dd, J = 6.3, 13.6 Hz), 1.30 (3H, d, J = 6.1 Hz); MS (ESI$^+$) 447 | Ex 4 (Scheme 1) from methyl 4-hydroxy-3-methoxybenzoate,5-(4-pyridyl)-1,3,4-thiadiazol-2-yl amine and (R)-1-phenylpropan-2-ol |

TABLE 1-continued

| Ex. | Structure and Name | Data | Method |
|---|---|---|---|
| 117 | 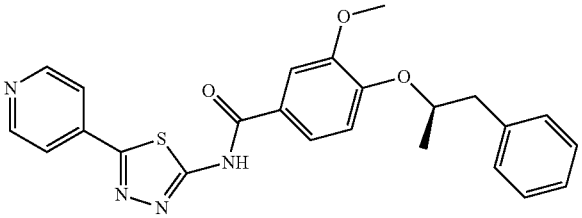<br>(R)-3-methoxy-4-((1-phenylpropan-2-yl)oxy)-N-(5-(pyridin-4-yl)-1,3,4-thiadiazol-2-yl)benzamide | H NMR (400 MHz, DMSO) 13.22 (1H, s), 8.81-8.79 (2H, m), 8.01-7.98 (2H, m), 7.87-7.81 (2H, m), 7.37-7.34 (4H, m), 7.29-7.22 (2H, m), 4.90 (1H, q, J = 6.1 Hz), 3.93 (3H, s), 3.10 (1H, dd, J = 6.2, 13.8 Hz), 2.94 (1H, dd, J = 6.1, 13.6 Hz), 1.30 (3H, d, J = 6.1 Hz); MS (ESI$^+$) 447 | Ex4 (Scheme 1) from methyl 4-hydroxy-3-methoxybenzoate,5-(4-pyridyl)-1,3,4-thiadiazol-2-yl amine and(S)-1-phenylpropan-2-ol |
| 118 | 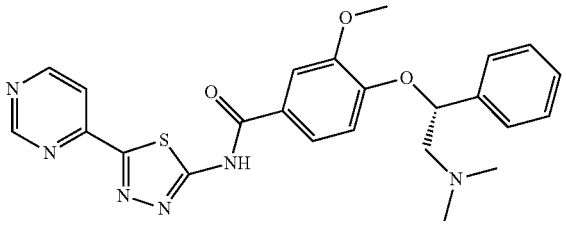<br>(R)-4-(2-(dimethylamino)-1-phenylethoxy)-3-methoxy-N-(5-(pyrimidin-4-yl)-1,3,4-thiadiazol-2-yl)benzamide | $^1$H NMR (400 MHz, DMSO) 12.89 (1H, s), 9.35 (1H, s), 9.03 (1H, d, J = 5.1 Hz), 8.29 (1H, d, J = 4.3 Hz), 7.83 (1H, d, J = 1.5 Hz), 7.69 (1H, dd, J = 1.6, 8.5 Hz), 7.48 (2H, d, J = 7.3 Hz), 7.40 (2H, dd, J = 7.5, 7.5 Hz), 7.32 (1H, dd, J = 7.2, 7.2 Hz), 7.09 (1H, d, J = 8.6 Hz), 5.71 (1H, dd, J = 4.0, 7.6 Hz), 3.98 (3H, s), 3.05-2.97 (1H, m), 2.73-2.69 (1H, m), 2.39 (6H, s); MS (ESI$^+$) 477 | Ex 6 (Scheme 1)from methyl 4-hydroxy-3-methoxybenzoate,5-(pyrimidin-4-yl)-1,3,4-thiadiazol-2-yl amine (Example 13 steps a and b) and (R)-2-(dimethylamino)-1-phenylethanol |
| 119 | 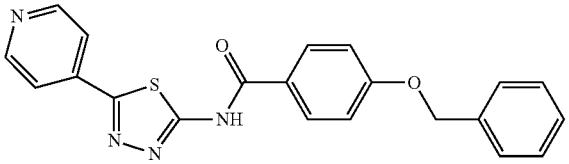<br>4-(benzyloxy)-N-(5-(pyridin-4-yl)-1,3,4-thiadiazol-2-yl)benzamide | $^1$H NMR (400 MHz, DMSO) 13.18 (1H, s), 8.71-8.69 (2H, m), 8.15 (2H, d, J = 8.9 Hz), 7.90-7.87 (2H, m), 7.49 (2H, d, J = 7.0 Hz), 7.42 (2H, dd, J = 7.3, 7.3 Hz), 7.39-7.34 (1H, m), 7.14 (2H, d, J = 8.9 Hz), 5.21 (2H, s); MS (ESI$^+$) 389 | Ex 4 step c (Scheme 1) from 5-(pyridin-4-yl)-1,3,4-thiadiazol-2-amine, and 4-(benzyloxy)benzoic acid |
| 120 | 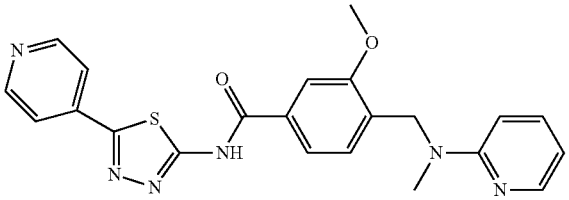<br>3-methoxy-4-((methyl(pyridin-2-yl)amino)methyl)-N-(5-(pyridin-4-yl)-1,3,4-thiadiazol-2-yl)benzamide | $^1$H NMR (400 MHz, DMSO) 13.51 (1H, s), 8.84 (2H, d, J = 6.1 Hz), 8.12-8.06 (3H, m), 7.96 (1H, dd, J = 8.1, 8.1 Hz), 7.91 (1H, s), 7.77 (1H, dd, J = 1.0, 7.8 Hz), 7.31 (1H, d, J = 7.8 Hz), 7.17 (1H, d, J = 8.8 Hz), 6.95 (1H, dd, J = 6.4, 6.4 Hz), 4.91 (2H, s), 4.01 (3H, s), 3.28 (3H, s); MS (ESI$^+$) 433 | Ex 40 (Scheme 4) from 5-(pyridin-4-yl)-1,3,4-thiadiazol-2-amine, methyl 4-(bromomethyl)-3-methoxybenzoate and N-methylpyridin-2-amine |
| 121 | 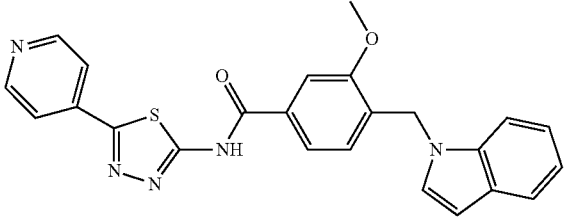<br>4-((1H-indol-1-yl)methyl)-3-methoxy-N-(5-(pyridin-4-yl)-1,3,4-thiadiazol-2-yl)benzamide | $^1$H NMR (400 MHz, DMSO) 13.33 (1H, s), 8.77 (2H, d, J = 6.1 Hz), 7.96 (2H, d, J = 6.1 Hz), 7.89 (1H, d, J = 1.3 Hz), 7.68-7.61 (2H, m), 7.53 (1H, d, J = 3.0 Hz), 7.46 (1H, d, J = 8.1 Hz), 7.18-7.13 (1H, m), 7.08 (1H, dd, J = 7.3, 7.3 Hz), 6.82 (1H, d, J = 8.1 Hz), 6.56 (1H, d, J = 3.3 Hz), 5.50 (2H, s), 4.06 (3H, s); MS (ESI$^+$) 442 | Ex 40 (Scheme 4) from 5-(pyridin-4-yl)-1,3,4-thiadiazol-2-amine, methyl 4-(bromomethyl)-3-methoxybenzoate and indole |

TABLE 1-continued

| Ex. | Structure and Name | Data | Method |
|---|---|---|---|
| 122 | 3-methoxy-4-(phenoxymethyl)-N-(5-(pyridin-4-yl)-1,3,4-thiadiazol-2-yl)benzamide | ¹H NMR (400 MHz, DMSO) 13.41 (1H, s), 8.78-8.75 (2H, m), 7.98-7.96 (2H, m), 7.86 (1H, s), 7.78 (1H, dd, J = 1.4, 7.9 Hz), 7.60 (1H, d, J = 7.9 Hz), 7.34-7.29 (2H, m), 7.03 (2H, d, J = 8.0 Hz), 6.97 (1H, dd, J = 7.3, 7.3 Hz), 5.16 (2H, s), 3.98 (3H, s); MS (ESI⁺) 419 | Ex40 (Scheme 4) from 5-(pyridin-4-yl)-1,3,4-thiadiazol-2-amine, methyl 4-(bromomethyl)-3-methoxybenzoate and phenol |
| 123 | 3-methoxy-4-((methyl(phenyl)amino)methyl)-N-(5-(pyridin-4-yl)-1,3,4-thiadiazol-2-yl)benzamide | ¹H NMR (400 MHz, DMSO) 13.31 (1H, s), 8.76-8.74 (2H, m), 7.97-7.94 (2H, m), 7.83 (1H, d, J = 1.5 Hz), 7.68 (1H, dd, J = 1.3, 7.8 Hz), 7.17-7.12 (2H, m), 7.09 (1H, d, J = 7.8 Hz), 6.65-6.39 (3H, m), 4.57 (2H, s), 3.98 (3H, s), 3.07 (3H, s); MS (ESI⁺) 432 | Ex 40 (Scheme 4) from 5-(pyridin-4-yl)-1,3,4-thiadiazol-2-amine, methyl 4-(bromomethyl)-3-methoxybenzoate and N-methylaniline |
| 124 | (R)-6-(2-hydroxy-2-methyl-1-phenylpropoxy)-N-(5-(pyridin-4-yl)-1,3,4-thiadiazol-2-yl)nicotinamide | ¹H NMR (400 MHz, DMSO) 13.31 (1H, s), 8.86 (1H, d, J = 2.5 Hz), 8.81-8.78 (2H, m), 8.41 (1H, dd, J = 2.5, 8.6 Hz), 8.00-7.98 (2H, m), 7.47 (2H, d, J = 7.1 Hz), 7.35 (2H, dd, J = 7.5, 7.5 Hz), 7.32-7.26 (1H, m), 7.13 (1H, d, J = 8.8 Hz), 6.03 (1H, s), 4.80 (1H, s), 1.25 (3H, s), 1.17 (3H, s); MS (ESI⁺) 448 | Ex 31 (Scheme 2) from 6-fluoro-N-(5-(pyridin-4-yl)-1,3,4-thiadiazol-2-yl)nicotinamide (Ex 31 step a) and (R)-2-methyl-1-phenylpropane-1,2-diol (Ex 29 step a) |
| 125 | (S)-6-((1-phenylpropan-2-yl)oxy)-N-(5-(pyridin-4-yl)-1,3,4-thiadiazol-2-yl)nicotinamide | ¹H NMR (400 MHz, DMSO) 13.39 (1H, s), 9.00 (1H, d, J = 2.5 Hz), 8.81-8.79 (2H, m), 8.41 (1H, dd, J = 2.5, 8.8 Hz), 8.01-7.99 (2H, m), 7.36-7.33 (4H, m), 7.28-7.22 (1H, m), 6.96 (1H, d, J = 8.8 Hz), 5.58-5.52 (1H, m), 3.10 (1H, dd, J = 6.8, 13.6 Hz), 2.99 (1H, dd, J = 6.1, 13.6 Hz), 1.36 (3H, d, J = 6.1 Hz); MS (ESI⁺) 418 | Ex 31 (Scheme 2) from 6-fluoro-N-(5-(pyridin-4-yl)-1,3,4-thiadiazol-2-yl)nicotinamide and (S)-1-phenylpropan-2-ol |
| 126 | (R)-6-((1-phenylpropan-2-yl)oxy)-N-(5-(pyridin-4-yl)-1,3,4-thiadiazol-2-yl)nicotinamide | ¹H NMR (400 MHz, DMSO) 13.39 (1H, s), 9.00 (1H, d, J = 2.5 Hz), 8.80 (2H, d, J = 6.1 Hz), 8.41 (1H, dd, J = 2.5, 8.6 Hz), 8.01-7.99 (2H, m), 7.35-7.33 (4H, m), 7.28-7.22 (1H, m), 6.96 (1H, d, J = 8.8 Hz), 5.58-5.52 (1H, m), 3.10 (1H, dd, J = 6.8, 13.6 Hz), 2.98 (1H, dd, J = 5.8, 13.6 Hz), 1.36 (3H, d, J = 6.3 Hz); MS (ESI⁺) 418 | Ex 31 step b (Scheme 2) from 6-fluoro-N-(5-(pyridin-4-yl)-1,3,4-thiadiazol-2-yl)nicotinamide (Ex 31 step a) and (R)-1-phenylpropan-2-ol |

TABLE 1-continued

| Ex. | Structure and Name | Data | Method |
|---|---|---|---|
| 127 | 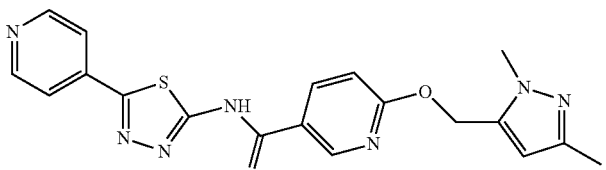<br>6-((1,3-dimethyl-1H-pyrazol-5-yl)methoxy)-N-(5-(pyridin-4-yl)-1,3,4-thiadiazol-2-yl)nicotinamide | ¹H NMR (400 MHz, DMSO) 13.45 (1H, s), 9.06 (1H, d, J = 2.5 Hz), 8.81 (2H, d, J = 6.3 Hz), 8.47 (1H, dd, J = 2.5, 8.6 Hz), 8.02-8.00 (2H, m), 7.09 (1H, d, J = 8.8 Hz), 6.21 (1H, s), 5.51 (2H, s), 3.84 (3H, s), 2.17 (3H, s); MS (ESI⁺) 408 | Ex 31 (Scheme 2) from 6-fluoro-N-(5-(pyridin-4-yl)-1,3,4-thiadiazol-2-yl)nicotinamide (Ex31 step a) and (1,3-dimethyl-1H-pyrazol-5-yl)methanol |
| 128 | 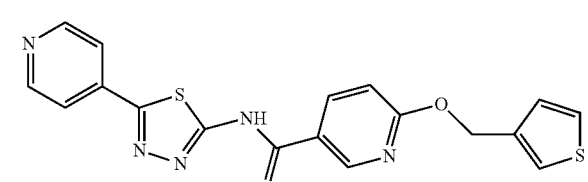<br>N-(5-(pyridin-4-yl)-1,3,4-thiadiazol-2-yl)-6-(thiophen-3-ylmethoxy)nicotinamide | ¹H NMR (400 MHz, DMSO) 13.44 (1H, s), 9.05 (1H, d, J = 2.5 Hz), 8.80 (2H, d, J = 5.8 Hz), 8.47 (1H, dd, J = 2.4, 8.7 Hz), 8.02-7.99 (2H, m), 7.67 (1H, d, J = 2.8 Hz), 7.62 (1H, dd, J = 2.9, 4.9 Hz), 7.28 (1H, d, J = 4.8 Hz), 7.08 (1H, d, J = 8.8 Hz), 5.51 (2H, s); MS (ESI⁺) 396 | Ex 31 (Scheme 2) from 6-fluoro-N-(5-(pyridin-4-yl)-1,3,4-thiadiazol-2-yl)nicotinamide (Example 31 step a) and thiophen-3-ylmethanol |
| 129 | 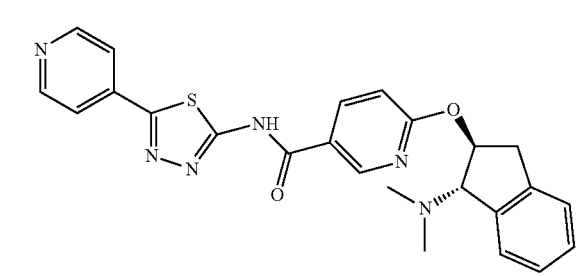<br>6-(((1S,2S)-1-(dimethylamino)-2,3-dihydro-1H-inden-2-yl)oxy)-N-(5-(pyridin-4-yl)-1,3,4-thiadiazol-2-yl)nicotinamide | ¹H NMR (400 MHz, DMSO) 13.24 (1H, s), 9.07 (1H, d, J = 2.5 Hz), 8.81-8.79 (2H, m), 8.46 (1H, dd, J = 2.5, 8.8 Hz), 8.01-7.99 (2H, m), 7.43-7.38 (1H, m), 7.35-7.32 (3H, m), 7.03 (1H, d, J = 8.6 Hz), 5.97-5.92 (1H, m), 4.46 (1H, d, J = 3.3 Hz), 3.58 (1H, dd, J = 6.8, 16.9 Hz), 2.93 (1H, dd, J = 3.8, 17.2 Hz), 2.35 (6H, s); MS (ESI⁺) 459 | Ex 32 (Scheme 2) from 6-fluoro-N-(5-(pyridin-4-yl)-1,3,4-thiadiazol-2-yl)nicotinamide (Ex 31 step a) and (1S,2S)-1-amino-2,3-dihydro-1H-inden-2-ol |
| 130 | 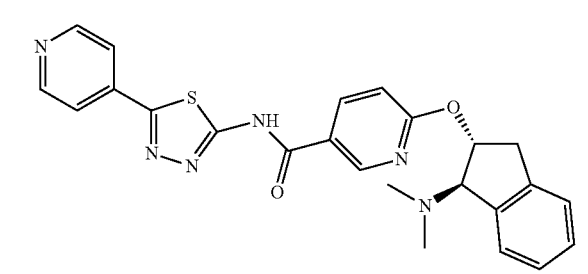<br>6-(((1R,2R)-1-(dimethylamino)-2,3-dihydro-1H-inden-2-yl)oxy)-N-(5-(pyridin-4-yl)-1,3,4-thiadiazol-2-yl)nicotinamide | ¹H NMR (400 MHz, DMSO) 13.3 (1H, s), 9.07 (1H, d, J = 2.3 Hz), 8.81-8.78 (2H, m), 8.45 (1H, dd, J = 2.4, 8.7 Hz), 8.02-7.98 (2H, m), 7.43-7.38 (1H, m), 7.33 (3H, dd, J = 4.7, 4.7 Hz), 7.03 (1H, d, J = 8.8 Hz), 5.96-5.91 (1H, m), 4.45 (1H, d, J = 3.0 Hz), 3.58 (1H, dd, J = 6.7, 17.1 Hz), 2.92 (1H, dd, J = 3.5, 17.2 Hz), 2.34 (6H, s); MS (ESI⁺) 459 | Ex 32 (Scheme 2) from 6-fluoro-N-(5-(pyridin-4-yl)-1,3,4-thiadiazol-2-yl)nicotinamide (Ex 31 step a) and (1R,2R)-1-amino-2,3-dihydro-1H-inden-2-ol |

TABLE 1-continued

| Ex. | Structure and Name | Data | Method |
|---|---|---|---|
| 131 | 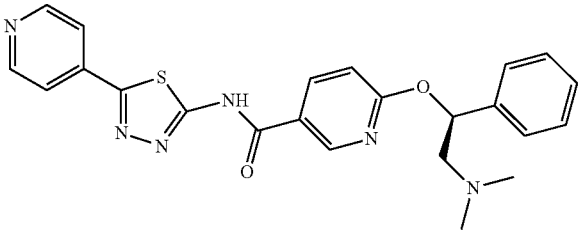<br>(S)-6-(2-(dimethylamino)-1-phenylethoxy)-N-(5-(pyridin-4-yl)-1,3,4-thiadiazol-2-yl)nicotinamide | ¹H NMR (400 MHz, DMSO) 12.54 (1H, s), 8.89 (1H, d, J = 2.5 Hz), 8.78-8.75 (2H, m), 8.43 (1H, dd, J = 2.5, 8.6 Hz), 7.97-7.94 (2H, m), 7.51 (2H, d, J = 7.1 Hz), 7.42 (2H, dd, J = 7.5, 7.5 Hz), 7.37-7.31 (1H, m), 7.09 (1H, d, J = 8.8 Hz), 6.47 (1H, dd, J = 3.8, 9.1 Hz), 3.16 (1H, dd, J = 9.0, 13.3 Hz), 2.84 (1H, dd, J = 3.7, 13.3 Hz), 2.45 (6H, s); MS (ESI⁺) 447 | Ex31 (Scheme 2) from 6-fluoro-N-(5-(pyridin-4-yl)-1,3,4-thiadiazol-2-yl)nicotinamide and (S)-2-(dimethylamino)-1-phenylethanol (Ex 6 step a starting from (S)-2-amino-1-phenylethanol) |
| 132 | 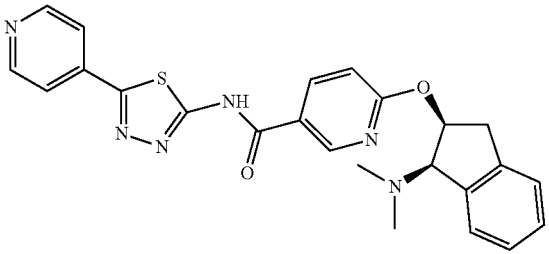<br>6-(((1R,2S)-1-(dimethylamino)-2,3-dihydro-1H-inden-2-yl)oxy)-N-(5-(pyridin-4-yl)-1,3,4-thiadiazol-2-yl)nicotinamide | ¹H NMR (400 MHz, DMSO) 13.09 (1H, br s), 9.06 (1H, d, J = 2.5 Hz), 8.82-8.78 (2H, m), 8.46 (1H, dd, J = 2.4, 8.7 Hz), 8.02-7.98 (2H, m), 7.45-7.41 (1H, m), 7.38-7.33 (3H, m), 7.02 (1H, d, J = 8.6 Hz), 6.03 (1H, q, J = 6.1 Hz), 4.60 (1H, d, J = 5.8 Hz), 3.41-3.35 (1H, m), 3.14 (1H, dd, J = 5.1, 16.7 Hz), 2.42 (6H, s); MS(ESI⁺) 459 | Ex 32 (Scheme 2) from 6-fluoro-N-(5-(pyridin-4-yl)-1,3,4-thiadiazol-2-yl)nicotinamide (Ex 31 step a) and (1R,2S)-1-amino-2,3-dihydro-1H-inden-2-ol |
| 133 | 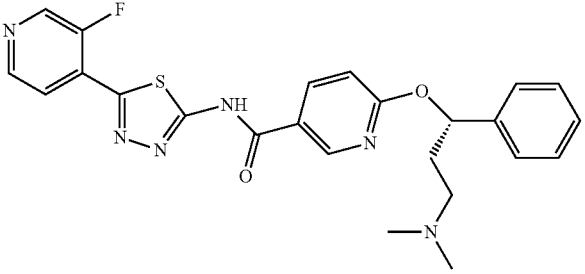<br>(S)-6-(3-(dimethylamino)-1-phenylpropoxy)-N-(5-(3-fluoropyridin-4-yl)-1,3,4-thiadiazol-2-yl)nicotinamide | ¹H NMR (400 MHz, DMSO) 8.76 (1H, d, J = 2.3 Hz), 8.68 (1H, d, J = 2.3 Hz), 8.46 (1H, d, J = 5.1 Hz), 8.30 (1H, dd, J = 2.4, 8.7 Hz), 8.13-8.08 (1H, m), 7.38 (2H, d, J = 7.3 Hz), 7.30 (2H, dd, J = 7.6, 7.6 Hz), 7.21 (1H, dd, J = 7.3, 7.3 Hz), 6.88 (1H, d, J = 8.6 Hz), 6.18 (1H, dd, J = 5.2, 8.0 Hz), 2.68 (2H, dd, J = 7.5, 7.5 Hz), 2.41 (6H, s), 2.25-2.14 (1H, m), 2.10-2.00 (1H, m); MS (ESI⁺) 479 | Ex 31 (Scheme 2) from 6-fluoronicotinic acid, 5-(3-fluoropyridin-4-yl)-1,3,4-thiadiazol-2-amine (Ex 14 step a) and (S)-3-(dimethylamino)-1-phenylpropan-1-ol (Ex 26 step a) |
| 134 | 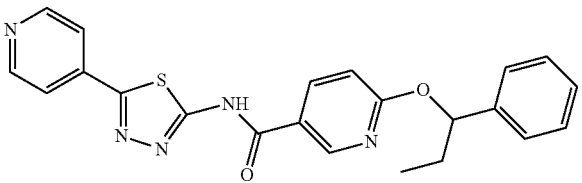<br>6-(1-phenylpropoxy)-N-(5-(pyridin-4-yl)-1,3,4-thiadiazol-2-yl)nicotinamide | ¹H NMR (400 MHz, DMSO) 13.36 (1H, s), 8.91 (1H, d, J = 2.5 Hz), 8.81-8.78 (2H, m), 8.42 (1H, dd, J = 2.5, 8.6 Hz), 8.01-7.98 (2H, m), 7.47 (2H, d, J = 7.1 Hz), 7.40 (2H, dd, J = 7.6, 7.6 Hz), 7.34-7.30 (1H, m), 7.10 (1H, d, J = 8.8 Hz), 6.16 (1H, dd, J = 6.7, 6.7 Hz), 2.11-1.92 (2H, m), 0.96 (3H, dd, J = 7.3, 7.3 Hz); MS (ESI⁺) 418 | Ex 34 (Scheme 2) from 6-fluoro-N-(5-(pyridin-4-yl)-1,3,4-thiadiazol-2-yl) nicotinamide (Ex 31 step a) and 1-phenylpropan-1-ol |

TABLE 1-continued

| Ex. | Structure and Name | Data | Method |
|---|---|---|---|
| 135 | 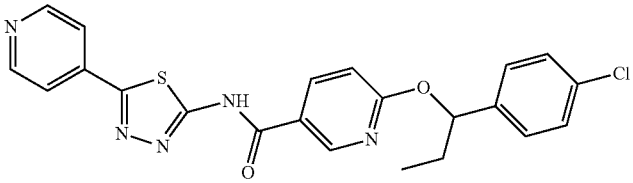<br>6-(1-(4-chlorophenyl)propoxy)-N-(5-(pyridin-4-yl)-1,3,4-thiadiazol-2-yl)nicotinamide | $^1$H NMR (400 MHz, DMSO) 13.33 (1H, s), 8.89 (1H, d, J = 2.5 Hz), 8.80-8.77 (2H, m), 8.43 (1H, dd, J = 2.5, 8.8 Hz), 7.99-7.97 (2H, m), 7.52-7.44 (4H, m), 7.09 (1H, d, J = 8.8 Hz), 6.14 (1H, dd, J = 6.6, 6.6 Hz), 2.09-1.91 (2H, m), 0.96 (3H, dd, J = 7.3, 7.3 Hz); MS (ESI$^+$) 452, 454 | Ex 34 (Scheme 2) from 6-fluoro-N-(5-(pyridin-4-yl)-1,3,4-thiadiazol-2-yl)nicotinamide (Ex 31 step a) and (4-chlorophenyl)propan-1-ol |
| 136 | 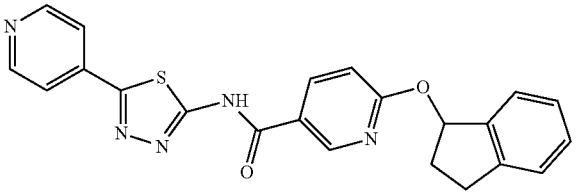<br>6-((2,3-dihydro-1H-inden-1-yl)oxy)-N-(5-(pyridin-4-yl)-1,3,4-thiadiazol-2-yl)nicotinamide | $^1$H NMR (400 MHz, DMSO) 11.51 (1H, s), 8.88 (1H, d, J = 2.3 Hz), 8.74-8.72 (2H, m), 8.42 (1H, dd, J = 2.4, 8.7 Hz), 7.92-7.89 (2H, m), 7.52-7.48 (2H, m), 7.42 (2H, dd. J = 7.6, 7.6 Hz), 7.36-7.32 (1H, m), 7.02 (1H, d, J = 8.8 Hz), 6.31 (1H, dd, J = 5.2, 8.0 Hz), 2.78 (2H, dd, J = 7.5, 7.5 Hz), 2.52 (6H, s), 2.39-2.26 (1H, m), 2.22-2.12 (1H, m); MS (ESI$^+$) 416 | Ex 35 (Scheme 2) from 6-chloro-N-(5-(pyridin-4-yl)-1,3,4-thiadiazol-2-yl)nicotinamide (Ex 35 step a) and 2,3-dihydro-1H-inden-1-ol |
| 137 | 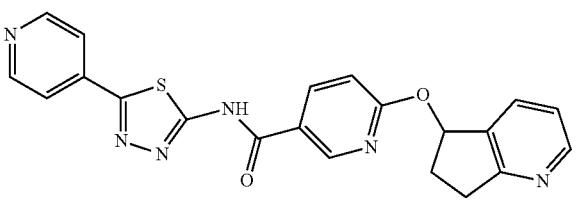<br>6-((6,7-dihydro-5H-cyclopenta[b]pyridin-5-yl)oxy)-N-(5-(pyridin-4-yl)-1,3,4-thiadiazol-2-yl)nicotinamide | $^1$H NMR (400 MHz, DMSO) 13.5 (1H, br s), 9.08 (1H, d, J = 2.5 Hz), 8.79-8.76 (2H, m), 8.55 (1H, dd, J = 1.6, 4.9 Hz), 8.46 (1H, dd, J = 2.8, 8.6 Hz), 7.99-7.96 (2H, m), 7.91 (1H, dd, J = 1.3, 7.6 Hz), 7.29 (1H, dd, J = 4.9, 7.7 Hz), 7.01 (1H, d, J = 8.6 Hz), 6.67 (1H, dd, J = 4.0, 7.1 Hz), 3.24-3.14 (1H, m), 3.02 (1H, ddd, J = 5.3, 9.0, 16.8 Hz), 2.78-2.69 (2H, m), 2.26-2.13 (1H, m); MS (ESI$^+$) 417 | Ex 35 (Scheme 2) from 6-chloro-N-(5-(pyridin-4-yl)-1,3,4-thiadiazol-2-yl)nicotinamide (Ex 35 step a) and 6,7-dihydro-5H-cyclopenta[b]pyridin-5-ol |
| 138 | 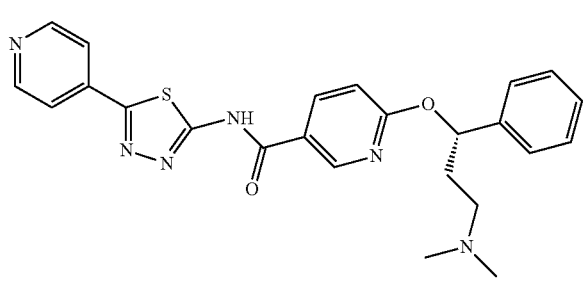<br>(S)-6-(3-(dimethylamino)-1-phenylpropoxy)-N-(5-(pyridin-4-yl)-1,3,4-thiadiazol-2-yl)nicotinamide | $^1$H NMR (400 MHz, DMSO) 11.51 (1H, s), 8.88 (1H, d, J = 2.3 Hz), 8.74-8.72 (2H, m), 8.42 (1H, dd, J = 2.4, 8.7 Hz), 7.92-7.89 (2H, m), 7.52-7.48 (2H, m), 7.42 (2H, dd, J = 7.6, 7.6 Hz), 7.36-7.32 (1H, m), 7.02 (1H, d, J = 8.8 Hz), 6.31 (1H, dd, J = 5.2, 8.0 Hz), 2.78 (2H, dd, J = 7.5, 7.5 Hz), 2.39-2.26 (1H, m), 2.22-2.12 (1H, m); MS (ESI$^+$) 461 | Example 35 (Scheme 2) Prepared from 6-chloro-N-(5-(pyridin-4-yl)-1,3,4-thiadiazol-2-yl)nicotinamide (Example 35 step a) and (S)-3-(dimethylamino)-1-phenylpropan-1-ol (Example 26 step a) |
| 139 | 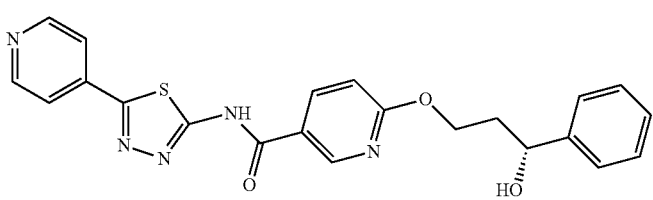<br>(R)-6-(3-hydroxy-3-phenylpropoxy)-N-(5-(pyridin-4-yl)-1,3,4-thiadiazol-2-yl)nicotinamide | $^1$H NMR (400 MHz, DMSO) 13.39 (1H, s), 9.00 (1H, d, J = 2.5 Hz), 8.79 (2H, d, J = 5.6 Hz), 8.43 (1H, dd, J = 2.4, 8.7 Hz), 7.99 (2H, d, J = 6.1 Hz), 7.44-7.36 (4H, m), 7.33-7.28 (1H, m), 7.01 (1H, d, J = 8.6 Hz), 5.43 (1H, d, J = 4.5 Hz), 4.84-4.78 (1H, m), 4.56-4.38 (2H, m), 2.12 (2H, q, J = 6.7 Hz); MS (ESI$^+$) 434 | Ex 35 (Scheme 2) from 6-chloro-N-(5-(pyridin-4-yl)-1,3,4-thiadiazol-2-yl)nicotinamide (Ex 35 step a) and (R)-1-phenyl-3-((triisopropylsilyl)oxy)-propan-1-ol (according to Ex 7 step a from (R)-1-phenylpropane-1,3-diol) |

TABLE 1-continued

| Ex. | Structure and Name | Data | Method |
|---|---|---|---|
| 140 | 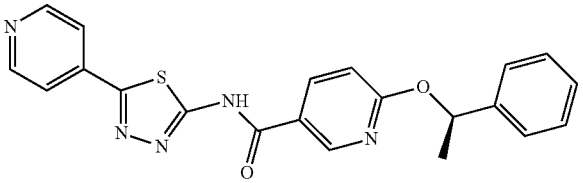<br>(R)-6-(1-phenylethoxy)-N-(5-(pyridin-4-yl)-1,3,4-thiadiazol-2-yl)nicotinamide | $^1$H NMR (400 MHz, DMSO) 13.32 (1H, br s), 8.89 (1H, d, J = 2.3 Hz), 8.74 (2H, d, J = 6.1 Hz), 8.38 (1H, dd, J = 2.5, 6.2 Hz), 7.95-7.92 (2H, m), 7.46 (2H, d, J = 7.3 Hz), 7.37, 2H, dd, J = 7.5, 7.5 Hz), 7.3-7.26 (1H, m), 7.03 (1H, d, J = .8. Hz), 6.31 (1H, q, J = 7.5 Hz), 1.62 (3H, d, J = 6.6 Hz); MS (ESI$^+$) 404 | Ex 35 (Scheme 2) from 6-chloro-N-(5-(pyridin-4-yl)-1,3,4-thiadiazol-2-yl)nicotinamide and (R)-1-phenylethanol |
| 141 | 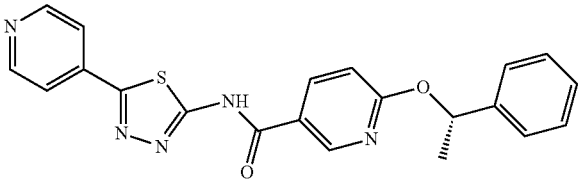<br>(S)-6-(1-phenylethoxy)-N-(5-(pyridin-4-yl)-1,3,4-thiadiazol-2-yl)nicotinamide | $^1$H NMR (400 MHz, DMSO) 13.31 (1H, s), 8.89 (1H, d, J = 2.3 Hz), 8.75-8.73 (2H, m), 8.38 (1H, dd, J = 2.5, 8.6 Hz), 7.95-7.93 (2H, m), 7.48-7.44 (2H, m), 7.37, (2H, dd, J = 7.6, 7.6 Hz), 7.3-7.26 (1H, m), 7.03 (1h, d, J = 8.8 Hz), 6.31 (1H, q, J = 6.5 Hz), 1.62 (3H, d, J = 6.6 Hz); MS (ESI$^+$) 404 | Ex 35 (Scheme 2) from 6-chloro-N-(5-(pyridin-4-yl)-1,3,4-thiadiazol-2-yl)nicotinamide and (S)-1-phenylethanol |
| 142 | 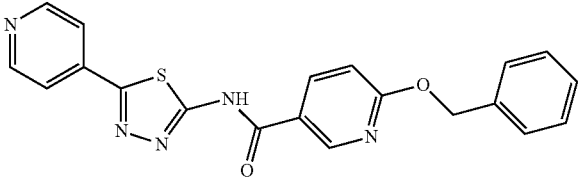<br>6-(benzyloxy)-N-(5-(pyridin-4-yl)-1,3,4-thiadiazol-2-yl)nicotinamide | $^1$H NMR (400 MHz, DMSO) 13.35 (1H, br s), 9.0 (1H, d, J = 2.3 Hz), 8.76-8.75 (2H, m), 8.42 (1H, dd, J = 2.5, 8.8 Hz), 7.97-7.95 (2H, m), 7.48 (2H, d, J = 7.1 Hz), 7.44-7.35 (3H, m), 7.07 (1H, d, J = 8.8 Hz), 5.48 (2H, s); MS (ESI$^+$) 390 | Ex 35 (Scheme 2) from 6-chloro-N-(5-(pyridin-4-yl)-1,3,4-thiadiazol-2-yl)nicotinamide and benzyl alcohol |
| 143 | 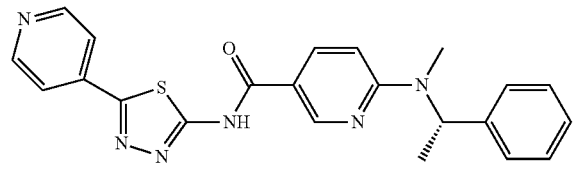<br>(S)-6-(methyl(1-phenylethyl)amino)-N-(5-(pyridin-4-yl)-1,3,4-thiadiazol-2-yl)nicotinamide | $^1$H NMR (400 MHz, DMSO) 13.10 (1H, s), 9.00 (1H, d, J = 2.3 Hz), 8.81-8.79 (2H, m), 8.31 (1H, dd, J = 2.5, 9.1 Hz), 8.01-7.98 (2H, m), 7.44-7.39 (2H, m), 7.36-7.32 (3H, m), 6.86 (1H, d, J = 9.3 Hz), 6.27 (1H, d, J = 4.8 Hz), 2.87 (3H, s), 1.62 (3H, d, J = 7.1 Hz); MS (ESI$^+$) 417 | Ex 36 (Scheme 2) from 6-fluoro-N-(5-(pyridin-4-yl)-1,3,4-thiadiazol-2-yl)nicotinamide (Ex 31 step a) and (S)-N-methyl-1-phenylethanamine |
| 144 | 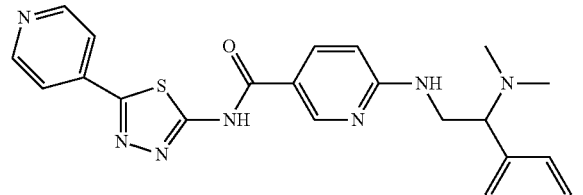<br>6-((2-(dimethylamino)-2-phenylethyl)amino)-N-(5-(pyridin-4-yl)-1,3,4-thiadiazol-2-yl)nicotinamide | $^1$H NMR (400 MHz, DMSO) 12.91 (1H, s), 8.87 (1H, d, J = 2.5 Hz), 8.80-8.78 (2H, m), 8.08 (1H, dd, J = 2.1, 8.7 Hz), 7.99-7.97 (2H, m), 7.43-7.38 (2H, m), 7.35 (4H, d, J = 7.1 Hz), 6.66 (1H, d, J = 8.8 Hz), 3.98-3.90 (1H, m), 3.76-3.70 (2H, m), 2.20 (6H, s); MS (ESI$^+$) 446 | Ex 36 (Scheme 2) from 6-fluoro-N-(5-(pyridin-4-yl)-1,3,4-thiadiazol-2-yl)nicotinamide (Ex 31 step a) and $N^1,N^1$-dimethyl-1-phenylethane-1,2-diamine |

TABLE 1-continued

| Ex. | Structure and Name | Data | Method |
|---|---|---|---|
| 145 | 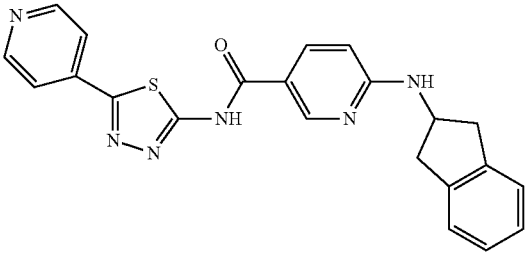<br>6-((2,3-dihydro-1H-inden-2-yl)amino)-N-(5-(pyridin-4-yl)-1,3,4-thiadiazol-2-yl)nicotinamide | $^1$H NMR (400 MHz, DMSO) 13.03 (1H, s), 8.93 (1H, d, J = 2.5 Hz), 8.79 (2H, d, J = 6.1 Hz), 8.15-8.10 (1H, m), 7.98 (2H, d, J = 5.8 Hz), 7.83 (1H, d, J = 6.6 Hz), 7.31 (2H, dd, J = 3.3, 5.3 Hz), 7.22 (2H, dd, J = 3.3, 5.6 Hz), 6.63 (1H, d, J = 8.8 Hz), 4.78 (1H, dd, J = 6.6, 12.6 Hz), 2.92 (2H, dd, J = 5.7, 16.0 Hz) two protons are obscured by the residual water signal; MS (ESI$^+$) 415 | Ex 36 (Scheme 2) from 6-fluoro-N-(5-(pyridin-4-yl)-1,3,4-thiadiazol-2-yl)nicotinamide (Ex 31 step a) and 2,3-dihydro-1H-inden-2-amine |
| 146 | 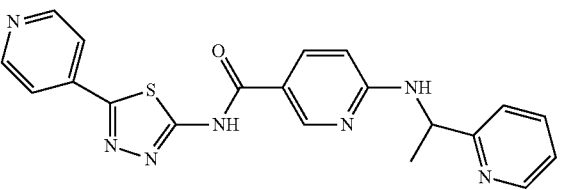<br>6-((1-(pyridin-2-yl)ethyl)amino)-N-(5-(pyridin-4-yl)-1,3,4-thiadiazol-2-yl)nicotinamide | $^1$H NMR (400 MHz, DMSO) 12.99 (1H, s), 8.83-8.77 (3H, m), 8.59 (1H, d, J = 4.8 Hz), 8.12 (1H, dd, J = 2.4, 9.0 Hz), 8.03-7.96 (3H, m), 7.82-7.77 (1H, m), 7.43 (1H, d, J = 8.1 Hz), 7.32-7.28 (1H, m), 6.72 (1H, d, J = 8.8 Hz), 5.33-5.28 (1H, m), 1.55 (3H, d, J = 6.8 Hz); MS (ESI$^+$) 404 | Ex 36 (Scheme 2) from 6-fluoro-N-(5-(pyridin-4-yl)-1,3,4-thiadiazol-2-yl)nicotinamide (Ex 31 step a) and 1-(pyridin-2-yl)ethanamine |
| 147 | 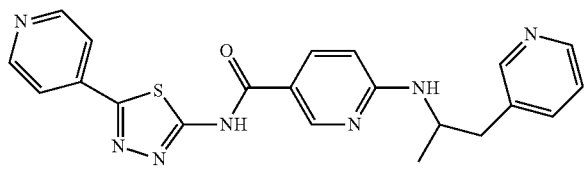<br>6-((1-(pyridin-3-yl)propan-2-yl)amino)-N-(5-(pyridin-4-yl)-1,3,4-thiadiazol-2-yl)nicotinamide | $^1$H NMR (400 MHz, DMSO) 12.99 (1H, s), 8.87 (1H, d, J = 2.3 Hz), 8.81-8.78 (2H, m), 8.50 (1H, d, J = 1.8 Hz), 8.44 (1H, dd, J = 1.4, 4.7 Hz), 8.09 (1H, dd, J = 2.4, 9.0 Hz), 8.00-7.97 (2H, m), 7.71 (1H, d, J = 7.8 Hz), 7.53 (1H, d, J = 7.8 Hz), 7.35 (1H, dd, J = 4.7, 7.7 Hz), 6.58 (1H, d, J = 8.8 Hz), 4.44-4.34 (1H, m), 2.89 (2H, dd, J = 2.1, 6.4 Hz), 1.21 (3H, d, J = 6.6 Hz); MS (ESI$^+$) 418 | Example 36 (Scheme 2) from 6-fluoro-N-(5-(pyridin-4-yl)-1,3,4-thiadiazol-2-yl)nicotinamide (Ex 31 step a) and 1-(pyridin-3-yl)propan-2-amine |
| 148 | 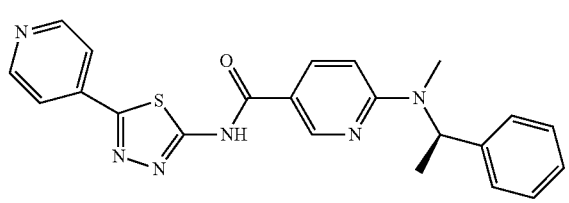<br>(R)-6-(methyl(1-phenylethyl)amino)-N-(5-(pyridin-4-yl)-1,3,4-thiadiazol-2-yl)nicotinamide | $^1$H NMR (400 MHz, DMSO) 13.09 (1H, s), 9.00 (1H, d, J = 2.5 Hz), 8.81-8.78 (2H, m), 8.31 (1H, dd, J = 2.5, 9.1 Hz), 8.01-7.98 (2H, m), 7.44-7.39 (2H, m), 7.37-7.32 (3H, m), 6.86 (1H, d, J = 9.1 Hz), 6.30 (1H, d, J = 5.3 Hz), 2.87 (3H, s), 1.62 (3H, d, J = 6.8 Hz); MS (ESI$^+$) 417 | Ex 36 (Scheme 2) from 6-fluoro-N-(5-(pyridin-4-yl)-1,3,4-thiadiazol-2-yl)nicotinamide (Ex 31 step a) and (R)-N-methyl-1-phenylethanamine |
| 149 | 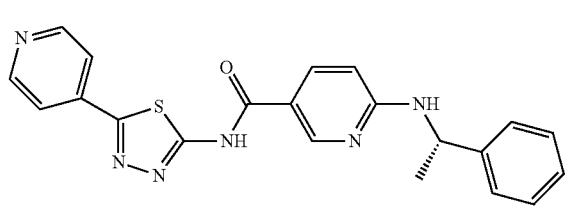<br>(S)-6-((1-phenylethyl)amino)-N-(5-(pyridin-4-yl)-1,3,4-thiadiazol-2-yl)nicotinamide | $^1$H NMR (400 MHz, DMSO) 12.98 (1H, s), 8.83 (1H, d, J = 2.5 Hz), 8.80-8.77 (2H, m), 8.10 (1H, dd, J = 2.4, 9.0 Hz), 8.03-7.96 (3H, m), 7.44 (2H, d, J = 7.3 Hz), 7.37 (2H, dd, J = 7.6, 7.6 Hz), 7.27 (1H, dd, J = 7.2, 7.2 Hz), 6.64 (1H, d, J = 8.8 Hz), 5.24-5.24 (1H, m), 1.52 (3H, d, J = 6.8 Hz); MS (ESI$^+$) 403 | Ex 36 (Scheme 2) from 6-fluoro-N-(5-(pyridin-4-yl)-1,3,4-thiadiazol-2-yl) nicotinamide (Ex e 31 step a) and (S)-1-phenylethanamine |

TABLE 1-continued

| Ex. | Structure and Name | Data | Method |
|---|---|---|---|
| 150 | 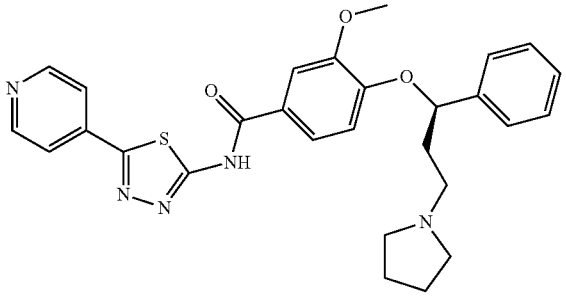<br>(R)-3-methoxy-4-(1-phenyl-3-(pyrrolidin-1-yl)propoxy)-N-(5-(pyridin-4-yl)-1,3,4-thiadiazol-2-yl)benzamide | $^1$H NMR (400 MHz, DMSO) 8.62 (2H, d, J = 5.8 Hz), 7.81 (2H, d, J = 6.1 Hz), 7.71 (1H, d, J = 2.0 Hz), 7.53 (1H, dd, J = 1.9, 8.5 Hz), 7.36-7.27 (4H, m), 7.21 (1H, dd, J = 7.2, 7.2 Hz), 6.84 (1H, d, J = 8.6 Hz), 5.46 (1H, dd, J = 5.1, 7.8 Hz), 3.85 (3H, s), 2.67 (6H, s), 2.70-2.60 (6H, m), 2.63 (6H, s), 2.00-1.91 (1H, m), 1.72-1.67 (4H, m); MS (ESI$^+$) 516 | Example 9 (Scheme 1) Prepared from methyl 4-hydroxy-3-methoxybenzoate, 5-(4-pyridyl)-1,3,4-thiadiazol-2-yl amine and (S)-3-chloro-1-phenylpropan-1-ol |
| 151 | 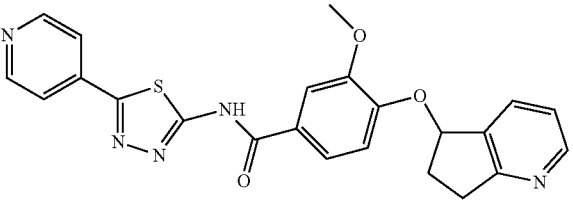<br>4-((6,7-dihydro-5H-cyclopenta[b]pyridin-5-yl)oxy)-3-methoxy-N-(5-(pyridin-4-yl)-1,3,4-thiadiazol-2-yl)benzamide | $^1$H NMR (400 MHz, DMSO) 13.29 (1H, s), 8.82-8.79 (2H, m), 8.58 (1H, dd, J = 1.5, 5.1 Hz), 8.02-7.99 (2H, m), 7.93-7.85 (3H, m), 7.43 (1H, d, J = 8.3 Hz), 7.32 (1H, dd, J = 4.8, 7.6 Hz), 6.09 (1H, dd, J = 3.5, 6.8 Hz), 3.90 (3H, s), 3.23-3.13 (1H, m), 3.01 (1H, ddd, J = 5.1, 9.1, 16.9 Hz), 2.77-2.66 (1H, m), 2.16 (1H, ddd, J = 5.1, 8.9, 17.6 Hz); MS (ESI$^+$) 446 | Ex4 (Scheme 1) from methyl 4-hydroxy-3-methoxybenzoate, 6,7-dihydro-5H-cyclopenta[b]pyridin-5-ol and 5-(pyridin-4-yl)-1,3,4-thiadiazol-2-amine |
| 152 | 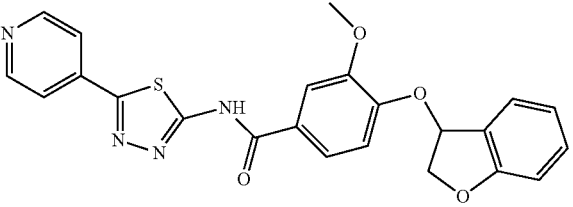<br>4-((2,3-dihydrobenzofuran-3-yl)oxy)-3-methoxy-N-(5-(pyridin-4-yl)-1,3,4-thiadiazol-2-yl)benzamide | $^1$H NMR (400 MHz, DMSO) 13.27 (1H, s), 8.81-8.79 (2H, m), 8.01-7.98 (2H, m), 7.92-7.87 (2H, m), 7.54 (1H, d, J = 7.6 Hz), 7.43-7.36 (2H, m), 7.04-6.99 (2H, m), 6.25 (1H, dd, J = 1.5, 6.1 Hz), 4.81 (1H, dd, J = 6.2, 11.2 Hz), 4.61 (1H, dd, J = 1.9, 11.2 Hz), 3.89 (3H, s); MS (ESI$^+$) 447 | Ex 4 (Scheme 1) from methyl 4-hydroxy-3-methoxybenzoate, 2,3-dihydrobenzofuran-3-ol and 5-(pyridin-4-yl)-1,3,4-thiadiazol-2-amine |
| 153 | 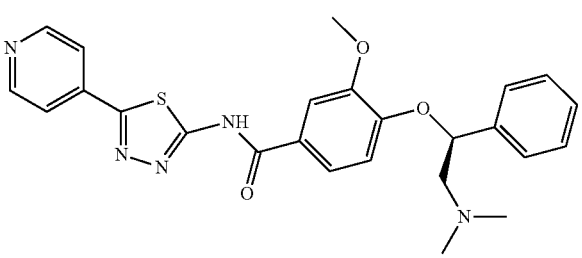<br>(S)-4-(2-(dimethylamino)-1-phenylethoxy)-3-methoxy-N-(5-(pyridin-4-yl)-1,3,4-thiadiazol-2-yl)benzamide | $^1$H NMR (400 MHz, DMSO) 12.89 (1H, s), 8.79-8.77 (2H, m), 7.98-7.96 (2H, m), 7.83 (1H, d, J = 2.0 Hz), 7.67 (1H, dd, J = 2.0, 8.6 Hz), 7.50-7.46 (2H, m), 7.40 (2H, dd, J = 7.5, 7.5 Hz), 7.34-7.30 (1H, m), 7.09 (1H, d, J = 8.8 Hz), 5.71 (1H, dd, J = 4.3, 7.8 Hz), 3.98 (3H, s), 3.00 (1H, dd, J = 8.0, 13.3 Hz), 2.70 (1H, dd, J = 4.2, 13.3 Hz), 2.38 (6H, s); MS (ESI$^+$) 476 | Ex 6 (Scheme 1) from (S)-2-amino-1-phenylethanol, methyl 4-hydroxy-3-methoxybenzoate and 5-(pyridin-4-yl)-1,3,4-thiadiazol-2-amine |

TABLE 1-continued

| Ex. | Structure and Name | Data | Method |
|---|---|---|---|
| 154 | 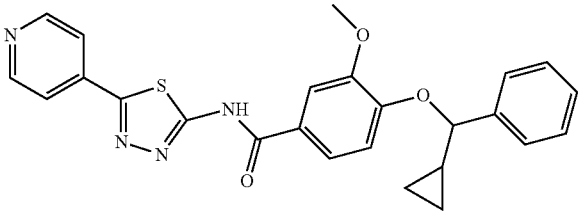<br>4-(cyclopropyl(phenyl)methoxy)-3-methoxy-N-(5-(pyridin-4-yl)-1,3,4-thiadiazol-2-yl)benzamide | $^1$H NMR (400 MHz, DMSO) 13.10 (1H, s), 8.75-8.72 (2H, m), 7.94-7.92 (2H, m), 7.77 (1H, d, J = 2.0 Hz), 7.60 (1H, dd, J = 2.0, 8.6 Hz), 7.45-7.41 (2H, m), 7.35 (2H, dd, J = 7.5, 7.5 Hz), 7.28-7.24 (1H, m), 6.92 (1H, d, J = 8.6 Hz), 4.91 (1H, d, J = 8.3 Hz), 3.94 (3H, s), 1.39-1.32 (1H, m), 0.69-0.63 (1H, m), 0.54-0.49 (3H, m); MS (ESI$^+$) 459 | Ex 4 (Scheme 1) from methyl 4-hydroxy-3-methoxybenzoate, cyclopropyl(phenyl)-methanol and 5-(pyridin-4-yl)-1,3,4-thiadiazol-2-amine |
| 155 | 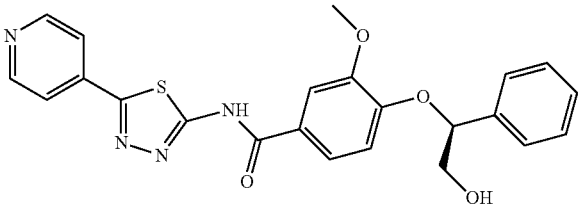<br>(S)-4-(2-hydroxy-1-phenylethoxy)-3-methoxy-N-(5-(pyridin-4-yl)-1,3,4-thiadiazol-2-yl)benzamide | $^1$H NMR (400 MHz, DMSO) 13.21 (1H, s), 8.8-8.78 (2H, m), 8.0-7.98 (2H, m), 7.84 (1H, d, J = 2.0 Hz), 7.68 (1H, dd, J = 82.1, 8.5 Hz), 7.46 (2H, d, J = 7.1 Hz), 7.4, 2H, dd, J = 7.5, 7.5 Hz), 7.35-7.3 (1H, m), 7.07 (1H, d, J = 8.6 Hz), 5.55 (1H, dd, J = 4.0, 7.3 Hz), 5.23 (1H, dd, J = 5.7, 5.7 Hz), 3.99 (3H, s), 3.91-383 (1H, m), 3.74-3.66 (1H, m); MS (ESI$^+$) 449 | Ex 7 (Scheme 1) from (R)-1-phenylethane-1,2-diol, methyl 4-hydroxy-3-methoxybenzoate and 5-(pyridin-4-yl)-1,3,4-thiadiazol-2-amine |
| 156 | 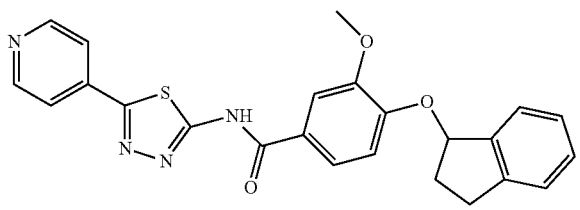<br>4-((2,3-dihydro-1H-inden-1-yl)oxy)-3-methoxy-N-(5-(pyridin-4-yl)-1,3,4-thiadiazol-2-yl)benzamide | $^1$H NMR (400 MHz, DMSO) 13.22 (1H, s), 8.77-8.75 (2H, m), 7.97-7.95 (2H, m), 7.88-7.82 (2H, m), 7.44-7.34 (4H, m), 7.29-7.23 (1H, m), 5.99 (1H, dd, J = 3.5, 6.6 Hz), 3.84 (3H, s), 3.12-3.03 (1H, m), 2.96-2.87 (1H, m), 2.68-2.54 (1H, m), 2.12-2.02 (1H, m); MS (ESI$^+$) 443 | Ex 4 (Scheme 1) from methyl 4-hydroxy-3-methoxybenzoate, 2,3-dihydro-1H-inden-1-ol and 5-(pyridin-4-yl)-1,3,4-thiadiazol-2-amine |
| 157 | 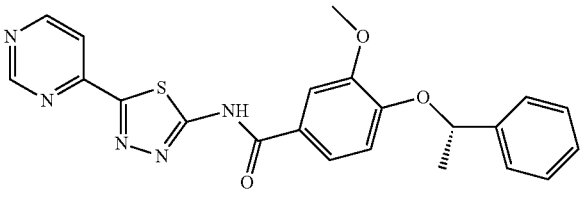<br>(S)-3-methoxy-4-(1-phenylethoxy)-N-(5-(pyrimidin-4-yl)-1,3,4-thiadiazol-2-yl)benzamide | $^1$H NMR (400 MHz, DMSO) 13.19 (1H, s), 9.33 (1H, d, J = 1.3 Hz), 9.01 (1H, d, J = 5.3 Hz), 8.26 (1H, dd, J = 1.3, 5.3 Hz), 7.79 (1H, d, J = 2.0 Hz), 7.66 (1H, dd, J = 2.0, 8.6 Hz), 7.49 (2H, d, J = 7.1 Hz), 7.36 (2H, dd, J = 7.6, 7.6 Hz), 7.27 (1H, dd, J = 7.3, 7.3 Hz), 7.01 (1H, d, J = 8.6 Hz), 5.7-5.64 (1H, m), 3.93 (3H, s), 1.59 (3H, d, J = 6.3 Hz); MS (ESI$^+$) 434 | Ex 13 step c (Scheme 1) from methyl 4-hydroxy-3-methoxybenzoate, (R)-1-phenylethanol and 5-(pyrimidin-4-yl)-1,3,4-thiadiazol-2-amine (Example 13 step a and b) |

TABLE 1-continued

| Ex. | Structure and Name | Data | Method |
|---|---|---|---|
| 158 | 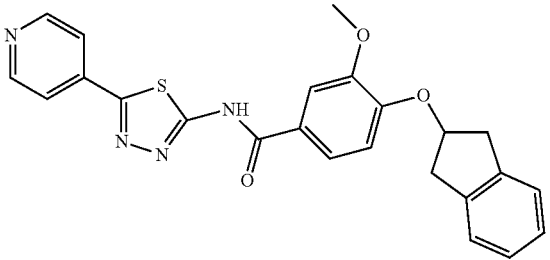<br>4-((2,3-dihydro-1H-inden-2-yl)oxy)-3-methoxy-N-(5-(pyridin-4-yl)-1,3,4-thiadiazol-2-yl)benzamide | $^1$H NMR (400 MHz, DMSO) 13.23 (1H, s), 8.77-8.74 (2H, m), 7.97-7.95 (2H, m), 7.85 (1H, dd, J = 2.0, 8.6 z), 7.8 (1H, d, J = 2.0 Hz), 7.31-7.24 (3H, m), 7.21-7.18 (2H, m), 5.38-5.33 (1H, m), 3.81 (3H, s), 3.43 (2H, dd, J = 5.8, 17.2 Hz), 3.07 (2H, dd, J = 1.9, 17.1 Hz); MS (ESI$^+$) 445 | Ex 4 (Scheme 1) from methyl 4-hydroxy-3-methoxybenzoate, 2,3-dihydro-1H-inden-2-ol and 5-(pyridin-4-yl)-1,3,4-thiadiazol-2-amine |
| 159 | 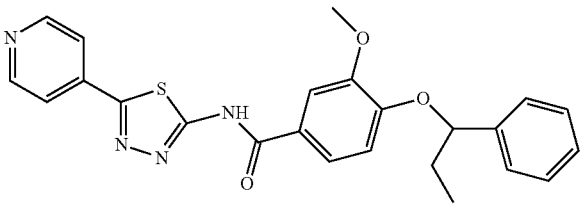<br>3-methoxy-4-(1-phenylpropoxy)-N-(5-(pyridin-4-yl)-1,3,4-thiadiazol-2-yl)benzamide | $^1$H NMR (400 MHz, DMSO) 13.09 (1H, s), 8.68-8.66 (2H, m), 7.88-7.85 (2H, m), 7.71 (1H, dd, J = 2.0 Hz), 7.55 (1H, dd, J = 2.1, 8.5 Hz), 7.35-7.26 (4H, m), 7.21-7.17 (1H, m), 6.9 (1H, d, J = 8.8 Hz), 5.34 (1H, dd, J = 6.6, 6.6 Hz), 3.86 (3H, s), 1.96-1.87 (1H, m), 1.82-1.73 (1H, m), 0.87 (3H, dd, J = 7.3, 7.3 Hz); MS (ESI$^+$) 447 | Ex 4 (Scheme 1) Prepared from methyl 4-hydroxy-3-methoxybenzoate, 1-phenylpropan-1-ol and 5-(pyridin-4-yl)-1,3,4-thiadiazol-2-amine |
| 160 | 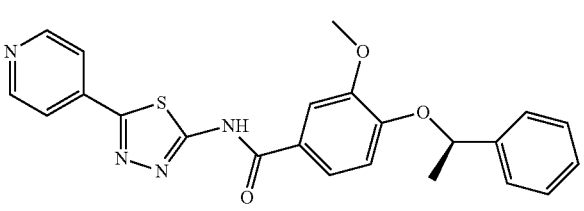<br>(R)-3-methoxy-4-(1-phenylethoxy)-N-(5-(pyridin-4-yl)-1,3,4-thiadiazol-2-yl)benzamide | $^1$H NMR (400 MHz, DMSO) 13.16 (1H, s), 8.75-8.71 (2H, m), 7.91 (2H, d, J = 4.5 Hz), 7.79 (1H, d, J = 2.0 Hz), 7.64 (1H, dd, J = 2.1, 8.5 Hz), 7.42 (2H, d, J = 7.2 Hz), 7.36 (2H, dd, J = 7.5, 7.5 Hz), 7.27 (1H, dd, J = 7.3, 7.3 Hz), 6.99 (1H, d, J = 8.7 Hz), 5.69-5.62 (1H, m), 3.92 (3H, s), 1.60 (3H, d, J = 6.4 Hz); MS (ESI$^+$) 433 | Ex 4 (Scheme 1) from methyl 4-hydroxy-3-methoxybenzoate, (S)-1-phenylethanol, 5-(pyridin-4-yl)-1,3,4-thiadiazol-2-amine |
| 161 | 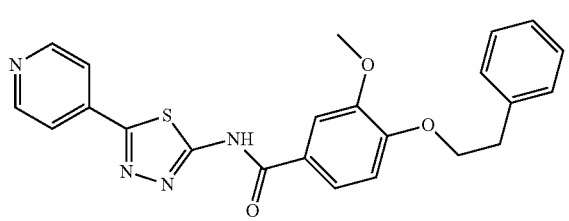<br>3-methoxy-4-phenethoxy-N-(5-(pyridin-4-yl)-1,3,4-thiadiazol-2-yl)benzamide | $^1$H NMR (400 MHz, DMSO) 13.19 (1H, s), 8.77-8.74 (2H, m), 7.97-7.94 (2H, m), 7.82-7.79 (2H, m), 7.39-7.30 (4H, m), 7.26-7.17 (2H, m), 4.30 (2H, dd, J = 7.0, 7.0 Hz), 3.88 (3H, s), 3.10 (2H, dd, J = 7.0, 7.0 Hz); MS (ESI$^+$) 433 | Ex18 (Scheme 1) from methyl 4-hydroxy-3-methoxybenzoate, (2-bromoethyl)benzene and 5-(pyridin-4-yl)-1,3,4-thiadiazol-2-amine |
| 162 | 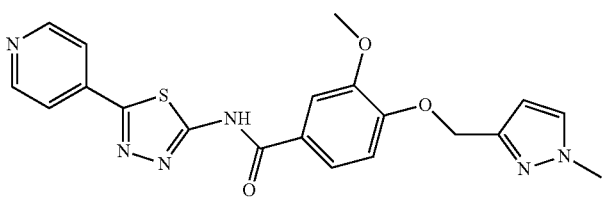<br>3-methoxy-4-((1-methyl-1H-pyrazol-3-yl)methoxy)-N-(5-(pyridin-4-yl)-1,3,4-thiadiazol-2-yl)benzamide | $^1$H NMR (400 MHz, DMSO) 13.19 (1H, s), 8.77-8.74 (2H, m), 7.97-7.94 (2H, m), 7.83-7.79 (2H, m), 7.69 (1H, d, J = 2.1 Hz), 7.31 (1H, d, J = 9.2 Hz), 6.34 (1H, d, J = 2.3 Hz), 5.10 (2H, s), 3.87 (3H, s), 3.85 (3H, s); MS (ESI$^+$) 423 | Ex18 (Scheme 1) from methyl 4-hydroxy-3-methoxybenzoate, 3-(chloromethyl)-1-methyl-1H-pyrazole and 5-(pyridin-4-yl)-1,3,4-thiadiazol-2-amine |

TABLE 1-continued

| Ex. | Structure and Name | Data | Method |
|---|---|---|---|
| 163 | 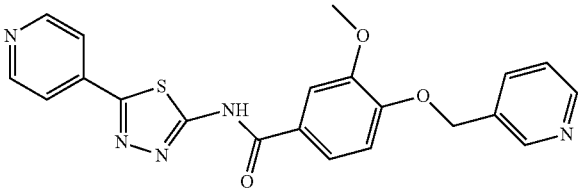<br>3-methoxy-4-(pyridin-3-ylmethoxy)-N-(5-(pyridin-4-yl)-1,3,4-thiadiazol-2-yl)benzamide | $^1$H NMR (400 MHz, DMSO) 13.24 (1H, s), 8.77-8.75 (2H, m), 8.71 (1H, d, J = 1.8 Hz), 8.58 (1H, dd, J = 1.6, 4.9 Hz), 7.97-7.95 (2H, m), 7.92-7.88 (1H, m), 7.83 (2H, d, J = 7.7 Hz), 7.47 (1H, dd, J = 4.7, 8.0 Hz), 7.29 (1H, d, J = 8.8 Hz), 5.27 (2H, s), 3.90 (3H, s); MS (ESI$^+$) 420 | Ex 18 (Scheme 1) from methyl 4-hydroxy-3-methoxybenzoate, 3-(chloromethyl)pyridine and 5-(pyridin-4-yl)-1,3,4-thiadiazol-2-amine |
| 164 | 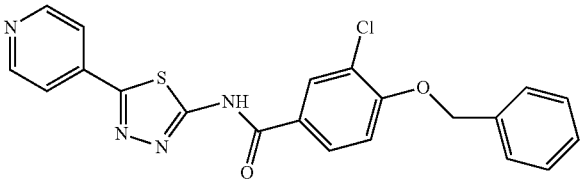<br>4-(benzyloxy)-3-chloro-N-(5-(pyridin-4-yl)-1,3,4-thiadiazol-2-yl)benzamide | $^1$H NMR (400 MHz, DMSO) 13.30 (1H, s), 8.77-8.74 (2H, m), 8.31 (1H, d, J = 2.3 Hz), 8.16 (1H, dd, J = 2.3, 8.7 Hz), 7.97-7.95 (2H, m), 7.51 (2H, d, J = 7.0 Hz), 7.47-7.42 (3H, m), 7.40-7.35 (1H, m), 5.36 (2H, s); MS (ESI$^+$) 423/425 | Ex18 (Scheme 1) from methyl 3-chloro-4-hydroxybenzoate, benzyl bromide and 5-(pyridin-4-yl)-1,3,4-thiadiazol-2-amine |
| 165 | 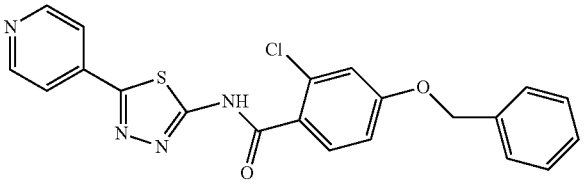<br>4-(benzyloxy)-2-chloro-N-(5-(pyridin-4-yl)-1,3,4-thiadiazol-2-yl)benzamide | $^1$H NMR (400 MHz, DMSO) 13.36 (1H, s), 8.77-8.74 (2H, m), 7.98-7.95 (2H, m), 7.71 (1H, d, J = 8.7 Hz), 7.48 (2H, d, J = 7.0 Hz), 7.42 (2H, dd, J = 7.3, 7.3 Hz), 7.39-7.35 (1H, m), 7.29 (1H, d, J = 2.4 Hz), 7.14 (1H, dd, J = 2.4, 8.7 Hz), 5.25 (2H, s); MS (ESI$^+$) 423/425 | Ex18 (Scheme 1) from methyl 2-chloro-4-hydroxybenzoate, benzyl bromide and 5-(pyridin-4-yl)-1,3,4-thiadiazol-2-amine |
| 166 | 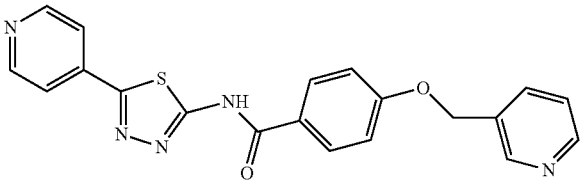<br>4-(pyridin-3-ylmethoxy)-N-(5-(pyridin-4-yl)-1,3,4-thiadiazol-2-yl)benzamide | $^1$H NMR (400 MHz, DMSO) 13.21 (1H, s), 8.77-8.71 (3H, m), 8.58 (1H, dd, J = 1.6, 4.8 Hz), 8.18 (2H, d, J = 8.9 Hz), 7.97-7.90 (3H, m), 7.46 (1H, dd, J = 5.1, 7.8 Hz), 7.23 (2H, d, J = 8.9 Hz), 5.30 (2H, s); MS (ESI$^+$) 390 | Ex18 (Scheme 1) from methyl 4-hydroxybenzoate, 3-(chloromethyl)pyridine and 5-(pyridin-4-yl)-1,3,4-thiadiazol-2-amine |
| 167 | 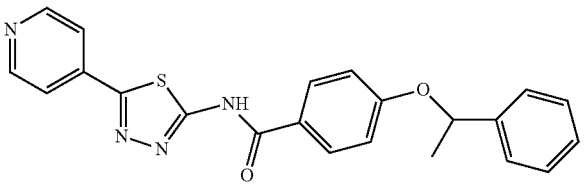<br>4-(1-phenylethoxy)-N-(5-(pyridin-4-yl)-1,3,4-thiadiazol-2-yl)benzamide | $^1$H NMR (400 MHz, DMSO) 13.11 (1H, s), 8.76-8.73 (2H, m), 8.07 (2H, d, J = 8.9 Hz), 7.96-7.93 (2H, m), 7.44 (2H, d, J = 7.2 Hz), 7.37 (2H, dd, J = 7.5, 7.5 Hz), 7.28 (1H, dd, J = 7.3, 7.3 Hz), 7.08 (2H, d, J = 9.0 Hz), 5.73-5.66 (1H, m), 1.60 (3H, d, J = 6.3 Hz); MS (ESI$^+$) 402 | Ex18 (Scheme 1) from methyl 4-hydroxybenzoate, (1-bromoethyl)benzene and 5-(pyridin-4-yl)-1,3,4-thiadiazol-2-amine |

TABLE 1-continued

| Ex. | Structure and Name | Data | Method |
|---|---|---|---|
| 168 | 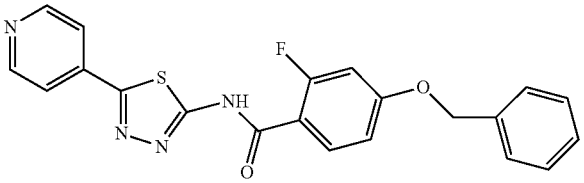<br>4-(benzyloxy)-2-fluoro-N-(5-(pyridin-4-yl)-1,3,4-thiadiazol-2-yl)benzamide | $^1$H NMR (400 MHz, DMSO) 13.14 (1H, s), 8.75-8.73 (2H, m), 7.95-7.93 (2H, m), 7.83 (1H, dd, J = 8.7, 8.7 Hz), 7.49 (2H, d, J = 7.0 Hz), 7.45-7.36 (3H, m), 7.09 (1H, dd, J = 2.2, 12.8 Hz), 7.01 (1H, dd, J = 2.3, 8.7 Hz), 5.24 (2H, s); MS (ESI$^+$) 407 | Ex 4 step c (Scheme 1) from 5-(pyridin-4-yl)-1,3,4-thiadiazol-2-amine and 4-(benzyloxy)-2-fluorobenzoic acid |
| 169 | 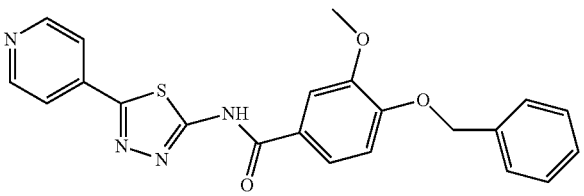<br>4-(benzyloxy)-3-methoxy-N-(5-(pyridin-4-yl)-1,3,4-thiadiazol-2-yl)benzamide | $^1$H NMR (400 MHz, DMSO) 13.20 (1H, s), 8.77-8.74 (2H, m), 7.97-7.94 (2H, m), 7.84-7.79 (2H, m), 7.48 (2H, d, J = 6.9 Hz), 7.44-7.36 (3H, m), 7.25 (1H, d, J = 8.4 Hz), 5.22 (2H, s), 3.90 (3H, s); MS (ESI$^+$) 419 | Ex 4 step c (Scheme 1) from 5-(pyridin-4-yl)-1,3,4-thiadiazol-2-amine and 4-(benzyloxy)-3-methoxybenzoic acid |
| 170 | 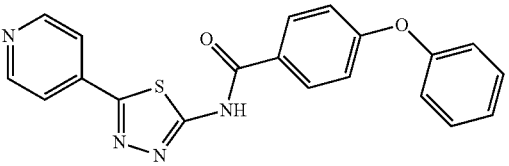<br>4-phenoxy-N-(5-(pyridin-4-yl)-1,3,4-thiadiazol-2-yl)benzamide | $^1$H NMR (400 MHz, DMSO) 13.30 (1H, s), 8.75-8.72 (2H, m), 8.20 (2H, d, J = 8.9 Hz), 7.95-7.92 (2H, m), 7.51-7.46 (2H, m), 7.30-7.24 (1H, m), 7.16 (2H, d, J = 7.8 Hz), 7.10 (2H, d, J = 8.9 Hz); MS (ESI$^+$) 375 | Ex 4 step c (Scheme 1) from 4-phenoxybenzoic acid and 5-(pyridin-4-yl)-1,3,4-thiadiazol-2-amine |
| 171 | 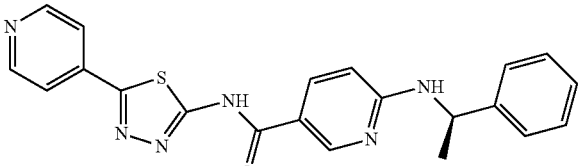<br>(R)-6-((1-phenylethyl)amino)-N-(5-(pyridin-4-yl)-1,3,4-thiadiazol-2-yl)nicotinamide | $^1$H NMR (400 MHz, DMSO) 12.97 (1H, s), 8.83 (1H, d, J = 2.5 Hz), 8.80-8.77 (2H, m), 8.11 (1H, dd, J = 2.4, 9.0 Hz), 8.04-7.97 (3H, m), 7.44 (2H, d, J = 7.3 Hz), 7.37 (2H, dd, J = 7.7, 7.7 Hz), 7.27 (1H, dd, J = 7.2, 7.2 Hz), 6.64 (1H, d, J = 8.6 Hz), 5.24-5.24 (1H, m), 1.52 (3H, d, J = 6.8 Hz); MS (ESI$^+$) 403 | Ex 36 (scheme 3) from (R)-1-phenylethanamine and 6-chloro-N-(5-pyridin-4-yl)-1,3,4-thiadiazol-2-yl)nicotinamide (Ex 35 step a) |
| 172 | 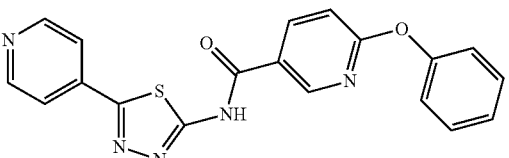<br>6-phenoxy-N-(5-(pyridin-4-yl)-1,3,4-thiadiazol-2-yl)nicotinamide | $^1$H NMR (400 MHz, DMSO) 13.5 (1H, s), 8.90-8.89 (1H, m), 8.75-8.73 (2H, m), 8.54-8.51 (1H, m), 7.95-7.93 (2H, m), 7.5-7.46 (2H, m), 7.31-7.29 (1H, m), 7.23-7.18 (3H, m); MS (ESI$^+$) 376 | Ex 4 step c from 6-phenoxynicotinic acid and 5-(pyridin-4-yl)-1,3,4-thiadiazol-2-amine |

TABLE 1-continued

| Ex. | Structure and Name | Data | Method |
|---|---|---|---|
| 173 | 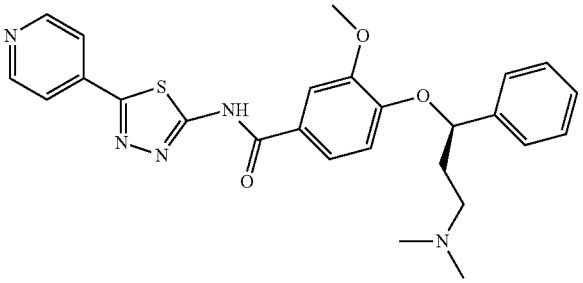<br>(R)-4-(3-(dimethylamino)-1-phenylpropoxy)-3-methoxy-N-(5-(pyridin-4-yl)-1,3,4-thiadiazol-2-yl)benzamide | $^1$H NMR (400 MHz, DMSO) 12.34 (1H, s), 8.77-8.74 (2H, m), 7.96-7.93 (2H, m), 7.83 (1H, d, J = 2.0 Hz), 7.66 (1H, dd, J = 2.0, 8.6 Hz), 7.46 (2H, d, J = 7.1 Hz), 7.41 (2H, dd, J = 7.6, 7.6 Hz), 7.33 (1H, dd, J = 7.2, 7.2 Hz), 6.98 (1H, d, J = 8.8 Hz), 5.56 (1H, dd, J = 5.2, 8.0 Hz), 3.97 (3H, s), 2.33 (6H, s),2.27-2.15 (1H, m), 2.08-1.97 (1H, m) two protons are obscured by the residual water signal; MS(ESI$^+$) 490 | Ex 11 (Scheme 1) from (R)-4-(3-(dimethylamino)-1-phenylpropoxy)-3-methoxybenzoic (Ex 11 step b) and 5-(pyridin-4-yl)-1,3,4-thiadiazol-2-amine |
| 174 | 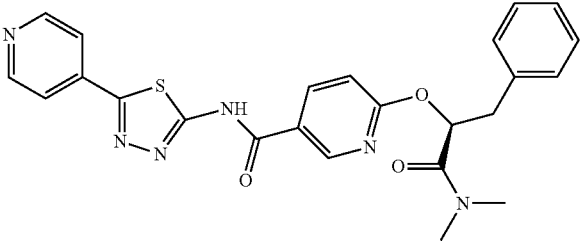<br>(S)-6-((1-(dimethylamino)-1-oxo-3-phenylpropan-2-yl)oxy)-N-(5-(pyridin-4-yl)-1,3,4-thiadiazol-2-yl)nicotinamide | $^1$H NMR (400 MHz, DMSO) 13.37 (1H, s), 8.90 (1H, d, J = 2.5 Hz), 8.81-8.78 (2H, m), 8.42 (1H, dd, J = 2.4, 8.7 Hz), 8.01-7.98 (2H, m), 7.43-7.34 (4H, m), 7.33-7.26 (1H, m), 7.07 (1H, d, J = 8.8 Hz), 5.88 (1H, dd, J = 6.2, 7.7 Hz), 3.22-3.17 (2H, m), 3.06 (3H, s), 2.85 (3H, s); MS (ESI$^+$) 475 | Ex 31 (Scheme 2) from 6-fluoro-N-(5-(pyridin-4-yl)-1,3,4-thiadiazol-2-yl)nicotinamide (Ex 31 step a) and (S)-2-hydroxy-N-dimethyl-3-phenylpropanamide (Ex 33 step a) |
| 175 | 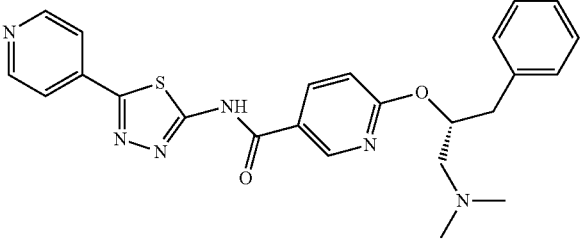<br>(R)-6-((1-(dimethylamino)-3-phenylpropan-2-yl)oxy)-N-(5-(pyridin-4-yl)-1,3,4-thiadiazol-2-yl)nicotinamide | $^1$H NMR (400 MHz, DMSO) 12.53 (1H, s), 8.96 (1H, d, J = 2.5 Hz), 8.78-8.76 (2H, m), 8.41 (1H, dd, J = 2.5, 8.6 Hz), 7.97-7.95 (2H, m), 7.32 (4H, d, J = 6.3 Hz), 7.30-7.21 (1H, m), 6.94 (1H, d, J = 8.6 Hz), 5.78-5.70 (1H, m), 3.16-2.99 (2H, m), 2.82-2.65 (2H, m), 2.37 (6H, s); MS (ESI$^+$) 461 | Ex 33 (Scheme 2) from 6-fluoro-N-(5-(pyridin-4-yl)-1,3,4-thiadiazol-2-yl)nicotinamide (Ex 31 step a) and (R)-2-hydroxy-3-phenylpropanoic acid |
| 176 | 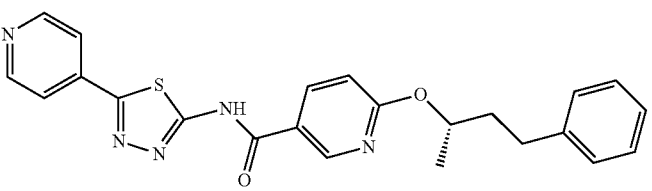<br>(S)-6-((4-phenylbutan-2-yl)oxy)-N-(5-(pyridin-4-yl)-1,3,4-thiadiazol-2-yl)nicotinamide | $^1$H NMR (400 MHz, DMSO) 13.39 (1H, s), 8.99 (1H, d, J = 2. 3Hz), 8.81 (2H, s), 8.43 (1H, dd, J = 2.5, 8.6 Hz), 8.01 (2H, d, J = 3.3 Hz), 7.35-7.30 (2H, m), 7.27-7.22 (3H, m), 6.99 (1H, d, J = 8.6 Hz), 5.37-5.29 (1H, m), 2.81-2.67 (2H, m), 2.14-1.93 (2H, m), 1.40 (3H, d, J = 6.2 Hz); MS (ESI$^+$) 432 | Ex 31 (Scheme 2) from 6-fluoro-N-(5-(pyridin-4-yl)-1,3,4-thiadiazol-2-yl) nicotinamide (Ex 31 step a) and (S)-4-phenylbutan-2-ol |

TABLE 1-continued

| Ex. | Structure and Name | Data | Method |
|---|---|---|---|
| 177 | 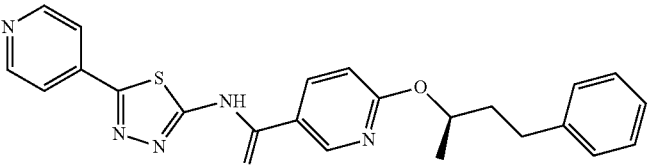<br>(R)-6-((4-phenylbutan-2-yl)oxy)-N-(5-(pyridin-4-yl)-1,3,4-thiadiazol-2-yl)nicotinamide | $^1$H NMR (400 MHz, DMSO) 13.39 (1H, s), 8.99-8.97 (1H, m), 8.81-8.77 (2H, m), 8.43 (1H, dd, J = 2.1, 8.7 Hz), 8.01-7.97 (2H, m), 7.35-7.30 (2H, m), 7.27-7.22 (3H, m), 6.99 (1H, d, J = 8.8 Hz), 5.37-5.29 (1H, m), 2.81-2.68 (2H, m), 2.14-1.94 (2H, m), 1.40 (3H, d, J = 6.1 Hz); MS (ESI$^+$) 418 | Ex 31 (Scheme 2) from 6-fluoro-N-(5-(pyridin-4-yl)-1,3,4-thiadiazol-2-yl)nicotinamide (Ex 31 step a) and (R)-4-phenylbutan-2-ol |
| 178 | 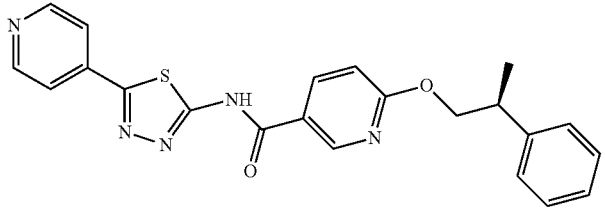<br>(S)-6-(2-phenylpropoxy)-N-(5-(pyridin-4-yl)-1,3,4-thiadiazol-2-yl)nicotinamide | $^1$H NMR (400 MHz, DMSO) 13.41 (1H, s), 9.01 (1H, s), 8.83 (2H, s), 8.42 (1H, d, J = 6.8 Hz), 8.04-8.01 (2H, m), 7.40-7.37 (4H, m), 7.31-7.26 (1H, m), 6.98 (1H, d, J = 8.6 Hz), 4.59-4.47 (2H, m), 3.33-3.28 (1H, m), 1.38 (3H, d, J = 7.1 Hz); MS (ESI$^+$) 418 | Ex 31 (Scheme 2) from 6-fluoro-N-(5-(pyridin-4-yl)-1,3,4-thiadiazol-2-yl)nicotinamide (Ex 31 step a) and (S)-2-phenylpropan-1-ol |
| 179 | 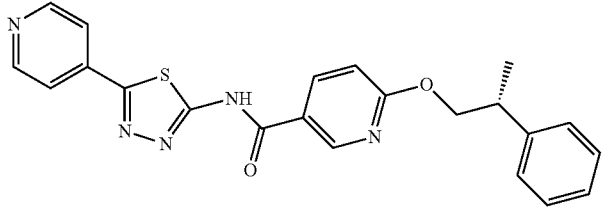<br>(R)-6-(2-phenylpropoxy)-N-(5-(pyridin-4-yl)-1,3,4-thiadiazol-2-yl)nicotinamide | $^1$H NMR (400 MHz, DMSO) 13.41 (1H, s), 9.01 (1H, s), 8.82 (2H, s), 8.42 (1H, d, J = 8.3 Hz), 8.02 (2H, s), 7.40-7.37 (4H, m), 7.31-7.26 (1H, m), 6.98 (1H, d, J = 8.6 Hz), 4.58-4.46 (2H, m), 3.33-3.28 (1H, m), 1.38 (3H, d, J = 7.1 Hz); MS (ESI$^+$) 418 | Ex 31 (Scheme 2) from 6-fluoro-N-(5-(pyridin-4-yl)-1,3,4-thiadiazol-2-yl)nicotinamide (Ex 31 step a) and (R)-2-phenylpropan-1-ol |
| 180 | 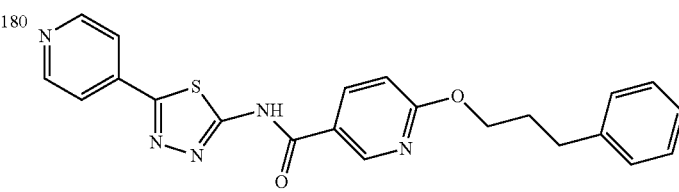<br>6-(3-(4-methoxyphenyl)propoxy)-N-(5-(pyridin-4-yl)-1,3,4-thiadiazol-2-yl)nicotinamide | $^1$H NMR (400 MHz, DMSO) 13.40 (1H, s), 9.01 (1H, d, J = 2.5 Hz), 8.81 (2H, d, J = 5.8 Hz), 8.44 (1H, dd, J = 2.5, 8.6 Hz), 8.02-7.99 (2H, m), 7.21 (2H, d, J = 8.8 Hz), 7.05 (1H, d, J = 8.8 Hz), 6.92-6.89 (2H, m), 4.40 (2H, dd, J = 6.4, 6.4 Hz), 3.78 (3H, s), 2.74 (2H, dd, J = 7.6, 7.6 Hz), 2.13-2.04 (2H, m); MS (ESI$^+$) 448 | Ex 31 (Scheme 2) from 6-fluoro-N-(5-(pyridin-4-yl)-1,3,4-thiadiazol-2-yl)nicotinamide (Ex 31 step a) and 3-(4-methoxyphenyl)propan-1-ol |
| 181 | 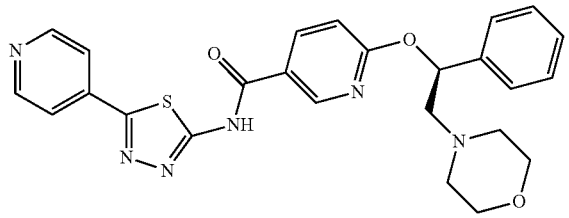<br>(S)-6-(2-morpholino-1-phenylethoxy)-N-(5-(pyridin-4-yl)-1,3,4-thiadiazol-2-yl)nicotinamide | $^1$H NMR (400 MHz, CDCl$_3$) 9.05 (1H, d, J = 2.3 Hz), 8.79-8.76 (2H, m), 8.42 (1H, dd, J = 2.5, 8.8 Hz), 7.86-7.84 (2H, m), 7.44 (2H, d, J = 7.1 Hz), 7.36-7.27 (3H, m), 6.98 (1H, d, J = 8.6 Hz), 6.53 (1H, dd, J = 3.8, 8.8 Hz), 3.68-3.58 (4H, m), 3.11-3.03 (1H, m), 2.76-2.70 (1H, m), 2.65-2.54 (4H, m); MS (ESI$^+$) 489 | Ex 39 (Scheme 2) from (S)-1-phenylethane-1,2-diol and 6-fluoro-N-(5-(pyridin-4-yl)-1,3,4-thiadiazol-2-yl)nicotinamide (Ex 31 step a) |

TABLE 1-continued

| Ex. | Structure and Name | Data | Method |
|---|---|---|---|
| 182 | 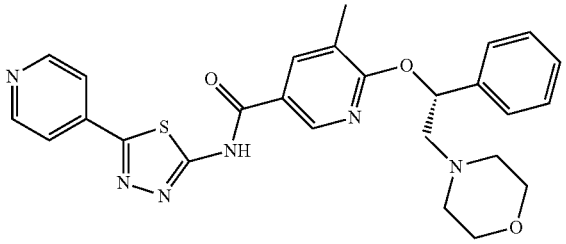<br>(R)-5-methyl-6-(2-morpholino-1-phenylethoxy)-N-(5-(pyridin-4-yl)-1,3,4-thiadiazol-2-yl)nicotinamide | $^1$H NMR (400 MHz, CDCl$_3$) 8.85 (1H, d, J = 2.3 Hz), 8.77-8.74 (2H, m), 8.17 (1H, d, J = 1.5 Hz), 7.85-7.83 (2H, m), 7.46-7.43 (2H, m), 7.36-7.27 (3H, m), 6.56 (1H, dd, J = 4.0, 8.3 Hz), 3.63-3.58 (4H, m), 3.05 (1H, dd, J = 8.3, 13.6 Hz), 2.78 (1H, dd, J = 4.0, 13.6 Hz), 2.64-2.53 (4H, m), 2.35 (3H, s); MS (ESI$^+$) 503 | Ex 20 (Scheme 2) from 6-chloro-5-methylnicotinic acid, 5-(4-pyridyl)-1,3,4-thiadiazol-2-yl amine (Ex 20 step a) and (R)-2-morpholino-1-phenylethanol (Example 39 steps a-b) |
| 183 | 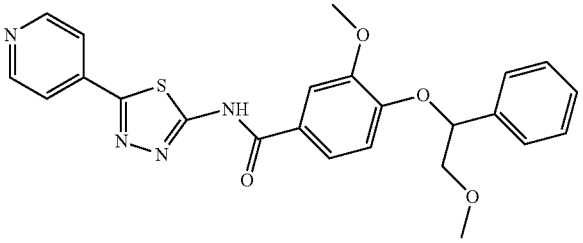<br>3-methoxy-4-(2-methoxy-1-phenylethoxy)-N-(5-(pyridin-4-yl)-1,3,4-thiadiazol-2-yl)benzamide | $^1$H NMR (400 MHz, DMSO) 13.21 (1H, s), 8.80-8.78 (2H, m), 8.00-7.98 (2H, m), 7.84 (1H, d, J = 2.3 Hz), 7.68 (1H, dd, J = 2.0, 8.6 Hz), 7.51-7.47 (2H, m), 7.41 (2H, dd, J = 7.5, 7.5 Hz), 7.36-7.32 (1H, m), 7.07 (1H, d, J = 8.8 Hz), 5.77 (1H, dd, J = 3.7, 7.7 Hz), 3.99 (3H, s), 3.84 (1H, dd, J = 7.7, 11.0 Hz), 3.65 (1H, dd, J = 3.4, 11.0 Hz), 3.40 (3H, s); MS (ESI$^+$) 463 | Ex 4 (Scheme 1) from methyl 4-hydroxy-3-methoxybenzoate, 5-(pyridin-4-yl)-1,3,4-thiadiazol-2-amine and 2-methoxy-1-phenylethanol (according to WO 2012138648) |
| 184 | 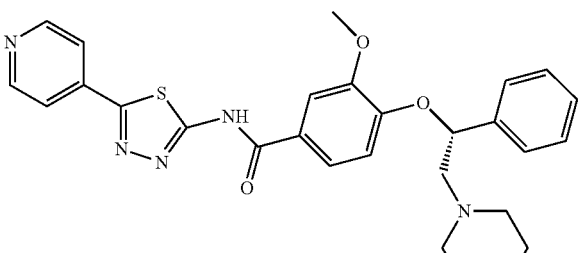<br>(R)-3-methoxy-4-(2-morpholino-1-phenylethoxy)-N-(5-(pyridin-4-yl)-1,3,4-thiadiazol-2-yl)benzamide | $^1$H NMR (400 MHz, DMSO) 13.15 (1H, s), 8.79 (2H, d, J = 6.1 Hz), 7.99-7.96 (2H, m), 7.83 (1H, d, J = 2.0 Hz), 7.67 (1H, dd, J = 2.0, 8.6 Hz), 7.48 (2H, d, J = 7.3 Hz), 7.40 (2H, dd, J = 7.5, 7.5 Hz), 7.32 (1H, dd, J = 7.2, 7.2 Hz), 7.10 (1H, d, J = 8.8 Hz), 5.75 (1H, dd, J = 3.9, 7.7 Hz), 3.98 (3H, s), 3.59 (4H, dd, J = 4.7, 4.7 Hz), 3.03-2.94 (1H, m), 2.73-2.58 (5H, m); MS (ESI$^+$) 518 | Ex. 10 (Scheme 1) from (S)-2-amino-1-phenylethanol, methyl 4-hydroxy-3-methoxybenzoate, 1-bromo-2-(2-bromoethoxy)ethane, and 5-(4-pyridyl)-1,3,4-thiadiazol-2-yl amine |
| 185 | 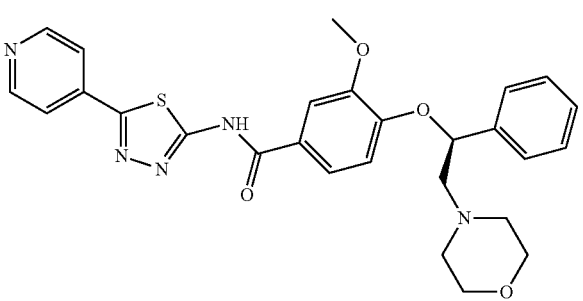<br>(S)-3-methoxy-4-(2-morpholino-1-phenylethoxy)-N-(5-(pyridin-4-yl)-1,3,4-thiadiazol-2-yl)benzamide | $^1$H NMR (400 MHz, DMSO) 13.15 (1H, s), 8.80-8.77 (2H, m), 7.99-7.96 (2H, m), 7.83 (1H, d, J = 2.3 Hz), 7.67 (1H, dd, J = 2.0, 8.6 Hz), 7.48 (2H, d, J = 7.1 Hz), 7.40 (2H, dd, J = 7.6, 7.6 Hz), 7.31 (1H, dd, J = 7.2, 7.2 Hz), 7.10 (1H, d, J = 8.8 Hz), 5.75 (1H, dd, J = 4.0, 7.8 Hz), 3.98 (3H, s), 3.59 (4H, dd, J = 4.7, 4.7 Hz), 2.99 (1H, dd, J = 8.0, 13.5 Hz), 2.72-2.58 (5H, m); MS (ESI$^+$) 518 | Ex. 10 (Scheme 1) from (R)-2-amino-1-phenylethanol, methyl 4-hydroxy-3-methoxybenzoate, 1-bromo-2-(2-bromoethoxy)ethane, and 5-(4-pyridyl)-1,3,4-thiadiazol-2-yl amine |

TABLE 1-continued

| Ex. | Structure and Name | Data | Method |
|---|---|---|---|
| 186 | 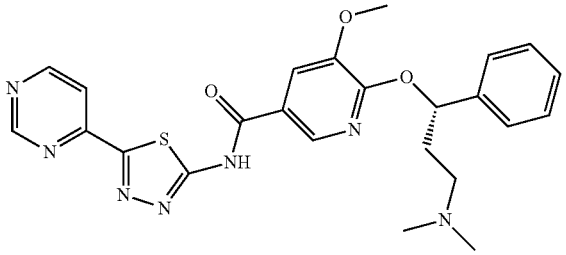<br>(S)-6-(3-(dimethylamino)-1-phenylpropoxy)-5-methoxy-N-(5-(pyrimidin-4-yl)-1,3,4-thiadiazol-2-yl)nicotinamide | $^1$H NMR (400 MHz, DMSO) 9.29 (1H, d, J = 1.5 Hz), 8.95 (1H, d, J = 5.3 Hz), 8.45 (1H, d, J = 2.0 Hz), 8.24 (1H, dd, J = 1.5, 5.3 Hz), 8.01 (1H, d, J = 1.8 Hz), 7.49 (2H, d, J = 7.3 Hz), 7.42 (2H, dd, J = 7.6, 7.6 Hz), 7.35-7.31 (1H, m), 6.37 (1H, dd, J = 5.4, 8.0 Hz), 3.98 (3H, s), 2.78-2.73 (2H, m), 2.51 (6H, s), 2.39-2.29 (1H, m), 2.22-2.12 (1H, m); MS (ESI$^+$) 492 | Ex. 20 (Scheme 2) from 6-chloro-5-methoxynicotinic acid, 5-(pyrimidin-4-yl)-1,3,4-thiadiazol-2-yl amine (Ex. 13 steps a and b) and (S)-3-(dimethylamino)-1-phenylpropan-1-ol (Ex. 26 step a) |
| 187 | 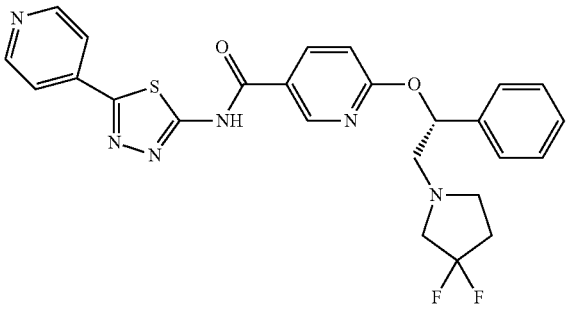<br>(R)-6-(2-(3,3-difluoropyrrolidin-1-yl)-1-phenylethoxy)-N-(5-(pyridin-4-yl)-1,3,4-thiadiazol-2-yl)nicotinamide | $^1$H NMR (400 MHz, DMSO) 13.37 (1H, s), 8.92 (1H, d, J = 1.8 Hz), 8.80 (2H, d, J = 5.1 Hz), 8.44 (1H, dd, J = 1.9, 8.5 Hz), 8.00 (2H, d, J = 5.3 Hz), 7.52 (2H, d, J = 7.3 Hz), 7.45-7.38 (2H, m), 7.35 (1H, dd, J = 7.1, 7.1 Hz), 7.14 (1H, d, J = 8.6 Hz), 6.39 (1H, dd, J = 3.7, 8.2 Hz), 3.18-3.02 (3H, m), 2.96-2.85 (3H, m), 2.30-2.19 (2H, m); MS (ESI$^+$) 509 | Ex. 39 (Scheme 2) from 6-fluoro-N-(5-(pyridin-4-yl)-1,3,4-thiadiazol-2-yl)nicotinamide (Ex. 31 step a), (R)-1-phenylethane-1,2-diol and 3,3-difluoropyrrolidine. |
| 188 | 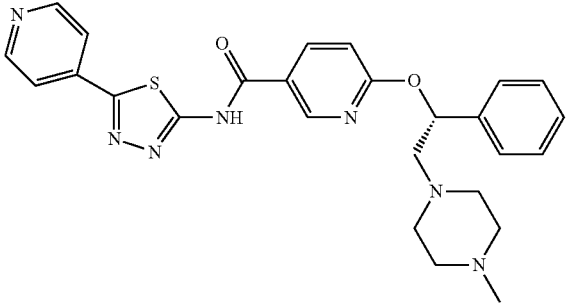<br>(R)-6-(2-(4-methylpiperazin-1-yl)-1-phenylethoxy)-N-(5-(pyridin-4-yl)-1,3,4-thiadiazol-2-yl)nicotinamide | $^1$H NMR (400 MHz, CDCl$_3$) 9.04 (1H, d, J = 2.3 Hz), 8.78-8.76 (2H, m), 8.41 (1H, dd, J = 2.7, 8.7 Hz), 7.86-7.83 (2H, m), 7.45-7.42 (2H, m), 7.35-7.30 (2H, m), 7.26-7.26 (1H, m), 6.96 (1H, d, J = 8.6 Hz), 6.51 (1H, dd, J = 3.7, 8.7 Hz), 3.10 (1H, dd, J = 8.7, 13.8 Hz), 2.78-2.72 (1H, m), 2.70-2.58 (4H, m), 2.45-2.33 (4H, m), 2.24 (3H, s); MS (ESI$^+$) 502 | Ex.39 (Scheme 2) from 6-fluoro-N-(5-(pyridin-4-yl)-1,3,4-thiadiazol-2-yl)nicotinamide (Ex. 31 step a), (S)-1-phenylethane-1,2-diol and 1-methylpiperazine |
| 189 | 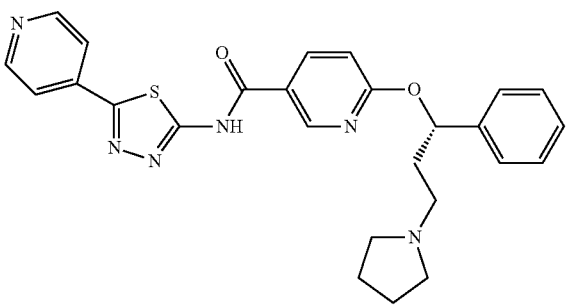<br>(S)-6-(1-phenyl-3-(pyrrolidin-1-yl)propoxy)-N-(5-(pyridin-4-yl)-1,3,4-thiadiazol-2-yl)nicotinamide | $^1$H NMR (400 MHz, DMSO) 8.87 (1H, d, J = 2.5 Hz), 8.73-8.70 (2H, m), 8.42 (1H, dd, J = 2.5, 8.6 Hz), 7.90-7.87 (2H, m), 7.50 (2H, d, J = 7.1 Hz), 7.42 (2H, dd, J = 7.5, 7.5 Hz), 7.36-7.32 (1H, m), 7.00 (1H, d, J = 8.8 Hz), 6.32 (1H, dd, J = 5.2, 8.0 Hz), 3.03-2.94 (6H, m), 2.39-2.30 (1H, m), 2.26-2.16 (1H, m), 1.87 (4H, dd, J = 6.3, 6.3 Hz); MS (ESI$^+$) 487 | Ex. 38 (Scheme 2) from 6-fluoro-N-(5-(pyridin-4-yl)-1,3,4-thiadiazol-2-yl)nicotinamide (Ex. 31 step a), (S)-3-iodo-1-phenylpropanol and pyrrolidine |

TABLE 1-continued

| Ex. | Structure and Name | Data | Method |
|---|---|---|---|
| 190 | 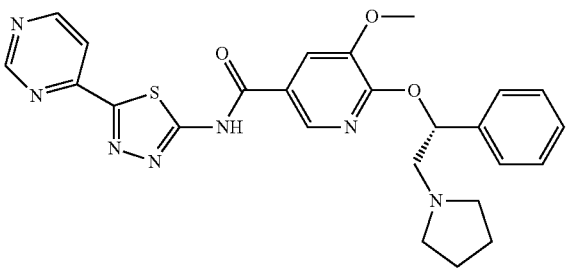<br>(R)-5-methoxy-6-(1-phenyl-2-(pyrrolidin-1-yl)ethoxy)-N-(5-(pyrimidin-4-yl)-1,3,4-thiadiazol-2-yl)nicotinamide | $^1$H NMR (400 MHz, DMSO) 9.32 (1H, d, J = 1.3 Hz), 8.99 (1H, d, J = 5.3 Hz), 8.46 (1H, d, J = 2.0 Hz), 8.27 (1H, dd, J = 1.3, 5.3 Hz), 8.03 (1H, d, J = 1.8 Hz), 7.51 (2H, d, J = 7.1 Hz), 7.42 (2H, dd, J = 7.5, 7.5 Hz), 7.36-7.32 (1H, m), 6.53 (1H, dd, J = 3.8, 8.8 Hz), 4.00 (3H, s), 3.36-3.28 (1H, m), 3.19-3.11 (1H, m), 2.95-2.87 (4H, m), 1.80 (4H, s); MS (ESI$^+$) 504 | Ex. 20 (Scheme 2) from 6-chloro-5-methoxynicotinic acid, 5-(pyrimidin-4-yl)-1,3,4-thiadiazol-2-yl amine (Ex. 13 steps a and b), and (R)-1-phenyl-2-(pyrrolidin-1-yl)ethanol (prepared according to Ex. 39 steps a and b starting from (R)-1-phenylethane-1,2-diol and pyrrolidine) |
| 191 | 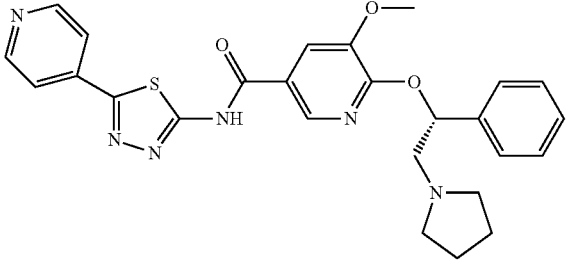<br>(R)-5-methoxy-6-(1-phenyl-2-(pyrrolidin-1-yl)ethoxy)-N-(5-(pyridin-4-yl)-1,3,4-thiadiazol-2-yl)nicotinamide | $^1$H NMR (400 MHz, DMSO) 12.36 (1H, s), 8.76 (2H, d, J = 4.9 Hz), 8.44 (1H, s), 8.03 (1H, s), 7.94 (2H, d, J = 4.9 Hz), 7.50 (2H, d, J = 7.3 Hz), 7.41 (2H, dd, J = 7.3, 7.3 Hz), 7.34 (1H, dd, J = 7.0, 7.0 Hz), 6.55-6.49 (1H, m), 4.00 (3H, s), 3.19-3.10 (2H, m), 2.92-2.83 (4H, m), 1.83-1.75 (4H, m); MS (ESI$^+$) 503 | Ex. 20 (Scheme 2) from 6-chloro-5-methoxynicotinic acid, 5-(4-pyridyl)-1,3,4-thiadiazol-2-yl amine and (R)-1-phenyl-2-(pyrrolidin-1-yl)ethanol (prepared according to Ex. 39 steps a and b starting from (R)-1-phenylethane-1,2-diol and pyrrolidine) |
| 192 | 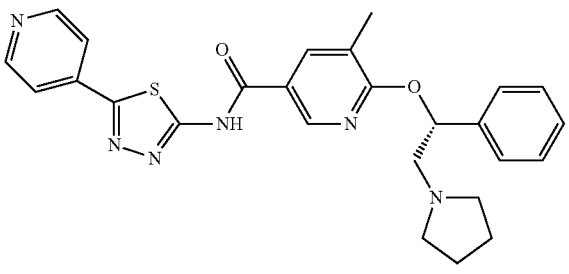<br>(R)-5-methyl-6-(1-phenyl-2-(pyrrolidin-1-yl)ethoxy)-N-(5-(pyridin-4-yl)-1,3,4-thiadiazol-2-yl)nicotinamide | $^1$H NMR (400 MHz, DMSO) 12.28 (1H, s), 8.77-8.74 (2H, m), 8.72 (1H, d, J = 2.3 Hz), 8.31 (1H, d, J = 1.3 Hz), 7.96-7.93 (2H, m), 7.51 (2H, d, J = 7.1 Hz), 7.41 (2H, dd, J = 7.5, 7.5 Hz), 7.33 (1H, dd, J = 7.2, 7.2 Hz), 6.51 (1H, dd, J = 3.8, 8.3 Hz), 3.32-3.27 (1H, m), 3.17-3.14 (1H, m), 2.92-2.84 (4H, m), 2.39 (3H, s), 1.82-1.75 (4H, m); MS (ESI$^+$) 487 | Ex. 20 (Scheme 2) from 6-chloro-5-methylnicotinic acid, 5-(4-pyridyl)-1,3,4-thiadiazol-2-yl amine and (R)-1-phenyl-2-(pyrrolidin-1-yl)ethanol (prepared according to Ex. 39 steps a and b starting from (R)-1-phenylethane-1,2-diol and pyrrolidine) |
| 193 | 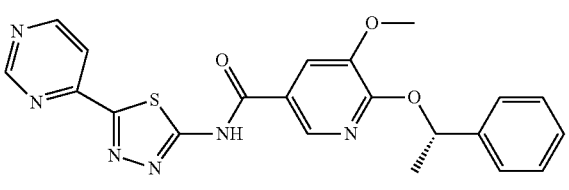<br>(S)-5-methoxy-6-(1-phenylethoxy)-N-(5-(pyrimidin-4-yl)-1,3,4-thiadiazol-2-yl)nicotinamide | $^1$H NMR (400 MHz, DMSO) 13.39 (1H, s), 9.39 (1H, d, J = 1.5 Hz), 9.06 (1H, d, J = 5.3 Hz), 8.52 (1H, d, J = 2.0 Hz), 8.32 (1H, dd, J = 1.5, 5.3 Hz), 8.04 (1H, d, J = 2.0 Hz), 7.50 (2H, d, J = 7.3 Hz), 7.42 (2H, dd, J = 7.6, 7.6 Hz), 7.35-7.31 (1H, m), 6.41 (1H, q, J = 6.5 Hz), 3.99 (3H, s), 1.68 (3H, d, J = 6.6 Hz); MS (ESI$^+$) 435 | Ex. 20 (Scheme 2) from 6-chloro-5-methoxynicotinic acid, 5-(pyrimidin-4-yl)-1,3,4-thiadiazol-2-yl amine (Ex. 13 steps a and b), and (S)-1-phenylethanol. |

TABLE 1-continued

| Ex. | Structure and Name | Data | Method |
|---|---|---|---|
| 195 | 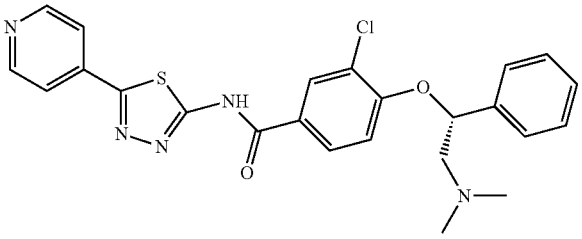<br>(R)-3-chloro-4-(2-(dimethylamino)-1-phenylethoxy)-N-(5-(pyridin-4-yl)-1,3,4-thiadiazol-2-yl)benzamide | $^1$H NMR (400 MHz, DMSO) 12.78 (1H, s), 8.79-8.76 (2H, m), 8.29 (1H, d, J = 2.3 Hz), 8.02 (1H, dd, J = 2.1, 8.7 Hz), 7.98-7.95 (2H, m), 7.50 (2H, d, J = 7.3 Hz), 7.43 (2H, dd, J = 7.5, 7.5 Hz), 7.37-7.29 (2H, m), 5.89 (1H, dd, J = 3.9, 8.0 Hz), 3.08 (1H, dd, J = 8.1, 13.4 Hz), 2.82 (1H, dd, J = 3.8, 13.4 Hz), 2.44 (6H, s); MS (ESI$^+$) 480/482 | Ex. 194 (Scheme 1) from (S)-tert-butyl (2-hydroxy-2-phenylethyl)carbamate (Ex. 10 step a), methyl 3-chloro-4-hydroxybenzoate and 5-(4-pyridyl)-1,3,4-thiadiazol-2-yl amine |
| 197 | 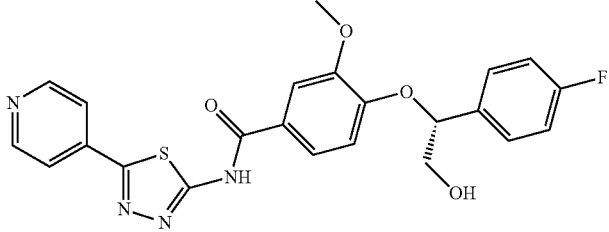<br>(R)-4-(1-(4-fluorophenyl)-2-hydroxyethoxy)-3-methoxy-N-(5-(pyridin-4-yl)-1,3,4-thiadiazol-2-yl)benzamide | $^1$H NMR (400 MHz, DMSO) 13.15 (1H, br. s), 8.76-8.73 (2H, m), 7.95-7.93 (2H, m), 7.79 (1H, d, J = 2.1 Hz), 7.64 (1H, dd, J = 2.1, 8.5 Hz), 7.46 (2H, dd, J = 5.5, 8.7 Hz), 7.18 (2H, dd, J = 8.9, 8.9 Hz), 7.05 (1H, d, J = 8.8 Hz), 5.53 (1H, dd, J = 4.3, 7.0 Hz), 5.17 (1H, dd, J = 5.6, 5.6 Hz), 3.93 (3H, s), 3.85-3.77 (1H, m), 3.69-3.62 (1H, m); MS (ESI$^+$) 467 | Ex. 7 (Scheme 1) from 4-fluorostyrene and AD-mix α, methyl 4-hydroxy-3-methoxybenzoate and 5-(4-pyridyl)-1,3,4-thiadiazol-2-yl amine |
| 198 | 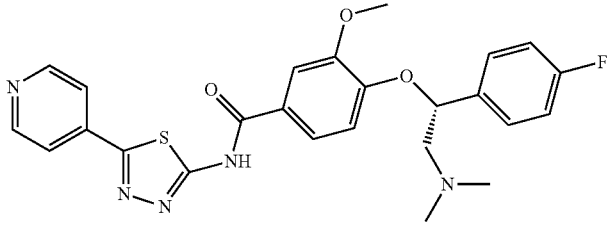<br>(R)-4-(2-(dimethylamino)-1-(4-fluorophenyl)ethoxy)-3-methoxy-N-(5-(pyridin-4-yl)-1,3,4-thiadiazol-2-yl)benzamide | $^1$H NMR (400 MHz, DMSO) 8.80 (2H, d, J = 4.5 Hz), 8.00 (2H, d, J = 4.8 Hz), 7.87-7.84 (1H, m), 7.70 (1H, d, J = 8.6 Hz), 7.55 (2H, dd, J = 5.8, 8.1 Hz), 7.25 (2H, dd, J = 8.7, 8.7 Hz), 7.13 (1H, d, J = 8.6 Hz), 5.79 (1H, dd, J = 4.3, 7.6 Hz), 3.99 (3H, s), 3.11-3.02 (1H, m), 2.86-2.74 (1H, m), 2.45 (6H, s); MS (ESI$^+$) 494 | Ex. 6 (Scheme 1) from (R)-2-amino-1-(4-fluorophenyl)ethanol hydrochloride, methyl 4-hydroxy-3-methoxybenzoate and 5-(4-pyridyl)-1,3,4-thiadiazol-2-yl amine |
| 199 | 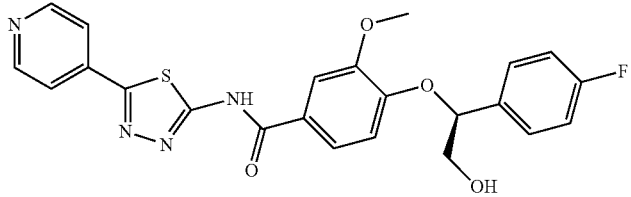<br>(S)-4-(1-(4-fluorophenyl)-2-hydroxyethoxy)-3-methoxy-N-(5-(pyridin-4-yl)-1,3,4-thiadiazol-2-yl)benzamide | $^1$H NMR (400 MHz, DMSO) 13.15 (1H, s), 8.76-8.73 (2H, m), 7.95-7.93 (2H, m), 7.79 (1H, d, J = 2.1 Hz), 7.65 (1H, dd, J = 2.1, 8.5 Hz), 7.46 (2H, dd, J = 5.5, 8.7 Hz), 7.18 (2H, dd, J = 8.9, 8.9 Hz), 7.05 (1H, d, J = 8.9 Hz), 5.53 (1H, dd, J = 4.2, 7.1 Hz), 5.16 (1H, dd, J = 5.6, 5.6 Hz), 3.93 (3H, s), 3.85-3.77 (1H, m), 3.69-3.61 (1H, m); MS (ESI$^+$) 467 | Ex. 7 (Scheme 1) from 4-fluorostyrene and AD-mix β, methyl 4-hydroxy-3-methoxybenzoate and 5-(4-pyridyl)-1,3,4-thiadiazol-2-yl amine |

| Ex. | Structure and Name | Data | Method |
|---|---|---|---|
| 200 | 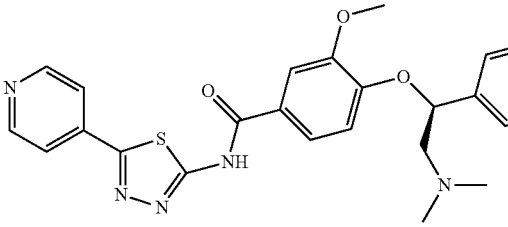(S)-4-(2-(dimethylamino)-1-(4-fluorophenyl)ethoxy)-3-methoxy-N-(5-(pyridin-4-yl)-1,3,4-thiadiazol-2-yl)benzamide | $^1$H NMR (400 MHz, DMSO) 8.80-8.77 (2H, m), 7.99-7.96 (2H, m), 7.83 (1H, d, J = 2.0 Hz), 7.69 (1H, dd, J = 2.0, 8.6 Hz), 7.55-7.51 (2H, m), 7.23 (2H, dd, J = 9.0, 9.0 Hz), 7.11 (1H, d, J = 8.6 Hz), 5.73 (1H, dd, J = 4.8, 7.6 Hz), 3.97 (3H, s), 2.97 (1H, dd, J = 7.7, 13.0 Hz), 2.70 (1H, dd, J = 4.7, 13.5 Hz), 2.36 (6H, s); MS (ESI$^+$) 494 | Ex. 6 (Scheme 1) from (S)-2-amino-1-(4-fluorophenyl)ethanol hydrochloride, methyl 4-hydroxy-3-methoxybenzoate and 5-(4-pyridyl)-1,3,4-thiadiazol-2-yl amine |

EXAMPLE 194

Formation of (R)-4-(2-(dimethylamino)-1-phenylethoxy)-3-fluoro-N-(5-(pyridin-4-yl)-1,3,4-thiadiazol-2-yl)benzamide (Compound 1-VII, Scheme 1)

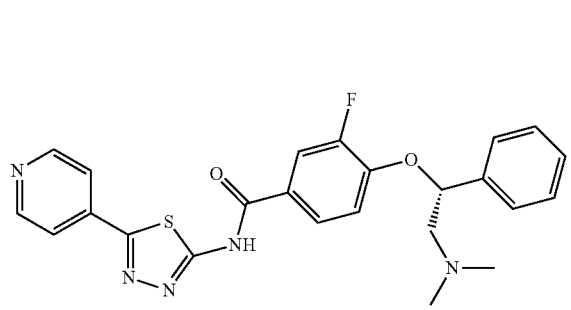 [SMILES: CN(C)C[C@H](Oc1ccc(C(=O)Nc2nnc(-c3ccncc3)s2)cc1F)c1ccccc1]

a) (R)-methyl 4-(2-amino-1-phenylethoxy)-3-fluorobenzoate (Compound of Formula 1-IV, Scheme 1)

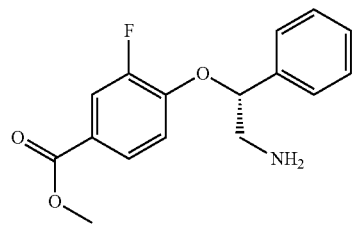 [SMILES: COC(=O)c1ccc(O[C@@H](CN)c2ccccc2)c(F)c1]

Following the general procedure outlined for Example 10, steps b and c, starting from (S)-tert-butyl (2-hydroxy-2-phenylethyl)carbamate (0.6 g, 2.5 mmol, 1.2 eq., Example 10 step a) and methyl 3-fluoro-4-hydroxybenzoate (0.36 g, 2.1 mmol, 1.0 eq.), (R)-methyl 4-(2-amino-1-phenylethoxy)-3-fluorobenzoate was isolated as a clear oil (0.152 g, 58% yield). $^1$H NMR (400 MHz, CDCl$_3$) 7.71 (1H, dd, J=2.0, 11.6 Hz), 7.61-7.58 (1H, m), 7.35 (4H, d, J=4.3 Hz), 7.32-7.27 (1H, m), 6.79 (1H, dd, J=8.5, 8.5 Hz), 5.24 (1H, dd, J=3.9, 7.7 Hz), 3.84 (3H, s), 3.23 (1H, dd, J=7.6, 13.6 Hz), 3.11 (1H, dd, J=4.0, 13.6 Hz).

b) (R)-methyl 4-(2-(dimethylamino)-1-phenylethoxy)-3-fluorobenzoate (Compound of Formula 1-IV, Scheme 1)

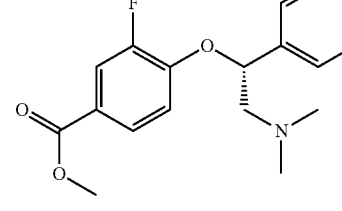

A mixture of (R)-methyl 4-(2-amino-1-phenylethoxy)-3-fluorobenzoate (0.15 g, 0.52 mmol, 1 eq.), formic acid (0.6 mL) and formaldehyde (37 wt % in water, 1.1 mL) was stirred at 85° C. for 5 hours and then at ambient temperature for a further 16 hours. The reaction was evaporated and the resultant residue was partitioned between dichloromethane (5 mL) and 2M aqueous sodium hydroxide (4.5 mL). The organic phase was separated and the aqueous phase extracted with dichloromethane (2×5 mL). The combined extracts were dried with magnesium sulfate and evaporated in vacuo. The resultant oil was dissolved in methanol and the solution loaded onto a Biotage SCX-2 cartridge (2 g). The cartridge was washed through with methanol and the product eluted with ammonia in methanol (3.5M), evaporation in vacuo yielded (R)-methyl 4-(2-(dimethylamino)-1-phenylethoxy)-3-fluorobenzoate as a clear oil (0.122 g, 74% yield). $^1$H NMR (400 MHz, CDCl$_3$) 7.69 (1H, dd, J=2.1, 11.7 Hz), 7.61-7.57 (1H, m), 7.37-7.30 (4H, m), 7.29-7.26 (1H, m), 6.80 (1H, dd, J=8.3, 8.3 Hz), 5.41 (1H, dd, J=3.4, 8.5 Hz), 3.84 (3H, s), 3.02 (1H, dd, J=8.5, 13.8 Hz), 2.66 (1H, dd, J=3.3, 13.6 Hz), 2.39 (6H, s).

c) (R)-4-(2-(dimethylamino)-1-phenylethoxy)-3-fluoro-N-(5-(pyridin-4-yl)-1,3,4-thiadiazol-2-yl)benzamide (Compound of Formula 1-VII, Scheme 1)

To a stirred solution of (R)-methyl 4-(2-(dimethylamino)-1-phenylethoxy)-3-fluorobenzoate (0.122 g, 0.38 mmol, 1 eq.) in methanol (3 mL) was added 2M aqueous sodium hydroxide solution (380 μL, 0.76 mmol, 2 eq.) and the resulting mixture stirred at ambient temperature for 24 hours. The pH was adjusted to 6 with 2M hydrochloric acid and the solvents removed in vacuo to afford crude (R)-4-(2-(dimethylamino)-1-phenylethoxy)-3-fluorobenzoic acid which was used in the subsequent step without further purification. A solution of (R)-4-(2-(dimethylamino)-1-phenylethoxy)-3-fluorobenzoic acid (0.38 mmol, 1 eq.), 5-(4-pyridyl)-1,3,4-thiadiazol-2-yl amine (0.075 g, 0.42 mmol, 1.1 eq.), HATU (0.22 g, 0.57 mmol, 1.5 eq.) and diisopropylethylamine (80 µL, 0.46 mmol, 1.2 eq.) in NMP (1.5 mL) was stirred at 70° C. for 29.5 hours. The reaction was diluted with water (10 mL) and the precipitate collected by filtration, washed with water then dried in vacuo. The crude reaction was purified by preparative HPLC followed by trituration with hot water to afford (R)-4-(2-(dimethylamino)-1-phenylethoxy)-3-fluoro-N-(5-(pyridin-4-yl)-1,3,4-thiadiazol-2-yl)benzamide as a tan solid (0.057 g, 32% yield). $^1$H NMR (400 MHz, DMSO) 12.75 (1H, s), 8.79-8.76 (2H, m), 8.04 (1H, dd, J=2.2, 12.2 Hz), 7.98-7.95 (2H, m), 7.91 (1H, dd, J=1.3, 8.6 Hz), 7.51 (2H, d, J=7.3 Hz), 7.43 (2H, dd, J=7.5, 7.5 Hz), 7.38-7.30 (2H, m), 5.83 (1H, dd, J=3.9, 8.2 Hz), 3.10 (1H, dd, J=7.9, 13.6 Hz), 2.79 (1H, dd, J=3.8, 13.4 Hz), 2.43 (6H, s); MS (ESI$^+$) 464.

EXAMPLE 201

Measurement of NOX1 Inhibitory Activities

The activity of the compounds according to the invention is tested in the inhibition or reduction of NOX1 activity in the following assays Fluorescence Assay Reactive oxygen species (ROS) production generated by hNOX1 enzyme was measured by fluorescence in both cellular and membrane-based assays using the Amplex® Red reagent. In the presence of horseradish peroxidase (HRP), the Amplex® Red reagent (10-acetyl-3,7-dihydroxyphenoxazine, AR), which is a colorless and nonfluorescent derivative of dihydroresorufin, reacts with $H_2O_2$ with a 1:1 stoichiometry to produce highly fluorescent resorufin at an excitation and emission wavelengths of 544 nm and 590 nm, respectively.

Materials

Membranes from CHO cells overexpressing hNox1 were prepared as previously described (Palicz et al., 2001, *J. Biol. Chem*, 76, 3090). After resuspension in sonication buffer (11% sucrose, 120 mM NaCl, 1 mM EGTA in PBS, pH 7.4), cells were broken by sonication and centrifuged (200 g, 10 min). The supernatant was layered onto a 17/40% (w/v) discontinuous sucrose gradient and centrifuged (150,000 g for 30 min). Membrane fractions were collected from the 17/40% interface, aliquoted in 10 µl samples and were stored at −80° C. Protein concentration was determined with Bradford reagent. Flavin Adenine Dinucleotide (FAD) (catalog # F6625-500MG), MgCl$_2$ (catalog # M8266-100G), Phosphatidic Acid (PA) (catalog # P3591-50MG) were purchased from Sigma-Aldrich. Horseradish peroxidase (HRP) (catalog #10108090001) was purchased from Roche. NADPH (catalog #A1395, 0500) was purchased from Applichem. Amplex red (AR) (catalog # A22177) was purchased from Invitrogen. 96 well polypropylene and black plates were purchased from Milian (catalog #055529 and #055218, respectively). FLUOstar OPTIMA microplate reader was supplied by BMG Labtech (Germany). Zephyr® Compact Liquid Handling Workstation was supplied by PerkinElmer (Germany).

Assay 1: ROS Production Measurement on hNOX1 Membranes hNOX1 Membrane Assay Buffer All solutions were placed on ice and protected from light. The final concentration in the 1× hNOX1 membrane fluorescent assay buffer was PBS pH7, 6 µM FAD, 15 µM PA, 1 mM MgCl$_2$, 12.5 µM AR, 0.02 u/ml, 125 ng membranes, 1.5 µg of cofactors and 30 µM NADPH.

The NADPH was dissolved in water at a concentration of 12 mM and was transferred in a metal transfer plate kept at 4° C. The NADPH was added to the assay plate to initiate the reaction just before the measurement.

Compound Dilution

Serial dilution (1:3, 10 serial dilution) of the compounds was performed in 100% DMSO in 96 well polypropylene plate—Row B-H Column 1-10, Row A, Column 1-10 contained reference compound. Starting concentration was 10$^{-2}$ M (10 mM). Final concentration in assay was 10$^{-4}$ M (100 µM). Compounds were diluted twice in PBS buffer by transferring 30 µl/well of PBS into 30 µl/well compounds sample in DMSO using Zephyr® Compact Liquid Handling Workstation. Control wells-columns 1 and 12-contained 60 µl DMSO in 50% PBS pH7.

Reaction Mixture and Assays

Reaction mixture is dispensed using Zephyr® Compact Liquid Handling Workstation. 90 µl of mix with membrane were dispensed into 96 well black plates—Column 2-11, Column 1 Row A-D, Column 12 Row E-H. 90 µl of control mix were dispensed into assay plate—Column 1 Row E-H, Column 12 Row A-D, which are wells for measuring background signal. 2 µl of compounds were dispensed into each well of assay plate using Zephyr® Compact Liquid Handling Workstation. The reaction mixture with compounds was incubated in assay plates for 20 min at 37° C. in a Titramax microplate incubator with gentle agitation. 10 µl of NADPH is dispensed to the assay plate. Fluorescence reading was recorded with the FLUOstar OPTIMA microplate reader for 10 min at 37° C. (8 cycles, 1 cycle duration 55 sec).

Assay 2: ROS Production Measurement on hNOX1 Cells

For the cell based-assay, NOX1 expression is induced with tetracycline and the phorbol 12-myristate 13-acetate (PMA) was used to stimulate the production of hydrogen peroxide in T-REx™-CHO-hNOX1 cells.

Cell Buffer

Buffer to be used for cells consisted of HBSS buffer with 1% glucose. 24 hours before the assay, the compounds are incubated with tetracycline (1 mg/ml) in DMEM/F12 supplemented with 10% serum and 1% penicillin and streptomycin. The day of the assay, cells are detached with trypsin and then centrifuged at 1200 rpm for 5 min. Media is aspirated and the cells are resuspended in cell buffer. The cells are counted and resuspended to 2.5. 10$^6$ cells/ml. The cell pellet is kept on ice.

hNOX1 Cell Fluorescence Assay Buffer

All solutions were placed on ice and protected from light. The final concentration in the 1× hNOX1 cellular fluorescent assay buffer are HBSS/5% Glc pH7, 25 µM AR, 0.45 u/ml HRP, 100 nM PMA and 50,000 cells/100 µl reaction mixture. HRP is transferred in a metal transfer plate kept at 4° C. HRP is added to the assay plate to initiate the reaction just before the measurement. AR reagent is added in the mixes just before the dispensing of mixes in the black 96 microplates.

Compound Dilution

Same as described in the ROS production measurement on hNOX1 membranes above.

Reaction Mixture and Assays

Same as described above with the following exceptions:

Mix with cells induced by tetracycline and stimulated by PMA, are in column 2-11, Column 1 Row A-D, Column 12 Row E-H which are wells for measuring full signal.

Mix with non induced cells and stimulated by PMA Column 1 Row E-H, Column 12 Row A-D, which are wells for measuring background signal Incubation of the reaction mixture with compounds 10 min 10 µl of HRP are added to the entire assay plate to initiate the reaction Fluorescence reading is recorded during 12 cycles and obtained and used for calculations and the slope from data points read time 1 min to 12 minutes are determined and used for calculations.

The Table 2 below summarizes the percentage of inhibition of NOX activity as measured by the above described assay 1 and expressed by their inhibitory constant calculated by non linear regression analysis using GraphPad Prism Software (GraphPad Software Co., San Diego, Calif.):

TABLE 2

| Compound no | Nox1 inhibitory constant Ki (µM) |
| --- | --- |
| (1) | 0.018 |
| (7) | 0.022 |
| (9) | 0.029 |
| (10) | 0.049 |
| (19) | 0.22 |
| (22) | 0.018 |
| (24) | 0.062 |
| (29) | 0.064 |
| (34) | 0.045 |
| (37) | 0.038 |
| (39) | 0.1 |
| (40) | 0.19 |
| (43) | 0.079 |
| (45) | 0.077 |
| (46) | 0.035 |
| (51) | 0.021 |
| (52) | 0.018 |
| (53) | 0.019 |
| (63) | 0.031 |
| (65) | 0.051 |
| (66) | 0.066 |
| (67) | 0.075 |
| (68) | 0.072 |
| (69) | 0.055 |
| (75) | 0.09 |
| (80) | 0.027 |
| (82) | 0.038 |
| (83) | 0.08 |
| (85) | 0.037 |
| (86) | 0.074 |
| (89) | 0.091 |
| (90) | 0.1 |
| (91) | 0.078 |
| (92) | 0.032 |
| (93) | 0.052 |
| (96) | 0.014 |
| (98) | 0.074 |
| (102) | 0.087 |
| (103) | 0.013 |
| (105) | 0.019 |
| (106) | 0.022 |
| (108) | 0.092 |
| (111) | 0.075 |
| (114) | 0.037 |
| (115) | 0.11 |
| (116) | 0.046 |
| (120) | 0.093 |
| (121) | 0.035 |
| (134) | 0.071 |

TABLE 2-continued

| Compound no | Nox1 inhibitory constant Ki (µM) |
| --- | --- |
| (136) | 0.047 |
| (149) | 0.078 |
| (151) | 0.015 |
| (152) | 0.038 |
| (154) | 0.033 |
| (157) | 0.11 |
| (158) | 0.022 |
| (161) | 0.079 |
| (162) | 0.095 |
| (168) | 0.1 |
| (174) | 0.096 |
| (178) | 0.085 |
| (180) | 0.032 |
| (182) | 0.037 |
| (183) | 0.055 |
| (185) | 0.089 |
| (187) | 0.055 |
| (197) | 0.024 |
| (198) | 0.025 |
| (199) | 0.047 |
| (200) | 0.11 |

EXAMPLE 202

In Vivo Angiogenesis Assay

Angiogenesis was assessed in male C57BL/6 mice (20-22 g) ordered from Elevage Janvier (France). Angioreactors ordered from Amsbio (Directed in vivo angiogenesis Assay ref 3450-048-K) were prepared according to kit instructions. Briefly, implant grade silicone cylinders closed at one end, called angioreactors, are filled with 20 µl of Trevigen's PathClear® basement membrane extract (BME) premixed with or without angiogenic-modulating factors. A mix of VEGF (10 µg) and FGF (50 µg) ordered from Peprotech was used. Two angioreactors per mouse are then implanted subcutaneously in the dorsal flank of the mice. Accompanied with the onset of angiogenesis, vascular endothelial cells proceed to grow into the BME and form vessels in the angioreactor. As early as 15 days post-implantation, there are enough cells to determine an effective dose response to angiogenic modulating factors using a FITC-Lectin detection system. Mice are treated with a compound of the invention by oral gavage (10 ml/kg) from D0 to D14.

EXAMPLE 203

In Vivo Dextran Sulfate Sodium-induced Colitis

Colitis was induced by 3.5% Dextran Sulfate Sodium (36.000-50.000 MW from MP Biomedical) in drinking water for 5 days. Mice were treated with a compound of the invention by oral gavage (10 ml/kg) from D0 to D5. A last administration was done 2 h before the euthanasia of animals on D5. Mice were euthanatized and colons were removed, cleaned and stored at −80° C. until NADPH-dependent superoxide generation was assayed by chemiluminescence in tissue using lucigenin.

EXAMPLE 204

In Vivo TNBS-induced Colitis Model

The compounds of the inventions are tested in a model of Trinitrobenzene sulfonate (TNBS)-induced colitis where intestinal inflammation is induced by TNBS administered intra-rectally in C57Bl/6 mice for 4 weeks. Animals are treated with a compound of the invention for 4 weeks by oral gavage. Chemokines and myeloperoxidase activity (phagocyte marker) is measured in colon homogenates. Immune cell infiltration is accessed by histological examination of hematoxylin-eosin stained.

EXAMPLE 205

In Vivo Model of Atherosclerosis

The compounds of the inventions are tested in a model of atherosclerosis as follows. Six-week-old ApoE−/− male mice are rendered diabetic by 5 daily intraperitoneal (IP) injections of streptozotocin (Sigma-Aldrich) at a dose of 55 mg/kg. A subgroup of diabetic and nondiabetic ApoE−/− mice are administered a compound of the invention, by daily gavage for 10 weeks. After 10 weeks, animals are anaesthetised by sodium pentobarbitone IP (100 mg/kg body weight; Euthatal, Sigma-Aldrich) and organs were rapidly dissected. Assessment of plaque area is undertaken using en face analysis, after staining with Sudan IV-Herxheimer's solution (BDH, Poole UK). Paraffin sections of aorta are used to stain for nitrotyrosine (Millipore), F4/80 (Abcam), monocyte chemoattractant protein 1 (MCP-1; BioVision) and 4-Hydroxynonenal (4-HNE) (Abcam).

EXAMPLE 206

In Vivo Acetic Acid Induced Pain Model

The compounds of the inventions are tested in a model of pain as follows. Mice are injected with acetic acid (0.5% i.p.). This treatment induces a recognizable writhing response in control animals. The number of writhes is counted for 10 minutes beginning 5 minutes after injection of acetic acid. 12 mice are studied per group. The test is performed partially blind. Compounds of the invention are administered p.o. 60 minutes before the test (i.e. 55 minutes before acetic acid), and compared with a vehicle control group. Morphine (16 mg/kg, p.o.) administered 60 minutes before the test (i.e. 55 minutes before acetic acid) is used as analgesic reference substance.

EXAMPLE 207

In Vivo UV-induced Pain Model

The compounds of the inventions are tested in a model of pain as follows. Mouse inflammatory pain is induced by exposing the plantar surface of the hind paw to 350 mJoules/ $cm^2$ ultra-violet radiation. Thermal hyperalgesia is assessed using Hargreaves test prior to UVB and 2 days post-UVB. Mechanical hyperalgesia is assessed using a digital Randall-Selitto device prior to UVB and 3 days post-UVB. All animals are euthanized on day 3 following the dRS (digital Randall-Selitto) test. Plasma samples and ipsilateral paw are collected. Administration of compounds of the invention is made for 3 days, once daily.

EXAMPLE 208

In Vivo Capsaicin-induced Pain Model

The compounds of the inventions are tested in a model of pain as follows. Rat inflammatory pain is induced by injecting 10 µg of Capsaicin to the subcutaneous plantar surface of the hind paw. Mechanical allodinia is assessed using the electronic Von Frey test prior to Capsaicin challenge and 30, 60, 90' post challenge. Administration of compounds of the invention is made 60' before the Capsaicin challenge.

EXAMPLE 209

In Vivo Rheumatoid Arthritis Pain Model

The compounds of the inventions are tested in a model of pain as follows. Male DBA (Dilute Brown Non-Agouti) mice are subjected to an intradermal injection of the emulsion at the base of the tail. On study day 21, the animals are given a collagen challenge to induced arthritis. Animals are then treated with compounds of the invention up to Day 42. At day 42, mechanical allodinia is assessed using the electronic Von Frey test. Body weight and clinical signs are monitored all along the study as well. The joins are collected and fixed in PFA and the arthritis score is then quantified after H&E staining.

EXAMPLE 210

In Vivo Model of Influenza

The compounds of the inventions are tested in a model of influenza as follows. A/Puerto Rico/8/34 (PR8) virus is grown and titrated for 50% lethal and 50% mouse infectious doses (LD50 and MID50, respectively) by administering serial ten-fold dilutions of egg-grown virus stock to 6-week old female B6 mice. Lethality, as defined by loss of greater than 25% original body weight, or infection, defined by positive Egg Infectious Dose (EID) titers in the lungs at day 3 post infection, are used as endpoints to determine $LD_{50}$ (Lethal Dose) or $MID_{50}$ (Mouse Infection Dose) titers respectively, in the method described by Reed and Muench.

C57Bl/6 mice are infected intranasally at 5-8 weeks of age with 50 MID50 or 20 MID50 of PR8 under sedation by intraperitoneal administration of 2,2,2,-tribromoethanol in tert-amyl alcohol (Avertin; Sigma-Aldrich). Mice are weighed daily. Mice which never dropped below 100% of original body weight are presumed to be uninfected and are omitted from longitudinal studies. The calculated 1 $LD_{50}$ is equivalent to 1000 $MID_{50}$. Mice are treated with compound of the invention for 14 days and Body Weight and mortality are followed. At D14 mice are euthanized and lungs were homogenized for virus titration and quantification of inflammatory chemokines and cytokines by ELISA.

EXAMPLE 211

In Vivo MPTP Mouse Model of Parkinson's Disease

The compounds of the inventions are tested in a model of Parkinson's Disease as follows. Chosen compounds of the present invention are infused directly in the lateral ventricles of mice, using Alzet osmotic minipump connected to a catheter. 3 different concentrations are tested. One day after the initiation of infusion, mice are injected every 2 hours with MPTP (1-methyl-4-phenyl-1,2,3,6-tetrahydropyridine), in a total of 3 injections for one day. Seven days after the MPTP injections all animals are sacrificed. For biochemical analysis, brains are collected and snap frozen for posterior preparation of total protein lysates from SN (substantia nigra) and ST (striatum) or for the measurements of dopamine levels. For immunohistochemical analysis, animals are intracardially perfused with saline and 4% paraformaldehyde in PBS, brains are then removed, and immersion-fixed in 4% paraformaldehyde overnight and cryoprotected in 30% sucrose. The following outcomes are evaluated:
a) The number of TH-positive Dopaminergic (DA) neurons in the substantia nigra (SN) by stereologic counting and the dopamine content in the striatum by HPLC are analyzed;
b) Alpha-Synuclein aggregation and pS129 alpha-synuclein levels are measured by immunohistochemistry and western-blot respectively.

The invention claimed is:
1. An amido thiadiazole compound according to Formula (I):

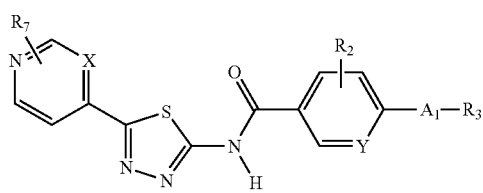

wherein X is selected from $CR^1$ and N; Y is selected from CH or N; $A_1$ is selected from —$OCHR^5$—, —$NR^4$—$CHR^5$—, —$CH_2NR^4$— and —$CH_2$—O—; $R^1$ is selected from H, halogen and optionally substituted $C_1$-$C_6$ alkyl; $R^2$ is selected from H, halogen, optionally substituted alkoxy, optionally substituted alkoxy $C_1$-$C_6$ alkyl, optionally substituted $C_1$-$C_6$ alkyl, optionally substituted amino, optionally substituted $C_1$-$C_6$ alkyl amino, optionally substituted heterocycloalkyl, optionally substituted $C_1$-$C_6$ alkyl heterocycloalkyl, optionally substituted amino $C_1$-$C_6$ alkyl, optionally substituted alkoxy $C_1$-$C_6$ alkyl, —O—$R^8$ and —$NR^9R^{10}$; $R^3$ is a group of formula —$(CHR^6)_n$-$A_2$ or $R^3$ forms with the moiety $CHR^5$ from $A_1$ an optionally substituted ring selected from optionally substituted aryl and optionally substituted heteroaryl, or $R^3$ forms with the moiety $NR^4$ from $A_1$ an optionally substituted ring selected from optionally substituted aryl, optionally substituted heteroaryl; n is an integer from 0 to 4; $R^4$ is selected from H and optionally substituted alkyl; $A_2$ is an optionally substituted ring selected from optionally substituted aryl and optionally substituted heteroaryl; $R^5$ is selected from H, optionally substituted $C_1$-$C_6$ alkyl, optionally substituted amino $C_1$-$C_6$ alkyl, optionally substituted alkoxy $C_1$-$C_6$ alkyl, optionally substituted heterocycloalkyl $C_1$-$C_6$ alkyl, optionally substituted aminocarbonyl, optionally substituted $C_2$-$C_8$ cycloalkyl and optionally substituted amino $C_1$-$C_6$ alkyl; $R^6$ is selected from H, optionally substituted $C_1$-$C_6$ alkyl, optionally substituted amino, optionally substituted $C_1$-$C_6$ alkyl amino and hydroxy and wherein $R^6$ groups are independently selected for each repeating unit ($CHR^6$); $R^7$ is selected from H, halogen and optionally substituted $C_1$-$C_6$ alkyl; $R^8$ is selected from H, optionally substituted $C_1$-$C_6$ alkyl, optionally substituted amino $C_1$-$C_6$ alkyl, optionally substituted heterocycloalkyl, optionally substituted $C_2$-$C_8$ cycloalkyl, optionally substituted heterocycloalkyl $C_1$-$C_6$ alkyl, optionally substituted $C_2$-$C_8$ cycloalkyl $C_1$-$C_6$ alkyl, optionally substituted alkoxy, optionally substituted amino $C_1$-$C_6$ alkyl; optionally substituted aryl $C_1$-$C_6$ alkyl and optionally substituted heteroaryl $C_1$-$C_6$ alkyl; $R^9$ and $R^{10}$ are independently selected from H, optionally substituted $C_1$-$C_6$ alkyl, optionally substituted amino $C_1$-$C_6$ alkyl, optionally substituted heterocycloalkyl, optionally substituted $C_2$-$C_8$ cycloalkyl, optionally substituted heterocycloalkyl $C_1$-$C_6$ alkyl, optionally substituted $C_2$-$C_8$ cycloalkyl $C_1$-$C_6$ alkyl, optionally substituted alkoxy, optionally substituted alkoxy $C_1$-$C_6$ alkyl, optionally substituted aryl $C_1$-$C_6$ alkyl and optionally substituted heteroaryl $C_1$-$C_6$ alkyl, optionally substituted amino $C_1$-$C_6$ alkyl; as well as tautomers, geometrical isomers, optically active forms and pharmaceutically acceptable salts thereof.

2. The amido thiadiazole compound according to claim 1, wherein X is N.

3. The amido thiadiazole compound according to claim 1, wherein X is $CR^1$.

4. The amido thiadiazole compound according to claim 1, wherein Y is CH.

5. The amido thiadiazole compound according to claim 1, wherein Y is N.

6. The amido thiadiazole compound according to claim 1, wherein $A_1$ is —$OCHR^5$—.

7. The amido thiadiazole compound according to claim 1, wherein $A_1$ is —$NR^4$—$CHR^5$.

8. The amido thiadiazole compound according to claim 1, wherein $A_1$ is —$CH_2NR^4$.

9. The amido thiadiazole compound according to claim 1, wherein $A_1$ is —$CH_2$—O—.

10. The amido thiadiazole compound according to claim 1, wherein n is selected from 0, 1 and 2.

11. The amido thiadiazole compound according to claim 1 selected from the following group:
  4-(1-phenylethoxy)-3-(piperidin-4-ylmethoxy)-N-(5-(pyridin-4-yl)-1,3,4-thiadiazol-2-yl)benzamide;
  3-(2-hydroxyethoxy)-4-(1-phenylethoxy)-N-(5-(pyridin-4-yl)-1,3,4-thiadiazol-2-yl)benzamide;
  5-chloro-6-(2-(dimethylamino)-1-(pyridin-2-yl)ethoxy)-N-(5-(pyridin-4-yl)-1,3,4-thiadiazol-2-yl)nicotinamide;
  3-methoxy-4-(1-phenylethoxy)-N-(5-(pyridin-4-yl)-1,3,4-thiadiazol-2-yl)benzamide;
  3-methoxy-4-(1-(pyridin-2-yl)ethoxy)-N-(5-(pyridin-4-yl)-1,3,4-thiadiazol-2-yl)benzamide;
  4-(2-(dimethylamino)-1-phenylethoxy)-3-methoxy-N-(5-(pyridin-4-yl)-1,3,4-thiadiazol-2-yl)benzamide;
  4-(2-hydroxy-1-phenylethoxy)-3-methoxy-N-(5-(pyridin-4-yl)-1,3,4-thiadiazol-2-yl)benzamide;
  4-(3-hydroxy-1-phenylpropoxy)-3-methoxy-N-(5-(pyridin-4-yl)-1,3,4-thiadiazol-2-yl)benzamide;
  3-methoxy-4-(1-phenyl-3-(pyrrolidin-1-yl)propoxy)-N-(5-(pyridin-4-yl)-1,3,4-thiadiazol-2-yl)benzamide;
  3-methoxy-4-(1-phenyl-2-(pyrrolidin-1-yl)ethoxy)-N-(5-(pyridin-4-yl)-1,3,4-thiadiazol-2-yl)benzamide;
  4-(3-(dimethylamino)-1-phenylpropoxy)-3-methoxy-N-(5-(pyridin-4-yl)-1,3,4-thiadiazol-2-yl)benzamide;
  3-methoxy-4-(2-(methylamino)-1-phenylethoxy)-N-(5-(pyridin-4-yl)-1,3,4-thiadiazol-2-yl)benzamide;
  3-methoxy-4-(1-(pyridin-3-yl)ethoxy)-N-(5-(pyrimidin-4-yl)-1,3,4-thiadiazol-2-yl)benzamide;
  N-(5-(3-fluoropyridin-4-yl)-1,3,4-thiadiazol-2-yl)-3-methoxy-4-(1-(pyridin-3-yl)ethoxy)benzamide;
  3-methoxy-N-(5-(3-methylpyridin-4-yl)-1,3,4-thiadiazol-2-yl)-4-(1-phenylethoxy)benzamide;
  3-methoxy-N-(5-(2-methylpyridin-4-yl)-1,3,4-thiadiazol-2-yl)-4-(1-phenylethoxy)benzamide;
  4-((1H-imidazol-4-yl)methoxy)-3-methoxy-N-(5-(pyridin-4-yl)-1,3,4-thiadiazol-2-yl)benzamide;
  3-methoxy-N-(5-(pyridin-4-yl)-1,3,4-thiadiazol-2-yl)-4-(pyrimidin-2-ylmethoxy)benzamide;

3-methoxy-4-((1-methyl-1H-imidazol-2-yl)methoxy)-N-(5-(pyridin-4-yl)-1,3,4-thiadiazol-2-yl)benzamide;
5-methyl-6-(1-phenylethoxy)-N-(5-(pyridin-4-yl)-1,3,4-thiadiazol-2-yl)nicotinamide;
5-chloro-6-(1-phenylethoxy)-N-(5-(pyridin-4-yl)-1,3,4-thiadiazol-2-yl)nicotinamide;
5-((2-methoxyethyl)amino)-6-(1-phenylethoxy)-N-(5-(pyridin-4-yl)-1,3,4-thiadiazol-2-yl)nicotinamide;
6-(benzyloxy)-5-chloro-N-(5-(pyridin-4-yl)-1,3,4-thiadiazol-2-yl)nicotinamide;
6-(benzyloxy)-5-(4-methylpiperazin-1-yl)-N-(5-(pyridin-4-yl)-1,3,4-thiadiazol-2-yl)nicotinamide;
5-methoxy-6-((1-phenylethyl)amino)-N-(5-(pyridin-4-yl)-1,3,4-thiadiazol-2-yl)nicotinamide;
6-(3-(dimethylamino)-1-phenylpropoxy)-5-methoxy-N-(5-(pyridin-4-yl)-1,3,4-thiadiazol-2-yl)nicotinamide;
6-(2-hydroxy-1-phenylethoxy)-5-methoxy-N-(5-(pyridin-4-yl)-1,3,4-thiadiazol-2-yl)nicotinamide;
6-(2-hydroxy-2-phenylethoxy)-5-methoxy-N-(5-(pyridin-4-yl)-1,3,4-thiadiazol-2-yl)nicotinamide;
5-chloro-6-(2-hydroxy-2-methyl-1-phenylpropoxy)-N-(5-(pyridin-4-yl)-1,3,4-thiadiazol-2-yl)nicotinamide;
5-chloro-6-(2-(dimethylamino)-1-(pyridin-2-yl)ethoxy)-N-(5-(pyridin-4-yl)-1,3,4-thiadiazol-2-yl)nicotinamide;
6-(2-(dimethylamino)-1-phenylethoxy)-N-(5-(pyridin-4-yl)-1,3,4-thiadiazol-2-yl)nicotinamide;
6-((1-(dimethylamino)-2,3-dihydro-1H-inden-2-yl)oxy)-N-(5-(pyridin-4-yl)-1,3,4-thiadiazol-2-yl)nicotinamide;
6((1-(dimethylamino)-3-phenylpropan-2-yl)oxy)-N-(5-(pyridin-4-yl)-1,3,4-thiadiazol-2-yl)nicotinamide;
6-((1-phenylpropan-2-yl)oxy)-N-(5-(pyridin-4-yl)-1,3,4-thiadiazol-2-yl)nicotinamide;
6-(1-(pyridin-3-yl)ethoxy)-N-(5-(pyridin-4-yl)-1,3,4-thiadiazol-2-yl)nicotinamide;
6-((1-(pyridin-3-yl)ethyl)amino)-N-(5-(pyridin-4-yl)-1,3,4-thiadiazol-2-yl) nicotinamide;
6-(1-phenylethoxy)-N-(5-(pyridin-4-yl)-1,3,4-thiadiazol-2-yl)-5-((tetrahydro-2H-pyran-4-yl)methoxy)nicotinamide;
6-(3-morpholino-1-phenylpropoxy)-N-(5-(pyridin-4-yl)-1,3,4-thiadiazol-2-yl)nicotinamide;
6-(2-morpholino-1-phenylethoxy)-N-(5-(pyridin-4-yl)-1,3,4-thiadiazol-2-yl)nicotinamide;
4-(isoindolin-2-ylmethyl)-3-methoxy-N-(5-(pyridin-4-yl)-1,3,4-thiadiazol-2-yl)benzamide;
6-(benzyloxy)-5-methoxy-N-(5-(pyridin-4-yl)-1,3,4-thiadiazol-2-yl)nicotinamide;
5-methoxy-6-(1-phenyl ethoxy)-N-(5-(pyridin-4-yl)-1,3,4-thiadiazol-2-yl) nicotinamide;
2-methyl-6-(1-phenylethoxy)-N-(5-(pyridin-4-yl)-1,3,4-thiadiazol-2-yl)nicotinamide;
2-methyl-6-(1-(pyridin-2-yl)ethoxy)-N-(5-(pyridin-4-yl)-1,3,4-thiadiazol-2-yl)nicotinamide;
6-(benzyloxy)-2-methyl-N-(5-(pyridin-4-yl)-1,3,4-thiadiazol-2-yl)nicotinamide;
5-methoxy-6-(1-(pyridin-2-yl)ethoxy)-N-(5-(pyridin-4-yl)-1,3,4-thiadiazol-2-yl)nicotinamide;
5-chloro-6-(1-(pyridin-2-yl)ethoxy)-N-(5-(pyridin-4-yl)-1,3,4-thiadiazol-2-yl)nicotinamide;
6-(benzyloxy)-5-((2-(dimethylamino)ethyl)amino)-N-(5-(pyridin-4-yl)-1,3,4-thiadiazol-2-yl)nicotinamide;
6-(benzyloxy)-5-methyl-N-(5-(pyridin-4-yl)-1,3,4-thiadiazol-2-yl)nicotinamide;
5-((2-(dimethylamino)ethyl)amino)-6-(1-phenylethoxy)-N-(5-(pyridin-4-yl)-1,3,4-thiadiazol-2-yl)nicotinamide;
6-(1-phenylethoxy)-N-(5-(pyridin-4-yl)-1,3,4-thiadiazol-2-yl)-5-((((tetrahydro-2H-pyran-4-yl)methyl)amino) nicotinamide;
5-(((1-methylpiperidin-4-yl)methyl)amino)-6-(1-phenylethoxy)-N-(5-(pyridin-4-yl)-1,3,4-thiadiazol-2-yl) nicotinamide;
5-(methylamino)-6-(1-phenylethoxy)-N-(5-(pyridin-4-yl)-1,3,4-thiadiazol-2-yl)nicotinamide;
6-(benzyloxy)-5-(methylamino)-N-(5-(pyridin-4-yl)-1,3,4-thiadiazol-2-yl)nicotinamide;
6-(3-(dimethylamino)-1-phenylpropoxy)-5-methyl-N-(5-(pyridin-4-yl)-1,3,4-thiadiazol-2-yl)nicotinamide;
5-chloro-6-(3-(dimethylamino)-1-phenylpropoxy)-N-(5-(pyridin-4-yl)-1,3,4-thiadiazol-2-yl)nicotinamide;
6-(2-(dimethylamino)-1-phenylethoxy)-5-methoxy-N-(5-(pyridin-4-yl)-1,3,4-thiadiazol-2-yl)nicotinamide;
5-chloro-6-(2-(dimethylamino)-1-phenylethoxy)-N-(5-(pyridin-4-yl)-1,3,4-thiadiazol-2-yl)nicotinamide;
6-(2-(dimethylamino)-1-phenylethoxy)-5-methyl-N-(5-(pyridin-4-yl)-1,3,4-thiadiazol-2-yl)nicotinamide;
5-((3-(dimethylamino)propyl)amino)-6-(1-phenylethoxy)-N-(5-(pyridin-4-yl)-1,3,4-thiadiazol-2-yl) nicotinamide;
5-((2-hydroxyethyl)amino)-6-(1-phenylethoxy)-N-(5-(pyridin-4-yl)-1,3,4-thiadiazol-2-yl)nicotinamide;
5-(((1-methyl-1H-imidazol-4-yl)methyl)amino)-6-(1-phenylethoxy)-N-(5-(pyridin-4-yl)-1,3,4-thiadiazol-2-yl)nicotinamide;
5-((1-methylpiperidin-4-yl)amino)-6-(1-phenylethoxy)-N-(5-(pyridin-4-yl)-1,3,4-thiadiazol-2-yl)nicotinamide;
5-((2-morpholinoethyl)amino)-6-(1-phenylethoxy)-N-(5-(pyridin-4-yl)-1,3,4-thiadiazol-2-yl)nicotinamide;
5-(4-methylpiperazin-1-yl)-6-(1-phenylethoxy)-N-(5-(pyridin-4-yl)-1,3,4-thiadiazol-2-yl)nicotinamide;
5-(dimethylamino)-6-(1-phenylethoxy)-N-(5-(pyridin-4-yl)-1,3,4-thiadiazol-2-yl)nicotinamide;
5-methoxy-6-((1-(pyridin-3-yl)ethyl)amino)-N-(5-(pyridin-4-yl)-1,3,4-thiadiazol-2-yl)nicotinamide;
6-(2-(dimethylamino)-1-(pyridin-2-yl)ethoxy)-5-methoxy-N-(5-(pyridin-4-yl)-1,3,4-thiadiazol-2-yl) nicotinamide;
5-(dimethylamino)-6-(3-(dimethylamino)-1-phenylpropoxy)-N-(5-(pyridin-4-yl)-1,3,4-thiadiazol-2-yl) nicotinamide;
6-(3-(dimethylamino)-1-phenylpropoxy)-5-(methylamino)-N-(5-(pyridin-4-yl)-1,3,4-thiadiazol-2-yl)nicotinamide;
3-methoxy-N-(5-(pyridin-4-yl)-1,3,4-thiadiazol-2-yl)-4-(pyridin-4-ylmethoxy)benzamide;
3-methoxy-4-(1-(pyridin-3-yl)ethoxy)-N-(5-(pyridin-4-yl)-1,3,4-thiadiazol-2-yl)benzamide;
4-((1,3-dimethyl-1H-pyrazol-5-yl)methoxy)-3-methoxy-N-(5-(pyridin-4-yl)-1,3,4-thiadiazol-2-yl)benzamide;
4-((2,3-dihydro-1H-inden-1-yl)oxy)-3-methoxy-N-(5-(pyridin-4-yl)-1,3,4-thiadiazol-2-yl)benzamide;
3-methoxy-N-(5-(pyridin-4-yl)-1,3,4-thiadiazol-2-yl)-4-((1,2,3,4-tetrahydronaphthalen-1-yl)oxy)benzamide;
3-methoxy-N-(5-(pyridin-4-yl)-1,3,4-thiadiazol-2-yl)-4-(thiazol-4-ylmethoxy)benzamide;
3-methoxy-N-(5-(pyridin-4-yl)-1,3,4-thiadiazol-2-yl)-4-(thiazol-2-ylmethoxy)benzamide;
3-(2-(dimethylamino)ethoxy)-4-(1-phenylethoxy)-N-(5-(pyridin-4-yl)-1,3,4-thiadiazol-2-yl)benzamide;

3-(2-methoxyethoxy)-4-(1-phenylethoxy)-N-(5-(pyridin-4-yl)-1,3,4-thiadiazol-2-yl)benzamide;
3-((1-methylpiperidin-4-yl)methoxy)-4-(1-phenylethoxy)-N-(5-(pyridin-4-yl)-1,3,4-thiadiazol-2-yl)benzamide;
3-methoxy-4-((2-methylpyridin-3-yl)methoxy)-N-(5-(pyridin-4-yl)-1,3,4-thiadiazol-2-yl)benzamide;
3-methoxy-4-((5-methylpyridin-2-yl)methoxy)-N-(5-(pyridin-4-yl)-1,3,4-thiadiazol-2-yl)benzamide;
3-methoxy-4-((5-methylisoxazol-3-yl)methoxy)-N-(5-(pyridin-4-yl)-1,3,4-thiadiazol-2-yl)benzamide;
3-methoxy-4-((4-methoxybenzyl)oxy)-N-(5-(pyridin-4-yl)-1,3,4-thiadiazol-2-yl)benzamide;
4-((2-fluorobenzyl)oxy)-3-methoxy-N-(5-(pyridin-4-yl)-1,3,4-thiadiazol-2-yl)benzamide;
3-methoxy-4-(pyridin-2-ylmethoxy)-N-(5-(pyridin-4-yl)-1,3,4-thiadiazol-2-yl)benzamide;
4-((4-fluorobenzyl)oxy)-3-methoxy-N-(5-(pyridin-4-yl)-1,3,4-thiadiazol-2-yl)benzamide;
3-methoxy-4-((5-methyl-1,2,4-oxadiazol-3-yl)methoxy)-N-(5-(pyridin-4-yl)-1,3,4-thiadiazol-2-yl)benzamide
4-((5-cyclopropylisoxazol-3-yl)methoxy)-3-methoxy-N-(5-(pyridin-4-yl)-1,3,4-thiadiazol-2-yl)benzamide;
3-methoxy-4-((1-methyl-1H-1,2,4-triazol-5-yl)methoxy)-N-(5-(pyridin-4-yl)-1,3,4-thiadiazol-2-yl)benzamide;
3-methoxy-4-((1-methyl-1H-imidazol-5-yl)methoxy)-N-(5-(pyridin-4-yl)-1,3,4-thiadiazol-2-yl)benzamide;
3-methoxy-4-(2-(1-methyl-1H-imidazol-2-yl)ethoxy)-N-(5-(pyridin-4-yl)-1,3,4-thiadiazol-2-yl)benzamide;
3-methoxy-4-(1-(pyridin-2-yl)ethoxy)-N-(5-(pyrimidin-4-yl)-1,3,4-thiadiazol-2-yl)benzamide;
N-(5-(3-fluoropyridin-4-yl)-1,3,4-thiadiazol-2-yl)-3-methoxy-4-(1-(pyridin-2-yl)ethoxy)benzamide;
N-(5-(3-fluoropyridin-4-yl)-1,3,4-thiadiazol-2-yl)-4-(3-hydroxy-1-phenylpropoxy)-3-methoxybenzamide;
N-(5-(3-fluoropyridin-4-yl)-1,3,4-thiadiazol-2-yl)-4-(2-hydroxy-1-phenylethoxy)-3-methoxybenzamide;
4-(2-(dimethylamino)-1-phenylethoxy)-N-(5-(3-fluoropyridin-4-yl)-1,3,4-thiadiazol-2-yl)-3-methoxybenzamide;
6-(3-(dimethylamino)-1-phenylpropoxy)-N-(5-(pyridin-4-yl)-1,3,4-thiadiazol-2-yl)-5-((tetrahydro-2H-pyran-4-yl)methoxy)nicotinamide;
5-chloro-6-(2-hydroxy-1-phenylethoxy)-N-(5-(pyridin-4-yl)-1,3,4-thiadiazol-2-yl)nicotinamide;
4-(3-hydroxy-1-phenylpropoxy)-3-methoxy-N-(5-(pyrimidin-4-yl)-1,3,4-thiadiazol-2-yl)benzamide;
4-(2-hydroxy-1-phenylethoxy)-3-methoxy-N-(5-(pyrimidin-4-yl)-1,3,4-thiadiazol-2-yl)benzamide;
4-(benzyloxy)-3-methoxy-N-(5-(pyrimidin-4-yl)-1,3,4-thiadiazol-2-yl)benzamide;
4-(benzyloxy)-N-(5-(3-fluoropyridin-4-yl)-1,3,4-thiadiazol-2-yl)-3-methoxybenzamide;
4-(2-(dimethylamino)-1-phenylethoxy)-3-methoxy-N-(5-(3-methylpyridin-4-yl)-1,3,4-thiadiazol-2-yl)benzamide;
6-(2-(dimethylamino)-1-phenylethoxy)-5-methoxy-N-(5-(pyrimidin-4-yl)-1,3,4-thiadiazol-2-yl)nicotinamide;
4-(2-(dimethylamino)-1-phenylethoxy)-3-methoxy-N-(5-(2-methylpyridin-4-yl)-1,3,4-thiadiazol-2-yl)benzamide;
3-methoxy-4-((1-phenylpropan-2-yl)oxy)-N-(5-(pyridin-4-yl)-1,3,4-thiadiazol-2-yl)benzamide;
4-(2-(dimethylamino)-1-phenylethoxy)-3-methoxy-N-(5-(pyrimidin-4-yl)-1,3,4-thiadiazol-2-yl)benzamide;
4-(benzyloxy)-N-(5-(pyridin-4-yl)-1,3,4-thiadiazol-2-yl)benzamide;
3-methoxy-4-((methyl(pyridin-2-yl)amino)methyl)-N-(5-(pyridin-4-yl)-1,3,4-thiadiazol-2-yl)benzamide;
4-((1H-indo-1-yl)methyl)-3-methoxy-N-(5-(pyridin-4-yl)-1,3,4-thiadiazol-2-yl)benzamide;
3-methoxy-4-(phenoxymethyl)-N-(5-(pyridin-4-yl)-1,3,4-thiadiazol-2-yl)benzamide;
3-methoxy-4-((methyl(phenyl)amino)methyl)-N-(5-(pyridin-4-yl)-1,3,4-thiadiazol-2-yl)benzamide;
6-(2-hydroxy-2-methyl-1-phenylpropoxy)-N-(5-(pyridin-4-yl)-1,3,4-thiadiazol-2-yl)nicotinamide;
6-((1-phenylpropan-2-yl)oxy)-N-(5-(pyridin-4-yl)-1,3,4-thiadiazol-2-yl)nicotinamide;
6-((1,3-dimethyl-1H-pyrazol-5-yl)methoxy)-N-(5-(pyridin-4-yl)-1,3,4-thiadiazol-2-yl)nicotinamide;
N-(5-(pyridin-4-yl)-1,3,4-thiadiazol-2-yl)-6-(thiophen-3-ylmethoxy)nicotinamide;
6-(3-(dimethylamino)-1-phenylpropoxy)-N-(5-(3-fluoropyridin-4-yl)-1,3,4-thiadiazol-2-yl)nicotinamide;
6-(1-phenylpropoxy)-N-(5-(pyridin-4-yl)-1,3,4-thiadiazol-2-yl)nicotinamide;
6-(1-(4-chlorophenyl)propoxy)-N-(5-(pyridin-4-yl)-1,3,4-thiadiazol-2-yl)nicotinamide;
6-((2,3-dihydro-1H-inden-1-yl)oxy)-N-(5-(pyridin-4-yl)-1,3,4-thiadiazol-2-yl)nicotinamide;
6-((6,7-dihydro-5H-cyclopenta[b]pyridin-5-yl)oxy)-N-(5-(pyridin-4-yl)-1,3,4-thiadiazol-2-yl)nicotinamide;
6-(3-(dimethylamino)-1-phenylpropoxy)-N-(5-(pyridin-4-yl)-1,3,4-thiadiazol-2-yl)nicotinamide;
6-(3-hydroxy-3-phenylpropoxy)-N-(5-(pyridin-4-yl)-1,3,4-thiadiazol-2-yl)nicotinamide;
6-(1-phenylethoxy)-N-(5-(pyridin-4-yl)-1,3,4-thiadiazol-2-yl)nicotinamide;
6-(benzyloxy)-N-(5-(pyridin-4-yl)-1,3,4-thiadiazol-2-yl)nicotinamide;
6-(methyl(1-phenylethyl)amino)-N-(5-(pyridin-4-yl)-1,3,4-thiadiazol-2-yl)nicotinamide;
6-((2-(dimethylamino)-2-phenylethyl)amino)-N-(5-(pyridin-4-yl)-1,3,4-thiadiazol-2-yl)nicotinamide;
6-((2,3-dihydro-1H-inden-2-yl)amino)-N-(5-(pyridin-4-yl)-1,3,4-thiadiazol-2-yl)nicotinamide;
6-((1-(pyridin-2-yl)ethyl)amino)-N-(5-(pyridin-4-yl)-1,3,4-thiadiazol-2-yl)nicotinamide;
6-((1-(pyridin-3-yl)propan-2-yl)amino)-N-(5-(pyridin-4-yl)-1,3,4-thiadiazol-2-yl)nicotinamide;
6-((1-phenylethyl)amino)-N-(5-(pyridin-4-yl)-1,3,4-thiadiazol-2-yl)nicotinamide;
4-((6,7-dihydro-5H-cyclopenta[b]pyridin-5-yl)oxy)-3-methoxy-N-(5-(pyridin-4-yl)-1,3,4-thiadiazol-2-yl)benzamide;
4-((2,3-dihydrobenzofuran-3-yl)oxy)-3-methoxy-N-(5-(pyridin-4-yl)-1,3,4-thiadiazol-2-yl)benzamide;
4-cyclopropyl(phenyl)methoxy)-3-methoxy-N-(5-(pyridin-4-yl)-1,3,4-thiadiazol-2-yl)benzamide;
3-methoxy-4-(1-phenylethoxy)-N-(5-(pyrimidin-4-yl)-1,3,4-thiadiazol-2-yl)benzamide;
4-((2,3-dihydro-1H-inden-2-yl)oxy)-3-methoxy-N-(5-(pyridin-4-yl)-1,3,4-thiadiazol-2-yl)benzamide;
3-methoxy-4-(1-phenylpropoxy)-N-(5-(pyridin-4-yl)-1,3,4-thiadiazol-2-yl)benzamide;
3-methoxy-4-phenethoxy-N-(5-(pyridin-4-yl)-1,3,4-thiadiazol-2-yl)benzamide;
3-methoxy-4-((1-methyl-1H-pyrazol-3-yl)methoxy)-N-(5-(pyridin-4-yl)-1,3,4-thiadiazol-2-yl)benzamide;
3-methoxy-4-(pyridin-3-ylmethoxy)-N-(5-(pyridin-4-yl)-1,3,4-thiadiazol-2-yl)benzamide;
4-(benzyloxy)-3-chloro-N-(5-(pyridin-4-yl)-1,3,4-thiadiazol-2-yl)benzamide;

4-(benzyloxy)-2-chloro-N-(5-(pyridin-4-yl)-1,3,4-thiadiazol-2-yl)benzamide;
4-(pyridin-3-ylmethoxy)-N-(5-(pyridin-4-yl)-1,3,4-thiadiazol-2-yl)benzamide;
4-(1-phenylethoxy)-N-(5-(pyridin-4-yl)-1,3,4-thiadiazol-2-yl)benzamide;
4-(benzyloxy)-2-fluoro-N-(5-(pyridin-4-yl)-1,3,4-thiadiazol-2-yl)benzamide;
4-(benzyloxy)-3-methoxy-N-(5-(pyridin-4-yl)-1,3,4-thiadiazol-2-yl)benzamide;
4-phenoxy-N-(5-(pyridin-4-yl)-1,3,4-thiadiazol-2-yl)benzamide;
6-phenoxy-N-(5-(pyridin-4-yl)-1,3,4-thiadiazol-2-yl)nicotinamide;
6-((1-(dimethylamino)-1-oxo-3-phenylpropan-2-yl)oxy)-N-(5-(pyridin-4-yl)-1,3,4-thiadiazol-2-yl)nicotinamide;
6-((4-phenylbutan-2-yl)oxy)-N-(5-(pyridin-4-yl)-1,3,4-thiadiazol-2-yl)nicotinamide;
6-(2-phenylpropoxy)-N-(5-(pyridin-4-yl)-1,3,4-thiadiazol-2-yl)nicotinamide;
6-(3-(4-methoxyphenyl)propoxy)-N-(5-(pyridin-4-yl)-1,3,4-thiadiazol-2-yl)nicotinamide;
5-methyl-6-(2-morpholino-1-phenylethoxy)-N-(5-(pyridin-4-yl)-1,3,4-thiadiazol-2-yl)nicotinamide;
3-methoxy-4-(2-methoxy-1-phenylethoxy)-N-(5-(pyridin-4-yl)-1,3,4-thiadiazol-2-yl)benzamide;
3-methoxy-4-(2-morpholino-1-phenylethoxy)-N-(5-(pyridin-4-yl)-1,3,4-thiadiazol-2-yl)benzamide;
3-methoxy-4-(2-morpholino-1-phenylethoxy)-N-(5-(pyridin-4-yl)-1,3,4-thiadiazol-2-yl)benzamide;
6-(3-(dimethylamino)-1-phenylpropoxy)-5-methoxy-N-(5-(pyrimidin-4-yl)-1,3,4-thiadiazol-2-yl)nicotinamide;
6-(2-(3,3-difluoropyrrolidin-1-yl)-1-phenylethoxy)-N-(5-(pyridin-4-yl)-1,3,4-thiadiazol-2-yl)nicotinamide;
6-(2-(4-methylpiperazin-1-yl)-1-phenylethoxy)-N-(5-(pyridin-4-yl)-1,3,4-thiadiazol-2-yl)nicotinamide;
6-(1-phenyl-3-(pyrrolidin-1-yl)propoxy)-N-(5-(pyridin-4-yl)-1,3,4-thiadiazol-2-yl)nicotinamide;
5-methoxy-6-(1-phenyl-2-(pyrrolidin-1-yl)ethoxy)-N-(5-(pyrimidin-4-yl)-1,3,4-thiadiazol-2-yl)nicotinamide;
5-methoxy-6-(1-phenyl-2-(pyrrolidin-1-yl)ethoxy)-N-(5-(pyridin-4-yl)-1,3,4-thiadiazol-2-yl)nicotinamide;
5-methyl-6-(1-phenyl-2-(pyrrolidin-1-yl)ethoxy)-N-(5-(pyridin-4-yl)-1,3,4-thiadiazol-2-yl)nicotinamide;
5-methoxy-6-(1-phenylethoxy)-N-(5-(pyrimidin-4-yl)-1,3,4-thiadiazol-2-yl)nicotinamide;
4-(2-(dimethylamino)-1-phenylethoxy)-3-fluoro-N-(5-(pyridin-4-yl)-1,3,4-thiadiazol-2-yl)benzamide;
3-chloro-4-(2-(dimethylamino)-1-phenylethoxy)-N-(5-(pyridin-4-yl)-1,3,4-thiadiazol-2-yl)benzamide;
4-(1-(4-fluorophenyl)-2-hydroxyethoxy)-3-methoxy-N-(5-(pyridin-4-yl)-1,3,4-thiadiazol-2-yl)benzamide; and
4-(2-(dimethylamino)-1-(4-fluorophenyl)ethoxy)-3-methoxy-N-(5-(pyridin-4-yl)-1,3,4-thiadiazol-2-yl)benzamide.

12. A pharmaceutical composition comprising at least one amido thiadiazole compound according to claim 1 and a pharmaceutically acceptable carrier, diluent or excipient thereof.

* * * * *